United States Patent
Rader et al.

(10) Patent No.: US 11,883,470 B2
(45) Date of Patent: Jan. 30, 2024

(54) COMPOSITIONS COMPRISING A LECITHIN CHOLESTEROL ACYLTRANSFERASE VARIANT AND USES THEREOF

(71) Applicant: The Trustees of the University of Pennsylvania, Philadelphia, PA (US)

(72) Inventors: Daniel Rader, Philadelphia, PA (US); Devin Christopher, Philadelphia, PA (US); Anna P. Tretiakova, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 814 days.

(21) Appl. No.: 16/320,350

(22) PCT Filed: Jul. 24, 2017

(86) PCT No.: PCT/US2017/043535
§ 371 (c)(1),
(2) Date: Jan. 24, 2019

(87) PCT Pub. No.: WO2018/022511
PCT Pub. Date: Feb. 1, 2018

(65) Prior Publication Data
US 2019/0282670 A1    Sep. 19, 2019

Related U.S. Application Data

(60) Provisional application No. 62/366,423, filed on Jul. 25, 2016.

(51) Int. Cl.
| | |
|---|---|
| *A61K 38/45* | (2006.01) |
| *A61K 48/00* | (2006.01) |
| *C12N 9/10* | (2006.01) |
| *C12N 15/86* | (2006.01) |
| *A61P 9/00* | (2006.01) |
| *C12P 21/02* | (2006.01) |
| *A61P 1/16* | (2006.01) |
| *A61K 38/00* | (2006.01) |

(52) U.S. Cl.
CPC .......... *A61K 38/45* (2013.01); *A61K 48/0058* (2013.01); *A61P 1/16* (2018.01); *A61P 9/00* (2018.01); *C12N 9/1029* (2013.01); *C12N 15/86* (2013.01); *C12P 21/02* (2013.01); *A61K 38/00* (2013.01); *C12N 2750/14143* (2013.01); *C12Y 203/01043* (2013.01)

(58) Field of Classification Search
None
See application file for complete search history.

(56) References Cited

U.S. PATENT DOCUMENTS

| | | | |
|---|---|---|---|
| 5,139,941 | A | 8/1992 | Muzyczka et al. |
| 5,478,745 | A | 12/1995 | Samulski et al. |
| 5,741,683 | A | 4/1998 | Zhou et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,491,907 | B1 | 12/2002 | Rabinowitz et al. |
| 6,596,535 | B1 | 7/2003 | Carter |
| 6,660,514 | B1 | 12/2003 | Zolotukhin et al. |
| 6,951,753 | B2 | 10/2005 | Shenk et al. |
| 7,094,604 | B2 | 8/2006 | Snyder et al. |
| 7,125,717 | B2 | 10/2006 | Carter |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,456,683 | B2 | 11/2008 | Takano et al. |
| 7,588,772 | B2 | 9/2009 | Kay et al. |
| 7,790,449 | B2 | 9/2010 | Gao et al. |

(Continued)

FOREIGN PATENT DOCUMENTS

| | | |
|---|---|---|
| CN | 102947453 A | 2/2013 |
| CN | 104520428 A | 4/2015 |

(Continued)

OTHER PUBLICATIONS

Gordon, David J,M.D., PhD., & Rifkind, Basil M,M.D., F.R.C.P. (1989). Current concepts: High-density lipoprotein—the clinical implications of recent studies. The New England Journal of Medicine, 321(19), 1311-1316. doi:https://doi.org/10.1056/NEJM198911093211907 (Year: 1989).*
Cohen et al. Multiple Rare Alleles Contribute to Low Plasma Levels of HDL Cholesterol. 2004. Science vol. 305(5685): 869-871 (Year: 2004).*
Gordon et al. High-Density Lipoprotein—The Clinical Implications of Recent Studies. 1986 Circulation 74, No. 6, 121: 7-1225 (Year: 1986).*

(Continued)

*Primary Examiner* — Samuel C Woolwine
*Assistant Examiner* — Tiffany Nicole Grooms
(74) *Attorney, Agent, or Firm* — Howson & Howson LLP; Cathy A. Kodroff

(57) ABSTRACT

A synthetic or recombinant human lecithin cholesterol acyltransferase (LCAT) variant is provided which comprises an LCAT enzyme having a substitution at position 114 based on the residue numbering of wild-type (WT) human LCAT [SEQ ID NO:1], wherein said variant is characterized by one or more of: (i) an esterification rate higher than the esterification rate of WT human LCAT; and/or (ii) an association with higher density lipoprotein levels as compared to subjects having WT LCAT. Also provided are vectors encoding the variant, compositions containing same, and methods of using the variant proteins and vectors for treatment of a variety of disorders associated with defective wt LCAT.

25 Claims, 28 Drawing Sheets
Specification includes a Sequence Listing.

(56) References Cited

U.S. PATENT DOCUMENTS

| | | | |
|---|---|---|---|
| 7,906,111 | B2 | 3/2011 | Wilson et al. |
| 7,943,374 | B2 | 5/2011 | Hildinger |
| 10,137,176 | B2 | 11/2018 | Wilson et al. |
| 10,889,832 | B2 | 1/2021 | Wilson et al. |
| 2002/0094324 | A1 | 7/2002 | Branellec et al. |
| 2002/0131956 | A1 | 9/2002 | Walsh et al. |
| 2004/0167088 | A1 | 8/2004 | Wickham et al. |
| 2007/0036760 | A1 | 2/2007 | Wilson et al. |
| 2009/0197338 | A1 | 8/2009 | Vandenberghe et al. |
| 2009/0227030 | A1 | 9/2009 | Gao et al. |
| 2012/0252877 | A1 | 10/2012 | Lo |
| 2013/0072548 | A1 | 3/2013 | Wright et al. |
| 2013/0259924 | A1 | 10/2013 | Bancel et al. |
| 2014/0155468 | A1 | 6/2014 | Gregory et al. |
| 2014/0252877 | A1 | 9/2014 | Turki |
| 2014/0348876 | A1 | 11/2014 | Jezek et al. |
| 2015/0065556 | A1 | 3/2015 | Birsoy et al. |
| 2015/0111955 | A1 | 4/2015 | High et al. |
| 2015/0293120 | A1 | 10/2015 | Lüking et al. |
| 2016/0000887 | A1 | 1/2016 | Wilson et al. |
| 2017/0101458 | A1 | 4/2017 | Wilson et al. |

FOREIGN PATENT DOCUMENTS

| | | | |
|---|---|---|---|
| EP | 1310571 | | 11/2002 |
| EP | 2489730 | | 8/2012 |
| EP | 2529020 | A1 | 12/2012 |
| JP | 2012-516357 | | 7/2012 |
| WO | WO-2003/042397 | | 5/2003 |
| WO | WO 2003/052051 | | 6/2003 |
| WO | WO-2004/108922 | | 12/2004 |
| WO | WO-2004108922 | A2 * | 12/2004 ........... C07K 14/775 |
| WO | WO-2005/033321 | | 4/2005 |
| WO | WO-2006/110689 | | 10/2006 |
| WO | WO-2011/020118 | | 2/2011 |
| WO | WO-2011/126808 | | 10/2011 |
| WO | WO-2012/177741 | | 12/2012 |
| WO | WO 2013/039969 | | 3/2013 |
| WO | WO-2013/049493 | | 4/2013 |
| WO | WO-2014/127196 | A1 | 8/2014 |
| WO | WO-2015/012924 | | 1/2015 |
| WO | WO-2015/051214 | | 4/2015 |
| WO | WO-2015/164723 | | 10/2015 |
| WO | WO-2015/0164778 | | 10/2015 |
| WO | WO-2015/164778 | | 10/2015 |
| WO | WO-2017/100682 | | 6/2017 |

OTHER PUBLICATIONS

NCBI Reference Sequence: NM_000229.1, 2014, *Homo sapiens* lecithin-cholesterol acyltransferase (LCAT), mRNA (Year: 2014).*

Lee et al. Analysis of human lecithin-cholesterol acyltransferase activity by carboxyl-terminal truncation. Biochimica et Biophysica Acta 1344 1997. 250-261 (Year: 1997).*

Spahr et al. Recombinant human lecithin-cholesterol acyltransferase Fc fusion: Analysis of N- and O-linked glycans and identification and elimination of a xylose-based. Protein Science 2013 vol. 22:1739-1753 (Year: 2013).*

Bryant et al., Lessons learned from the clinical development and market authorization of Glybera, Human Gene Therapy, vol. 24(2):55-64, Jun. 2013.

Buning et al., Recent developments in adeno-associated virus vector technology, Journal Gene Medicine, vol. 10(7):717-733, Jul. 2008.

Conca et al., Novel missense variants in LCAT and APOB genes in an Italian kindred with familial lecithin: cholesterol acyltransferase deficiency and hypobetalipoproteinemia, Journal of Clinical Lipidology, vol. 6(3):244-50, May 2012.

Cohen et al., Multiple Rare Alleles Contribute to Low Plasma Levels of HDL Cholesterol, Science, vol. 305(5685):869-72, Aug. 2004.

Elbers et al., Gene-Centric Meta-Analysis of Lipid Traits in African, East Asian and Hispanic Populations, PLoS One, vol. 7(2):e50198, Dec. 2012.

Fisher et al., Transduction with recombinant adeno-associated virus for gene therapy is limited by leading-strand synthesis, Journal Virology, vol. 70(1):520-532, Jan. 1996.

Goldbourt et al., Isolated Low HDL Cholesterol as a Risk Factor for Coronary Heart Disease Mortality, Arterioschelosis, Thrombosis, and Vascular Biology, vol. 17(1):10-13, Jan. 1997.

Gordon et al., High-density lipoprotein cholesterol and coronary heart disease in hypercholesterolemic men: The Lipid Research Clinics Coronary Primary Prevention Trial, Circulation., vol. 74:1217-1225, Dec. 1986.

Green and Sambrook, Molecular Cloning: A Laboratory Manual, Cold Spring Harbor Press, Cold Spring Harbor, NY (2012).

Grieger et al., Adeno-associated virus as a gene therapy vector: Vector development, production and clinical applications, Advance Biochem. Engineering/Biotechnology, vol. 99:119-145, Oct. 2005.

Kassim et al., Gene therapy in a humanized mouse model of familial hypercholesterolemia leads to marked regression of atherosclerosis, PLoS One, vol. 5(10):e13424, Oct. 2010.

Lock et al., Absolute Determination of Single-Stranded and Self-Complementary Adeno-Associated Viral Vector Genome Titers by Droplet Digital PCR, Human Gene Therapy Methods, vol. 25(2):115-25, Apr. 2014.

Marchot et al., Enzymatic activity and protein interactions in alpha/beta hydrolase fold proteins: moonlighting versus promiscuity, Protein and Peptide Letters, vol. 19(2):132-43, Feb. 2012.

Matagne et al., A codon-optimized Mecp2 transgene corrects breathing deficits and improves survival in a mouse model of Rett syndrome, Neurobiology of Disease, vol. 99:1-11, Mar. 2017.

McCarty et al., Self-complementary recombinant adeno-associated virus (scAAV) vectors promote efficient transduction independently of DNA synthesis, Gene Therapy, vol. 8(16):1248-1254, Aug. 2001.

Miyatake et al., Transcriptional targeting of herpes simplex virus for cell-specific replication, Journal Virology, vol. 71*7):5124-32, Jul. 1997.

Muthahari et al., Elucidation of Active Site Protective Residues in Rhizomucor miehei Lipase by Targeted Molecular Dynamics Approach, Procedia Chemistry, vol. 16:285-291, 2015.

Nathwani et al., Long-term safety and efficacy of factor IX gene therapy in hemophilia B, New England Journal of Medicine, vol. 371:1994-2004, Nov. 2014.

Peters et al., Theoretical investigation of the dynamics of the active site lid in Rhizomucor miehei lipase, Biophysical Journal, vol. 71(1):119-129, Jul. 1996.

Ossoli et al., Lipoprotein X Causes Renal Disease in LCAT Deficiency, PLoS One, vol. 11(2):e0150083, Feb. 2016.

Piper et al., The high-resolution crystal structure of the human LCAT, Journal of Lipid Research, vol. 56(9):1711-9, Sep. 2015.

Rousset et al., Effect of recombinant human lecithin cholesterol acyltransferase infusion on lipoprotein metabolism in mice, The Journal of Pharmacology and Experimental Therapeutics, vol. 335(1):140-148, Oct. 2010.

Sakai et al., Targeted disruption of the mouse lecithin:cholesterol acyltransferase (LCAT) gene. Generation of a new animal model for human LCAT deficiency, The Journal of Biological Chemistry, vol. 272(11):7506-7510, Mar. 1997.

Sandig et al., HBV-derived promoters direct liver-specific expression of an adenovirally transduced LDL receptor gene, vol. 3(11):1002-9, Nov. 1996.

Se'guret-mace' et al., Potential Gene Therapy for Lecithin-Cholesterol Acyltransferase (LCAT)-Deficient and Hypoalphalipoproteinemic Patients With Adenovirus-Mediated Transfer of Human LCAT Gene, Circulation, vol. 94(9):2177-2184, Nov. 1996.

Shamburek et al., Familial Lecithin:Cholesterol Acyltransferase Deficiency: First-in-Human Treatment with Enzyme Replacement, Journal Clinical Lipidology, vol. 10(2):356-367, Mar. 2016.

Thomson et al., A comprehensive comparison of multiple sequence alignments, Nucleic Acids Research, vol. 27(13): 2682-2690, Jul. 1999.

Tricoci et al., Infusion of Reconstructed High-Density Lipoprotein CSL112, in Patients with Atherosclerosis: Safety and Pharmacokinetic Results from a Phase 2a Randomized Clinical Trial, Journal of the American Heart Association, vol. 4(8):e002171, Aug. 2015.

(56) References Cited

OTHER PUBLICATIONS

Watson et al., Treatment of patients with cardiovascular disease with L-4F, an apo-A1 mimetic, did not improve select biomarkers of HDL function, Journal of Lipids Research, vol. 52:361-373, Feb. 2011.
Zhang et al., Adenovirus-adeno-associated virus hybrid for large-scale recombinant adeno-associated virus production, Human Gene Therapy, vol. 20(9):922-929, Sep. 2009.
International Search Report and Written Opinion dated Nov. 16, 2017, in International Patent Application No. PCT/US2017/43535, filed Jul. 24, 2017.
U.S. Appl. No. 62/366,423, filed Jul. 25, 2016.
Ajufo et al., Recent Developments in Gene Therapy for Homozygous Familial Hypercholesterolemia, Curr. Atheroscler. Re., vol. 18(22), Mar. 2016.
BioQuest, PBS (Phosphate Buffered Saline) (1X, ph 7.4) Preparation and Recipe, AAT Bioquest, retrieved Oct. 6, 2021 from https://www.aatbio.com/resources/buffer-preparations-and-recipes/pbs-phosphate-buffered-saline.
Boutin et al., Prevalence of serum IgG and neutralizing factors against adeno-associated virus (AAV) types 1, 2, 5, 6, 8, and 9 in the healthy population: implications for gene therapy using AAV vectors, Human Gene Therapy, vol. 21(6):704-712, Jun. 2010.
Carillo-Carrasco et al., Liver-directed recombinant adeno-associated viral gene delivery rescues a lethal mouse model of methylmalonic acidemia and provides long-term phenotypic correction, Human Gene Therapy, vol. 21:1147-1154, Sep. 2010.
Chandler et al., Liver-directed adeno-associated virus serotype 8 gene transfer rescues a lethal murine model of citrullinemia type 1, Gene Therapy, vol. 20:1188-1191, Oct. 2013.
Harrington et al., Neutralizing Antibodies Against Adeno-Associated Viral Capsids in Patients with mut Methylmalonic Acidemia, Human Gene Therapy, vol. 27(5):345-353, Jan. 2016.
Jiang et al., Effects of transient immunosuppression on adeno-associated, virus-mediated, liver-directed gene transfer in rhesus macaques and implications for human gene therapy, Blood, vol. 18(10):3321-3328, Nov. 2006.
Lagor et al., Overview of the LDL receptor: relevance to cholesterol metabolism and future approaches for the treatment of coronary heart disease, Journal of Receptor, Ligand and Channel Research, pp. 1-13, Dec. 2009.
Mimuro et al., Minimizing the Inhibitory Effect of Neutralizing Antibody for Efficient Gene Expression in the Liver With Adeno-associated Virus 8 Vectors, Molecular Therapy, vol. 21(2):318-323, Feb. 2013.
Scripps Laboratories, Phosphate Buffer Formulations: 10mM Sodium Phosphate, 150 mM Sodium Chloride, 0.05%, Sodium Azide, pH 7.2 0.1, retrieved Oct. 6, 2021 from http://scrippslabs.com/phosphate-buffer-formulations.
Maguire et al., Safety and Efficacy of Gene Transfer for Leber's Cogenital Amaurosis, New England Journal of Medicine, vol. 358(21):2240-2248, May 2008.
Somanathan et al., AAV vectors expressing LDLR gain-of-function variants demonstrate increased efficacy in mouse models of familial hypercholesterolemia, Circulation Research, vol. 115(6):591-599, Aug. 2014.
Zhang et al., Binding of Proprotein Convertase Subtilisin/Kexin Type 9 to Epidermal Growth Factor-like Repeat A of Low Density Lipoprotein Receptor Decreases Receptor Recycling and Increases Degradation, Journal of Biological Chemistry, American Society for Biochemistry and Molecular Biology, vol. 282(25):18602-18612, Jun. 2007.
Non-Final Office Action issued on U.S. Appl. No. 15/306,419, dated Feb. 18, 2022.
Office Action issued on Japanese Patent Application No. 2019-545363, with agent translation, dated Jan. 19, 2022.
Non-Final Office Action issued on U.S. Appl. No. 16/486,981, dated Nov. 26, 2021.
Office Action issued on Chinese Patent Application No. 201680081580.9, with agent translation, dated May 8, 2021.
Extended European Search Report issued on European Patent Application No. 21166865.2, dated Oct. 18, 2021.
AAl-Alif et al., LDLR-Gene therapy for familial hypercholesterolaemia: problems, progress, and perspectives, vol. 3(1):36, Dec. 2010.
Deng et al., Identification of amino acid residues in the ligand binding repeats of LDL receptor important for PCSK9 binding, Journal Lipid Research, vol. 60(3):516-527, Mar. 2019.
Gordon et al., High-density lipoprotein—the clinical implications of recent studies, The New England Journal of Medicine, vol. 9:1311-6, Nov. 1989.
Gong, et al., A gene expression atlas of the central nervous system based on bacterial artificial chromosomes, Nature, vol. 425(6961):917-25, Oct. 2003.
Greig et al., Characterization of AAV-mediated human factor VIII gene therapy in hemophilia A mice, Human Gene Therapy, vol. 28(5):392-402, May 2017.
Gu et al., Characterization of the role of EGF-A of low density lipoprotein receptor in PCSK9 binding, The Journal of Lipid Research, vol. 54(12):3345-3357, Dec. 2013.
Kassim et al., Adeno associated virus serotype 8 gene therapy leads to significant lowering of plasma cholesterol levels in humanized mouse models of homozygous and heterozygous familial hypercholesterolemia, Human Gene Therapy, vol. 24(1):19-26, Jan. 2013.
Maguire et al., Safety and efficacy of gene transfer for Leber's congenital amaurosis, New England Journal of Medicine, vol. 358(21):2240-2248, May 2008.
Nardini et al., Alpha/beta hydrolase fold enzymes: the family keeps growing, Current Opinion in Structural Biology, vol. 9(6):732-737, Dec. 1999.
Vaisman et al., Measurement of lecithin-cholesterol acyltransferase activity with the use of a Peptide-Proteoliposome substrate, Methods in Molecular Biology, vol. 1027:343-52, 2013.
Zelcer et al, LXR Regulates Cholesterol Uptake Through Idol-Dependent Ubiquitination of the LDL Receptor, Science, vol. 325(5936):100-104, Jul. 2009.
Wright et al., Identification of Factors that Contribute to Recombinant AAV2 Particle Aggregation and Methods to Prevent its Occurrence during Vector Purification and Formulation, Molecular Therapy, vol. 12(1):1710178, Jul. 2005.
Chen et al., Biodistribution of AAV8 Vectors Expressing Human Low-Density Lipoprotein Receptor in a Mouse Model of Homozygous Familial Hypercholesterolemia, Human Gene Therapy Clinical Development, vol. 24(4):154-460, Dec. 2013.
Suryanarayan et al., AAV vectors expressing LDLR gain-of-function variants demonstrate increased efficacy in mouse models of familial hypercholesterolemia, Circulation Research, American Heart Association, Inc., vol. 115(6):591-599, Aug. 2014.
Ezim et al., Recent Developments in Gene Therapy for Hypercholesterolemia, Current Atherosclerosis Reports, Current Science, vol. 18(5):1-9, Mar. 2016.
Nathwani et al., Enhancing transduction of the liver by adeno-associated viral vectors, Gene Therapy, vol. 16(1):60-69, Jan. 2009.
Non-Final Office Action dated Apr. 2, 2020 issued in corresponding U.S. Appl. No. 16/060,409, and Response dated Jul. 2, 2020.
Non-Final Office Action dated May 1, 2020 issued in corresponding U.S. Appl. No. 15/306,419.
Communication issued in corresponding European Patent Application No. 16825936.4, dated May 20, 2020.
Office Action dated Jun. 2, 2020 issued in corresponding Brazilian Patent Application No. BR112016024379-0, and translation provided by local Agent.
Office Action dated Aug. 31, 2020 issued in corresponding Colombian Patent Application No. NC2018/0007165, and Response filed Jan. 13, 2021.
Extended Search Report dated Dec. 1, 2020 issued in corresponding European Patent Application No. 18754347.5.
Office Action dated Dec. 16, 2020 issued in corresponding Japanese Patent Application No. 2018-530566, with unofficial translation provided by local Agent.
Final Office Action dated Dec. 28, 2020 issued in corresponding U.S. Appl. No. 15/306,419.
Dec. 18, 2017, WO, PCT/US2017/043535.

(56) References Cited

OTHER PUBLICATIONS

Cohen et al, Science, Multiple rare alleles contribute to low plasma levels of HDL cholesterol, vol. 305(5685):869-72, Aug. 2004.
Glukhova, et al, Nature Communications, Structure and function of lysosomal phospholipase A2 and lecithin:cholesterol acyltransferase, vol. 6:6250, Mar. 2015.
Piper, et al, The Journal of Lipid Research, The high-resolution crystal structure of human LCAT, vol. 56(9):1711-1719, Sep. 2015.
Lock et al., Rapid, Simple, and Versatile Manufacturing of Recombinant Adeno-Associated Viral Vectors at Scale, Human Gene Therapy, vol. 21(10):1259-1271, Oct. 2010.
Extended European Search Report dated Oct. 10, 2022 issued in corresponding European Patent Application No. 22165782.8 and response.
Non-Final Office Action dated Nov. 10, 2022 issued in corresponding U.S. Appl. No. 16/950,272 and response.
Office Action dated Jul. 13, 2022 issued in corresponding Israeli Patent Application No. 268276 and response.
Office Action dated Jul. 19, 2022 issued in corresponding Mexican Patent Application No. MX/A/2018/007080.
Office Action dated Feb. 27, 2023 issued in corresponding Mexican Patent Application No. MX/A/2018/007080.
Office Action dated Apr. 25, 2023 issued in corresponding Korean Patent Application No. 10-2019-7024773.
Ayyobi et al., Lecithin: cholesterol acyltransferase (LCAT) deficiency and risk of vascular disease: 25 year follow-up, Atherosclerosis, 177(2): 361-6, Dec. 2004.
Bell et al., No evidence for tumorigenesis of AAV vectors in a large-scale study in mice, Molecular Therapy: The journal of the American Society of Gene Therapy, 12(2): 299-306, Aug. 2005.
Bell et al., Analysis of tumors arising in male B6C3F1 mice with and without AAV vector delivery to liver, Molecular Therapeutics, 14(1): 34-44, May 2006.
Borysiewicz et al., Renal failure in familial lecithin: cholesterol acyltransferase deficiency, The Quarterly Journal of Medicine, 51(204): 411-26, 1982.
Calabresi et al., The molecular basis of lecithin:cholesterol acyltransferase deficiency syndromes: a comprehensive study of molecular and biochemical findings in 13 unrelated Italian families, Arteriosclerosis, Thrombosis, and Vascular Biology, 25(9): 1972-8, Sep. 2005.
Calcedo et al., Worldwide epidemiology of neutralizing antibodies to adeno-associated viruses, Journal of Infectious Disease, 199(3): 381-90, Feb. 2009.
Chandler et al., Vector design influences hepatic genotoxicity after adeno-associated virus gene therapy, Journal of Clinical Investigation, 125(2): 870-80, Feb. 2015.
Cogan et al., Corneal opacity in LCAT disease, Cornea, 11(6): 595-9, Nov. 1992.
Couto et al., Direct exposure of mouse spermatozoa to very high concentrations of a serotype-2 adeno-associated virus gene therapy vector fails to lead to germ cell transduction, Human Gene Therapy, 15(3): 287-91, Mar. 2004.
Donsante et al., Observed incidence of tumorigenesis in longterm rodent studies of rAAV vectors, Gene Therapy, 8(17): 1343-6, Sep. 2001.
Favaro et al., Host and vector-dependent effects on the risk of germline transmission of AAV vectors, Molecular Therapy: The journal of the American Society of Gene Therapy, 17(6):1022-30, Jun. 2009.
Ferla et al., Non-clinical safety and efficacy of an AAV2/8 vector administered intravenously for treatment of Mucopolysaccharidosis Type VI. Molecular Therapy Methods & Clinical Development, 6: 143-58, Sep. 2017.
Fountoulakis et al., The P274S Mutation of Lecithin-Cholesterol Acyltransferase (LCAT) and Its Clinical Manifestations in a Large Kindred. American Journal of Kidney Diseases, 74(4):510-522, Oct. 2019.
Freeman et al., The Effects of MEDI6012 on Lipoproteins in Familial LCAT Deficiency Patients and a New NMR Method for Quantifying Lipoprotein-X, Circulation, 136(Supp. 1):A16097, Nov. 2017.
Frohlich et al., Plasma lipoprotein abnormalities in heterozygotes for familial lecithin:cholesterol acyltransferase deficiency. Metabolism: Clinical and Experimental, 37(1):3-8, Jan. 1988.
Funke et al., Genetic and phenotypic heterogeneity in familial lecithin: cholesterol acyltransferase (LCAT) deficiency. Six newly identified defective alleles further contribute to the structural heterogeneity in this disease. The Journal of Clinical Investigation, 91(2):677-83, Feb. 1993.
Gao et al., Clades of adeno-associated viruses are widely disseminated in human tissues, Journal of Virology, 78(12):6381-8, Jun. 2004.
Geller et al., Genetic and secondary causes of severe HDL deficiency and cardiovascular disease, Journal of Lipid Research, 59(12):2421-35, Dec. 2018.
George et al., Hemophilia B Gene Therapy with a High-Specific-Activity Factor IX Variant, The New England Journal of Medicine, 377(23):2215-27, Dec. 2017.
Gil-Farina et al., Recombinant AAV integration is not associated with hepatic genotoxicity in nonhuman primates and patients. Molecular therapy: The Journal of the American Society of Gene Therapy, 24(6):1100-5, Jun. 2016.
Glomset, The plasma lecithins:cholesterol acyltransferase reaction, Journal of Lipid Research, 9(2):155-67, Mar. 1968.
Graham et al., Characteristics of a human cell line transformed by DNA from human adenovirus type 5, Journal General Virology, 36(1):59-74, Jul. 1997.
Greig et al., Non-clinical study examining AAV8.TBG.hLDLR vector-associated toxicity in chow-fed wild-type and LDLR(+/−) Rhesus macaques, Human Gene Therapy Clinical Development, 28(1):39-50, Mar. 2017.
Holleboom et al., Proteinuria in early childhood due to familial LCAT deficiency caused by loss of a disulfide bond in lecithin:cholesterol acyl transferase, Atherosclerosis, 216(1):161-5, May 2011.
Holleboom et al., High prevalence of mutations in LCAT in patients with low HDL cholesterol levels in The Netherlands: identification and characterization of eight novel mutations, Human Mutation, 32(11):1290-8, Nov. 2011.
Horina et al., Long-term follow-up of a patient with lecithin cholesterol acyltransferase deficiency syndrome after kidney transplantation, Transplantation, 56(1):233-6, Jul. 1993.
Imbasciati et al., Renal lesions in familial lecithincholesterol acyltransferase deficiency. Ultrastructural heterogeneity of glomerular changes, American Journal of Nephrology, 6(1):66-70, 1986.
Jakob et al., No evidence for germline transmission following prenatal and early postnatal AAV-mediated gene delivery, Journal of Gene Medicine, 7(5):630-7, May 2005.
Jonas, Lecithin cholesterol acyltransferase, Biochimica et Biophysica acta, 1529(1-3):245-56, Dec. 2000.
Kay et al., Evidence for gene transfer and expression of factor IX in haemophilia B patients treated with an AAV vector, Nature Genetics, 24(3):257-61, Mar. 2000.
Kuivenhoven et al., The molecular pathology of lecithin:cholesterol acyltransferase (LCAT) deficiency syndromes, Journal of Lipid Research, 38(2):191-205, Feb. 1997.
Lambert et al., Analysis of glomerulosclerosis and atherosclerosis in lecithin cholesterol acyltransferase-deficient mice, The Journal of Biological Chemistry, 276(18):15090-8, May 2001.
Li et al., Assessing the potential for AAV vector genotoxicity in a murine model, Blood, 117(12):3311-9, Mar. 2011.
Li et al., Adeno-associated virus capsid antigen presentation is dependent on endosomal escape, Journal of Clinical Investigation, 123(3):1390-401, Mar. 2013.
Lynn et al., Uptake and metabolism of lipoprotein-X in mesangial cells. Molecular and Cellular Biochemistry, 175(1-2):187-94, Oct. 1997.
Manno et al., Successful transduction of liver in hemophilia by AAV-Factor IX and limitations imposed by the host immune response, Nature Medicine, 12:342-7, Feb. 2006.

(56) References Cited

OTHER PUBLICATIONS

McCarty et al., Integration of adeno-associated virus (AAV) and recombinant AAV vectors, Annual Reviews of Genetics, 38:819-45, Dec. 2004.

Melnick et al., Association of 20 milli-micron particles with adenoviruses, Journal of Bacteriology, 90(1):271-4, Jul. 1965.

Miller, Glybera and the future of gene therapy in the European Union, Nature Reviews Drug Discovery, 11:419, Apr. 2012.

Murayama et al., Effects of plasma infusion on plasma lipids, apoproteins and plasma enzyme activities in familial lecithin:cholesterol acyltransferase deficiency, European Journal of Clinical Investigation, 14(2):122-9, Apr. 1984.

Myhre et al., Renal failure in familial lecithin-cholesterol acyltransferase deficiency, Nephron, 18(4):239-48, 1977.

Najafian et al., AJKD Atlas of Renal Pathology: Lecithin-Cholesterol Acyltransferase (LCAT) Deficiency, American Journal of Kidney Diseases, 70(1):e5-e6, Jul. 2017.

Nathwani et al., Adenovirus-associated virus vector mediated gene transfer in hemophilia B, New England Journal of Medicine, 365:2357-65, Dec. 2011.

Ng et al., Disruption of the murine lecithin:cholesterol acyltransferase gene causes impairment of adrenal lipid delivery and up-regulation of scavenger receptor class B type I, The Journal of Biological Chemistry, 272(25):15777-81, Jun. 1997.

Ng et al., Hypertriglyceridemia in lecithin-cholesterol acyltransferase-deficient mice is associated with hepatic overproduction of triglycerides, increased lipogenesis, and improved glucose tolerance, Journal of Biological Chemistry, 279(9):7636-42, Feb. 2004.

Nichols et al., Effects of guanidine hydrochloride on human plasma high density lipoproteins, Biochimica et Biophysica Acta, 446(1):226-39, Sep. 1976.

Nishiwaki et al., Human lecithin:cholesterol acyltransferase deficiency: in vivo kinetics of low-density lipoprotein and lipoprotein-X, Arteriosclerosis, Thrombosis, and Vascular Biology, 26(6):1370-5, Jun. 2006.

Norum et al., The effect of plasma transfusion on the plasma cholesterol esters in patients with familial plasma lecithin: cholesterol acyltransferase deficiency, Scandinavian Journal of Clinical and Laboratory Investigation, 22(4):339-42, Dec. 1968.

Norum et al., Plasma lipoproteins in familial lecithin:cholesterol acyltransferase deficiency: physical and chemical studies of low and high density lipoproteins, Journal of Clinical Investigation, 50(5):1131-40, May 1971.

Panescu et al., Recurrence of lecithin cholesterol acyltransferase deficiency after kidney transplantation, Nephrology, Dialysis, Transplantation, 12(11):2430-2, Nov. 1997.

Peloso et al., Association of low-frequency and rare coding sequence variants with blood lipids and coronary heart disease in 56,000 whites and blacks, American Journal of Human Genetics, 94(2):223-32, Feb. 2014.

Penaud-Budloo et al., Adeno-associated virus vector genomes persist as episomal chromatin in primate muscle, Journal of Virology, 82(16):7875-85, Aug. 2008.

Rangarajan et al., AAV5-Factor VIII Gene Transfer in Severe Hemophilia A, The New England Journal of Medicine, 377(26):2519-30, Dec. 2017.

Rosas et al., Patterns of scAAV vector insertion associated with oncogenic events in a mouse model for genotoxicity, Molecular Therapeutics, 20(11):2098-110, Nov. 2012.

Shamburek et al., Safety and Tolerability of ACP-501, a Recombinant Human Lecithin: Cholesterol Acyltransferase, in a Phase 1 Single-Dose Escalation Study, Circulation Research, 118(1):73-82, Jan. 2016.

Simioni et al., X-linked thrombophilia with a mutant factor IX (factor IX Padua), The New England Journal of Medicine, 361(17):1671-5, Oct. 2009.

Sparks et al., Effect of cholesterol on the charge and structure of apolipoprotein A-I in recombinant high density lipoprotein particles, The Journal of Biological Chemistry, 268(31):23250-7, Nov. 1993.

Strom et al., Lecithin: Cholesterol Acyltransferase (LCAT) Deficiency: renal lesions with early graft recurrence, Ultrastructural Pathology, 35(3):139-45, Feb. 2011.

Vaisman et al., LCAT Enzyme Replacement Therapy Reduces LpX and Improves Kidney Function in a Mouse Model of Familial LCAT Deficiency, The Journal of Pharmacology and Experimental Therapeutics, 368:423-34, Mar. 2019.

Viestenz, et al. Histopathology of corneal changes in lecithin-cholesterol acyltransferase deficiency, Cornea, 21(8):834-7, Nov. 2002.

Vitali et al., Is Low-Density Lipoprotein Cholesterol the Key to Interpret the Role of Lecithin:Cholesterol Acyltransferase in Atherosclerosis? Circulation, 138(10):1008-11, Sep. 2018.

Vrabec et al., Ophthalmic observations in lecithin cholesterol acyltransferase deficiency, Archives of Ophthalmology, 106(2):225-9, Feb. 1988.

Yee et al., Changes in lipoprotein profile and urinary albumin excretion in familial LCAT deficiency with lipid lowering therapy, Atherosclerosis, 205(2):528-32, Aug. 2009.

Wang et al., Adeno-associated virus vector as a platform for gene therapy delivery, Nature Reviews Drug Discovery, 18(5):358-78, May 2019.

Zhu et al., A novel in vivo lecithin-cholesterol acyltransferase (LCAT)-deficient mouse expressing predominantly LpX is associated with spontaneous glomerulopathy, The American Journal of Pathology, 165(4):1269-78, Oct. 2004.

* cited by examiner

FIG. 7A
FIG. 7B
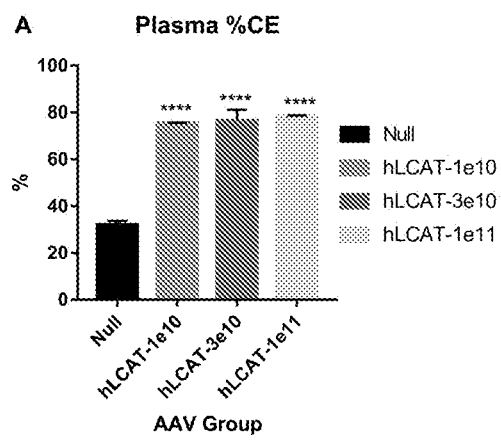
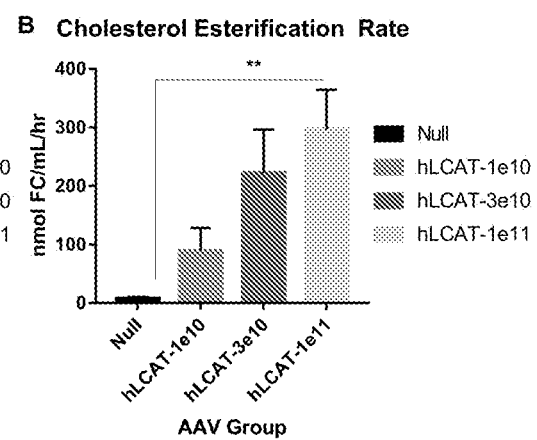
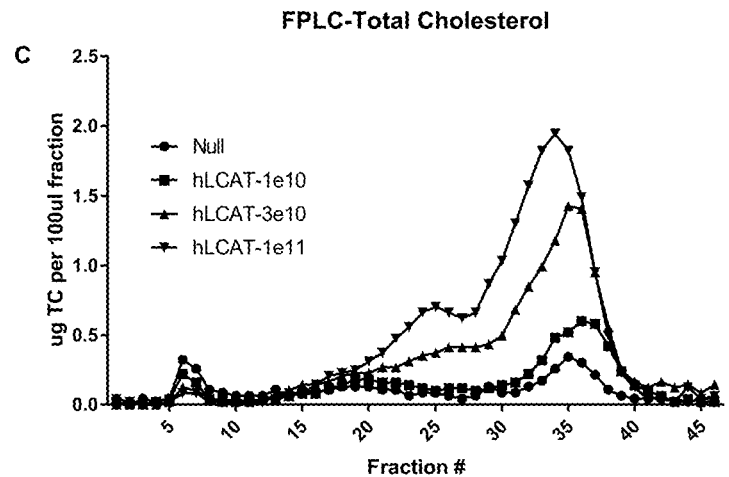
FIG. 7C

FIG. 8A
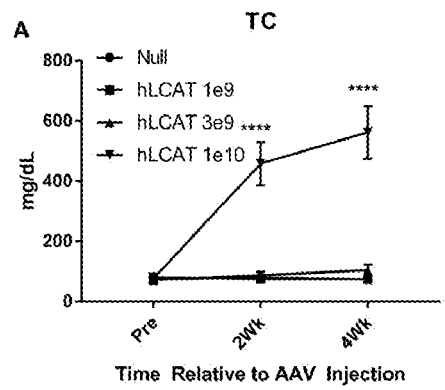
FIG. 8B
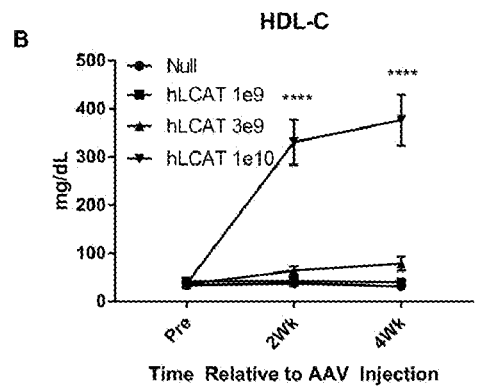
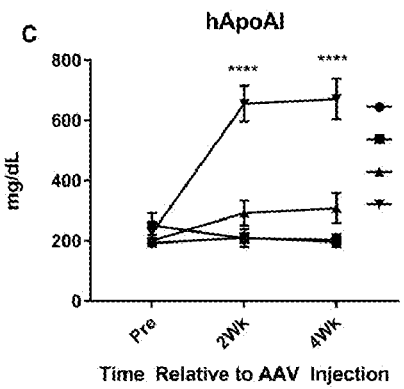
FIG. 8C
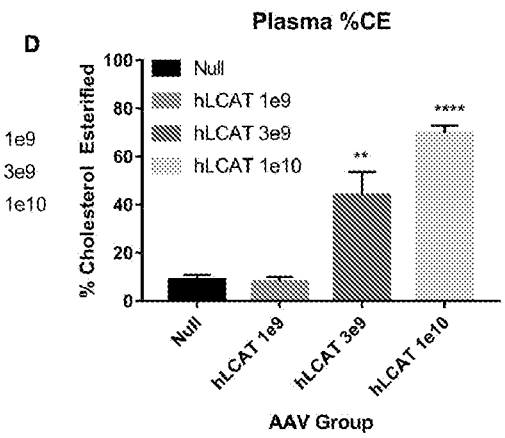
FIG. 8D
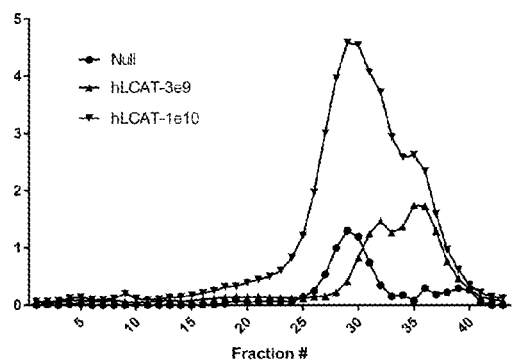
FIG. 8E FIG. 10A
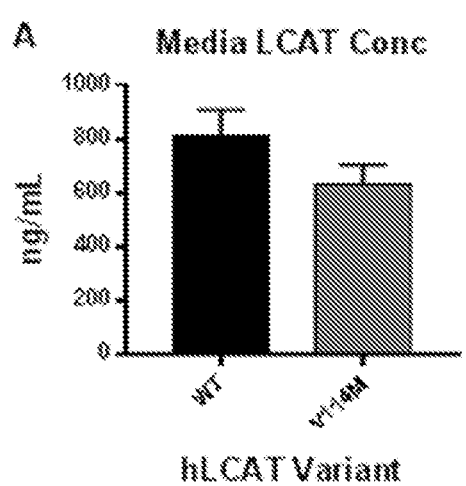
FIG. 10B
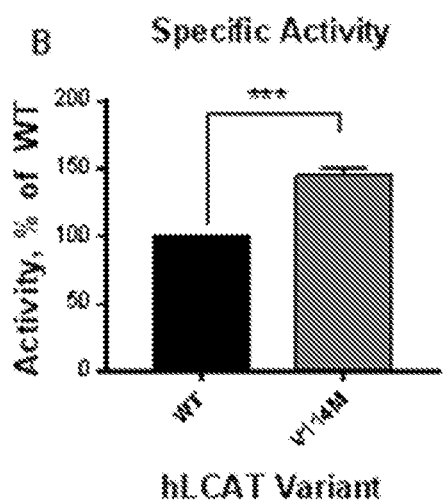
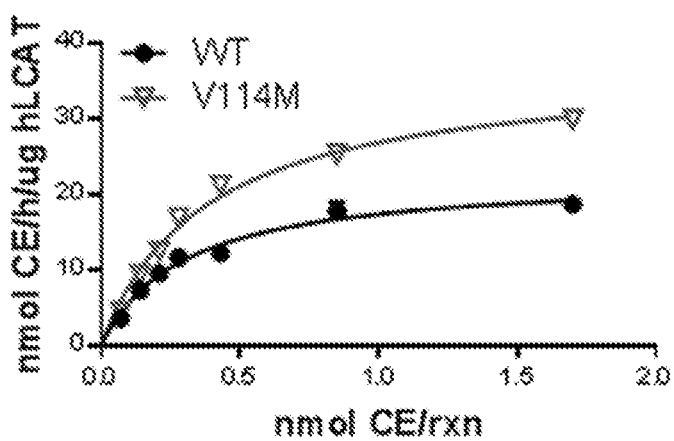
FIG. 10C FIG. 12A
FIG. 12B
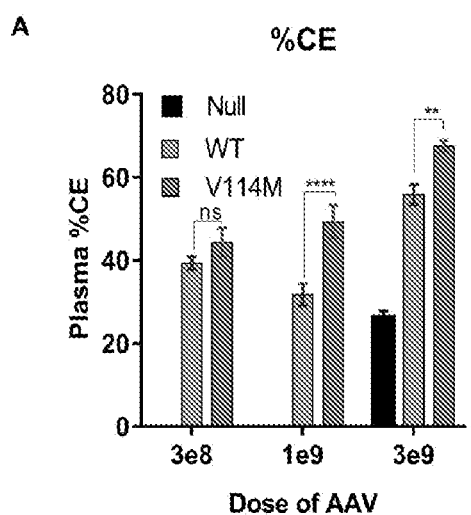
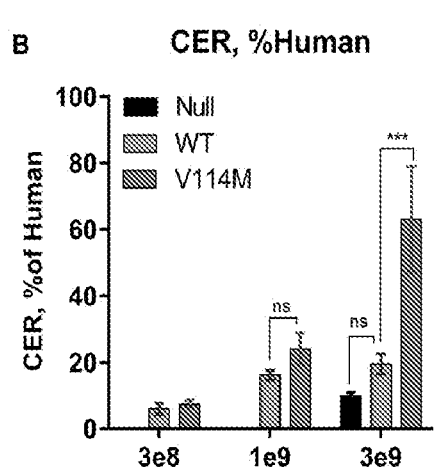
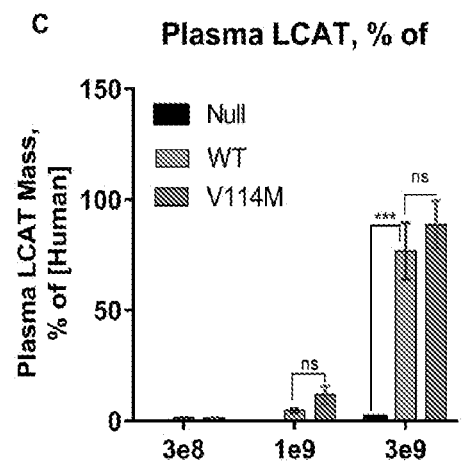
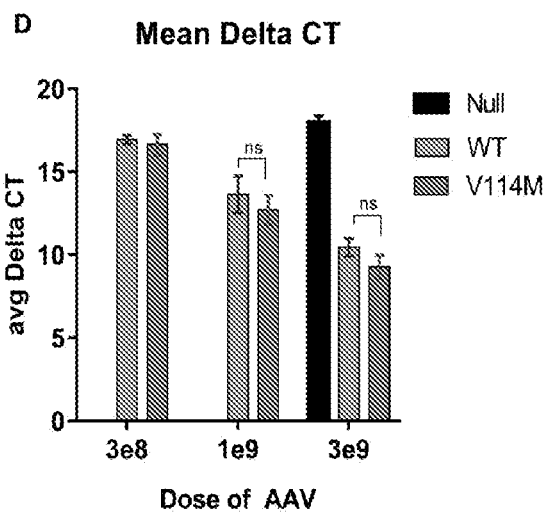
FIG. 12C
FIG. 12D FIG. 14A
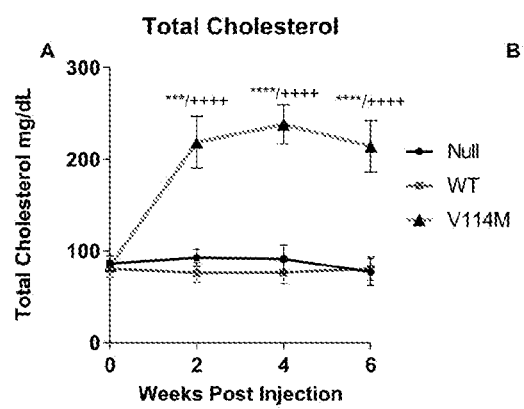
FIG. 14B
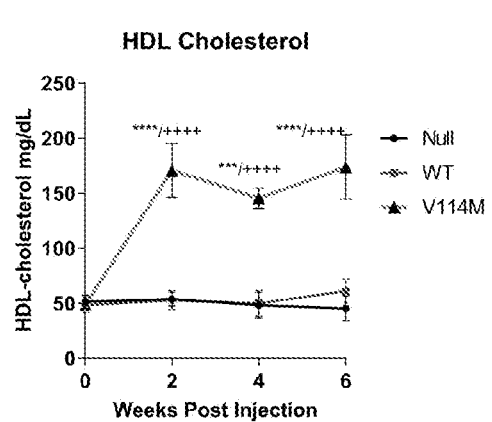
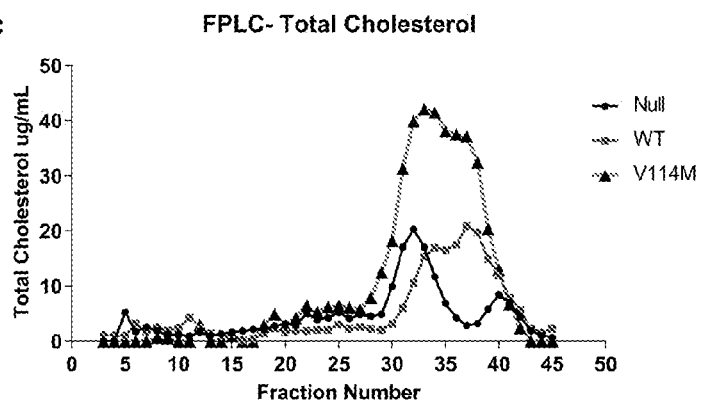
FIG. 14C FIG. 19A
FIG. 19B
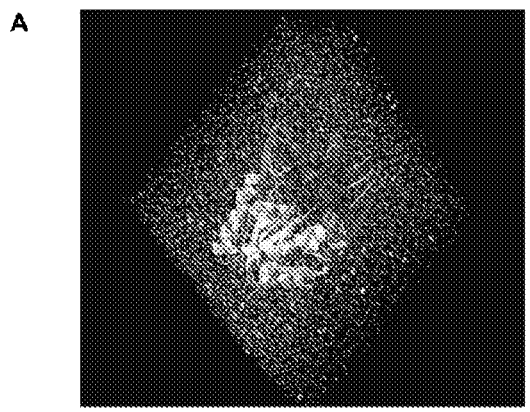
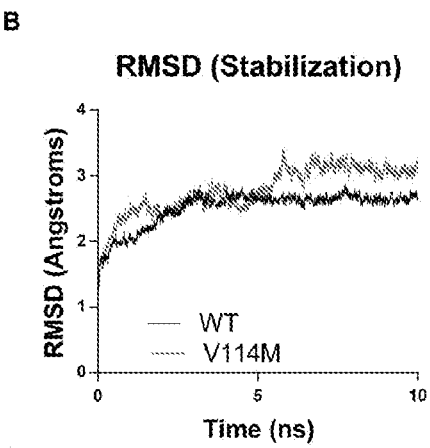
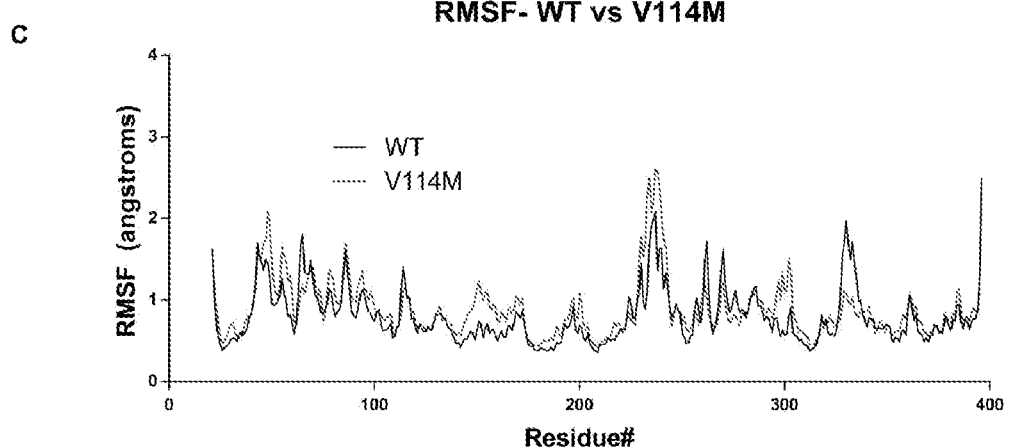
FIG. 19C FIG. 20A
FIG. 20B
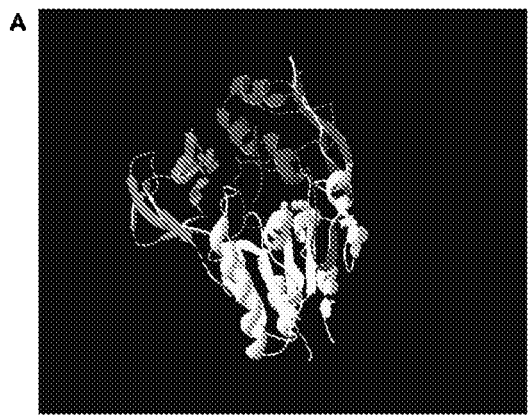 
FIG. 20C
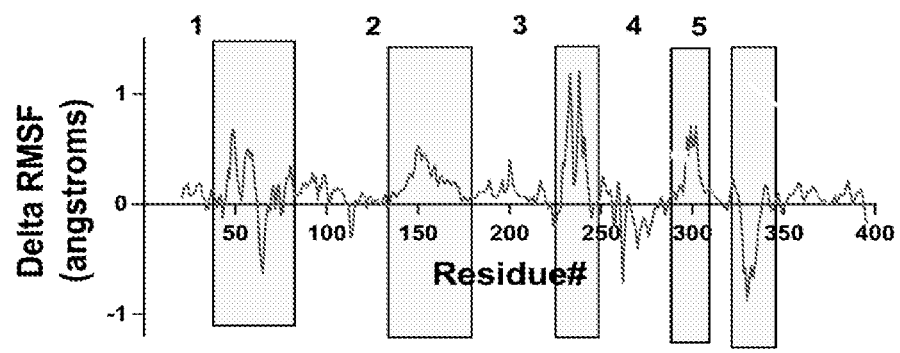
FIG. 20D
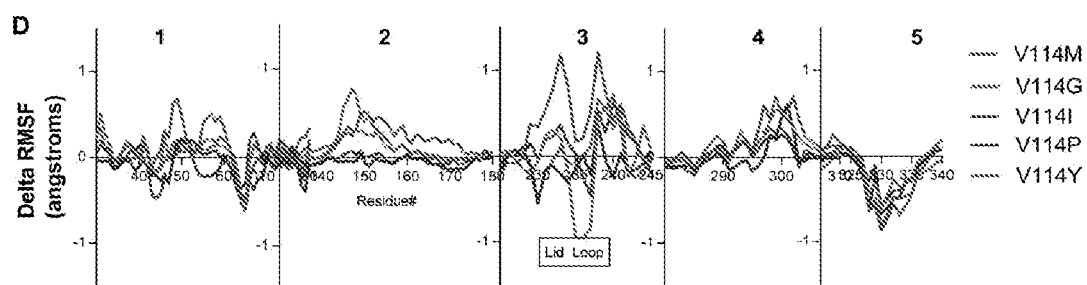

FIG. 24A

```
SEQ ID NO: 2   ATGGGGCCGCCCGGCTCCCCATGGCAGTGGGTGACGCTGCTGCTGGGGCTGCTGCTCCCT
SEQ ID NO: 5   ATGGGTCCCCCCGGTTCACCCTGGCAGTGGGTGACCCTGCTGCTGGGTCTGCTGCTGCCC
SEQ ID NO: 4   ATGGGCCCCCCCGGCAGCCCCTGGCAGTGGGTGACCCTGCTGCTGGGCCTGCTGCTGCCC
SEQ ID NO: 3   ATGGGGCCCCCGGGAGCCCCTGGCAGTGGGTGACCCTGCTGCTGGGGCTGCTGCTGCCC
SEQ ID NO: 6   ATGGGACCTCCTGGAAGCCCTTGGCAGTGGGTGACCCTGCTGCTGGGACTGCTGCTGCCT
               ***** ** ** **    ** ************* *********** ******* **

SEQ ID NO: 2   CCTGCCGCCCCCTTCTGGCTCCTCAATGTGCTCTTCCCCCCGCACACCACGCCCAAGGCT
SEQ ID NO: 5   CCCGCTGCTCCCTTTTGGCTGCTGAACGTGCTGTTTCCCCCCATACCACCCCCAAGGCT
SEQ ID NO: 4   CCCGCTGCTCCCTTTTGGCTGCTGAACGTGCTGTTTCCCCCCACACCACCCCCAAGGCT
SEQ ID NO: 3   CCCGCCGCCCCCTTCTGGCTGCTGAACGTGCTGTTCCCCCCCACACCACCCCCAAGGCC
SEQ ID NO: 6   CCTGCCGCCCCTTTCTGGCTGCTGAACGTGCTGTTCCCTCCTCACACCACCCCTAAGGCC
               ** ** ** ** ** ***** ** ** ***** ** ** ** ** ***** ** *****

SEQ ID NO: 2   GAGCTCAGTAACCACACACGGCCCGTCATCCTCGTGCCCGGCTGCCTGGGGAATCAGCTA
SEQ ID NO: 5   GAACTGTCAAATCATACCCGCCCCGTGATCCTGGTGCCCGGTTGCCTGGGTAATCAGCTG
SEQ ID NO: 4   GAACTGAGCAACCACACCCGGCCCGTGATTCTGGTGCCCGGCTGTCTGGGCAACCAGCTG
SEQ ID NO: 3   GAGCTGAGCAACCACACCCGGCCCGTGATCCTGGTGCCCGGTGCCTGGGGAACCAGCTG
SEQ ID NO: 6   GAGCTGAGCAACCACACCCGGCCTGTGATCCTGGTGCCTGGCTGCCTGGGAAACCAGCTG
               ** **    ** ** ** ** ** ** ** ** ***** ** ** ***** ** *****

SEQ ID NO: 2   GAAGCCAAGCTGGACAAACCAGATGTGGTGAACTGGATGTGCTACCGCAAGACAGAGGAC
SEQ ID NO: 5   GAAGCTAAGCTGGACAAGCCCGACGTGGTGAATTGGATGTGCTACCGCAAGACCGAAGAC
SEQ ID NO: 4   GAAGCTAAGCTGGACAAGCCCGACGTGGTGAACTGGATGTGTTACCGGAAGACCGAAGAC
SEQ ID NO: 3   GAGGCCAAGCTGGACAAGCCCGACGTGGTGAACTGGATGTGCTACCGGAAGACCGAGGAC
SEQ ID NO: 6   GAGGCCAAGCTGGACAAGCCTGACGTGGTGAACTGGATGTGCTACCGGAAGACCGAGGAC
               ** ** *********** ** ** ******* ******** ***** ***** ** ***

SEQ ID NO: 2   TTCTTCACCATCTGGCTGGATCTCAACATGTTCCTACCCCTTGGGGTAGACTGCTGGATC
SEQ ID NO: 5   TTTTTTACCATCTGGCTGGACCTGAATATGTTTCTGCCCCTGGGTGTGGACTGCTGGATC
SEQ ID NO: 4   TTTTTTACCATTTGGCTGGACCTGAACATGTTTCTGCCCCTGGGCGTGGACTGTTGGATT
SEQ ID NO: 3   TTCTTCACCATCTGGCTGGACCTGAACATGTTCCTGCCCCTGGGGGTGGACTGCTGGATC
SEQ ID NO: 6   TTCTTCACCATCTGGCTGGACCTGAACATGTTCCTGCCTCTGGGAGTGGACTGCTGGATC
               ** ** ***** ******** ** ** ***** ** ** ** ** ** ***** *****

SEQ ID NO: 2   GATAACACCAGGGTTGTCTACAACCGGAGCTCTGGGCTCGTGTCCAACGCCCCTGGTGTC
SEQ ID NO: 5   GACAATACCCGCGTGGTGTACAATCGCTCATCAGGTCTGGTGTCAAACGCTCCCGGTGTG
SEQ ID NO: 4   GACAACACCCGGGTGGTGTACAACCGGAGCAGCGGCCTGGTGAGCAACGCTCCCGGCGTG
SEQ ID NO: 3   GACAACACCCGGGTGGTGTACAACCGGAGCAGCGGGCTGGTGAGCAACGCCCCCGGGGTG
SEQ ID NO: 6   GACAACACCCGGGTGGTGTACAACCGGAGCAGCGGACTGGTGAGCAACGCCCCTGGAGTG
               ** ** *** * ** ** ***** **         ** ** ***    ***** ** **
```

FIG. 24B

```
SEQ ID NO: 2    CAGATCCGCGTCCCTGGCTTTGGCAAGACCTACTCTGTGGAGTACCTGGACAGCAGCAAG
SEQ ID NO: 5    CAGATCCGCGTGCCCGGTTTTGGTAAGACCTACTCAGTGGAATACCTGGACTCATCAAAG
SEQ ID NO: 4    CAGATTCGGGTGCCCGGCTTTGGCAAGACCTACAGCGTGGAATACCTGGACAGCAGCAAG
SEQ ID NO: 3    CAGATCCGGGTGCCCGGGTTCGGGAAGACCTACAGCGTGGAGTACCTGGACAGCAGCAAG
SEQ ID NO: 6    CAGATCCGGGTGCCTGGATTCGGAAAGACCTACAGCGTGGAGTACCTGGACAGCAGCAAG
                ***** ** ** ** ** ** ** ********     ***** *********       ***

SEQ ID NO: 2    CTGGCAGGGTACCTGCACACACTGGTGCAGAACCTGGTCAACAATGGCTACGTGCGGGAC
SEQ ID NO: 5    CTGGCTGGTTACCTGCATACCCTGGTGCAGAATCTGGTGAATAACGGTTACGTGCGCGAC
SEQ ID NO: 4    CTGGCTGGCTACCTGCACACCCTGGTGCAGAACCTGGTGAACAACGGCTACGTGCGGGAC
SEQ ID NO: 3    CTGGCCGGGTACCTGCACACCCTGGTGCAGAACCTGGTGAACAACGGGTACGTGCGGGAC
SEQ ID NO: 6    CTGGCCGGATACCTGCACACCCTGGTGCAGAACCTGGTGAACAACGGATACGTGCGGGAC
                *****  ** ********  ** *********** ***** ** ** ** ******** ***

SEQ ID NO: 2    GAGACTGTGCGCGCCGCCCCCTATGACTGGCGGCTGGAGCCCGGCCAGCAGGAGGAGTAC
SEQ ID NO: 5    GAAACCGTGCGCGCTGCTCCCTACGACTGGCGCCTGGAACCCGGTCAGCAGGAAGAATAC
SEQ ID NO: 4    GAAACCGTGCGGGCTGCTCCCTACGACTGGCGGCTGGAACCCGGCCAGCAGGAAGAATAC
SEQ ID NO: 3    GAAACCGTGCGGGCCGCCCCCTACGACTGGCGGCTGGAGCCCGGGCAGCAGGAGGAGTAC
SEQ ID NO: 6    GAGACAGTGCGGGCCGCCCCTTACGACTGGCGGCTGGAGCCTGGACAGCAGGAGGAGTAC
                ** **  *****  ** ** ** ** ******** ***** ** ** ******** ** ***

SEQ ID NO: 2    TACCGCAAGCTCGCAGGGCTGGTGGAGGAGATGCACGCTGCCTATGGGAAGCCTGTCTTC
SEQ ID NO: 5    TACCGCAAGCTGGCTGGTCTGGTGGAAGAAATGCACGCTGCTTACGGTAAGCCCGTGTTT
SEQ ID NO: 4    TACCGGAAGCTGGCTGGCCTGGTGGAAGAAATGCACGCTGCTTACGGCAAGCCCGTGTTT
SEQ ID NO: 3    TACCGGAAGCTGGCCGGGCTGGTGGAGGAGATGCACGCCGCCTACGGGAAGCCCGTGTTC
SEQ ID NO: 6    TACCGGAAGCTGGCCGGACTGGTGGAGGAGATGCACGCCGCCTACGGAAAGCCTGTGTTC
                ***** *****  ** ** ******** ** ******** ** ** ** ***** ** **

SEQ ID NO: 2    CTCATTGGCCACAGCCTCGGCTGTCTACACTTGCTCTATTTCCTGCTGCGCCAGCCCCAG
SEQ ID NO: 5    CTGATCGGTCATTCACTGGGTTGCCTGCATCTGCTGTACTTTCTGCTGCGCCAGCCCCAG
SEQ ID NO: 4    CTGATTGGCCACAGCCTGGGCTGTCTGCATCTGCTGTACTTTCTGCTGCGGCAGCCCCAG
SEQ ID NO: 3    CTGATCGGGCACAGCCTGGGGTGCCTGCACCTCCTGTACTTCCTGCTGCGGCAGCCCCAG
SEQ ID NO: 6    CTGATCGGACACAGCCTGGGCTGCCTGCATCTGCTGTACTTCCTGCTGCGGCAGCCTCAG
                ** ** ** **          ** ** ** ** ** *  ** ** ** ******** ***** ***

SEQ ID NO: 2    GCCTGGAAGGACCGCTTTATTGATGGCTTCATCTCTCTTGGGGCTCCCTGGGGTGGCTCC
SEQ ID NO: 5    GCTTGGAAGGACCGCTTTATCGACGGTTTTATCTCACTGGGTGCTCCCTGGGGTGGTTCA
SEQ ID NO: 4    GCTTGGAAGGACCGGTTTATTGACGGCTTTATTAGCCTGGGCGCTCCCTGGGGCGGCAGC
SEQ ID NO: 3    GCCTGGAAGGACCGGTTCATCGACGGGTTCATCAGCCTGGGGGCCCCTGGGGAGGGAGC
SEQ ID NO: 6    GCCTGGAAGGACCGGTTCATCGACGGATTCATCAGCCTGGGAGCCCCTTGGGGAGGAAGC
                ** *********** ** ** ** **  **              ** ** ** ***** **

SEQ ID NO: 2    ATCAAGCCCATGCTGGTCTTGGCCTCAGGTGACAACCAGGGCATCCCCATCATGTCCAGC
SEQ ID NO: 5    ATCAAGCCCATGCTGGTGCTGGCTTCAGGTGACAATCAGGGTATCCCCATCATGTCATCA
SEQ ID NO: 4    ATTAAGCCCATGCTGGTGCTGGCTAGCGGCGACAACCAGGGCATTCCCATTATGAGCAGC
SEQ ID NO: 3    ATCAAGCCCATGCTGGTGCTGGCCAGCGGGGACAACCAGGGGATCCCCATCATGAGCAGC
SEQ ID NO: 6    ATCAAGCCTATGCTGGTGCTGGCCAGCGGAGACAACCAGGGAATCCCTATCATGAGCAGC
                ** ***** ********  ****       ** ***** ** ** **  ***
```

FIG. 24C

```
SEQ ID NO: 2    ATCAAGCTGAAAGAGGAGCAGCGCATAACCACCACCTCCCCCTGGATGTTTCCCTCTCGC
SEQ ID NO: 5    ATCAAGCTGAAGGAAGAACAGCGCATCACCACCACCTCACCCTGGATGTTTCCCTCACGC
SEQ ID NO: 4    ATTAAGCTGAAGGAAGAACAGCGGATTACCACCACCAGCCCCTGGATGTTTCCCAGCCGG
SEQ ID NO: 3    ATCAAGCTGAAGGAGGAGCAGCGGATCACCACCACCAGCCCCTGGATGTTCCCCAGCCGG
SEQ ID NO: 6    ATCAAGCTGAAGGAGGAGCAGCGGATCACCACCACCAGCCCTTGGATGTTCCCTAGCCGG
                  ** ******** **  ** *****  ** *********    ** ******* **       **

SEQ ID NO: 2    ATGGCGTGGCCTGAGGACCACGTGTTCATTTCCACACCCAGCTTCAACTACACAGGCCGT
SEQ ID NO: 5    ATGGCTTGGCCCGAAGACCACGTGTTTATCTCAACCCCCTCATTTAATTACACCGGTCGC
SEQ ID NO: 4    ATGGCTTGGCCCGAAGACCACGTGTTTATTAGCACCCCCAGCTTTAACTACACCGGCCGG
SEQ ID NO: 3    ATGGCCTGGCCCGAGGACCACGTGTTCATCAGCACCCCCAGCTTCAACTACACCGGGCGG
SEQ ID NO: 6    ATGGCCTGGCCTGAGGACCACGTGTTCATCAGCACCCCTAGCTTCAACTACACCGGACGG
                *****  ***** ** ***********      **  **       ** ** *****  ** **

SEQ ID NO: 2    GACTTCCAACGCTTCTTTGCAGACCTGCACTTTGAGGAAGGCTGGTACATGTGGCTGCAG
SEQ ID NO: 5    GACTTTCAGCGCTTTTTTGCTGACCTGCATTTTGAAGAAGGTTGGTACATGTGGCTGCAG
SEQ ID NO: 4    GACTTTCAGCGGTTTTTTGCTGACCTGCACTTTGAAGAAGGCTGGTACATGTGGCTGCAG
SEQ ID NO: 3    GACTTCCAGCGGTTCTTCGCCGACCTGCACTTCGAGGAGGGTGGTACATGTGGCTGCAG
SEQ ID NO: 6    GACTTCCAGCGGTTCTTCGCCGACCTGCACTTCGAGGAGGGCTGGTACATGTGGCTGCAG
                *****  **  ** **  ** ** ********  ** **  ** ** ******************

SEQ ID NO: 2    TCACGTGACCTCCTGGCAGGACTCCCAGCACCTGGTGTGGAAGTATACTGTCTTTACGGC
SEQ ID NO: 5    TCACGCGACCTGCTGGCTGGTCTGCCCGCTCCCGGTGTGGAAGTGTACTGCCTGTACGGT
SEQ ID NO: 4    AGCCGGGACCTGCTGGCTGGCCTGCCCGCTCCCGGCGTGGAAGTGTACTGTCTGTACGGC
SEQ ID NO: 3    AGCCGGGACCTGCTGGCCGGGCTGCCCGCCCCGGGGTGGAGGTGTACTGCCTGTACGGG
SEQ ID NO: 6    AGCCGGGACCTGCTGGCCGGACTGCCTGCCCCTGGAGTGGAGGTGTACTGCCTGTACGGA
                  **   *****  *****    **  **    **  *****  ** ***** ** *****

SEQ ID NO: 2    GTGGGCCTGCCCACGCCCCGCACCTACATCTACGACCACGGCTTCCCCTACACGGACCCT
SEQ ID NO: 5    GTGGGTCTGCCCACCCCCCGCACCTACATCTACGACCACGGTTTTCCCTACACCGACCCC
SEQ ID NO: 4    GTGGGCCTGCCCACCCCCCGGACCTACATTTACGACCACGGCTTTCCCTACACCGACCCC
SEQ ID NO: 3    GTGGGGCTGCCCACCCCCCGGACCTACATCTACGACCACGGGTTCCCCTACACCGACCCC
SEQ ID NO: 6    GTGGGACTGCCTACCCCTCGGACCTACATCTACGACCACGGATTCCCTTACACCGACCCT
                *****  *****  ** **   ** ********  **********  ** ** *****  *****

SEQ ID NO: 2    GTGGGTGTGCTCTATGAGGATGGTGATGACACGGTGGCGACCCGCAGCACCGAGCTCTGT
SEQ ID NO: 5    GTGGGTGTGCTGTACGAAGACGGTGACGACACCGTGGCTACCCGCTCAACCGAACTGTGC
SEQ ID NO: 4    GTGGGCGTGCTGTACGAAGACGGCGACGACACCGTGGCTACCCGGAGCACCGAACTGTGT
SEQ ID NO: 3    GTGGGGGTGCTGTACGAGGACGGGGACGACACCGTGGCCACCCGGAGCACCGAGCTGTGC
SEQ ID NO: 6    GTGGGAGTGCTGTACGAGGACGGAGACGACACCGTGGCCACCCGGAGCACCGAGCTGTGC
                *****  *****  ** **  **  ** ** ***** *****  *****    ***** ** **

SEQ ID NO: 2    GGCCTGTGGCAGGGCCGCCAGCCACAGCCTGTGCACCTGCTGCCCCTGCACGGGATACAG
SEQ ID NO: 5    GGTCTGTGGCAGGGTCGCCAGCCCCAGCCCGTGCATCTGCTGCCCCTGCATGGTATCCAG
SEQ ID NO: 4    GGCCTGTGGCAGGGCCGGCAGCCCCAGCCCGTGCATCTGCTGCCCCTGCACGGCATTCAG
SEQ ID NO: 3    GGGCTGTGGCAGGGGCGGCAGCCCCAGCCCGTGCACCTCCTGCCCCTGCACGGGATCCAG
SEQ ID NO: 6    GGACTGTGGCAGGGACGGCAGCCTCAGCCTGTGCATCTGCTGCCTCTGCACGGAATCCAG
                ** ********** ** *****  ***** ***** *****  ***** *****  ** ***
```

FIG. 24D

```
SEQ ID NO: 2    CATCTCAACATGGTCTTCAGCAACCTGACCCTGGAGCACATCAATGCCATCCTGCTGGGT
SEQ ID NO: 5    CATCTGAATATGGTGTTTTCAAATCTGACCCTGGAACATATCAACGCTATCCTGCTGGGT
SEQ ID NO: 4    CACCTGAACATGGTGTTTAGCAACCTGACCCTGGAACACATTAACGCTATTCTGCTGGGC
SEQ ID NO: 3    CACCTGAACATGGTGTTCAGCAACCTGACCCTGGAGCACATCAACGCCATCCTGCTGGGG
SEQ ID NO: 6    CACCTGAACATGGTGTTCAGCAACCTGACCCTGGAGCACATCAACGCCATCCTGCTGGGA
                ** ** ** ***** **    ** ********** ** ** ** ** ** ********

SEQ ID NO: 2    GCCTACCGCCAGGGTCCCCCTGCATCCCCGACTGCCAGCCCAGAGCCCCCGCCTCCTGAA
SEQ ID NO: 5    GCTTACCGCCAGGGTCCCCCCGCTTCACCCACCGCTTCACCCGAACCCCCACCCCCCGAG
SEQ ID NO: 4    GCTTACCGGCAGGGCCCCCCCGCTAGCCCCACCGCTAGCCCCGAACCCCCACCCCCCGAG
SEQ ID NO: 3    GCCTACCGGCAGGGCCCCCCGCCAGCCCCACCGCCAGCCCCGAGCCCCCACCCCCCGAG
SEQ ID NO: 6    GCCTACCGGCAGGGACCTCCTGCCAGCCCTACCGCCAGCCCTGAGCCTCCTCCTCCTGAG
                ** ***** ***** ** ** **    ** ** **    ** ** ** ** ** ** **

SEQ ID NO: 2    TAA
SEQ ID NO: 5    TGA
SEQ ID NO: 4    TGA
SEQ ID NO: 3    TGA
SEQ ID NO: 6    TGA
                * *
``` hLCAT gene frag V114A

COMPOSITIONS COMPRISING A LECITHIN CHOLESTEROL ACYLTRANSFERASE VARIANT AND USES THEREOF

STATEMENT REGARDING FEDERALLY SPONSORED RESEARCH OR DEVELOPMENT

This invention was made with government support under grant number P01HL059407 awarded by the National Institutes of Health. The government has certain rights in the invention.

Reference to an Electronic Sequence Listing

The electronic sequence listing filed herewith named "UPN-16771OPCT_ST25.txt" with size of 162,000 bytes, created on date of Jul. 24, 2017, and the contents of the electronic sequence listing (e.g., the sequences and text therein) are incorporated herein by reference in entirety.

BACKGROUND OF THE INVENTION

Atherosclerosis is a polygenic complex disease of mammals characterized by the deposits or plaques of lipids and other blood derivatives in the arterial walls (aorta, coronary arteries, and carotid). These plaques can be calcified to a greater or lesser extent according to the progression of the process. They are also associated with the accumulation of fatty deposits consisting mainly of cholesterol esters in the arteries. Cholesterol accumulates in the foam cells of the arterial wall, thereby narrowing the lumen and decreasing the flow of blood. This is accompanied by a thickening of the arterial wall, with hypertrophy of the smooth muscle, the appearance of foam cells and the accumulation of the fibrous tissue. Hypercholesterolemia can therefore result in very serious cardiovascular pathologies such as infarction, peripheral vascular disease, stroke, sudden death, cardiac decompensation, cerebral vascular accidents and the like.

Cholesterol is carried in the blood by various lipoproteins including very low-density lipoprotein (VLDL), low-density lipoproteins (LDL) and high-density lipoproteins (HDL). VLDL is synthesized in the liver and is converted to LDL in the blood, supplying the peripheral tissues with cholesterol. In contrast, HDL captures cholesterol from the peripheral tissues and transports them to the liver where they are converted to bile acids and excreted. The development of atherosclerosis and the risk of coronary heart disease (CHD) is inversely correlated with levels of HDL in the serum. See, e.g., Gordon et al. (1989) N. Engl. J. Med. 321: 1311; and Goldbourt et al. (1997) Thromb Vasc. Biol. 17: 107. Studies have demonstrated that the risk for developing clinical atherosclerosis in men drops 2-3% with every 1 mg/dL increase in the concentration of HDL in plasma (Gordon et al. (1989) N. Engl. J. Med. 321: 1311). Low HDL cholesterol often occurs in the context of central obesity and diabetes in conjunction with other features of metabolic syndrome (Goldbourt et al., supra). Since high concentrations of HDL have a protective effect against the development of premature atherosclerosis, conversely, it has also been suggested that low HDL cholesterol levels are associated with an increased risk of CHD (Gordon et al. (1986) Circulation 74: 1217). It is well known that levels of LDL cholesterol are positively associated with risk for CHD. It has been established that plasma concentrations of LDL cholesterol can be reduced by treatment with statins, inhibitors of the cholesterols biosynthesis enzyme 3-hydroxyl-3-methylglutary Coenzyme A reductase and this treatment has been used as a successful approach for reducing the risk for atherosclerosis where the primary indication is high LDL level. However, it remains unclear whether statins are beneficial for patients whose primary lipid abnormality is low HDL cholesterol.

Lecithin Cholesterol Acyltransferase (LCAT) is a plasma enzyme secreted by the liver. LCAT is responsible for esterification of free cholesterol in the blood compartment, a process that is essential for the formation of mature, functional high density lipoproteins (HDL). Inherited loss of function mutations in the LCAT gene are the cause of two autosomal recessive diseases, Fish Eye Disease (FED) and Familial LCAT deficiency (FLD). FED is characterized by low plasma HDL and corneal opacities. FLD is characterized by extremely low levels of high density lipoprotein cholesterol (HDL-C), anemia, corneal opacities, and chronic progressive renal disease leading to end-stage kidney disease as early as the third decade of life. Currently, there is no specific FDA-approved treatment for either disease. Patients are managed symptomatically.

EP24897301A1 describes a modified LCAT protein in which LCAT proteins are fused to an immunoglobulin G (IgG) constant (Fc) domain. Modifications having C31Y and an L4 or N5 substitution are provided.

US2015/28447A1 describes agonist binding proteins that specifically bind to human LCAT. Such binding proteins include human antibodies.

LCAT-V114M is a naturally occurring variant of LCAT. In human studies, this variant is associated with higher levels of HDL. See, e.g., Jonathan C. Cohen, et al., Science, Vol 305, Issue 5685, pp 896-872 (2004) and Clara C. Elbers, et al, PLoS One, Vol 7, Issue 12, e50198 (2012).

What are still needed are effective compositions and methods for treating a variety of cholesterol-related disorders.

SUMMARY OF THE INVENTION

LCAT variant proteins with increased enzymatic activity and/or stability and constructs useful for expressing same in situ are provided. These proteins and nucleic acid molecules expressing same are useful in methods for treatment of a variety of conditions including, e.g., cardiovascular disease (CVD), which includes, e.g., coronary artery disease and coronary heart disease, atherosclerosis, renal disease, inflammatory disorders and disorders associated with thrombosis using these modified LCAT proteins.

In one aspect, a synthetic or recombinant human lecithin cholesterol acyltransferase (LCAT) protein variant is provided, which comprises: an LCAT enzyme having a substitution at position 114 based on the residue numbering of wild-type (WT) human LCAT (SEQ ID NO:1), wherein said variant is characterized by one or more of: (i) an esterification rate higher than the esterification rate of WT human LCAT; and/or (ii) an association with higher density lipoprotein levels as compared to subjects having WT LCAT. In one embodiment, the substitution is a proline (P). In certain embodiments, the substitution is selected from Ala (A), Cys (C), Asp (D), Glu (E), Phe (F), Gly (G), His (H), Ile (I), Lys (K), Leu (L), Asn (N), Pro (P), Gln (Q), Arg (R), Ser (S), Thr (T), Trp (W) or Tyr (Y). In certain other embodiments, the variant is Met (M). In still other embodiments, the variant is not Met.

In a further aspect, a pharmaceutical composition which comprises at least one LCAT protein variant and one or more of a carrier, excipient, or preservative, is provided herein.

In still another aspect, a synthetic or recombinant nucleic acid molecule is provided with encodes the wild-type LCAT protein or an LCAT protein variant having the substitution at position 114, based on the residue numbering of SEQ ID NO:1. In one embodiment, the nucleic acid molecule is codon-optimized. Additionally or alternatively, the LCAT protein variant is LCAT-V114M (SEQ ID NO: 7). In certain embodiments, the substitution is Pro. selected from Ala (A), Cys (C), Asp (D), Glu (E), Phe (F), Gly (G), His (H), Ile (I), Lys (K), Leu (L), Asn (N), Pro (P), Gln (Q), Arg (R), Ser (S), Thr (T), Tip (W) or Tyr (Y). In still other embodiments, the variant is not Met.

In yet another aspect, a recombinant vector is provided. The recombinant viral vector comprises an expression cassette containing, at a minimum, comprising (a) a nucleic acid coding sequence for the wild-type LCAT protein or a recombinant human LCAT variant comprising: an amino acid substitution at amino acid position 114 based on the residue numbering of normal human LCAT, wherein said variant is characterized by one or more of: (i) an esterification rate higher than the esterification rate of WT human LCAT, (ii) an association with higher density lipoprotein levels as compared to subjects having WT LCAT; and (b) regulatory sequences which direct expression of the LCAT variant in a host cell, said regulatory sequences being operably linked to the LCAT coding sequence. In one embodiment, the nucleic acid coding sequence is codon-optimized. In one embodiment, the vector is a viral vector. In a further embodiment, the vector is an AAV.

In still a further aspect, a pharmaceutical composition is provided which comprises at least one viral vector and one or more of a carrier, excipient, or preservative.

In yet another aspect, a method for preferentially increasing high density lipoprotein levels is provided. The method involves delivering an LCAT protein variant and/or a viral vector expressing the wild-type LCAT protein or a variant thereof, to a subject in need thereof. The variant used may be the naturally occurring 114Met variant, or an engineered variant, such as the 114Pro variant. The variant selected is characterized by one or more of: (i) an esterification rate higher than the esterification rate of WT human LCAT; and/or (ii) an association with higher density lipoprotein levels as compared to subjects having WT LCAT.

In one aspect, a method for treating Fish Eye Disease (FED) is provided. In still another aspect, a method for treating LCAT deficiency (FLD) is provided. In still a further embodiment, a method for treating coronary artery disease/atherosclerosis is provided. In yet another embodiment, a method for treating anemia, corneal opacities, and/or chronic progressive renal disease associated with FED or FLD is provided. In yet another embodiment, a composition provided herein can be useful for improving renal function, delaying the need for a kidney transplant, or preventing the need for a kidney transplant.

Other aspects and advantages of the invention will be readily apparent from the following detailed description of the invention.

BRIEF DESCRIPTION OF THE DRAWINGS

In all the figures presented herein unless otherwise indicated, * indicates $p<0.05$,  indicates $p<0.005$, * indicates $p<0.0005$ and **** indicates $p<0.00005$ relative to WT. Errors bars indicate standard error.

In FIGS. 6A-6D,7A-7C, 8A-8E, 9A-9C, 12A-12D, 14A-14C, 15A-15D, 21A-21C and 22A-22D, * indicates $p<0.05$,  indicates $p<0.005$, * indicates $p<0.0005$ and **** indicates $p<0.00005$ relative to AAV-Null injected mice.

FIGS. 6A-6D provide line graphs showing that 3e10 GC of AAV8-TBG-hLCAT significantly increases plasma lipids in LCAT KO mice. We tested three more doses of AAV-hLCAT in LCAT KO mice (N=5) and measured plasma lipids out to 6 weeks post injection. Mice injected with 3e11 GC per mouse and 1e11 GC per mouse of AAV-hLCAT had significant increases in plasma total cholesterol (TC, FIG. 6A), HDL-cholesterol (HDL-c, FIG. 6B) and phospholipids (FIG. 6C). No differences were seen in alanine aminotransferase (ALT) (FIG. 6D).

FIGS. 7A-7C provide graphs showing that 1e10 GC of AAV8-TBG-hLCAT normalized plasma % CE in LCAT KO mice. All AAV-hLCAT injected mice had significantly elevated plasma % CE (FIG. 7A). We also measured total plasma cholesterol esterification rate (CER) in these mice (FIG. 7B) and measured total cholesterol in FPLC fractions of pooled plasma samples from each group (FIG. 7C).

FIGS. 8A-8E provide graphs showing that 3e9 GC of AAV8-TBG-hLCAT significantly increases plasma % CE in LCAT KO/hApoAI mice. We injected LCAT KO/hApoAI transgenic mice with one of three indicated doses of AAV-hLCAT or AAV-Null and measured plasma lipids out to 6 weeks post injection. Mice that were injected with 1e10 GC per mouse of AAV-hLCAT had significantly increased plasma total cholesterol (FIG. 8A), HDL-cholesterol (FIG. 8B) and hApoAI (FIG. 8C). We also measured plasma % CE in these mice (FIG. 8D) and measured total cholesterol in FPLC fractions of pooled plasma samples from each group (FIG. 8E).

FIGS. 9A-9C provide bar graphs showing that plasma LCAT mass is dose dependent and comparable between experiments. We measured plasma LCAT mass in AAV injected mice, 6 weeks after injection by monoclonal ELISA. Shown in (FIG. 9A) are the plasma LCAT concentrations in injected LCAT KO mice, in (FIG. 9B) are the concentrations in LCAT KO/hApoAI transgenic mice and shown in (FIG. 9C) is a comparison of the average plasma LCAT concentration from the two separate experiments, demonstrating that the concentration is comparable at the same dose.

FIGS. 10A-10C provide graphs showing that the LCAT variant V114M is more effective than WT LCAT in promoting cholesterol esterification. The WT and V114M variants of human LCAT were generated as described herein. Medium containing the recombinant proteins was subsequently collected to test activity. LCAT concentration in the reaction mix was assessed by ELISA. Results indicate no statistically significant differences between the two experimental mixtures in LCAT protein concentration (FIG. 10A). The activity of WT and V114M was tested against reconstituted HDL, containing human ApoA-I and $^3$H-cholesterol. Activity was expressed as esterified cholesterol (CE) released as nmol/h/gg LCAT. The V114M variant has approximately 150% the activity of WT LCAT (FIG. 10B). Error bar indicates standard error. Enzymatic activity was defined by calculating the rate of enzymatic reaction according to the model of Michaelis-Menten (FIG. 10C). Results indicate that V114M displays significantly higher Vmax (the maximum esterification rate achieved by the system, at saturating concentration of substrate) and Km (the concentration of substrate at which the reaction rate is half of Vmax) compared to WT. This results further support increased enzyme activity compared to WT protein.

FIGS. 12A-12D provide bar graphs showing that 3e9 GC of AAV8-TBG-hLCAT-V114M significantly increases plasma % CE and CER while AAV8-TBG-hLCAT WT does not. Plasma percent cholesterol ester in injected mice calculated from plasma lipids measured 6 weeks after injection (FIG. 12A). We also measured whole plasma cholesterol esterification rate (CER) in AAV-injected mice at this same time point and expressed it here as percentage of normal human whole plasma CER (FIG. 12B). Plasma hLCAT concentrations 6 weeks after injection as measured by polyclonal ELISA also expressed as % of normal human plasma concentration (FIG. 12C). Lastly, we examined gene expression, here we show human LCAT delta CT values for AAV injected mice (N=7), normalized to mouse beta-actin and 18S (FIG. 12D).

FIGS. 14A-14C provide line graphs showing that 3e9 GC of AAV8-TBG-hLCAT-V114M induces large increases in total cholesterol and HDL cholesterol in LCAT KO/hApoAI transgenic mice. We injected groups of LCAT KO/hApoAI transgenic mice with 3e9 GC of AAV-hLCAT-WT, AAV-hLCAT-V114M or control AAV-Null and measured plasma lipids before and after injection. Animals injected with AAV-hLCAT-V114M had substantial increases in total cholesterol (FIG. 14A) and HDL-cholesterol (FIG. 14B). We also measured plasma % CE in these mice and measured total cholesterol in FPLC fractions of pooled plasma samples from each group (FIG. 14C). In AAV-hLCAT injected mice, we see a shift towards a human-like bimodal HDL-C distribution.

FIGS. 15A-15D provide bar graphs showing that 3e9 GC of AAV8-TBG-hLCAT-V114M increases plasma CER in LCAT KO/hApoAI transgenic mice while AAV8-TBG-hLCAT-WT does not. We measured plasma lipids in AAV injected mice. 6 weeks after injection, both AAV-hLCAT injected groups had a plasma % CE within the normal range at approximately 60% (FIG. 15A). The plasma % CE acquires were also normalized to that of human and plotted in FIG. 15B. The AAV-hLCLAT-V114M has significantly elevated CER while the WT group did not. WT hLCAT and hLCAT-V114M were expressed equally as measured by plasma LCAT mass (FIG. 15C) and RT-PCR (FIG. 15D).

FIGS. 19A-19C provide data showing molecular dynamics simulation of hLCAT-V114M. Image showing the crystal structure of LCAT submerged in a water box, ready for simulation (FIG. 19A). Line graph showing change in root-mean-square-deviation (RMSD) stabilization over the 10 ns simulation time (FIG. 19B). Black line represents WT-LCAT, red line represents LCAT-V114M. We then plotted the root-mean-square fluctuation (RMSF) of each residue of WT human LCAT and LCAT-V114M over 10 ns simulation (FIG. 19C) in order to compare the predicted structures.

FIGS. 20A-20D provide data showing that molecular dynamics simulation of hLCAT variants suggests V114M may increase flexibility of the lid loop. Image showing the location of V114M within the LCAT structure (FIG. 20A). Image showing the active site lid-loop (FIG. 20B). Lid loop is shown in light blue. The catalytic triad/active site is labeled in green. V114M is labeled in red. We plotted the delta-RMSF for each residue of LCAT-V114M relative to WT hLCAT (FIG. 20C). We highlighted the five regions of hLCAT that are most dramatically affected by the V114M mutation. Close-up of delta-RMSF plots showing selected LCAT-114 variants (FIG. 20D). The five numbered panels represent the highlighted regions in 16B. Center panel (number 3) shows the delta-RMSF values in the lid loop region.

FIGS. 21A-21C provide bar graphs showing that codon optimized hLCAT variants significantly increase plasma lipids in BL6 mice. We designed four codon optimized variants of human LCAT, v1, v11, v26, and v20, and expressed them in AAVs. We injected C57/BL6 mice (N=4) with one of two doses of these vectors, AAV8-TBG-hLCAT (WT) or AAV8-TBG-Null then measured plasma lipids out to 6 weeks post-injection. We measured total cholesterol (FIG. 21A), HDL-C(FIG. 21B) and calculated % cholesterol esterified (FIG. 21C).

FIGS. 22A-22D provide line graphs showing that codon optimized hLCAT significantly increase plasma lipids in LCAT KO mice. We designed four codon optimized variants of human LCAT, v1, v11, v26, and v201, and expressed them in AAVs. We injected LCAT KO mice (N=7) with 1e10 GC of one of these new vectors, AAV-hLCAT (WT) or AAV-Null then measured plasma lipids out to 8 weeks post-injection. We measured total cholesterol (FIG. 22A), HDL-C(FIG. 22B), and calculated non-HDL cholesterol (FIG. 22C) and % cholesterol esterified (FIG. 22D).

FIGS. 24A-24D provide information of an alignment of wild-type human LCAT [SEQ ID NO:2] coding sequence with codon-optimized human LCAT coding sequences, SEQ ID NO: 3 (v1), SEQ ID NO: 4 (v11), SEQ ID NO: 5 (v26) and SEQ ID NO: 6 (v201).

DETAILED DESCRIPTION OF THE INVENTION

Figure 1:
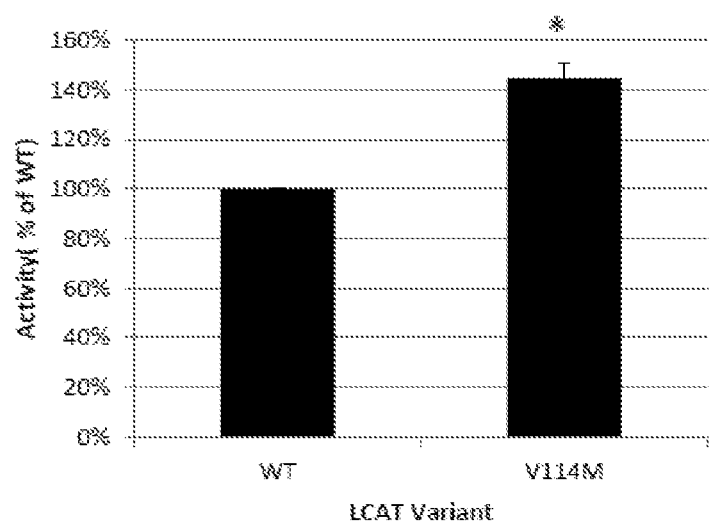
FIG. 1 is a bar chart showing the activity of LCAT-V114M on recombinant HDL particles. We expressed the WT and V114M variants of human LCAT in 293 cells and harvested the media to test activity. LCAT activity (esterification rate) was measured on $^3$H labeled recombinant HDL particles and was normalized to protein concentration as measured by ELISA. The V114M variant has approximately 150% the activity of WT LCAT.

The present invention provides LCAT protein variants which have increased activity, as measured in vitro and/or in an animal model, as compared to the wild-type (WT) LCAT V114 (numbering based on the position in human LCAT in the protein containing the wild-type signal peptide). The protein variant may be delivered in protein form, or expressed in situ from a viral vector, such as an adeno-associated virus (AAV). Further provided herein are compositions useful for delivery of these protein variants and vectors, and methods of use thereof. Delivery of these variants to subjects in need thereof via a number of routes, is useful for increasing high density lipoprotein levels. These variants are also useful in treating one or more conditions including, e.g., Fish Eye Disease (FED), Familial Lecithin Cholesterol Acyltransferase Deficiency (FLD), coronary artery disease, atherosclerosis, anemia, corneal opacities, and/or chronic progressive renal disease.

I. LCAT Variants

The term "LCAT" or "lecithin-cholesterol acyltransferase," as used herein, refers to a wild type glycoprotein enzyme that catalyzes the synthesis of cholesterol esters and lysolecithin from phosphatidylcholine and unesterified cholesterol present in lipoproteins. This enzyme is produced primarily by the liver and circulates in blood reversibly bound to lipoproteins. Human LCAT has a polypeptide mass of 49 kDa, or around 67 kDa with added carbohydrate mass. As used herein, the term "human LCAT" or "hLCAT" protein refers to the sequence in UniProtKB/Swiss-Prot: P04180.1, which includes a native signal peptide (residues 1-24), reproduced in SEQ ID NO: 1.

The LCAT variants described herein refer to changes at residue position 114 (Valine) relative to the residue positions of the amino acid sequence of the human LCAT of SEQ ID NO: 1. The novel variants (LCAT-V114X) provided herein specifically exclude the naturally-occurring LCAT-V 114M variant. Thus, if the initial methionine (start) is removed (aa 1), the relative position of the valine substituted with another amino acid would be position 113; similarly, if the signal peptide were removed (aa 1-24 of SEQ ID NO: 1), the relative position of the substituted valine would be residue 90. Thus, if a heterologous signal peptide is substituted for the native signal peptide show in SEQ ID NO: 1, the relative position of the substituted valine could be readily determined. Similarly, one of skill in the art can still readily identify the relative position 114, if the human LCAT contains amino acid substitutions at other positions with the LCAT protein, contains an N-terminal truncation and/or a C-terminal truncation, and/or is in a fusion protein.

As used herein, "LCAT-V114X" refers to a novel LCAT variant comprising a mutation at residue position 114 (Valine) relative to the residue positions of the amino acid sequence of the human LCAT of SEQ ID NO: 1, wherein X indicates any amino acid other than V. In one embodiment, X represents A, C, D, E, F, G, H, I, K, L, N, P, Q, R, S, T, W and Y. In some embodiments, X represents F, I, L, P or Q. In some embodiments, X does not represent M.

As used herein, "LCAT-V114M" refers to a naturally occurring variant of LCAT comprising a Met at residue position 114 (Valine) relative to the residue positions of the amino acid sequence of the human LCAT of SEQ ID NO: 1. In human studies, this variant is associated with higher levels of HDL. See, e.g., Jonathan C. Cohen, et al., Science, Vol 305, Issue 5685, pp 896-872 (2004) and Clara C. Elbers, et al, PLoS One, Vol 7, Issue 12, e50198 (2012).

In one embodiment, provided herein is a recombinant protein comprising: (a) the wild-type human LCAT protein or the human LCAT protein variant as described herein; and/or (b) a polypeptide tag. As used herein, the term "polypeptide tag" refers to a short amino acid sequence incorporated into the wild-type human LCAT protein or a variant thereof that facilitates the identification and/or purification of the protein to which it is attached. In one example, a useful polypeptide tag for the Anchor is a Myc tag. In another example, a polypeptide tag is a FLAG Tag. In another embodiment, a polypeptide tag is a NE Tag. In still another embodiment, a polypeptide tag is a HA-Tag. In still another example, a polypeptide tag is a His or poly-His Tag. In one embodiment, a poly peptide tag is 6×His Tag. In one embodiment, a poly peptide tag is V5 Tag. Other suitable tags include without limitation, chitin binding protein (CBP), maltose binding protein (MBP), Strep-tag and glutathione-S-transferase (GST), a tobacco etch virus (TEV) protease recognition site, a cleavage tag or a fluorescent tag. "Cleavage tag" refers to a polypeptide tag that allows the polypeptide to be cleaved at that site by an enzymatic or other mechanism. A cleavage tag might be selected from a human rhinovirus 3C protease (3C/PreScission) or PSP cleavage tag, an EKT (Enterokinase) cleavage tag, a FXa (Factor Xa) cleavage tag, a TEV (tobacco echovirus) cleavage tag, and a thrombin cleavage tag. Still other suitable cleavage tags or polypeptide tags may be publicly or commercially available and be readily used by one of skill in the art. Additionally, the recombinant protein might comprise 1, 2, 3, 4, 5 or more polypeptide tag(s). In an example, the recombinant protein comprises a V5 tag and a 6 ×His tag. In one embodiment, a polypeptide tag is located at the C-terminus of the wild-type human LCAT protein or the human LCAT protein variant as described herein. Alternatively or additionally, a polypeptide tag is located at the N-terminus of the wild-type human LCAT protein or the human LCAT protein variant as described herein.

```
SEQ ID NO: 1: >sp|P04180|LCAT_HUMAN Phosphatidyl-
choline-sterol acyltransferase
OS = Homo sapiens GN = LCAT PE = 1 SV = 1
MGPPGSPWQWVTLLLGLLLPPAAPFWLLNVLFPPHTTPKAELSNHTRPVI

LVPGCLGNQLEAKLDKPDVVNWMCYRKTEDFFTIWLDLNMFLPLGVDCWI

DNTRVVYNRSSGLVSNAPGVQIRVPGFGKTYSVEYLDSSKLAGYLHTLVQ

NLVNNGYVRDETVRAAPYDWRLEPGQQEEYYRKLAGLVEEMHAAYGKPVF

LIGHSLGCLHLLYFLLRQPQAWKDRFIDGFISLGAPWGGSIKPMLVLASG

DNQGIPIMSSIKLKEEQRITTTSPWMFPSRMAWPEDHVFISTPSFNYTGR

DFQRFFADLHFEEGWYMWLQSRDLLAGLPAPGVEVYCLYGVGLPTPRTYI

YDHGFPYTDPVGVLYEDGDDTVATRSTELCGLWQGRQPQPVHLLPLHGIQ

HLNMVFSNLTLEHINAILLGAYRQGPPASPTASPEPPPPE.
```

Suitably, the LCAT-V114M variant or the LCAT-V114X variants provided herein are characterized by one or more of: (i) an esterification rate higher than the esterification rate of WT human LCAT; and/or (ii) an association with higher density lipoprotein levels as compared to human subjects having WT LCAT. In certain embodiments, the LCAT-V114X variants are further characterized by having at least: an esterification rate higher than WT LCAT and/or an esterification rate of at least that of the naturally-occurring human LCAT V114M variant, and/or improved stability or half-life as compared to the human LCAT V114M mutant, and/or a higher binding level or association level with high density lipoprotein (HDL). Further, in certain embodiments, these variants are characterized by the ability to increase circulating plasma HDL levels in the absence of increasing LDL levels. LDL levels may be unaffected and/or may be modulated (increased or decreased).

A variety of in vitro assays are known for measuring LCAT activity. See, e.g., Examples 2, 4, 5, 6 and 8 below. This is a modification of the LCAT assay described in Vaisman, B L and Remaley A T, Methods Mol Biol, 2013, 1027: 343-352. Still other in vitro assays may be selected by one of skill in the art.

Alternatively or in addition, an animal model may be used to measure LCAT activity. Examples of suitable models are the mouse model provided in Examples 3, 4, 5, 6, and 8 below. Other suitable assays may be selected by one of skill in the art. See, e.g., N. Sakai et al, J Biol Chem, 1997 Mar 14; 272(11):7506-10; and S. Se'geret-Mac, et al, Circulation, 1996; 94:2177-2184.

Amino acid residues may be referenced herein by their 3-letter or 1-letter code. A list of common amino acids is provided below for convenience.

The term "amino acid substitution" and its synonyms described above are intended to encompass modification of an amino acid sequence by replacement of an amino acid with another, substituting, amino acid. In addition to the substitution of the LCAT-V114X variants, one or more other amino acid substitutions may be present. Preferably, the substitutions selected are not associated with any disease or disorder. Such a substitution may be a conservative substitution. It may also be a non-conservative substitution. The term conservative, in referring to two amino acids, is intended to mean that the amino acids share a common property recognized by one of skill in the art. For example, amino acids having hydrophobic nonacidic side chains, amino acids having hydrophobic acidic side chains, amino acids having hydrophilic nonacidic side chains, amino acids having hydrophilic acidic side chains, and amino acids having hydrophilic basic side chains. Both naturally occurring and non-naturally occurring amino acids are known in the art and may be used as substituting amino acids in embodiments. Methods for replacing an amino acid are well known to the skilled in the art and include, but are not limited to, mutations of the nucleotide sequence encoding the amino acid sequence. Reference to "one or more" herein is intended to encompass the individual embodiments of, for example, 1, 2, 3, 4, 5, 6, or more.

| Amino Acid Residue | 3-Letter Code | 1-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In one embodiment, the variant may have a substitution of A, C, D, E, F, G, H, I, K, L, N, P, Q, R, S, T, W and Y at position 114 relative to the residue positions of the amino acid sequence of the human LCAT of SEQ ID NO: 1. See, SEQ ID NOs: 8, 9, 10, 11, 12, 13, 14, 15, 16, 17, 18, 19, 20, 21, 22, 23, 24, and 25, for the amino acid sequences of said variants. Alternatively, the variant may have a substitution of M at position 114 relative to the residue positions of the amino acid sequence of the human LCAT of SEQ ID NO: 1. See, SEQ ID NO: 7. In one embodiment, the variant may have a substitution of Pro (P) [SEQ ID NO: 19]. In other embodiments, the substitutions are selected from Ala (A) (See SEQ ID NO: 8 for the amino acid sequence of the corresponding hLCAT variant), Cys (C) (See SEQ ID NO: 9 for the amino acid sequence of the corresponding hLCAT variant), Asp (D) (See SEQ ID NO: 10 for the amino acid sequence of the corresponding hLCAT variant), Glu (E) (See SEQ ID NO: 11 for the amino acid sequence of the corresponding hLCAT variant), Phe (F) (See SEQ ID NO: 12 for the amino acid sequence of the corresponding hLCAT variant), Gly (G) (See SEQ ID NO: 13 for the amino acid sequence of the corresponding hLCAT variant), His (H) (See SEQ ID NO: 14 for the amino acid sequence of the corresponding hLCAT variant), Ile (I) (See SEQ ID NO: 15 for the amino acid sequence of the corresponding hLCAT variant), Lys (K) (See SEQ ID NO: 16 for the amino acid sequence of the corresponding hLCAT variant), Leu (L) (See SEQ ID NO: 17 for the amino acid sequence of the corresponding hLCAT variant), Asn (N) (See SEQ ID NO: 18 for the amino acid sequence of the corresponding hLCAT variant), Gln (Q) (See SEQ ID NO: 20 for the amino acid sequence of the corresponding hLCAT variant), Arg (R) (See SEQ ID NO: 21 for the amino acid sequence of the corresponding hLCAT variant), Ser (S) (See SEQ ID NO: 22 for the amino acid sequence of the corresponding hLCAT variant), Thr (T) (See SEQ ID NO: 23 for the amino acid sequence of the corresponding hLCAT variant), Trp (W) (See SEQ ID NO: 24 for the amino acid sequence of the corresponding hLCAT variant), or Tyr (Y) (See SEQ ID NO: 25 for the amino acid sequence of the corresponding hLCAT variant).

Optionally, these LCAT variants may have additional amino acid substitutions. For example, P406L has been described. See, e.g., Conca, Paola, et al. "Novel missense variants in LCAT and APOB genes in an Italian kindred with familial lecithin: cholesterol acyltransferase deficiency and hypobetalipoproteinemia." Journal of clinical lipidology 6.3 (2012): 244-250. Other substitutions may be selected.

Additionally, an LCAT variant may have truncation at the N-terminus and/or C-terminus. An example of an N-terminal truncation (or the mature functional enzyme) may be a deletion of all or a portion of the signal peptide (aa 1-24 of SEQ ID NO: 1). Optionally, an N-terminal truncation may be longer than 24 amino acids, e.g., 25 to 30 amino acids. Such an LCAT variant with an N-terminal truncation may be engineered to be a chimeric or fusion protein having a heterologous N-terminal peptide or protein portion. Such a peptide may be heterologous signal or leader peptide, or another peptide or protein. An example of a C-terminal truncation may involve deletion of about 30 amino acids, about 20 amino acids, about 10 amino acids, about 5 amino acids, or 1, 2, 3 or 4 amino acids. Such an LCAT variant with a C-terminal truncation may be engineered to be a chimeric or fusion protein having a heterologous C-terminal peptide or protein portion. The binding partner for such a chimeric or fusion protein may be from a single source or multiple sources. For example, such a binding partner may contain a heterologous signal or leader peptide, an optional linker or spacer sequence, an immunoglobulin chain, etc.

The LCAT variants described herein may be generated synthetically or recombinantly and used in protein form for a variety of purposes, including, e.g., enzyme therapy. Thus, pharmaceutical composition which comprises at least one LCAT protein variant as provided herein may be prepared using and one or more of a carrier, excipient, or preservative. Suitable non-active and additional active components of such a composition are described elsewhere in this document, incorporated by reference into this paragraph.

Provided herein is a synthetic or recombinant human lecithin cholesterol acyltransferase (LCAT) variant comprising: an LCAT enzyme having a substitution at position 114 based on the residue numbering of wild-type (WT) human LCAT (SEQ ID NO:1), wherein said variant is characterized by one or more of: (i) an esterification rate higher than the esterification rate of WT human LCAT; and/or (ii) an association with higher density lipoprotein levels as compared to subjects having WT LCAT. In one embodiment, the substitution at position 114 comprises an amino acid selected from A, C, D, E, F, G, H, I, K, L, N, P, Q, R, S, T, W and Y. In another embodiment, the substitution at position 114 comprises an amino acid Met. In one embodiment, the variant further comprises a second amino acid substitution at a second position. In one embodiment, the LCAT variant is truncated at the N-terminus or C-terminus. In one embodiment, the LCAT variant comprises a deletion in the native signal peptide, corresponding to amino acids 1 to 24 of SEQ ID NO: 1. In another embodiment, the LCAT variant is a chimeric protein comprising a heterologous signal peptide. In one embodiment, the LCAT variant is delivered as part of a fusion protein.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "Clustal Omega", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

II. Coding Sequences of LCAT Variants

In addition to the LCAT protein variants provided herein, nucleic acid sequences encoding these LCAT protein variants are provided. The nucleic acid sequence of human wild-type LCAT is reproduced in SEQ ID NO: 2. The nucleic acid sequence of naturally occurring human LCAT-V114M is reproduced in SEQ ID NO: 26. In one embodiment, a coding sequence which encodes a LCAT variant is provided. In one embodiment, a coding sequence encodes hLCAT-V 114M (SEQ ID NO: 7) is provided. In another embodiment, a coding sequence encodes hLCAT-V114P is provided. In other embodiments, a coding sequence is selected from SEQ ID NO: 27 (encoding hLCAT-V114A), SEQ ID NO: 28 (encoding hLCAT-V114C), SEQ ID NO: 29 (encoding hLCAT-V 114D), SEQ ID NO: 30 (encoding hLCAT-V 114E), SEQ ID NO: 31 (encoding hLCAT-V 114F), SEQ ID NO: 32 (encoding hLCAT-V114G), SEQ ID NO: 33 (encoding hLCAT-V114H), SEQ ID NO: 34 (encoding hLCAT-V114I), SEQ ID NO: 35 (encoding hLCAT-V114K), SEQ ID NO: 36 (encoding hLCAT-V 114L), SEQ ID NO: 37 (encoding hLCAT-V 114N), SEQ ID NO: 39 (encoding hLCAT-V 114Q), SEQ ID NO: 40 (encoding hLCAT-V 114R), SEQ ID NO: 41 (encoding hLCAT-V 114S), SEQ ID NO: 42 (encoding hLCAT-V 114T), SEQ ID NO: 43 (encoding hLCAT-V114W) and SEQ ID NO: 44 (encoding hLCAT-V114Y) is provided.

An exemplary method of mutagenesis to generating the variants described herein is shown in Example 8. The coding sequences for these variants may be generating using site-directed mutagenesis of the wild-type nucleic acid sequence. Alternatively or additionally, web-based or commercially available computer programs, as well as service based companies may be used to back translate the amino acids sequences to nucleic acid coding sequences, including both RNA and/or cDNA. See, e.g., backtranseq by EMBOSS, www_ebi_ac_uk/Tools/st/; Gene Infinity (www_geneinfinity_org/sms-/sms_backtranslation)_html); or ExPasy (www_expasy_org/tools/). In one embodiment, the RNA and/or cDNA coding sequences are designed for optimal expression in human cells. Codon-optimized coding regions can be designed by various different methods. This optimization may be performed using methods which are available on-line, published methods, or a company which provides codon optimizing services. One codon optimizing method is described, e.g., in WO2015/012924. Briefly, the nucleic acid sequence encoding the product is modified with synonymous codon sequences. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

In one aspect, the coding sequence for wild-type human LCAT or a human LCAT variant is a codon optimized sequence. In one embodiment, the optimization is useful to improve production, transcription, expression or safety in a subject. In another embodiment, the optimization is useful to increase efficacy of the resulting therapeutic compositions or treatment. In one embodiment, the human LCAT variant is LCAT-V 114M. In another embodiment, the human LCAT variant is LCAT-V114X. In one embodiment, the codon-optimized hLCAT coding sequence is characterized by improved translation rate as compared to wild-type hLCAT coding sequences. In one embodiment, the hLCAT coding sequence has about 86% identity to the coding sequence of the full-length wildtype (SEQ ID NO: 2) or that of hLCAT-V114M (SEQ ID NO: 26) or that of hLCAT-V114X. In one embodiment, the hLCAT coding sequence has about 83% identity to the coding sequence of the full-length wildtype (SEQ ID NO: 2) or that of hLCAT-V114M (SEQ ID NO: 26) or that of hLCAT-V114X. In one embodiment, the hLCAT coding sequence has about 82% identity to the coding sequence of the full-length wildtype (SEQ ID NO: 2) or that of hLCAT-V114M (SEQ ID NO: 26) or that of hLCAT-V114X. In another embodiment, the hLCAT coding sequence has about 85% identity to the coding sequence of the full-length wildtype (SEQ ID NO: 2) or that of hLCAT-V114M (SEQ ID NO: 26) or that of hLCAT-V114X. In one embodiment, the hLCAT coding sequence shares less than about 99%, less than about 98%, less than about 97%, less than about 96%, less than about 95%, less than about 94%, less than about 93%, less than about 92%, less than about 91%, less than about 90%, less than about 89%, less than about 88%, less than about 87%, less than about 86%, less than about 85%, less than about 84%, less than about 83%, less than about 82%, less than about 81%, less than about 80%, less than about 79%, less than about 78%, less than about 77%, less than about 76%, less than about 75%, less than about 74%, less than about 73%, less than about 72%, less than about 71%, less than about 70%, less than about 69%, less than about 68%, less than about 67%, less than about 66%, less than about 65%, less than about 64%, less than about 63%, less than about 62%, less than about 61% or less identity to the coding sequence of the full-length wildtype (SEQ ID NO: 2) or that of hLCAT-V114M (SEQ ID NO: 26) or that of hLCAT-V114X. In another embodiment, the hLCAT coding sequence shares about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61% or less identity to the coding sequence of the full-length wildtype (SEQ ID NO: 2) or that of hLCAT-V114M (SEQ ID NO: 26) or that of hLCAT-V114X. In one embodiment, provided herein is a codon optimized, engineered nucleic acid sequence encoding the wildtype hLCAT coding sequence [SEQ ID NO: 1] or hLCAT-V114M [SEQ ID NO: 7] or hLCAT-V114X, or a nucleic acid sequence at least about 95% identical thereto. In one embodiment, provided herein is a codon optimized, engineered nucleic acid sequence of SEQ ID NO: 3 (codon-optimized human LCAT coding sequence v1, hLCATco-v1), or a nucleic acid sequence at least about 95% identical thereto. In one embodiment, provided herein is a codon optimized, engineered nucleic acid sequence of SEQ ID NO: 4 (codon-optimized human LCAT coding sequence v11, hLCATco-v11), or a nucleic acid sequence at least about 95% identical thereto. In one embodiment, provided herein is a codon optimized, engineered nucleic acid sequence of SEQ ID NO: 5 (codon-optimized human LCAT coding sequence v26, hLCATco-v26), or a nucleic acid sequence at least about 95% identical thereto. In one embodiment, provided herein is a codon optimized, engineered nucleic acid sequence of SEQ ID NO: 6 (codon-optimized human LCAT coding sequence v1, hLCATco-v201), or a nucleic acid sequence at least about 95% identical thereto. In another embodiment, provided herein is a codon optimized, engineered nucleic acid sequence of SEQ ID NO: 63 (codon-optimized coding sequence v1 of human LCAT-V114M, hLCAT-V 114M-co-v1), or a nucleic acid sequence at least about 95% identical thereto.

In one embodiment, provided herein is a nucleic acid sequence comprising: (a) a coding sequence of the wild-type human LCAT protein or the human LCAT protein variant as described herein; and/or (b) a coding sequence encoding a polypeptide tag.

The terms "percent (%) identity", "sequence identity", "percent sequence identity", or "percent identical" in the context of nucleic acid sequences refers to the bases in the two sequences which are the same when aligned for correspondence. The length of sequence identity comparison may be over the full-length of the genome, the full-length of a gene coding sequence, or a fragment of at least about 500 to 5000 nucleotides, or as desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "Clustal Omega", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

In one embodiment, provided herein is a nucleic acid sequence comprising a coding sequence of the wild-type human LCAT protein or the human LCAT protein variant as described herein is engineered into any suitable genetic element, e.g., naked DNA, phage, transposon, cosmid, RNA molecule (e.g., mRNA), episome, etc., which transfers the hLCAT sequences carried thereon to a host cell, e.g., for generating nanoparticles carrying DNA or RNA, viral vectors in a packaging host cell and/or for delivery to a host cell in a subject. In one embodiment, the genetic element is a plasmid. The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, NY (2012).

III. Expression Cassette

In one aspect, an expression cassette comprising the coding sequence for the wild type human LCAT or a human LCAT variant as described herein is provided. In one embodiment, the coding sequence is a codon-optimized sequence as described herein. In one embodiment, the expression cassette comprises codon-optimized, engineered nucleic acid sequence selected from SEQ ID NOs: 3, 4, 5, 6, or 63; or a nucleic acid sequence at least about 95% identical thereto. In one embodiment, the expression cassette further comprising a coding sequence of a polypeptide tag. In one embodiment, the human LCAT variant is hLCAT-V114M (SEQ ID NO: 7).

In one embodiment, an expression cassette comprising provided herein is a nucleic acid sequence comprising: (a) a coding sequence of the wild-type human LCAT protein or the human LCAT protein variant as described herein; and (b) optionally, a coding sequence encoding a polypeptide tag.

In one embodiment, the expression cassette further comprises regulatory elements which direct expression of the sequence encoding the wild type human LCAT or a human LCAT variant. In one embodiment, the regulatory elements comprise a promoter. In a further embodiment, the promoter is a TBG promoter, a T7 promoter, a TBG-S1 promoter, an A1AT promoter, a LSP promoter, a TTR promoter, or a CMV promoter. In another embodiment, the regulatory elements comprise an enhancer. In a further embodiment, the enhancer(s) is selected from one or more of an APB enhancer, an ABPS enhancer, an alpha mic/bik enhancer, a TTR enhancer, an en34 enhancer, an ApoE enhancer, a CMV enhancer, or an RSV enhancer. In yet another embodiment, the regulatory elements comprise an intron. In a further embodiment, the intron is selected from CBA, human beta globin, IVS2, SV40, bGH, alpha-globulin, beta-globulin, collagen, ovalbumin, or p53. In one embodiment, the regulatory elements comprise a polyA. In a further embodiment, the polyA is a synthetic polyA or from bovine growth hormone (bGH), human growth hormone (hGH), SV40, rabbit β-globin (RGB), or modified RGB (mRGB). In another embodiment, the regulatory elements comprise a WPRE sequence. In yet another embodiment, the regulatory elements comprise a Kozak sequence.

As used herein, an "expression cassette" refers to a nucleic acid molecule which comprises the LCAT variant coding sequences, promoter, and may include other regulatory sequences therefor, which cassette may be engineered into a genetic element and/or packaged into the capsid of a viral vector (e.g., a viral particle). Typically, such an expression cassette for generating a viral vector contains the LCAT sequences described herein flanked by packaging signals of the viral genome and other expression control sequences such as those described herein.

The expression cassette typically contains a promoter sequence as part of the expression control sequences or the regulatory sequences. In one embodiment, a tissue specific promoter may be selected. For example, if a liver-specific promoter is desired, one may select from thyroxin binding globulin (TBG), or other liver-specific promoters [see, e.g., The Liver Specific Gene Promoter Database, Cold Spring Harbor, rulai.schl.edu/LSPD,]such as, e.g., alpha 1 antitrypsin (A1AT); human albumin (Miyatake et al., J. Virol., 71:5124 32 (1997), humAlb); hepatitis B virus core promoter (Sandig et al., Gene Ther., 3:1002 9 (1996)); TTR minimal enhancer/promoter; alpha-antitrypsin promoter; T7 promoter; and LSP (845 nt)25(requires intron-less scAAV). Other promoters, such as viral promoters, constitutive promoters, regulatable promoters [see, e.g., WO 2011/126808 and WO 2013/049493], or a promoter responsive to physiologic cues may be used may be utilized in the vectors described herein.

In addition to a promoter, an expression cassette and/or a vector may contain other appropriate "regulatory element" or "regulatory sequence", which comprise but not limited to enhancer; transcription factor; transcription terminator; efficient RNA processing signals such as splicing and polyadenylation signals (polyA); sequences that stabilize cytoplasmic mRNA, for example Woodchuck Hepatitis Virus (WHP) Posttranscriptional Regulatory Element (WPRE); sequences that enhance translation efficiency (i.e., Kozak consensus sequence); sequences that enhance protein stability; and when desired, sequences that enhance secretion of the encoded product. Examples of suitable polyA sequences include, e.g., SV40, bovine growth hormone (bGH), and TK polyA. Examples of suitable enhancers include, e.g., the alpha fetoprotein enhancer, the TTR minimal promoter/enhancer, LSP (TH-binding globulin promoter/alpha1-microglobulin/bikunin enhancer), amongst others.

These control sequences or the regulatory sequences are "operably linked" to the LCAT gene sequences. As used herein, the term "operably linked" refers to both expression control sequences that are contiguous with the gene of interest and expression control sequences that act in trans or at a distance to control the gene of interest.

It should be understood that the compositions in the expression cassette described herein are intended to be applied to other compositions, regimens, aspects, embodiments and methods described across the Specification.

IV. Vector

The expression cassette may be engineered onto a plasmid which is used for production of a viral vector. The minimal sequences required to package the expression cassette into an AAV viral particle are the AAV 5' and 3' ITRs, which may be of the same AAV origin as the capsid, or which of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the hLCAT coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

The abbreviation "sc" refers to self-complementary. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

An adeno-associated virus (AAV) viral vector is an AAV DNase-resistant particle having an AAV protein capsid into which is packaged nucleic acid sequences for delivery to target cells. An AAV capsid (cap) is composed of 60 capsid protein subunits, VP1, VP2, and VP3, that are arranged in an icosahedral symmetry in a ratio of approximately 1:1:10 to 1:1:20, depending upon the selected AAV. AAV serotypes may be selected as sources for capsids of AAV viral vectors (DNase resistant viral particles) including, e.g., AAV1, AAV2, AAV3, AAV4, AAV5, AAV6, AAV6.2, AAV7, AAV8, AAV9, rh10, AAVrh64R1, AAVrh64R2, rh8 [See, e.g., US Published Patent Application No. 2007-0036760-A1; US Published Patent Application No. 2009-0197338-A1; and EP 1310571]; or a variant thereof. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), WO 2006/110689, WO 2003/042397 (rh10), or yet to be discovered, or a recombinant AAV based thereon, or an artificial AAV, may be used as a source for the AAV capsid. These documents also describe other AAV which may be selected for generating AAV and are incorporated by reference. In some embodiments, an AAV cap for use in the viral vector can be generated by mutagenesis (i.e., by insertions, deletions, or substitutions) of one of the aforementioned AAV Caps or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps.

As used herein, relating to AAV, the term "variant" means any AAV sequence which is derived from a known AAV sequence, including those sharing at least 70%, at least 75%, at least 80%, at least 85%, at least 90%, at least 95%, at least 97%, at least 99% or greater sequence identity over the amino acid or nucleic acid sequence. In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3). In one embodiment, the AAV capsid shares at least 95% identity with the AAV8 vp3. In another embodiment, a self-complementary AAV is used.

As used herein, "artificial AAV" means, without limitation, an AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV, non-contiguous portions of the same AAV, from a non-AAV viral source, or from a non-viral source. An artificial AAV may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 and AAV2/8 are exemplary pseudotyped vectors. The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, NY (2012).

For packaging an expression cassette into virions, the ITRs are the only AAV components required in cis in the same construct as the gene of interest. In one embodiment, the coding sequences for the replication (rep) and/or capsid (cap) are removed from the AAV genome and supplied in trans or by a packaging cell line in order to generate the AAV vector. For example, as described above, a pseudotyped AAV may contain ITRs from a source which differs from the source of the AAV capsid. Additionally or alternatively, a chimeric AAV capsid may be utilized. Still other AAV components may be selected. Sources of such AAV sequences are described herein and may also be isolated or obtained from academic, commercial, or public sources (e.g., the American Type Culture Collection, Manassas, VA). Alternatively, the AAV sequences may be obtained through synthetic or other suitable means by reference to published sequences such as are available in the literature or in databases such as, e.g., GenBank®, PubMed®, or the like.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety. The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, NY (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

Optionally, the hLCAT genes described herein may be delivered via viral vectors other than rAAV. Such other viral vectors may include any virus suitable for gene therapy may be used, including but not limited to adenovirus; herpes virus; lentivirus; retrovirus; etc. Suitably, where one of these other vectors is generated, it is produced as a replication-defective viral vector.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

Optionally, the hLCAT genes described herein may be delivered via non-viral vectors. A "vector" as used herein is a biological or chemical moiety comprising a nucleic acid sequence which can be introduced into an appropriate host cell for replication or expression of said nucleic acid sequence. Common vectors include viral vectors and non-viral vectors. As used herein, a non-viral vector might be selected from naked DNA, phage, transposon, plasmids, cosmids (Phillip McClean, www_ndsu.edu/pubweb/-mcclean/-plsc731/cloning/cloning4_htm) and artificial chromosomes (Gong, Shiaoching, et al. "A gene expression atlas of the central nervous system based on bacterial artificial chromosomes." Nature 425.6961 (2003): 917-925).

"Plasmid" or "plasmid vector" generally is designated herein by a lower case p preceded and/or followed by a vector name. Plasmids, other cloning and expression vectors, properties thereof, and constructing/manipulating methods thereof that can be used in accordance with the present invention are readily apparent to those of skill in the art. In one embodiment, the nucleic acid sequence as described herein or the expression cassette as described herein are engineered into a suitable genetic element (a vector) useful for generating viral vectors and/or for delivery to a host cell, e.g., naked DNA, phage, transposon, cosmid, episome, etc., which transfers the ASL sequences carried thereon. The selected vector may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, NY.

The term "transgene" or "gene of interest" as used interchangeably herein means an exogenous and/or engineered protein-encoding nucleic acid sequence that is under the control of a promoter and/or other regulatory elements in an expression cassette, rAAV genome, recombinant plasmid or production plasmid, vector, or host cell described in this specification. In certain embodiments, the transgene is a nucleic acid sequence comprising a coding sequence of the wild-type hLCAT protein or a variant thereof as described herein. In some embodiments, the transgene is a codon optimized nucleic acid sequence set forth in SEQ ID NO: 3 (hLCATco-v1). In certain embodiments, the transgene is a codon optimized nucleic acid sequence set forth in SEQ ID NO: 63 (hLCAT-V114M-co-v1).

The term "exogenous" as used to describe a nucleic acid sequence or protein means that the nucleic acid or protein does not naturally occur in the position in which it exists in a chromosome, or host cell. An exogenous nucleic acid sequence also refers to a sequence derived from and inserted into the same host cell or subject, but which is present in a non-natural state, e.g. a different copy number, or under the control of different regulatory elements.

The term "heterologous" as used to describe a nucleic acid sequence or protein means that the nucleic acid or protein was derived from a different organism or a different species of the same organism than the host cell or subject in which it is expressed. The term "heterologous" when used with reference to a protein or a nucleic acid in a plasmid, expression cassette, or vector, indicates that the protein or the nucleic acid is present with another sequence or subsequence with which the protein or nucleic acid in question is not found in the same relationship to each other in nature.

As used herein, the term "host cell" may refer to the packaging cell line in which a vector (e.g., a recombinant AAV) is produced from a production plasmid. In the alternative, the term "host cell" may refer to any target cell in which expression of the transgene is desired. Thus, a "host cell," refers to a prokaryotic or eukaryotic cell that contains a exogenous or heterologous nucleic acid sequence that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion. In certain embodiments herein, the term "host cell" refers to cultures of cells of various mammalian species for in vitro assessment of the compositions described herein. In other embodiments herein, the term "host cell" refers to the cells employed to generate and package the viral vector or recombinant virus. Still in other embodiment, the term "host cell" is intended to reference the target cells of the subject being treated in vivo for the diseases or conditions as described herein. In a further embodiment, the term "host cell" is a liver cell.

As used herein, a "vector genome" refers to the nucleic acid sequence packaged inside the rAAV capsid which forms a viral particle. Such a nucleic acid sequence contains AAV inverted terminal repeat sequences (ITRs). In the examples herein, a vector genome contains, at a minimum, from 5' to 3', an AAV2 5' ITR, a coding sequence encoding a wild-type hLCAT protein or a variant thereof as described herein, and an AAV2 3' ITR. However, ITRs from a different source AAV other than AAV2 may be selected. Further, other ITRs may be used. Further, the vector genome contains regulatory sequences which direct is expression of the gene of interest.

In one aspect, provided herein is a recombinant viral vector which comprises an expression cassette comprising: (a) a nucleic acid coding sequence for the wild-type human LCAT (SEQ ID NO: 1); or a nucleic acid coding sequence for a synthetic or recombinant human lecithin cholesterol acyltransferase (LCAT) variant comprising: an amino acid substitution at amino acid residue position 114 based on the residue numbering of wt normal LCA, wherein said variant is characterized by one or more of: (i) an esterification rate higher than the esterification rate of WT human LCAT; (ii) an association with higher density lipoprotein levels as compared to subjects having WT LCAT; and (b) regulatory sequences which direct expression of the LCAT variant in a host cell, said regulatory sequences being operably linked to the LCAT coding sequence. In one embodiment, the recombinant viral vector is an adeno-associated virus (AAV). In a further embodiment, the AAV vector comprises a capsid selected from an AAV8, AAVrh64R1, AAV9, or AAVrh10 capsid. In one embodiment, the amino acid at position 114 is selected from A, C, D, E, F, G, H, I, K, L, N, P, Q, R, S, T, W and Y. In another embodiment, the variant has a M at position 114 of SEQ ID NO:1. In one embodiment, the LCAT variant is truncated at the N-terminus or C-terminus. In one embodiment, the LCAT variant is delivered as part of a fusion protein. In one embodiment, the expression cassette further comprising an optional coding sequence of a polypeptide tag. In one embodiment, the nucleic acid coding sequence is selected from SEQ ID NOs: 3, 26 and 63.

Exemplary vector genomes of AAV-TBG-hLCAT-V114M, AAV-TBG-hLCATco-v1, and AAV-TBG-hLCAT-V114M-co-v1 are reproduced in SEQ ID NOs: 70, 71 and 72 respectively. An exemplary plasmid for cloning and/or producing hLCAT-V114P variant (pcDNA3.1-hLCAT-V 114P) is reproduced in SEQ ID NO: 77.

It should be understood that the compositions in the vector described herein are intended to be applied to other compositions, regiments, aspects, embodiments and methods described across the Specification.

V. Pharmaceutical Composition

In one aspect, provided herein is a pharmaceutical composition which comprises at least one LCAT protein variant as described herein and one or more of a carrier, surfactant, excipient, or preservative.

In one aspect, provided herein is a pharmaceutical composition which comprises at least one viral or non-viral vector as described herein and one or more of a carrier, excipient, or preservative.

The pharmaceutical compositions described herein are designed for delivery to subjects in need thereof by any suitable route or a combination of different routes. Direct delivery to the liver (optionally via intravenous, via the hepatic artery, the portal vein, hepatic vein, bile duct, or by transplant), oral, inhalation, intranasal, intratracheal, intraarterial, intraocular, intravenous, intramuscular, subcutaneous, intradermal, and other parenteral routes of administration. The viral vectors or pharmaceutical compositions described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

The replication-defective viruses can be formulated with a physiologically acceptable carrier for use in gene transfer and gene therapy applications. In the case of AAV viral vectors, quantification of the genome copies ("GC") may be used as the measure of the dose contained in the formulation. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal). Alternative or additional method for performing AAV GC number titration is via oqPCR or digital droplet PCR (ddPCR) as described in, e.g., M. Lock et al, Hum Gene Ther Methods. 2014 April; 25(2):115-25. doi: 10.1089/hgtb.2013.131. Epub 2014 Feb 14, which is incorporated herein by reference.

Also, the replication-defective virus compositions can be formulated in dosage units to contain an amount of replication-defective virus that is in the range of about $1.0 \times 10^9$ GC to about $1.0 \times 10^{15}$ GC (to treat an average subject of 70 kg in body weight), and preferably $1.0 \times 10^{12}$ GC to $1.0 \times 10^{14}$ GC for a human patient. In another embodiment, the dose is less than about $1.5 \times 10^{11}$ GC/kg. For example, the dose of AAV virus may be about $3 \times 10^8$ GC/kg, about $1 \times 10^9$ GC/kg, about $3 \times 10^9$ GC/kg, about $5 \times 10^9$ GC/kg, about $1 \times 10^{10}$ GC/kg, about $3 \times 10^{10}$ GC/kg, about $5 \times 10^{10}$ GC/kg, or about $1 \times 10^{11}$ GC/kg.

In another example, the compositions may be formulated to deliver variant proteins in an amount of about 0.001 mg/kg to about 10 mg/kg.

The above-described recombinant vectors may be delivered to host cells according to published methods. The rAAV, preferably suspended in a physiologically compatible carrier, may be administered to a human or non-human mammalian subject. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and/or variants and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

VI. Methods

The viral vectors and other constructs described herein may be used in preparing a medicament for delivering a LCAT variant to a subject in need thereof, e.g., by expressing the variant in vivo, supplying LCAT variant having an increased half-life to a subject, and/or for treating elevated cholesterol levels, reduced HDL-c, elevated triglycerides, familial hypercholesterolemia, atherosclerosis, cardiovascular disease (coronary artery disease, cardiovascular disease, etc), renal disease or dysfunction, and/or another lipoprotein metabolic disorder.

As used herein, "disease", "disorder" and "condition" are used interchangeably, to indicate an abnormal state in a subject. In one embodiment, the disease is elevated cholesterol levels; reduced HDL-c; elevated triglycerides; reduced phospholipids; reduced plasma percent cholesterol esterified (% CE); reduced cholesterol esterification rate (CER); familial hypercholesterolemia; atherosclerosis; cardiovascular disease (coronary artery disease, cardiovascular disease, etc); renal disease or dysfunction; Fish Eye Disease (FED); familial LCAT deficiency (FLD); anemia, corneal opacities, and/or chronic progressive renal disease associated with FED or FLD; a deficiency or defect in wt LCAT function or activity; and/or another lipoprotein metabolic disorder.

In one embodiment, a method for treating a subject having a condition is provided, wherein the condition comprising one or more of: elevated cholesterol levels; reduced HDL-c; elevated triglycerides; reduced phospholipids; reduced plasma percent cholesterol esterified (% CE); reduced cholesterol esterification rate (CER); familial hypercholesterolemia; atherosclerosis; cardiovascular disease (coronary artery disease, cardiovascular disease, etc); renal disease or dysfunction; Fish Eye Disease (FED); familial LCAT deficiency (FLD); anemia, corneal opacities, and/or chronic progressive renal disease associated with FED or FLD; a deficiency or defect in wt LCAT function or activity; and/or another lipoprotein metabolic disorder.

A course of treatment may optionally involve repeat administration of the same viral vector (e.g., an AAV8 vector) or a different viral vector (e.g., an AAV8 and an AAVrh10). Still other combinations may be selected using the viral vectors described herein. For example, for liver-targeted delivery regimens may include, e.g., AAVrh64R1, AAV9, and/or AAVrh10 capsid. For vascular-targeted delivery regimens, AAV vectors having these or other AAV capsids may be selected; alternatively, other vectors may be selected. Similarly, for eye-targeted delivery regimens, AAV vectors having these or other AAV capsids may be selected; alternatively, other vectors may be selected. Optionally, the composition described herein may be combined in a regimen involving anti-lipid drugs (e.g., statins, monoclonal antibodies, etc), or protein-based therapies (including, e.g., delivery of a composition containing one or more LCAT variant proteins as described herein). In another embodiment, a treatment may be preceded by, followed by, or may include an ongoing regimen with probucol or a recombinant HDL infusion therapy. Probucol [4,4'-[propane-2,2-diylbis(thio)] bis(2,6-di-tert-butylphenol)] is an anti-hyperlipidemic drug originally developed for coronary artery disease and currently in clinical trials to evaluate its effects in diabetic nephropathy, reducing risk of cerebral hemorrhage without cardiovascular events, negating cognitive deterioration in dementia of the Alzheimer type, and severe hypercholesterolemia (in combination with cilostazol or valsartan). Examples of suitable moieties for HDL infusion therapies may include, e.g., APL180 (an ApoA1 mimetic; Novartis, also known as L-4F), See, e.g., CE Watson et al, Lipids Research, 52: 361-373 (Feb 2011), which provides the sequence and illustrative dosing. Other infusion therapies may utilize CLS112 (P. Tricoci, et al, J Am Heart Assoc. 2015; 4:e002171; CSL Limited; AEGIS-I) or CER-001 (a negatively charged lipoprotein particle which contains human recombinant ApoA-1 (also known as pre-beta HDL; Cerenis Therapeutics)). In one embodiment, a method for preferentially increasing high density lipoprotein levels in a subject (e.g., a human patient) is provided which involves an LCAT variant as provided herein, either by enzyme therapy or expressed from or a viral vector a subject in need thereof. The protein, variant or vector may be targeted to the liver, eye or vasculature, or may be delivered by other suitable means.

In another embodiment, a method for treating Fish Eye Disease (FED) is provided.

In still another embodiment, a method for treating familial LCAT deficiency (FLD) is provided.

In a further example, a method for treating anemia, corneal opacities, and/or chronic progressive renal disease associated with FED or FLD.

In a further example, a method for treating cardiovascular disease, coronary artery disease, renal disease, and/or renal dysfunction (e.g., diabetic nephropathy) are provided.

In still a further example, a method for treating a disorder or disease associated with a deficiency or defect in wt LCAT function or activity is provided herein.

"Atherosclerosis" refers to a condition characterized by the hardening and/or narrowing of the arteries caused by the buildup of athermatous plaque inside the arterial walls. The atheromatous plaque is divided in three components, (1) the atheroma, a nodular accumulation of a soft flaky material at the center of large plaques, composed of macrophages nearest the lumen of the artery; (2) underlying areas of cholesterol crystals; (3) calcification at the outer base of more advanced lesions. Indicators of atherosclerosis include, for example, the development of plaques in the arteries, their calcification, or the development of foam cells in arteries. The narrowing of the arteries can be determined by IMT, angiogram, calcium scan, ultrafast CT, or ultrasound.

The term "HDL" refers to the high-density lipoproteins.

The term "LDL", as used herein, means the low-density lipoproteins.

In yet another embodiment, a method for improving renal function, delaying the need for a kidney transplant, or preventing the need for a kidney transplant, is provided.

The term "treatment" or "treating" includes the administration to a subject in need of a pharmacologically active amount or a therapeutically effective amount of a modified LCAT protein which will inhibit, decrease or reverse development of, for example, a pathological atherosclerosis, inflammatory disorder, or thrombosis-related disorder. In another aspect, treatment as used herein means the administration, to a subject in need, of an amount of a compound of the invention, which, with respect to atherosclerosis, will increase HDL cholesterol levels. "Inhibiting," in connection with inhibiting atherosclerosis, is intended to mean preventing, retarding, stabilizing, or reversing formation or growth of atheromatous plaques, inflammatory disorder, or thrombosis-related disorder. Treatment of diseases and disorders herein is intended to also include therapeutic administration of a modified LCAT protein of the invention (or a pharmaceutical salt, derivative or prodrug thereof) or a pharmaceutical composition containing the modified LCAT protein to a subject believed to be in need of treatment for diseases and disorders, such as, for example, inflammatory disorders, thrombosis disorders, coronary heart disease and/or cardiovascular disease, high blood pressure, LCAT deficiency syndrome, high density lipoprotein levels, FED, FLD, coronary artery disease, anemia, renal disease and/or chronic progressive renal disease, Alzheimer's disease, corneal opacity, metabolic syndrome, dyslipidemia, myocardial infarction, stroke, peripheral vascular disease and/or critical limb ischemia, angina and the like. Treatment also encompasses administration of the modified LCAT protein, which may be administered directly, or via vector-mediated delivery (e.g., AAV-mediated delivery), or pharmaceutical composition to subjects not having been diagnosed as having a need thereof, i.e., prophylactic administration to the subject, for prevention of a condition or disorder. Generally, the subject is initially diagnosed by a licensed physician and/or authorized medical practitioner, and a regimen for prophylactic and/or therapeutic(acute or chronic) treatment via administration of the modified LCAT protein(s) or compositions of the invention is suggested, recommended or prescribed.

A variety of in vitro assays and in vivo animal models are known for measuring the methods described herein. See, e.g., Examples below. Alternatively or in addition, an animal model may be used to test rAAV vectors described herein for treating chronic progressive renal disease associated with FED or FLD, e.g., the LpX injection model by Ossoli et al (Ossoli, A. et al. Lipoprotein X Causes Renal Disease in LCAT Deficiency. PLoS One 11, e0150083 (2016)). The phrase "therapeutically effective amount" is the amount of a LCAT protein variant or a vector expressing a LCAT variant as described herein that will achieve the goal of improvement in disorder severity and the frequency of incidence. The improvement in disorder severity includes, for example with respect to atherosclerosis, prevention of accumulation of cholesterol in vessel walls increasing of blood levels of HDL cholesterol, the reversal of atherosclerosis, as well as slowing down the progression of atherosclerosis, prevention or treatment of inflammatory disorders, and prevention or treatment of thrombosis-relating conditions.

As used herein, the term "subject" is intended to mean a human or other mammal, exhibiting, or at risk of developing a disease, disorder or dysfunction associated with LCAT defects or deficiencies. Such clinical indications of these conditions are known in the art. A "subject" is a mammal, e.g., a human, mouse, rat, guinea pig, dog, cat, horse, cow, pig, or non-human primate, such as a monkey, chimpanzee, baboon or gorilla.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

The term "regulation" or variations thereof as used herein refers to the ability of a composition to inhibit one or more components of a biological pathway.

Unless defined otherwise in this specification, technical and scientific terms used herein have the same meaning as commonly understood by one of ordinary skill in the art and by reference to published texts, which provide one skilled in the art with a general guide to many of the terms used in the present application.

With regard to the description of these inventions, it is intended that each of the compositions herein described, is useful, in another embodiment, in the methods of the invention. In addition, it is also intended that each of the compositions herein described as useful in the methods, is, in another embodiment, itself an embodiment of the invention.

EXAMPLES

The following examples are illustrative only and are not intended to limit the present invention.

Here we performed the first studies of AAV-hLCAT as a therapeutic for FLD. We tested a total of five doses of AAV-hLCAT in LCAT KO mice and three doses in 'humanized' LCAT KO/hApoAI transgenic mice. For the purpose of these studies, we defined the MED, or minimally efficacious dose, as the dose that produced statistically significant increases in plasma % CE. We found that the MED in LCAT KO mice was 1e10 GC per mouse which is approximately equivalent to 5e11 GC per kg. The MED was reduced in LCAT KO/hApoAI transgenic mice, to 3e9 GC per mouse or 1.5e11 GC per kg. This dose is more than ten fold lower than the lowest dose used in recent AAV gene therapy trials for hemophilia B (Nathwani, A. C. et al. Long-term safety and efficacy of factor IX gene therapy in hemophilia B. N. Engl. J. Med. 371, 1994-2004 (2014)), which was 2e12 GC per kg.

Next, we tested the in vitro activity of the naturally-occurring LCAT variant V 114M that exist in the human population at measurable levels. Two naturally-occurring LCAT variants R123H and S232T served as controls. All three of these variants were found to be significantly associated with differential HDL-C levels in the human population in the heterozygous state. These associations, identified in people carrying a single variant allele in combination with a normal allele, suggest that the effect of these SNPs on the function of the enzyme is relatively strong and strong enough to overcome the effect of the normal allele. We found that in the case of two of these variants, R123H and VI 14M, the activity of these variants on recombinant HDL was consistent with their human lipid associations. Activity of the third variant, S232T was not found to be significantly different from WT, although the activity of this variant in general, was much more variable. It is possible that the mechanism by which this variant is associated with decreased HDL-C is not related to its enzymatic activity. However, when we further examined the V114M variant, which had a positive association with HDL-C, we found that it not only had increased activity in vitro at 160% of WT, but also in vivo, supporting that the increase in activity of this variant is responsible for its positive association.

When we expressed this gain of function variant of hLCAT using AAV2/8, we found that V114M, because of its increased activity, reduced the MED of the vector in both LCAT KO and LCAT KO/hApoAI mice. The use of V114M instead of WT hLCAT, reduced the MED from 1e10 GC per mouse to 3e9 GC per mouse in LCAT KO mice, and in LCAT KO/hApoAI mice, we concluded the MED was reduced from 3e9 GC per mouse to 1e9 GC per mouse. This dose of 1e9 GC per mouse is equivalent to 5e10 GC per kg, a dose that is 20fold lower than the approved dose of Glybera and 40 fold lower than the lowest dose used in the Hemophilia B trial. As we mentioned previously, when it comes to gene therapy, the lower the dose, the better. A lower dose reduces the risk of immune reactions against the vector and the transgene, as well as reduces the burden on production and price of the vector, which under good-manufacturing practice (GMP) can be quite expensive. This low dose is a promising start in the world of gene therapy for FLD.

Sequence optimization had less impact on the effectiveness of our vector to increase plasma lipids and % CE than described in published studies for other proteins, but one variant, hLCATv 1, did appear to be better than WT. Plasma LCAT mass and transcript levels can be studied to assess this construct for an improved transcript: protein ratio as compared to WT.

Recombinant enzyme therapy was shown to reduce renal dysfunction in an LCAT deficient patient (Shamburek, R. D. et al. Familial lecithin:cholesterol acyltransferase deficiency: First-in-human treatment with enzyme replacement. J. Clin. Lipidol. 10, 356-367 (2016)). This important finding suggests that FLD renal disease is potentially reversible upon the introduction of functional LCAT. If we can achieve a comparable plasma concentration of hLCAT using our AAV, it is reasonable to expect that our vector would improve or eliminate renal dysfunction perhaps even more effectively than recombinant enzyme therapy, as the plasma hLCAT concentration will be more stable. However, even if comparable plasma concentrations are not achieved, there may be therapeutic value to the patient in that the need for enzyme or other therapy may be reduced. In this patient, a recombinant hLCAT dose of 9 mg/dL normalized plasma % CE and the effect lasted for several days after each infusion. The peak plasma concentration of LCAT following the infusion of this dose was approximately 4 times that of the normal human plasma concentration, but the steady state plasma LCAT mass was approximately 120% of normal. The middle dose tested in this patient was 3 mg/dL. This dose had a steady state plasma LCAT concentration comparable to a normal individual and produced near normal % CE during the several days following infusion. We have shown that using AAV-hLCAT-V114M, we can reach a plasma LCAT concentration near normal, at approximately 80%, and produce normal % CE, using just 3e9 GC per mouse, or 1.5e 11 GC per kg of vector. We would expect that the therapeutic dose of our vector may be even lower than this, perhaps 5e10 GC per kg as we concluded in our studies, as the expression of hLCAT from the AAV genome will be constant and plasma concentrations will be stable, unlike with recombinant enzyme therapy.

An additional advantage of gene therapy over recombinant enzyme therapy, is the reduction in risk of immunity against the LCAT enzyme. Repeated treatments with recombinant enzyme comes with means the development antibodies against the enzyme is inevitable. The level of antibodies must be monitored and managed throughout the life of the patient to ensure the success of treatment. In certain embodiments, co-therapy with one or more immunosuppressive agents (e.g., steroids, etc) is used with a gene therapy approach. Such co-therapy may begin prior to, or at the time of administration. Such co-therapy with one or more immunosuppressive agent may be continued for days, weeks, or months following administration of vector, or shorter or longer periods, as determined.

Example 1—Generation of LCAT Variants

A series of human LCAT variants containing a single amino acid change at residue position 114, with respect to the numbering of SEQ ID NO:1, which includes the native hLCAT signal peptide (amino acids 1-24). The native amino acid at this position is valine; the variants generated included hLCAT-V114F; hLCAT-V114I; hLCAT-V114L; hLCAT-V114M; hLCAT-V114P; and hLCAT-V114Q. All LCAT variants were created using GeneStrand fragments [purchased from Eurofins Genomics], and cloning into the widely used expression plasmid, pcDNA3.1. GeneStrand fragments and plasmids were cut with the restriction enzymes KpnI and HindIII from New England Biolabs (NEB) and then the cut fragments were ligated into the plasmid backbones using T4 Ligase also from NEB. Expression plasmids containing each of these variants were used to assess activity as described below.

The hLCAT-V114M variant was cloned into an expression plasmid and its activity was tested in vitro on recombinant HDL particles. This variant was observed to have approximately 150% the activity of the common or WT variant (FIG. 1). Secondly, this variant was tested in vivo. Using adeno-associated virus, AAV2/8, as a vector, the WT and V114M variants of LCAT were expressed in the livers of separate LCAT KO mice. Groups of LCAT KO mice (n=5) were injected with $1\times10^{10}$ (1e10) genome copies (GC) of AAV2/8 expressing either the WT LCAT or LCAT-V114M, or a null control virus.

LCAT KO and LCAT KO/human ApoAI transgenic mice are maintained in our animal facility on chow diet. 6-10 week old male mice received single intraperitoneal injections of one of our adeno-associated viral vectors (AAV) (produced by Penn Vector Core) diluted in sterile PBS. Blood samples were collected prior to injection and every 2 weeks thereafter via retroorbital bleed. Animals were sacrificed 6 weeks after AAV injection. Plasma lipids were measured by AXCEL autoanalyzer.

For the animal studies described in the paragraph above, an AAV8 vector was generated using the expression cassette encoding the proteins. Using conventional triple transfection techniques, the vector was generated with an AAV8 capsid, with the expression cassette inserted between an AAV2 5' ITR and AAV2 3' ITR The hLCAT-V114M variant was expressed under the control of a human TBG promoter and the alpha-I-microglobulin/bikunin enhancer. AAV constructs also contained a chimeric intron sequence and SV40 poly-A sequence. The intron sequence used in these constructs is a chimera of intron sequences from human p-globulin and the human immunoglobulin heavy chain.

Figures 2A, 2B:
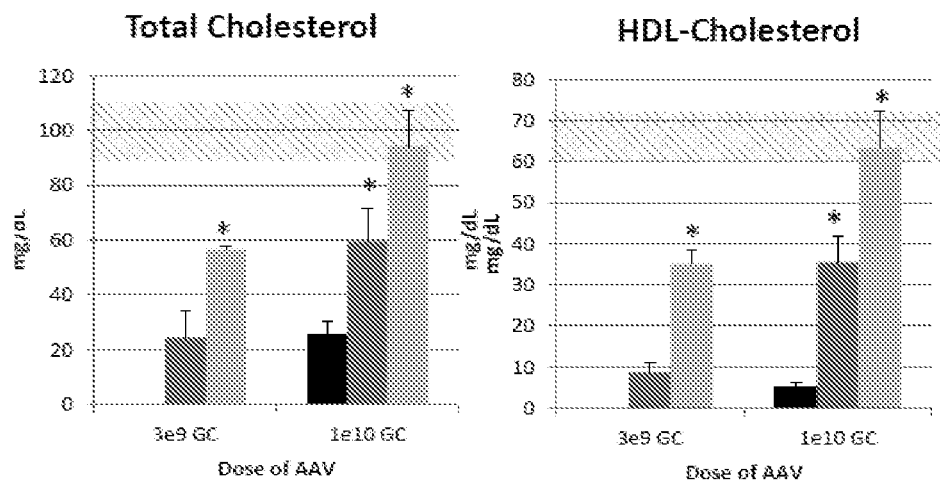
FIGS. 2A-2C show plasma lipids of total cholesterol (FIG. 2A), HDL-cholesterol (FIG. 2B), and percentage of cholesterol ester (FIG. 2C) 6 weeks post AAV-injection. LCAT KO mice were injected with one of three AAV vectors LCAT-WT, LCAT-V114M or Null control vector at a dose of $3\times10^9$ (3e9) GC or $1\times10^{10}$ (1e10) GC. 6 weeks after injection, blood was collected and plasma lipids including total cholesterol (TC) and HDL-cholesterol (HDL-c) were measured by AXCEL auto-analyzer. Mice who received a vector expressing LCAT had higher TC and HDL-c than mice who received null vector. Mice who received the V114M variant had higher TC and HDL-c than the mice who received the WT LCAT vector. Asterisks indicate $p<0.05$ as compared to Null. Error bars show standard deviation.
Figure 2C:
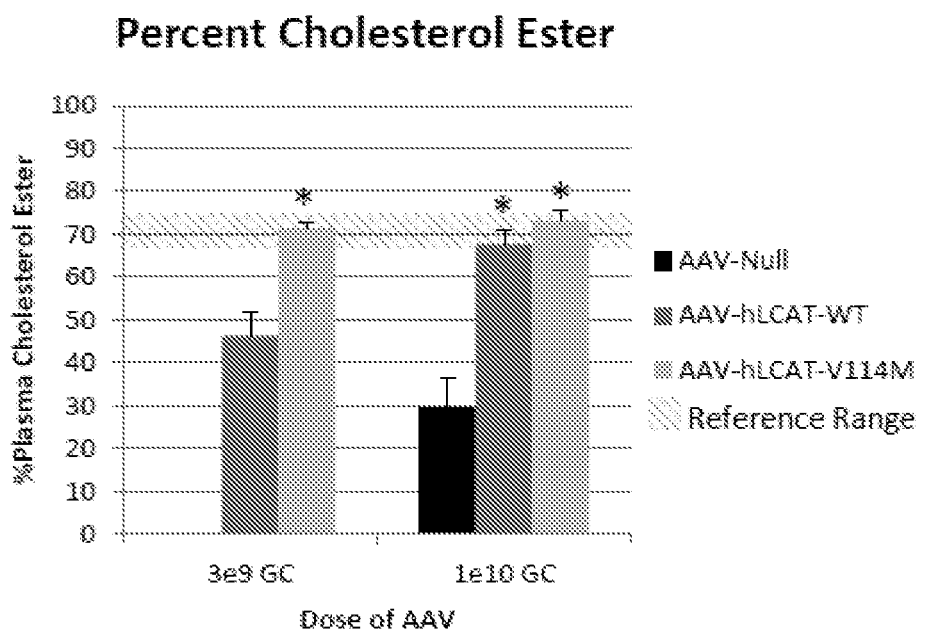
Figure 3A:
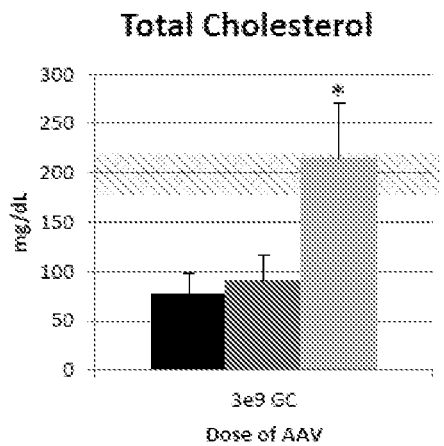
FIGS. 3A-3C are bar charts showing that $3\times10^9$ (3e9) genome copies (GC) of AAV-hLCAT-V114M normalizes plasma lipids in LCAT KO/hApoAI transgenic mice while $3\times10^9$ GC of AAV-hLCAT-WT does not. Groups of LCAT KO/hApoAI transgenic mice (n=5) received a single injection of $3\times10^9$ (3e9) GC of AAV-Null, AAV-hLCAT-WT or AAV-hLCAT-V114M. Shown are selected plasma lipids from injected mice, as measured by AXCEL auto-analyzer in plasma samples collected 6 weeks after injection. Mice that received AAV-hLCAT-V114M demonstrated significant increases in total cholesterol (FIG. 3A), HDL-cholesterol (FIG. 3B) and % CE (FIG. 3C), with levels in the normal range. However, while mice that received AAV-hLCAT-WT had normal plasma % CE, these mice did not have any significant increases in other plasma lipids. Asterisks indicate $p<0.05$ as compared to Null. Error bars indicate standard deviation.
Figure 3B:
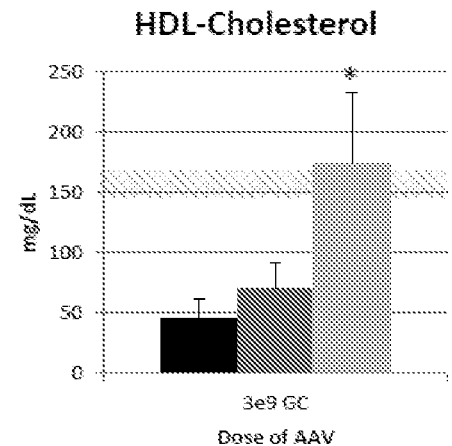
Figure 3C:
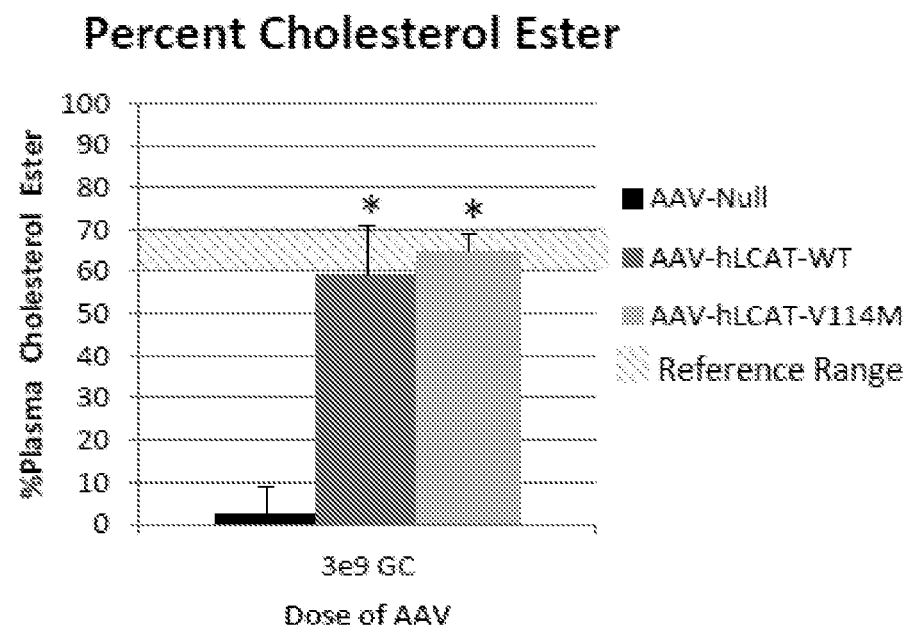
Figure 4:
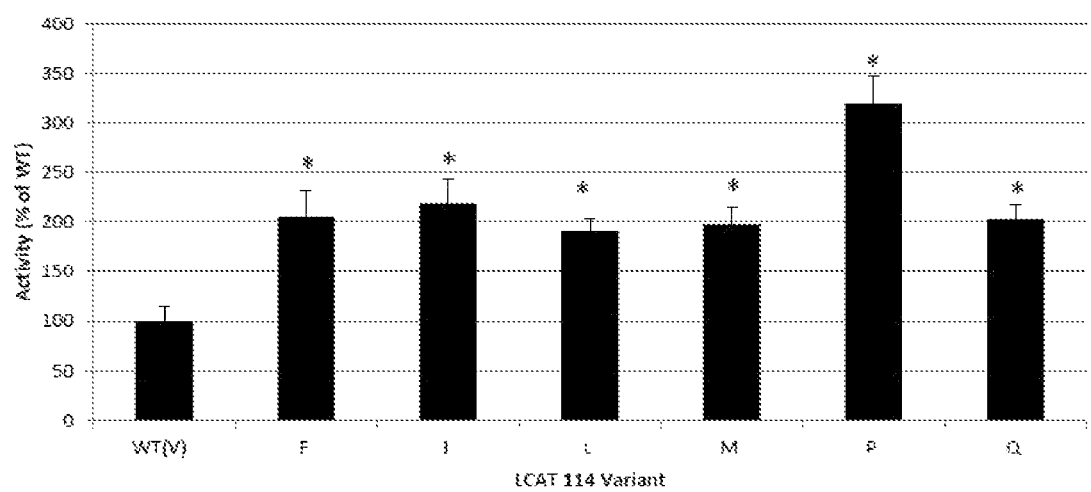
FIG. 4 is a bar chart showing that six hLCAT V114 variants have activity greater than WT human LCAT. We tested the in vitro activity of 20 versions of hLCAT, each with a different amino acid at position 114. Shown here are the six variants which have activity greater than the WT enzyme, which has Valine (V) at position 114. These variants are V114F (Phenylalanine), V114I (Isoleucine), V114L (Leucine), V114M (Methionine), V114P (Proline) and V114Q (Glutamine).

When plasma lipids were measured in these mice 6 weeks post-injection, we found that mice which were injected with either LCAT virus had elevated total cholesterol (TC) and HDL-cholesterol (HDL-c) as compared to null-virus injected controls (FIGS. 2A and 2B). However, mice who received the LCAT-V114M virus had higher TC and HDL-c as compared to the mice who received the WT virus. This is consistent with our in vitro activity data, demonstrating that this LCAT variant has greater activity than the WT, both in vitro and in an animal model.

Example 2—In Vitro LCAT Activity Assay

After thawing, HEK293 cells were passaged 2-3 times in standard serum medium (such as DMEM w/FBS). Cells were then adapted to serum free medium (Freestyle 293 Expression Medium from ThermoFisher catalog #12338026) by reducing the volume of serum containing medium each passage. A trypsin inhibitor (Thermo-Fisher #T6522) was added to media immediately after trypsinizing to prevent death of the cells. Once adapted, cells were plated at $3\times10^5$ cells per well, in 12-well plates for transient transfection. At approximately 80% confluency, or 24-48 hours later, cells were transfected using Lipofectamine. 4 µg of each plasmid DNA construct was used per well, with each construct repeated in triplicate wells. Media was changed 6 hours later and then collected 48 hours post-transfection. Media samples were aliquoted and frozen at −80° C. immediately after collection.

Recombinant HDL (rHDL) was prepared via cholate dialysis using POPC (Avanti Lipids #850457), ApoAI (purified from pooled human plasma) and free cholesterol (Avanti Lipids #250165) at a ratio of 2.7:1:0.11 respectively. Additionally, 3H labeled cholesterol was added to the rHDL at a ratio of 20uCi/mg ApoAI. Given that ApoAI is our limiting reagent, we calculated the amount of other reagents based on the mass of ApoAI that was to be used in the preparation. Briefly, appropriate volumes of POPC and cholesterol solutions were dried down under N2 gas then resuspended in TBS with EDTA, pH 7.4. The volume of TBS used for resuspension was calculated based on the volume of dialyzed ApoAI such that the total volume of the mixture going into dialysis was 4 mL/mg of ApoAI. 30 mg/mL cholate solution (in TBS with EDTA) was added to the suspension (94 µL/mg ApoAI) which was vortexed and then incubated at 37° C. for 90 minutes. Dialyzed ApoAI was then added to the mixture which was again vortexed and incubated at 37° C. for another 60 minutes. The final mixture was then dialyzed against 6×4L of TBS with EDTA, pH 7.4 over 72 hours. After dialysis, the rHDL was combined with an equal volume of 2% BSA with 10 mM BME (in TBS with EDTA) and stored at 4° C. until the assay was performed (within one week). Additional BME was added to the rHDL before setting up the reactions.

On ice, 60 µl of rHDL mixture, as prepared above, was pipetted into labeled tubes. Each reaction was run in triplicate. After inverting each media aliquot 5-7 times, 5 µL of media was added to each labeled tube containing rHDL. Reactions were then incubated in a 37° C. water bath for 2 hours. Upon removal from the water bath, reactions were terminated by the addition of 1 mL of cold 100% ethanol and placed on dry ice. Reactions were then stored at −20° C. overnight. Next, reactions were centrifuged at 13,000 rpm for 10 minutes to pellet any protein. The supernatant was moved into matching labeled glass culture tubes and then dried down using a centrifugal evaporator. Dried samples were resuspended in 50 µL chloroform containing unlabeled flash chromatograph (FC) and capillary electrophoresis (CE) carrier for thin layer chromatography (TLC). Labeled FC and CE in each sample was separated by TLC using 170:30:1 Hexane: DEE: Acetic Acid. Spots were cut and quantified using scintillation counting. LCAT activity for each sample was then calculated as percent of cholesterol esterified per hour. Background activity as measured in media samples from GFP transfected cells was subtracted out and then activity of each variant was normalized to LCAT concentration as measured by polyclonal ELISA (Biovendor #RD191122200R). Because exact activity values vary between rHDL preps, data is presented as relative to WT activity (calculated for each assay).

Example 3—Pre-clinical Development of AAV Based Gene Therapy for FLD—AAV.hLCAT in LCAT KO and LCAT KO/hApoA-1 transgenic mice The minimally efficacious dose (MED) of the WT human LCAT AAV vector was identified in LCAT KO and humanized LCAT KO/hApoA-I transgenic mice.
A. Dose Response of AAV8-TBG-hLCAT in LCAT KO Mice The MED of AAV8-TBG-hLCAT was determined in LCAT KO mice. The MED is defined as the lowest dose that produces a significant increase in plasma percent cholesterol esterified (% CE). We estimated the starting dose for our studies based on the doses used in human trials for other diseases. For reference, the therapeutic dose of Glybera (Bryant, L. M. et al. Lessons learned from the clinical development and market authorization of Glybera. Hum Gene Ther Clin Dev 24, 55-64 (2013)). The only gene therapy product approved in western medicine, and also an AAV based therapy, is 1e12 GC per kg of bodyweight, which is approximately equivalent to 3e10 GC per mouse. In the hemophilia trials, the starting dose of AAV was 2e11GC per kg (4e9 GC per mouse) and the highest dose was 2e12 GC per kg (4e10 GC per mouse) (Nathwani, A. C. et al. Long-term safety and efficacy of factor IX gene therapy in hemophilia B. N. Engl. J. Med. 371, 1994-2004 (2014)).[68] Based on these doses, we believed that our MED would be somewhere in the range of 3e9 to 3e10 GC per mouse.

Figure 5A:
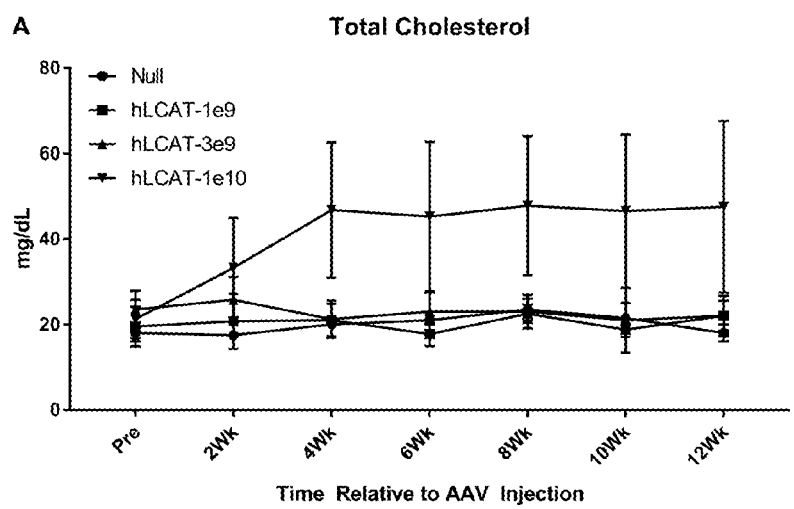
FIGS. 5A-5B provide line graphs showing that 1e10 GC of AAV8-TBG-hLCAT increases total cholesterol (FIG. 5A) and HDL-cholesterol (HDL-c, FIG. 5B) in LCAT KO mice. LCAT KO mice (N=4) were injected with one of three doses of AAV-hLCAT or AAV-Null as described in Example 3. Plasma lipids were measured over a period of 12 weeks. Mice that were injected with 1e10 GC of AAV-hLCAT demonstrated an increase in plasma TC (FIG. 5A) and HDL-C(FIG. 5A) although it was not statistically significant as compared to AAV-Null injected mice. Error bars indicate standard error.
Figure 5B:
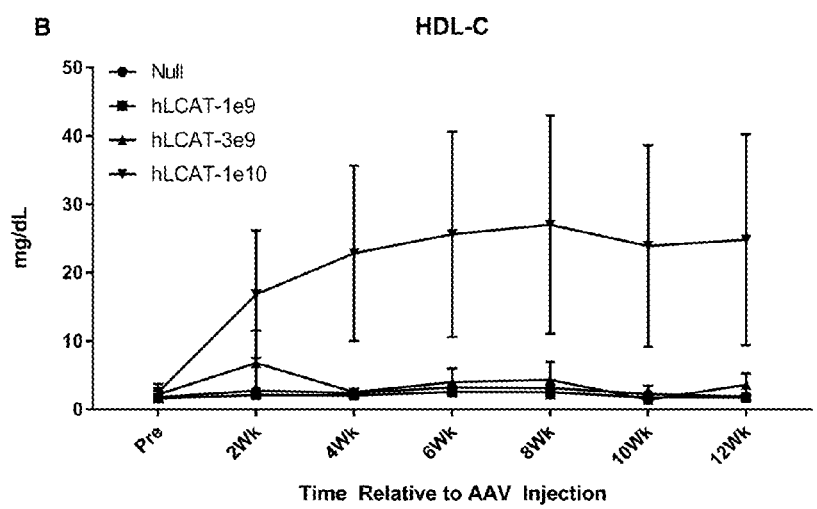

LCAT KO mice (N=4) were injected with the AAV8 with human WT LCAT under the control of the thyroxine-binding globulin (TBG) liver specific promoter, produced by Penn Vector core. Three low doses of vector, 1e9, 3e9 and 1e10 GC per mouse were utilized. Control mice were injected with 1e10 GC per mouse of AAV-Null. We measured total cholesterol (TC) and HDL-cholesterol (HDL-C) in these mice. Prior to injection, LCAT KO mice have low TC, less than 30 mg/dL with 90-100 mg/dL being normal, and very low HDL-C, typically below 5 mg/dL as compared to 65-75 mg/dL in a normal mouse. After injection, mice that received a dose of 1e10 GC did have increases in both TC, at 4 weeks post injection with 45f12 mg/dL, and HDL-C of 22±13 mg/dL, though these differences were not statistically significant in this experiment (FIGS. 5A and 5B). All mice in the 1e9 GC and 3e9 GC groups had lipids comparable to baseline. Lipids in the high dose group increased slightly until week 4 and then were stable out to 12 weeks post-injection.

Figure 6A:
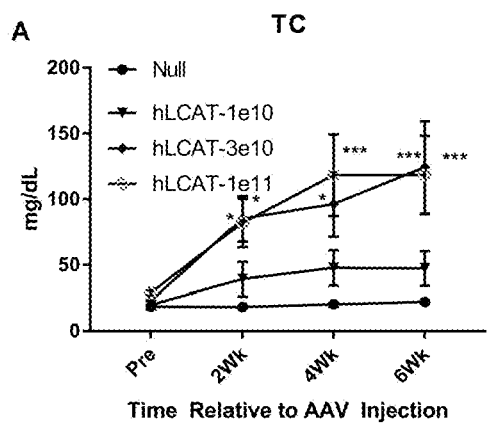
Figure 6B:
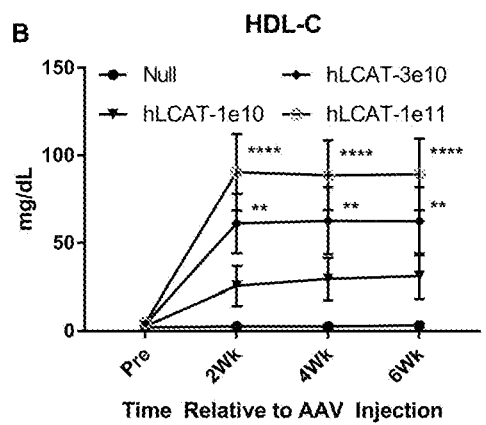
Figure 6C:
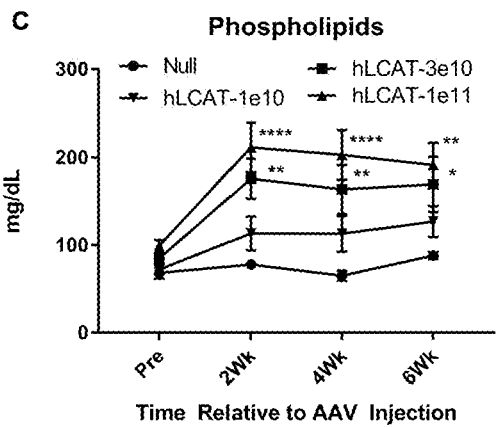
Figure 6D:
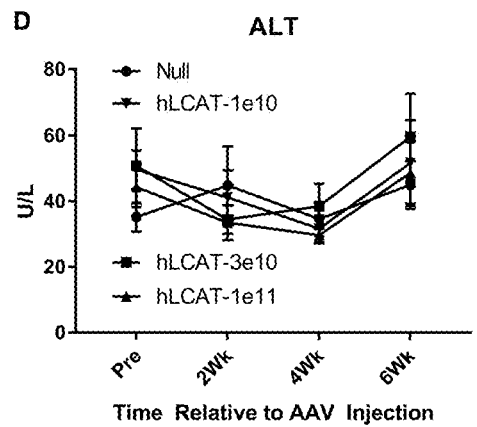

As we did not see any statistically significant differences in this first experiment, for the second experiment, two higher doses of AAV-hLCAT, 3e10 and 1e11 GC per mouse (N=5) were tested. A group of mice was also injected with 1e10 GC each, for comparison with the previous experiment. As in the previous experiment, a control group was injected with AAV-Null, this time at a dose of 1e11 GC per mouse. Both the middle and high dose groups in this experiment demonstrated statistically significant increases in TC and HDL-C (FIGS. 6A and 6B). The high dose 1e11 GC group had a mean TC of 116±18 mg/dL and HDL-C of 90f8 mg/dL, both values being above the normal range. The middle dose group, at 6 weeks post injection, had a mean TC of 118f12 mg/dL nearly identical to the high dose group. HDL-C in the middle dose group was lower at 60±7 mg/dL. The low dose group (1e10GC) was comparable to the previous experiment in that the mean TC was about 50 mg/dL but was not significantly different from null-injected control mice. Phospholipids in these mice followed a similar dose dependent pattern (FIG. 6C). No increase was seen in plasma ALTs in these mice (FIG. 6D).

All three AAV-hLCAT groups had percent plasma percent cholesterol esterified within the normal range at approximately 75% (FIG. 7A). Whole plasma cholesterol esterification rate (CER) in these mice was variable, but overall tended to increase consistent with the dose (FIG. 7B). Only the highest dose group had CER that was statistically significantly different from null injected mice. To examine cholesterol distribution and particle size we separated pooled plasma samples by FPLC (FIG. 7C). When we measured TC in these samples we see a dose dependent increase in the HDL peak, with higher doses skewing towards a larger particle size (towards the lower fraction numbers). This is consistent with an increase in mature HDL. Based on these experiments, we determined the MED of AAV-hLCAT to be 1e10 GC per mouse, which is approximately equivalent to 5e11 GC per kg.
B. Dose Response of AAV8-TBG-hLCAT in LCAT KO/hApoA-I Transgenic Mice ApoA-I is the primary protein component of HDL and is a potent activator of LCAT. It is known that human LCAT is activated more efficiently by human ApoA-I than its murine counterpart[103]. Given that the interaction between LCAT and its cofactor ApoA-I is species specific, and human LCAT is known to prefer human ApoAI over mouse ApoA-I, we anticipated that the MED of AAV8-TBG-hLCAT would be lower in LCAT KO/hApoA-I transgenic mice than in LCAT KO mice.

Only the three lower doses (N=5), 1e9 GC, 3e9 GC and 1e10 GC per mouse was tested in this experiment. Again, a control group was injected with AAV-Null. In these mice, 1e10 GC resulted in large and significant increases in TC and HDL-C as well as ApoA-I (FIGS. 8A, 8B and 8C). Mice in the high dose group (1e10 GC) had a mean TC of 580±32 mg/dL at 4 weeks post-injection, as compared to approximately 75±12 mg/dL at baseline. This TC value is well above the normal range for these mice, which is 175-225 mg/dL. The HDL-C in these mice ranged from 45±7 mg/dL in null injected controls, which were comparable to baseline, to 392 mg/dL in the 1e10 GC group. Again, this HDL-C is well above the normal range of normal ApoA-I tg mice, which is 140-160 mg/dL. 3e9 GC did not produce any statistically significant increases in plasma lipids, although the mice in this group did have a significant increase in their % CE, approaching normal at around 45% (FIG. 8D). The high dose group had a normal % CE around 60% which is considered normal for these mice. We also analyzed plasma FPLC profiles, the same as done in the previous experiment. Unlike in LCAT KO mice, LCAT KO/hApoA-I transgenic mice have a bimodal distribution of HDL-C which is more similar to a human FPLC profile than the single peak we see in LCAT KO mice (FIG. 8E). In our AAV injected LCAT KO/hApoA-I mice, we see that null injected mice have an abnormal HDL-C peak which is singular and large in size, at fraction 28, while the 3e9 GC injected mice have a more normal human-like bimodal distribution, albeit with less cholesterol (i.e. fewer particles) than the mice that received 1e10 GC. The high dose mice have much higher HDL-C peaks, which skew towards a larger size, indicating more mature HDLs. From this experiment, we conclude that the MED of AAV-hLCAT in LCAT KO/hApoAI mice is 3e9 GC per mouse, which is approximately equivalent to 1.5e 11 GC per kg. This is a half log below the MED in LCAT KO mice.

Figures 9A, 9B, 9C:
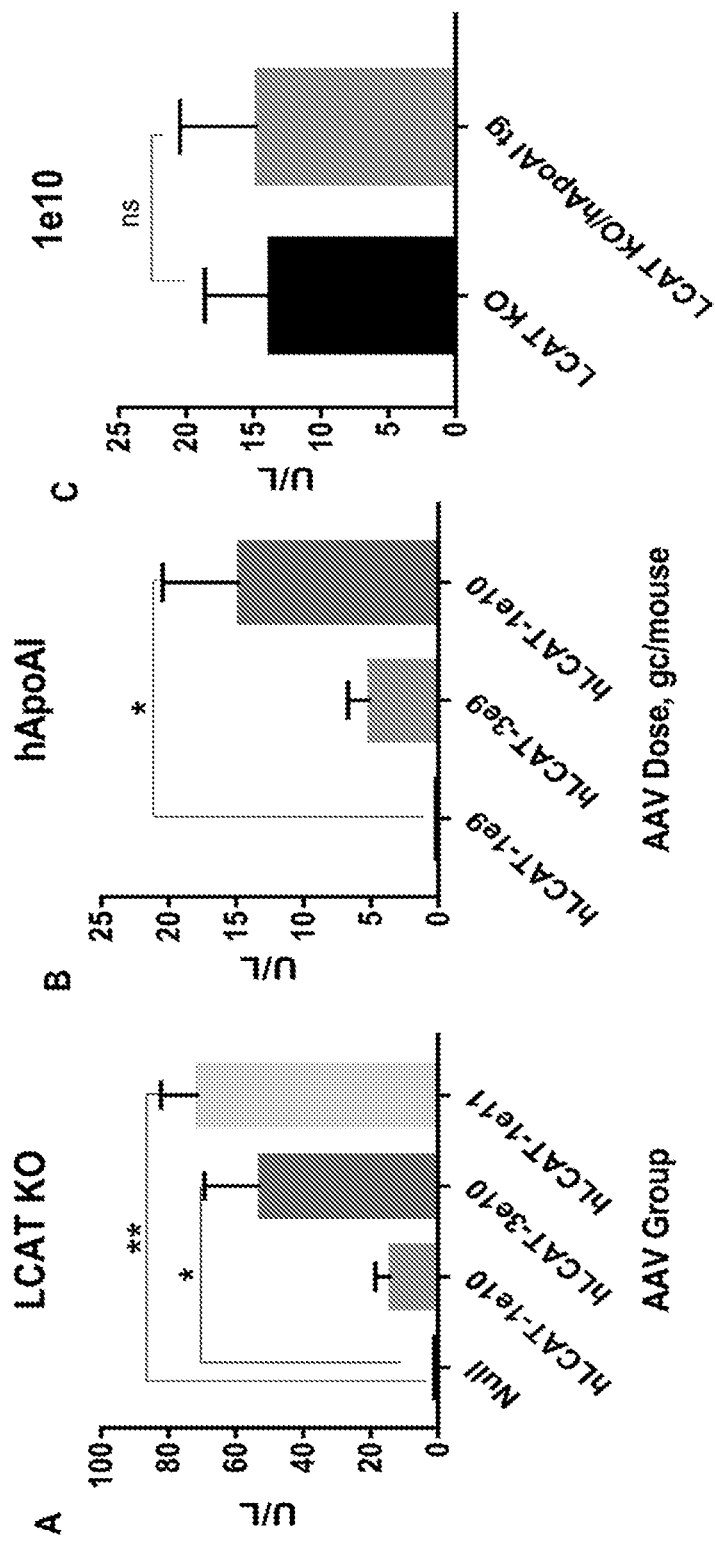

To ensure that our dilutions and dosing were consistent between the two experiments, we measured plasma LCAT mass in the mice from this example. Comparing plasma LCAT mass across these experiments reveals that LCAT mass is dose dependent, ranging from 5±2U/L at 3e9 GC, to 73±8 U/L at 1e11 GC per mouse (FIGS. 9A and 9B). In the 1e10 GC dose groups in both experiments the concentrations are comparable at around 14 U/L (FIG. 9C). This reassures us that dilution of the vector was consistent between the two experiments.

Example 4—Pre-Clinical Development of AAV Based Gene Therapy for FLD-AAV.hLCAT-V114M We characterized a naturally occurring gain of function variant of human LCAT, V114M, that has approximately 160% the activity of WT. The MED of a vector expressing this variant was determined then. hLCAT-V114M reduced the MED of our LCAT vector from 3e9 GC per mouse to 1e9 GC per mouse.

A. Identification of a Naturally-Occurring Gain-of-Function Variant in Human LCAT The hLCAT variant V114M is associated with increased HDL-C in the human population (Table 1) (Cohen, J. C. et al. Multiple rare alleles contribute to low plasma levels of HDL cholesterol. Science 305, 869-872 (2004)).

TABLE 1

Naturally-occurring missense LCAT variants associated in heterozygous state with significantly different HDL-C levels. Shown here is a summary of the three naturally occurring variants of LCAT identified in the human population at measurable levels.

| Variant | HDL-C | P-value | MAF | Frequency |
|---|---|---|---|---|
| V114M | Higher | 0.0045 | 9.42E−05 | 19/100,000 people |
| R123H | Lower | 3.14E−12 | 0.00068 | 136/100,000 people |
| S232T | Lower | 1.02E−10 | 0.02534 | 2500/100,000 people (1/40) |

First, we tested the in vitro activity of three variants, and the catalytic serine mutant negative control, S205G, to determine the effect of these mutations on enzyme activity. When tested on our exogenous substrate, recombinant HDL, V114M had increased specific activity relative to WT human LCAT, about 150%, consistent with its association with increased HDL-C(FIG. 10B). Additionally, R123H demonstrates reduced specific activity relative to WT, at 60±3%, also consistent with its HDL-C association. Specific activity of S232T was not significantly different from WT. It is important to note that although we did not measure gene expression in our transfected cells, that there was a wide range of LCAT concentrations in the media of transfected cells, ranging from around 500 ng/mL in the V114M transfections to around 1700 ng/mL in the R123H transfections (FIG. 10A). These differences however, should not affect the outcome of our next experiment as all activity calculations were normalized to the LCAT concentration. Next, in order to better understand the properties of V114M, potentially a gain-of-function variant, we also tested the specific activity of WT human LCAT and LCAT-V 114M on a range of substrate concentrations (FIG. 10C). Using a fit to the Michaelis-Menten equation, we calculated the $V_{max}$ and Km constants for both enzymes. While WT LCAT has a Vmax of 22.56 (95% CI 20.3-25.0) on our substrate, LCAT-V114M had a Vmax of 37.03 (95% CI 34.4-39.8) (Table 2). The Km of the two enzymes were comparable, at 0.3 (95% CI 0.22-0.39) and 0.38 (95% CI 0.31-0.44). Overall, these data suggest that V114M is in fact a gain-of-function variant of LCAT having higher activity than WT and that V114M does not affect lipid or substrate binding, but somehow affects efficiency of the active site.

TABLE 2

Kinetic study suggests V114M increases Vmax of LCAT

| LCAT Variant | Vmax | 95% CI | Km | 95% CI |
|---|---|---|---|---|
| WT | 22.56 | 20.3 to 25.0 | 0.30 | 0.22 to 0.39 |
| V114M | 37.03 | 34.4 to 39.8 | 0.38 | 0.31 to 0 44 |

B. Testing AAV8-TBG-hLCAT-V114M In Vivo: Determination of the MED

After confirming that hLCAT-V114M had increased activity in vitro relative to WT, this variant was tested in vivo to determine the MED of this new vector.

To confirm that hLCAT-V114M is indeed a gain-of-function variant in vivo and to determine if hLCAT-V 114M will lower the MED of our vector, we injected LCAT KO mice (N=7) with one of three doses of AAV expressing WT human LCAT (AAV-hLCAT-WT), human LCAT-V114M (AAV-hLCAT-V114M), or a Null control vector (AAV-Null). Three low doses were utilized in this experiment, 3e8 GC, 1e9 GC and 3e9GC per mouse. Additionally, we harvested livers from these mice 6 week post-injection to determine if WT LCAT and LCAT-V 114M are expressed equally.

Figure 11A:
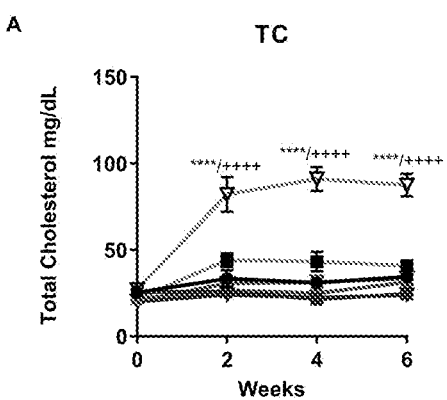
FIGS. 11A-11C provide line graphs showing that 3e9 GC of AAV8-TBG-hLCAT-V114M significantly increases plasma lipids in LCAT KO mice, while AAV8-TBG-hLCAT-WT does not. We injected groups of LCAT KO mice (N=7) with one of three doses of AAV, 3e8 GC, 1e9 GC or 3e9 GC per mouse. Mice received either AAV-hLCAT-WT, AAV-hLCAT-V114M or AAV-Null. We measured plasma lipids, including total cholesterol (FIG. 11A) and HDL-cholesterol (FIG. 11B) before and every 2 weeks after injection, until the animals were euthanized 6 weeks later. Mice that received 3e9 GC of AAV-hLCAT-V114M had significantly elevated TC and HDL-C. We also measured plasma % CE in these mice (FIG. 11C) and measured total cholesterol in FPLC fractions of pooled plasma samples from each group. HDL peak is at fraction 39. * indicates p<0.05, ** indicates p<0.005, * indicates p<0.0005 and **** indicates p<0.00005 relative to AAV-Null injected mice. ++indicate significance relative to AAV-hLCAT-WT injected mice.
Figure 11B:
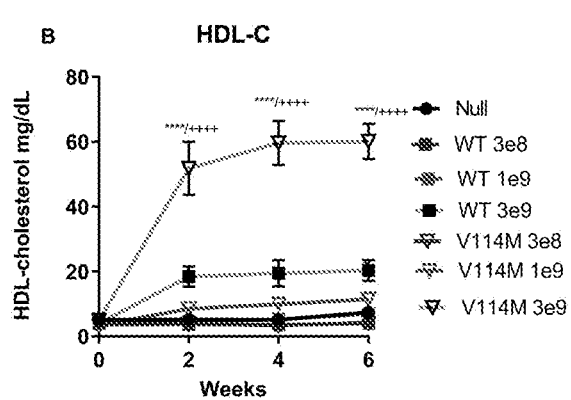
Figure 11C:
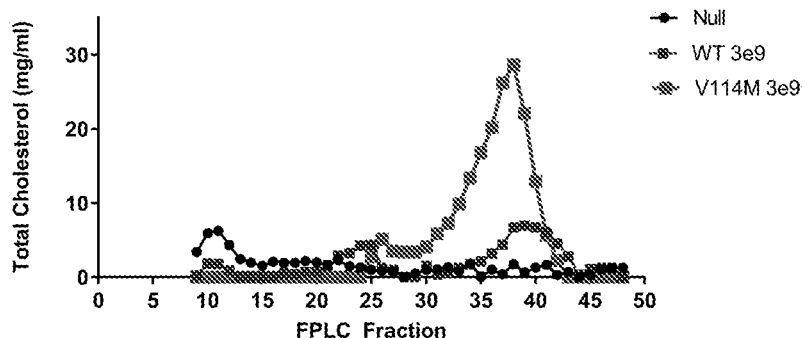

As before, we measured plasma lipids in injected mice. The mice in the high dose AAV-V114M group has significantly higher TC and HDL-C than mice in all of the other groups at 82±7 mg/dL and 59±4 mg/dL respectively, however, mice that received 3e9 GC of AAV-WT did not have significantly increased plasma TC, but did have significantly increased HDL-C, at 20±3 mg/dL, relative to AAV-Null, 8±2 mg/dL (FIGS. 11A and 11B). If the high dose hLCAT groups were compared, AAV-hLCAT-V114M had dramatically higher plasma TC, at 82±7 mg/dL as compared to 46±3 mg/dl in the WT group, and HDL-C, at 59±4 compared to 20±3 mg/dL in the WT group. When we fractionated pooled plasma samples by FPLC, mice in the high dose V114M group had more cholesterol in large HDL particles, fractions 30-36, than mice in the WT group, consistent with increased LCAT activity and more mature HDL particles.

Mice injected with AAV-hLCAT-V114M also had higher plasma % CE than WT injected mice at both 1e9GC and 3e9 GC (FIG. 12A). The MED of AAV-hLCAT-WT in this experiment was 3e9 GC per mouse, a half log below what we concluded in LCAT KO mice (Section A, Example 3), and the same as the MED in LCAT KO/hApoAI mice (Section B, Example 3). Mice injected with 3e9 of AAV-hLCAT-V114M had significantly higher plasma CER, about 60% of human plasma activity, than mice that received the same dose of AAV-WT, about 20% (FIG. 12B). WT and VI 14M were indeed expressed equally as measured by both RT-PCR and by ELISA for plasma LCAT mass (FIGS. 12C and 12D). Despite having similar plasma LCAT concentrations, the MED of AAV-hLCAT-V114M based on these data, is 1e9 GC per mouse, a half log below the MED of its WT counterpart.

Figure 13A:
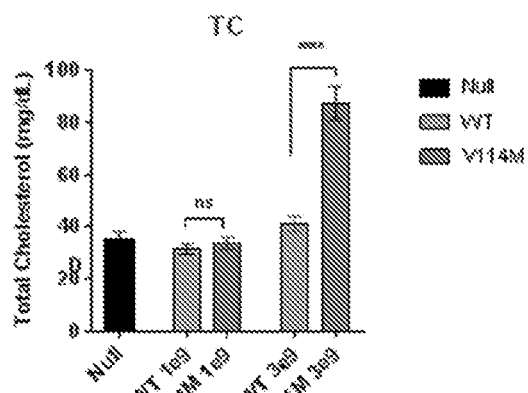
FIGS. 13A-13F provide bar graphs showing that the LCAT variant V114M is more effective than WT LCAT in vivo, even at very low doses. The experiment was run as described in Example 4. TC (FIG. 13A), HDL-C(FIG. 13B), plasma cholesterol ester content (expressed as CE % of Total cholesterol, FIG. 13C), % CE of said mice normalized to that of human (FIG. 13D), Plasma LCAT concentration determined by ELISA (FIG. 132E) and liver LCAT gene expression measured by RT-qPCR (FIG. 13F) were measured and plotted. * indicates p<0.05,  p<0.005, * p<0.0005 calculated using one-way ANOVA and Tukey's multiple comparison test.
Figure 13B:
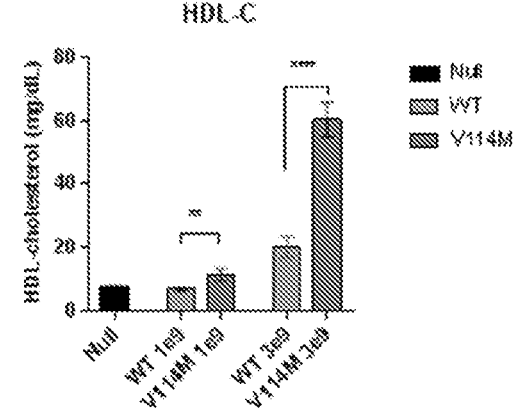
Figure 13C:
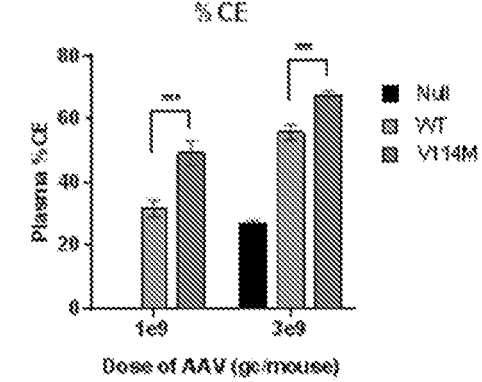
Figure 13D:
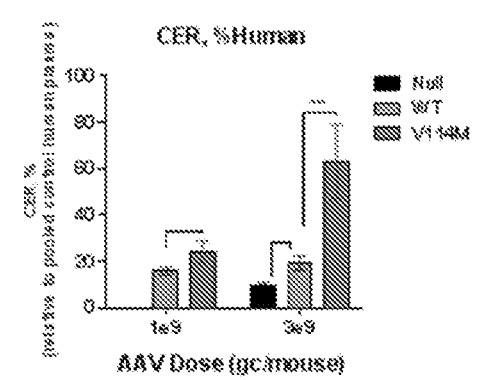
Figure 13E:
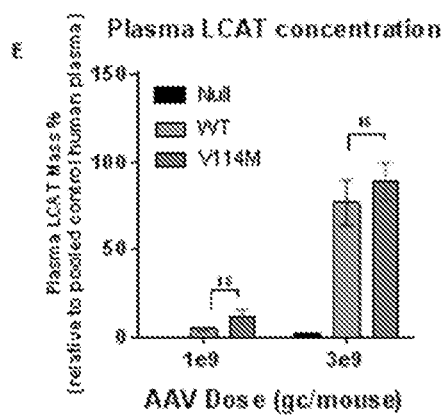
Figure 13F:
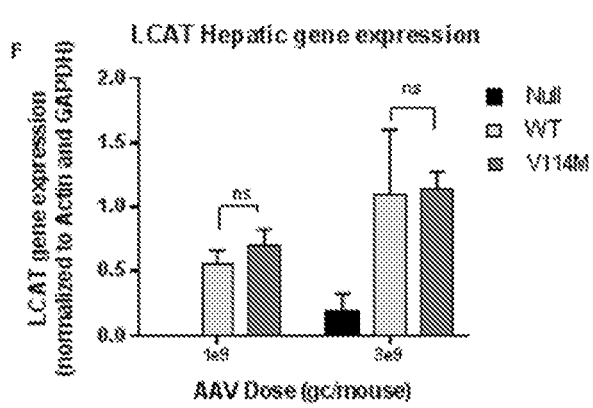

Furthermore, LCAT-V 114M demonstrates increased activity in vivo when expressed using adeno-associated virus (AAV) in LCAT deficient (LCAT KO) mice. Mice were injected with one of three AAV vectors LCAT-WT, LCAT-V114M or Null control vector, at 2 different doses (1e9 and 3e9 genome copies, gc/mouse). 6 weeks after injection, blood was collected and plasma lipids, LCAT concentration and plasma cholesterol esterification rate were measured. At the same time point, mice were sacrificed and liver was collected to measure LCAT gene expression via RT-qPCR Lipids at six weeks were measured using AXCEL autoanalyzer. Mice who received a vector expressing LCAT had higher TC (FIG. 13A) and HDL-C(FIG. 13B) than mice who received null vector. Mice that received the V114M variant had higher TC and HDL-C than the mice who received the WT LCAT vector. Mice that received a vector expressing LCAT V114M had higher plasma cholesterol ester content (expressed as CE % of Total cholesterol, FIG. 13C) and increased LCAT-mediated cholesterol esterification rate (CER, % human, FIG. 13D) compared to Null vector injected mice and WT LCAT injected mice. Plasma LCAT concentration was determined by ELISA (FIG. 13E) and liver LCAT gene expression was measured by RT-qPCR (FIG. 13F). Both WT and V114M LCAT vectors induced significant expression of LCAT gene and protein compared to Null vector. No difference was observed between WT and V114M in terms of protein and gene expression, demonstrating that the changes in functional parameters listed above are due to increased activity of V114M compared to WT LCAT.

In order to better predict what the therapeutic dose of AAV-V114M might be in human FLD, we again tested the AAVs in LCAT KO/hApoA-I transgenic mice. We tested a single dose in LCAT KO/hApo-I mice, 3e9 GC per mouse. Mice in the V114M group had significantly higher total TC and HDL-C compared to WT, at 208±15 mg/dL of TC in the V114M group at 6 weeks post injection and only 80±7 mg/dL in the WT group (FIG. 14A). HDL-C in AAV-hLCAT-V114M injected mice was 165f22 mg/dL, while WT injected mice remained at baseline at 57±6 mg/dL (FIG. 14B). The WT group in this experiment did not have any significant increases in plasma lipids relative to AAV-Null control injected mice. Plasma cholesterol FPLC profiles in injected mice demonstrate the expected human-like bimodal distribution of HDL particles, with V114M injected mice having much more HDL-C overall, but particularly in larger, more mature HDL particles, fractions 28-35 (FIG. 14C).

Figure 15A:
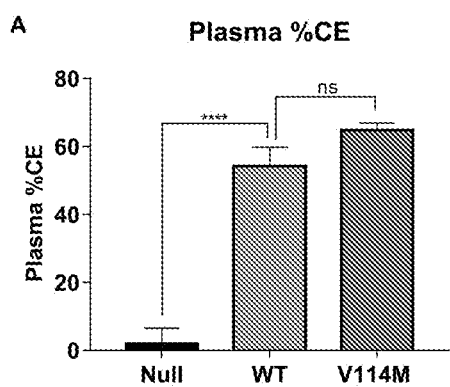
Figure 15B:
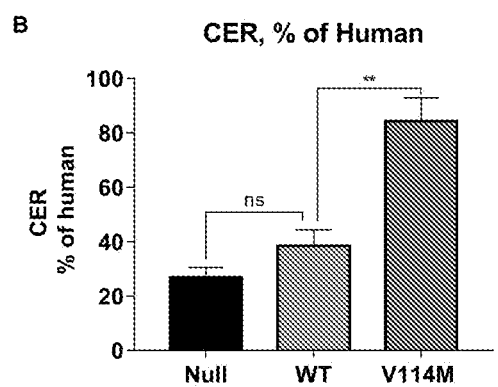
Figure 15C:
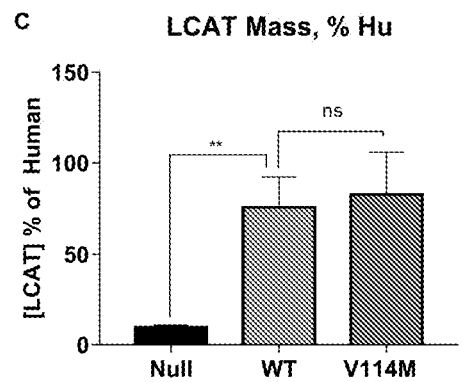
Figure 15D:
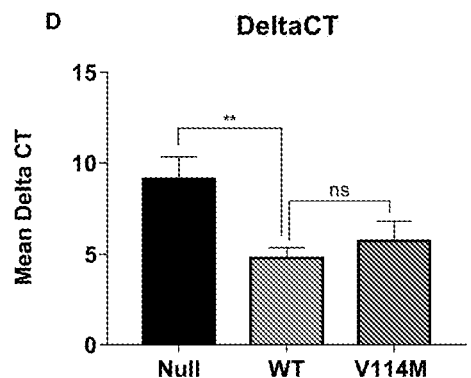

Unlike the experiment in LCAT KO mice, both LCAT injected groups had approximately 60% plasma CE, approaching a normal ratio, at 60% (FIG. 15A). Animals in the AAV-V114M group had significantly higher plasma CER, at about 80% of human, while the WT group had only 40% which was not significantly different from the AAV-Null injected group (FIG. 15B). Plasma LCAT concentration did not differ between the WT and V114M groups (FIG. 15C). WT hLCAT and LCAT-V114M were expressed equally in these mice expression was comparable for both constructs (FIG. 15D). The mean plasma LCAT mass in this experiment was comparable to the previous experiment as well, at around 80% of the normal human concentration. MED of AAV-hLCAT-V114M in these mice in under investigation. However, based on the data in LCAT KO mice, and the previous studies of AAV-hLCAT-WT in both LCAT KO and LCAT KO/hApoAI mice, it is estimated that the MED in these mice is at or below 1e9 GC per mouse, approximately equivalent to 5e10 GC per kg of bodyweight.

Figure 16A:
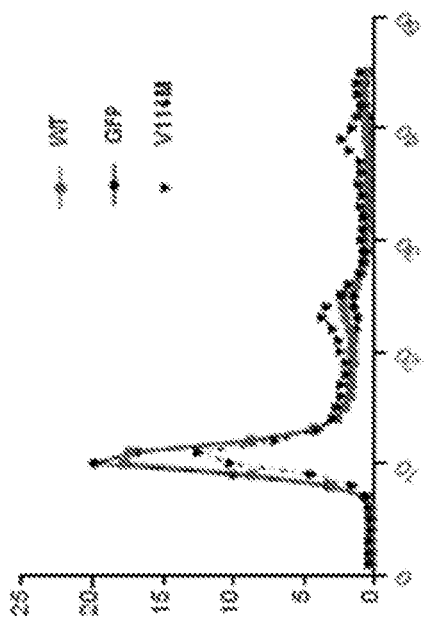
FIGS. 16A-16F provide graphs showing that hLCAT-V114M reduces LpX in FLD patient human plasma. We measured whole plasma cholesterol esterification rate (CER) in plasma of two LCAT deficient patients to confirm LCAT deficiency (FIG. 16A). $^3$H labeled FLD patient plasma was incubated with transfection media containing equal concentrations of either WT-LCAT or LCAT-V114M, or transfection media from control GFP transfection. After a 15-hour incubation at 37° C., we separated free cholesterol and cholesterol ester via TLC. Total percent cholesterol esterified in each sample after incubation, measured by scintillation counting of 3H label in FC and CE bands (FIG. 16B). Incubated plasma was fractionated by FPLC. Curves show percent of total counts per fraction for each sample (FIG. 16C). The peak at fraction 10 represents lipoprotein X (LpX), the peak at fraction 24 represents LDL and the peak at fraction 39 represents HDL. FPLC fractions across each peak were pooled and then free cholesterol and cholesterol ester were separated by TLC. Bars represent % of total counts present in each FPLC peak (FIGS. 16D-16F). VLDL peak corresponds with lipoprotein X (LpX). Black bars indicate % of counts in esterified cholesterol for that peak. * indicates $p<0.05$,  indicates $p<0.005$, * indicates $p<0.0005$ and **** indicates $p<0.00005$ relative to controls.
Figure 16B:
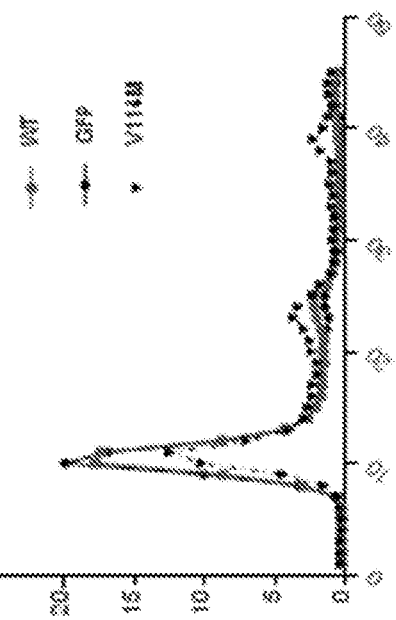
Figure 16C:
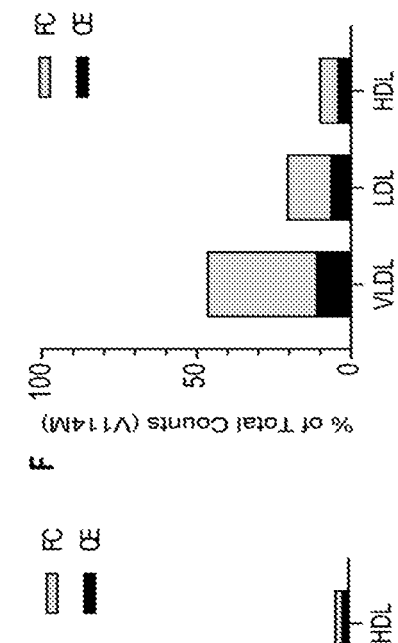
Figure 16D:
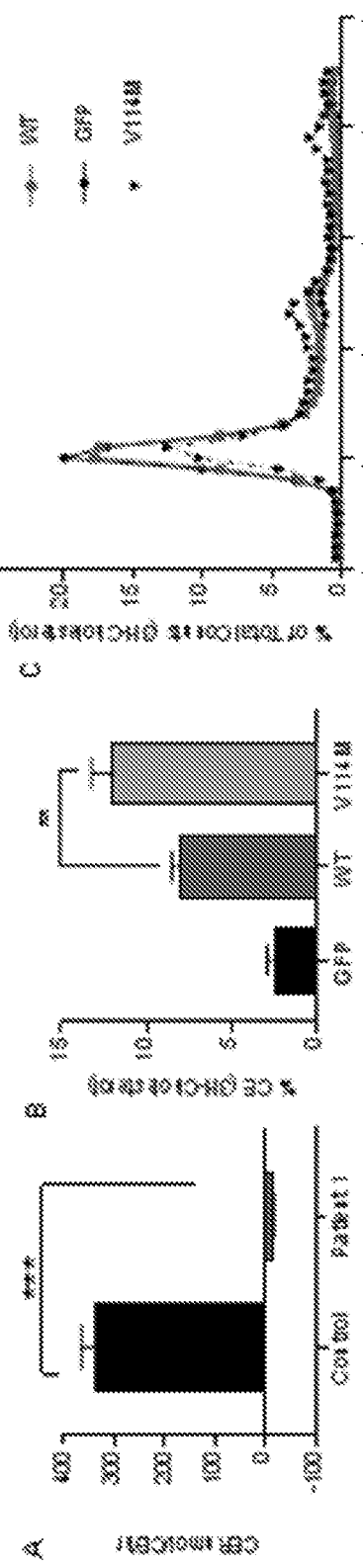
Figure 16E:
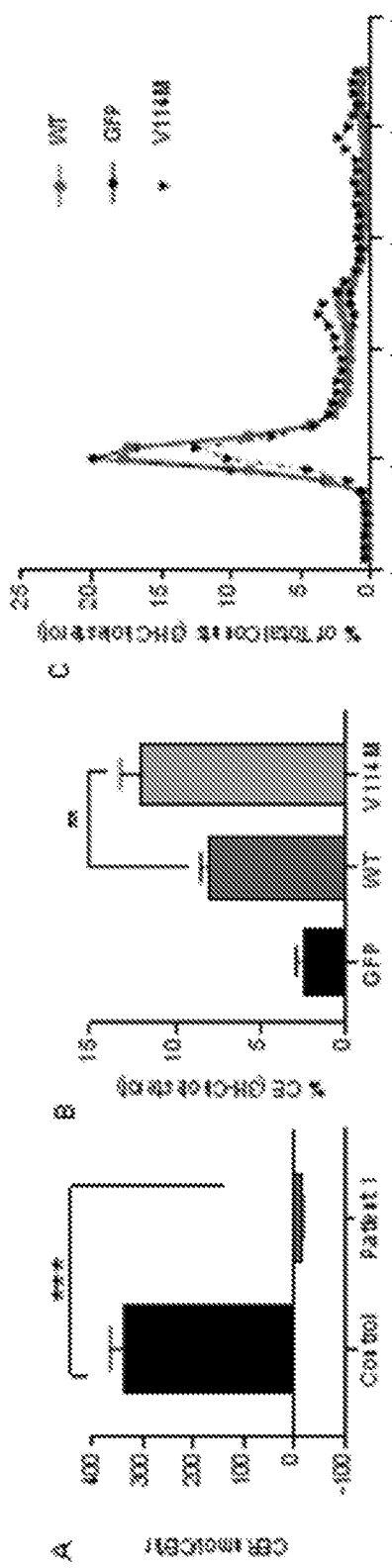
Figure 16F:
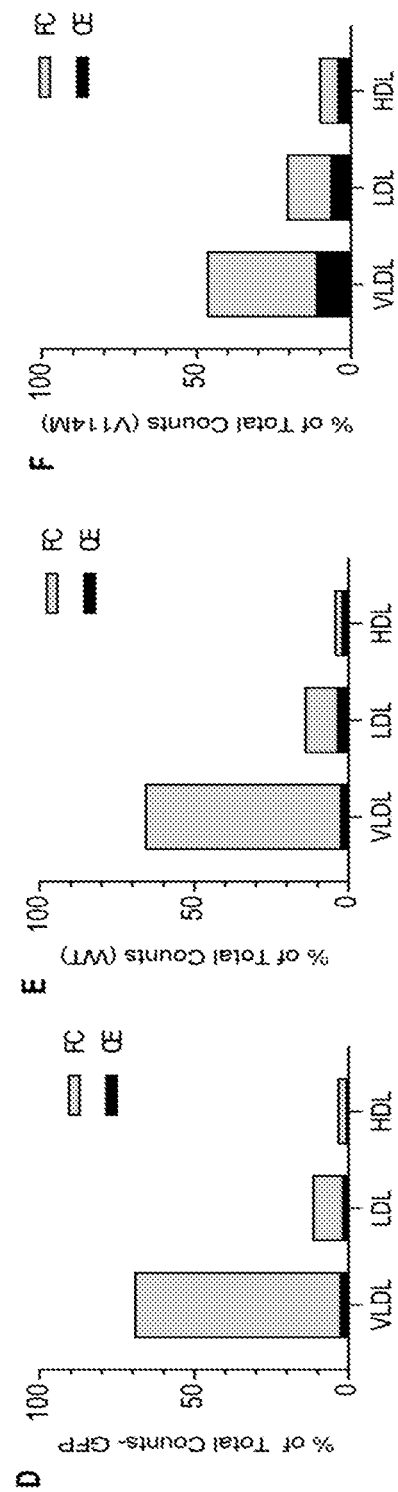

C. Examining the Effect of hLCAT-V114M on FLD Patient Plasma Lipid Profiles hLCAT-V114M has higher activity than WT hLCAT as demonstrated both in vitro and in vivo. hLCAT-V114M lowered the MED of the AAV8-TBG vector in both LCAT KO and LCAT KO/hApoA-I transgenic mice. The ability of hLCAT-V114M expressed in cell media, to normalize the plasma lipid profile of two FLD patients, was further tested. We examined the ability of this variant to normalize the plasma FPLC cholesterol profiles of two FLD patients. First, we measured CER in the plasma of two FLD patients, in order to confirm the absence of activity (FIG. 16A). Consistent with the FLD diagnosis, the plasma CER from both patients did not differ significantly from background levels. We measured a variety of plasma lipids in both patients and a healthy control (Table 3). Both patients have low HDL-C at 1.7 and 13.9 mg/dL, low ApoA-I concentrations at 46 and 36 mg/dL as well as low % CE at −9.79% and 13.64%, consistent with LCAT deficiency. To test the effect of LCAT-V 114M on the abnormal lipid profile of FLD patients, particularly the abnormal lipoprotein LpX, we incubated $^3$H labeled patient plasma with transfection media collected from transient transfection of HEK293 cells. LCAT concentration in each sample was measured by ELISA and then samples were diluted to match the concentrations before incubation, excluding GFP. After a 15-hour incubation, the plasma sample that was incubated with WT LCAT had total % CE at 8±1% as compared to GFP background at 2.5% (FIG. 16B). However, the plasma sample incubated with media containing hLCAT-V114M had total % CE of 12f3% (p=0.0037 compared to WT), a difference that is consistent with data from our previous in vitro assays. We fractionated these incubated samples by FPLC and using scintillation counting a reduction was observed in the amount of total cholesterol contained in the LpX peak in the sample that was incubated with hLCAT-V114M, fractions 8-13. In addition, the appearance of LDL, fractions 20-25, and HDL, fractions 37-41, was observed in this patient sample (FIG. 16C). In comparison, there was no decrease in the amount of cholesterol in the LpX peak, in the WT sample, and no visible HDL. However, WT LCAT did produce some LDL in this patient sample. When we examine the breakdown of FC and CE in each of these peaks, we see that while the LpX (VLDL) peak in the GFP incubated sample had under 5% CE, the same peak in the V114M sample contained over 10% CE (FIGS. 16D, 16E and 16F). Percent CE in the WT LpX peak remained similar to baseline, although there appeared to be small increases in the % CE in both the LDL and HDL peaks in the WT sample. Overall, these data suggest that hLCAT-V 114M is more effective at reducing LpX, thereby normalizing the FLD plasma lipid profile, than WT hLCAT.

TABLE 3

Plasma lipids in two FLD patients.

| Sample ID | Chol mg/dl | HDL mg/dl | non-HDL-C mg/dl | TG mg/dl | PL mg/dl | FC mg/dl | % CE % | Glu mg/dl | NEFA meq/l | ApoA-I mg/dl | ApoB mg/dl |
|---|---|---|---|---|---|---|---|---|---|---|---|
| Control plasma | 163 | 75.4 | 88 | 74 | 217 | 45 | 72.4 | 79 | 0.06 | 158 | 50 |
| Patient 1 | 194 | 16.7 | 177 | 349 | 402 | 213 | −9.8 | 110 | 0.24 | 46 | 23 |
| Patient 2 | 110 | 13.9 | 96 | 162 | 211 | 95 | 18.6 | 90 | 0.05 | 36 | 21 |

D. The LCAT Variant V114M is More Effective than WT LCAT in Promoting Reverse Cholesterol Transport (RCT) In Vivo Mice were injected with one of three AAV vectors LCAT-WT, LCAT-V114M or Null control vector, at the dose of 3e9 genome copies, gc/mouse. 12 weeks after injection, they underwent in vivo assessment of RCT efficiency. RCT, reverse cholesterol transport is the process by which HDL particles can promote efflux of unesterified cholesterol in excess from peripheral cells and transport it to the liver for excretion though the bile. LCAT is able to esterify cholesterol in HDL. Since CE is more hydrophobic than unesterified cholesterol, it migrates into the HDL core. As a result, LCAT activity ensures a constant gradient of unesterified cholesterol between the HDL surface and the core and indirectly promotes the further efflux of cholesterol from the cells. The ability of HDL to promote RCT is considered atheroprotective and agents potentially able to improve this pathway may represent a potential therapeutic strategy to prevent and reduce the formation of atherosclerotic plaque A.

Figure 17B:
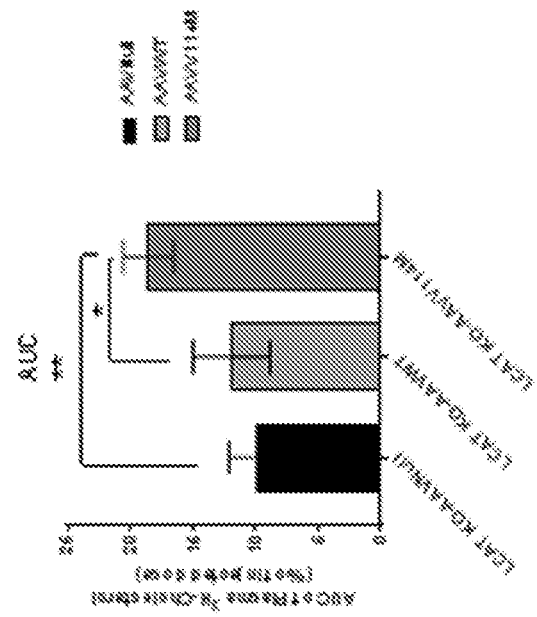
FIGS. 17A-17B provide graphs showing that the LCAT variant V114M is more effective than WT LCAT in promoting Reverse Cholesterol Transport (RCT) in vivo. The experiment was performed as described in Example 4, Section D. Cholesterol efflux from macrophages as shown by percentage of injected 3H Cholesterol are plotted in FIG. 17A. The relative RCT efficiency has been estimated by calculating the Area Under the Curve (AUC) of the graphs in FIG. 17B. Error bars indicate standard error. * indicates $p<0.05$,  $p<0.005$, * $p<0.0005$ calculated using One way ANOVA and Tukeys multiple comparison test.
Figure 17A:
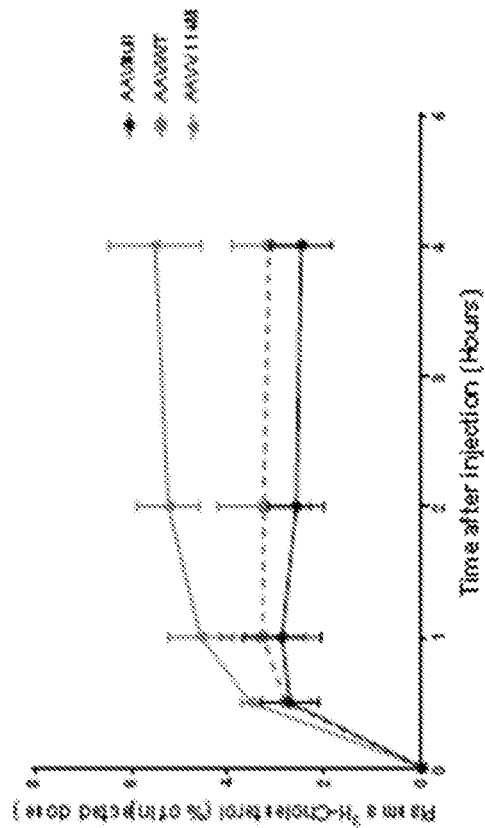

In this experiment, $^3$H-cholesterol nanoparticles were injected via tail vein. Post administration, the particles are readily taken up by macrophages and reappear in HDL and non-HDL particles. The rate of macrophage RCT was assessed by measuring the plasma radioactive tracer at different time points after injection. V114M is more efficient than WT LCAT in promoting cholesterol efflux from macrophages, as shown by the higher percentage of injected $^3$H Cholesterol detected in the circulation B (FIG. 17A). The relative RCT efficiency has been estimated by calculating the Area Under the Curve (AUC) of the graphs in FIG. 17B. Both the AAV-WT LCAT and V114M-LCAT treatments are associated with improved RCT compared to Null vector. However, mice injected with AAV-V 114M LCAT display significantly higher RCT efficiency compared to AAV WT LCAT injected mice.

E. Investigating the Mechanism of Gain-of-Function of hLCAT-V114M

Figure 18A:
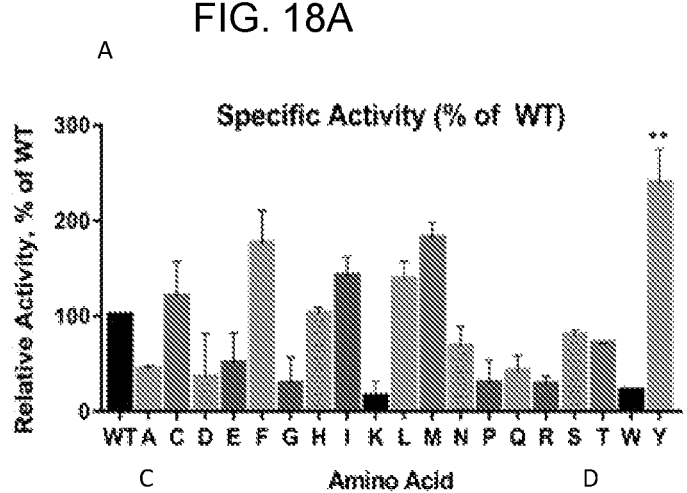
FIGS. 18A-18D provide graphs showing that activity of hLCAT-V114 variants correlates with amino acid size. We tested the activity of 20 hLCAT variants on rHDL, each with a different amino acid at position 11 (FIG. 18A). Activity of the variants was variable, but when we plotted the relationship between molecular weight of the amino acid and activity of the variant, we saw there was a strong correlation (FIG. 18B) with tryptophan being an outlier. If we remove this outlier and replot the relationship, we measure a correlation of 0.97 (FIG. 18C). Comparatively, if we plot the relationship between hydrophobicity index and activity we see no correlation (FIG. 18D).
Figure 18B:
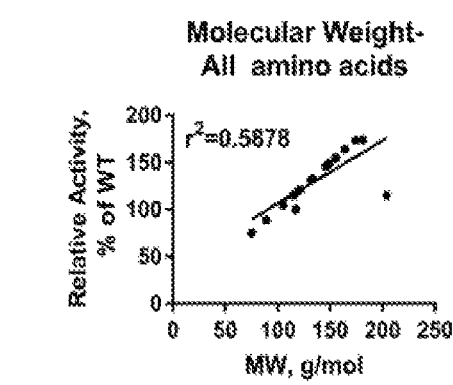
Figure 18C:
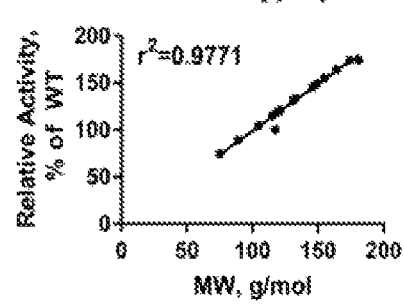
Figure 18D:
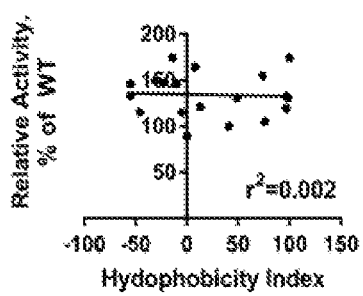

To examine the gain-of-function mechanism from an un-biased view, we created and tested the in vitro activity of 18 additional LCAT variants, each with one of the remaining amino acids at position 114. Specific activity of these variants ranged from 10% to 220% of WT (FIG. 18A). A positive correlation, with an $r^2$ value of 0.5878, was observed between the size of the amino acid (using molecular weight as a surrogate) and the activity of each variant (FIG. 18B). One amino acid (tryptophan) was an outlier. Upon exclusion of tryptophan from the analysis, the correlation reached 0.9771 (FIG. 18C). In contrast, the relationship between the hydrophobicity index of each amino acid and the activity of its associated variant was plotted in FIG. 18D, no correlation was observed.

To gain more insight regarding the possible mechanism of gain-of-function of LCAT-V 114M, this variant was modelled using molecular dynamics simulation (MDS), which like other in silico methods, combines the principles of physics and chemistry with computer technology to predict the outcome of a given set of inputs and parameters. In the case of MDS, the input in a three-dimensional structure, typically a representation of a protein derived from X-ray crystallography. The parameters are a set of physical principles which govern the movement of the atoms that make up the protein.

Three dimensional structures of WT LCAT and LCAT-V 114M were generated based on the recently published crystal structure (Piper, D. E. et al. The high-resolution crystal structure of human LCAT. J. Lipid Res. 56, 1711-1719 (2015)), and their behavior in a solvent-exposed (aqueous) environment was simulated over a period of 10 ns (FIG. 19A). Both structures achieved stability during this time period, as measured by root-mean-square-deviation (RMSD) (FIG. 19B). To examine local structural fluctuations over the course of the simulation, we plotted the root-mean-square-fluctuation (RMSF) values for each protein across the length of the amino acid sequence (FIG. 19C). Comparing two plots, there are several regions of the LCAT protein where V114M is to predict to alter local structural movement, one of these regions, residues 220-250, stands out as the region with the highest RMSF value, is the lid loop.

FIG. 20A shows the position Valine 114 within the LCAT protein structure. Valine 114 is positioned in the membrane associating region of LCAT, near the junction of the three domains. In FIG. 20B, the position of the lid loop which is the structure that partially blocks access to the active site can be observed. Based on these simulations, these regions of interest were selected: residues 45-75, 125-175, 220-250, 290-310 and 320-340 (FIG. 20C). Residues 45-75 fall in the membrane-associating domain. Residues 125-175 are located in the hydrolase domain, 290-310 and 320-340 are in the cap domain. Importantly, none of these regions contain any of residues that form the substrate-binding pocket, any of the catalytic triad or make up any other previous identified relevant structures. However, residues 220-250 make up the lid loop, a flexible loop which blocks access to the active site and is known to be important in enzyme activation and regulation (Peters, G. H., et al. Theoretical investigation of the dynamics of the active site lid in *Rhizomucor miehei* lipase. Biophys. J. 71, 119-129 (1996); and Muthahari, Y. A. & Hertadi, R Elucidation of Active Site Protective Residues in *Rhizomucor miehei* Lipase by Targeted Molecular Dynamics Approach. Procedia Chemistry 16, 285-291 (2015)). Furthermore, LCAT VI14G and V114P were modelled due to their relatively low activity; V114I was modelled because of its similarity to V11M, both in structure and activity; and V114Y was chosen because of its striking increase in specific activity. The delta-RMSF profiles of these 4 new variants were compared to LCAT-V114M (FIG. 20D), in five regions of interest, V114M stood out in that it is the only variant predicted to increase flexibility (delta-RMSF) across the entire lid loop.

Example 5—Pre-Clinical Development of AAV Based Gene Therapy for FLD-Testing Codon Optimized Variants of hLCAT To identify a variant that further increases the effectiveness of the vector and decreases the MED, four codon optimized variants of the human LCAT were compared.

Codon optimized sequences have been used to improve transgene expression in several preclinical studies of gene therapy (Greig, J. A. et al. Characterization of AAV-mediated human factor VIII gene therapy in hemophilia A mice. Hum. Gene Ther. (2017). doi:10.1089/hum.2016.128; and Matagne, V. et al. A codon-optimized Mecp2 transgene corrects breathing deficits and improves survival in a mouse model of Rett syndrome. Neurobiol. Dis. 99, 1-11 (2016)). Four codon optimized variants of human LCAT were compared side by side, to determine the best candidate. FIGS. 24A-24D provide information of an alignment of wild-type human LCAT coding sequence [SEQ ID NO: 1] with codon-optimized human LCAT coding sequences, v1 [SEQ ID NO: 3], v1 [SEQ ID NO: 4], v26 [SEQ ID NO: 5] and v201 [SEQ ID NO: 6]. Alignment statistics are further calculated and show an 86% (1122/1311) identity and 0% gaps (2/1311) between LCATco-v1 and WT, an 83% (1094/1319) identity and 0% gaps (0/1319) between LCATco-v 11 and WT, an 82% (1080/1320) identity and 0% gaps (2/1320) between LCATco-v26 and WT and an 85% (1102/1303) identity and 0% gaps (2/1303) between LCATco-v201 and WT.

Figure 21A:
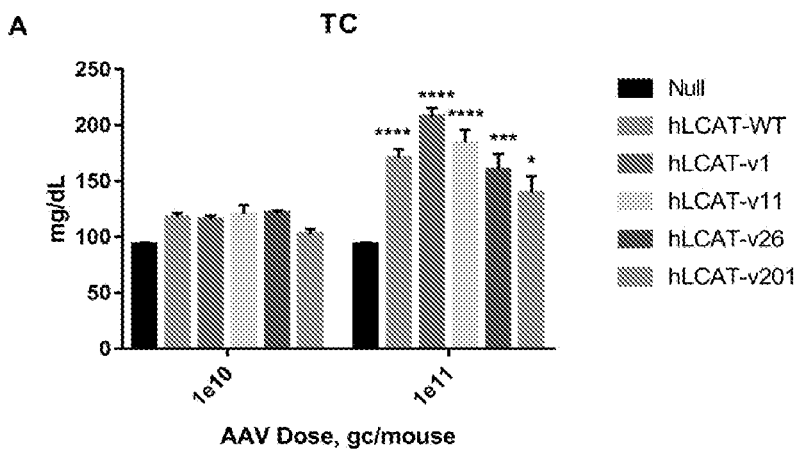
Figure 21B:
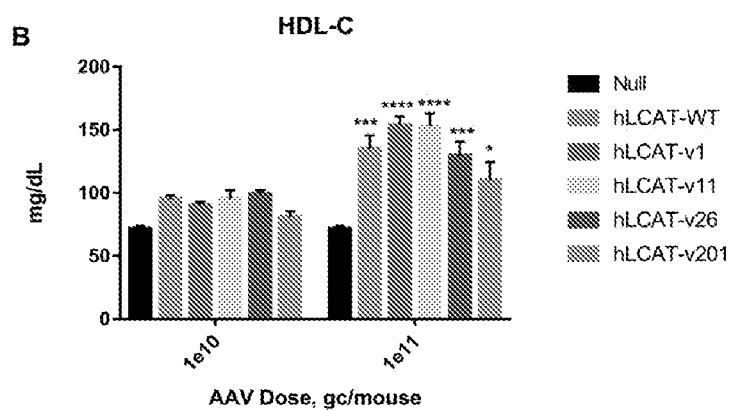
Figure 21C:
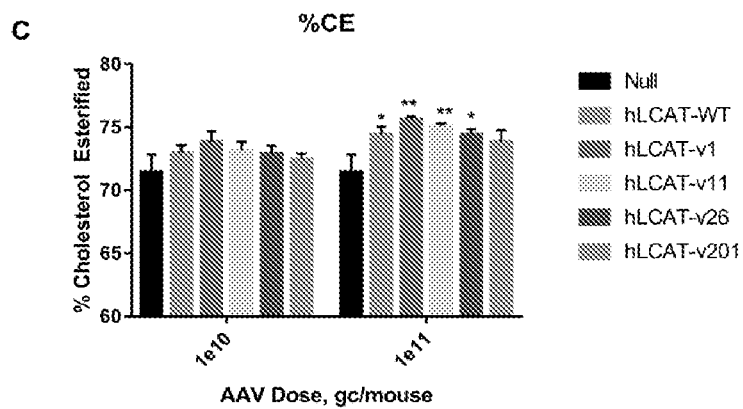

Following the in silico analysis of the many potential codon optimized LCAT variants, four candidates (variants 1 (v1), 11 (v11), 26 (v26) and 201(v201)) were selected for testing in vivo. Each variant was synthesized and then cloned into a plasmid for AAV production. For our pilot experiment we selected C57BL/6J mice and two doses, 1e10 GC per mouse and 1e11 GC per mouse (N=4), with AAV-Null and AAV-hLCAT-WT injected mice served as controls. We measured plasma lipids in these mice before injections and every 2 weeks after, as per our standard lab protocol. 6 weeks post-injection, none of the low dose groups had any significant differences in their plasma lipids relative to null injected mice (data not shown). The high dose hLCAT groups however, all had significantly increased TC and HDL-C relative to controls, with variant 1 (AAV-hLCAT-v1) having the highest TC at 201±6 mg/dL, and HDL-C at 152±3 mg/dL), followed by the AAV-hLCAT-v11, and hLCAT-WT groups (FIGS. 21A and 21B). Although the AAV-hLCAT-v1 group had the highest lipids, this was not statistically significantly different from any of the other AAV-hLCAT groups. With respect to plasma % CE, four of the five AAV-hLCAT groups had significantly elevated % CE relative to null, only AAV-hLCAT-v201 was not significant (FIG. 21C).

Figure 22A:
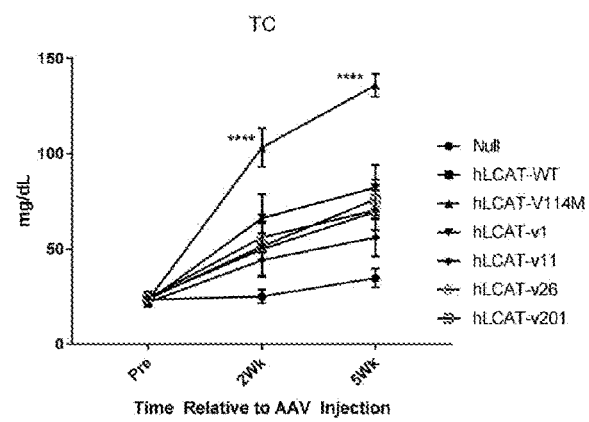
Figure 22B:
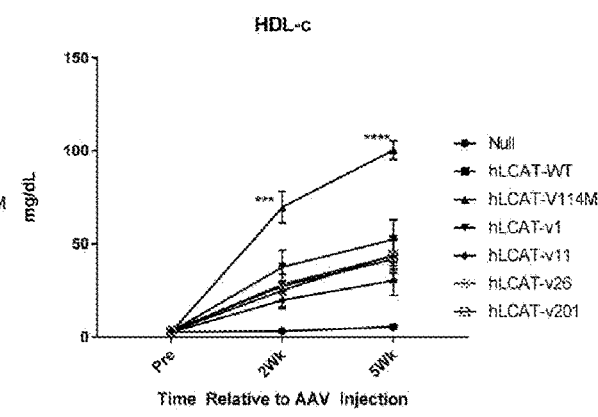
Figure 22C:
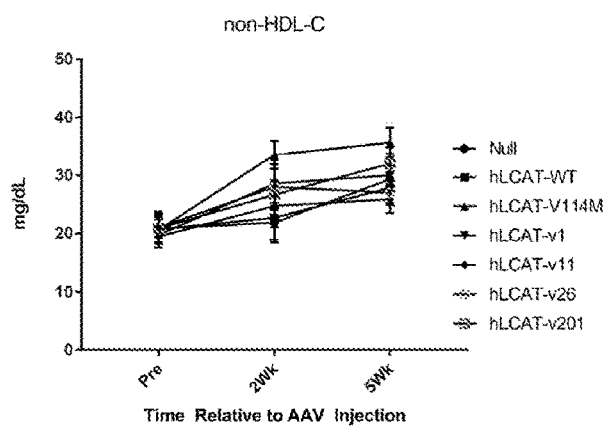
Figure 22D:
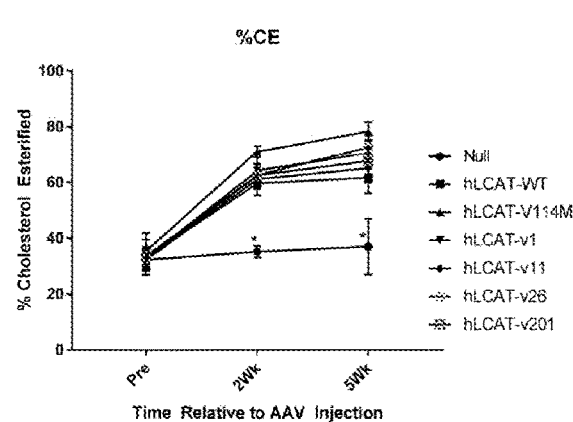
Figure 23A:
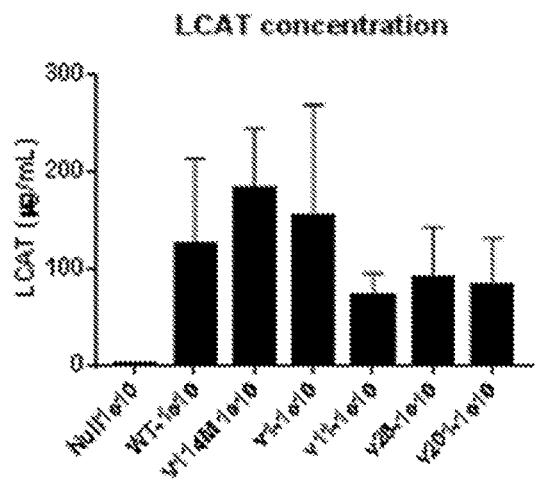
FIGS. 23A-23E provide bar graphs showing that testing strategies to increase LCAT efficacy by Codon Optimization of human LCAT cDNA. The experiment was run as described in the last paragraph of Example 5. Plasma LCAT concentration (FIG. 23A), TC (FIG. 23B), HDL-C(FIG. 23C), plasma cholesterol ester content (expressed as CE % of Total cholesterol, FIG. 23D) and liver LCAT gene expression measured by RT qPCR (FIG. 23E) were plotted and presented.
Figure 23B:
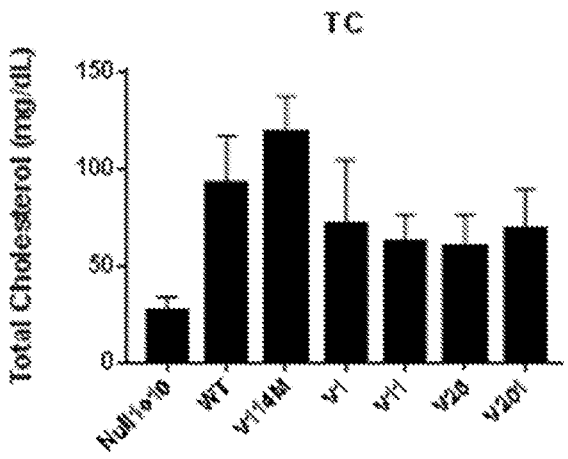
Figure 23C:
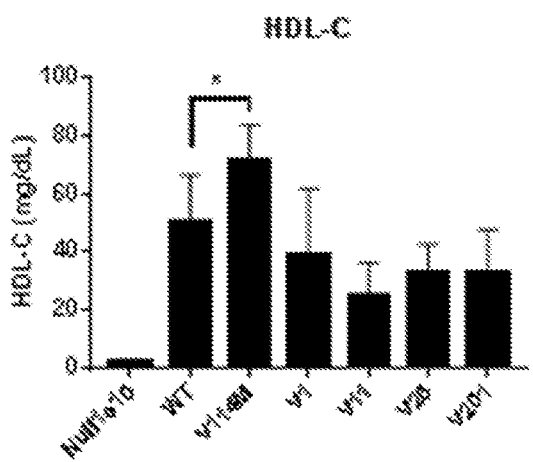
Figure 23D:
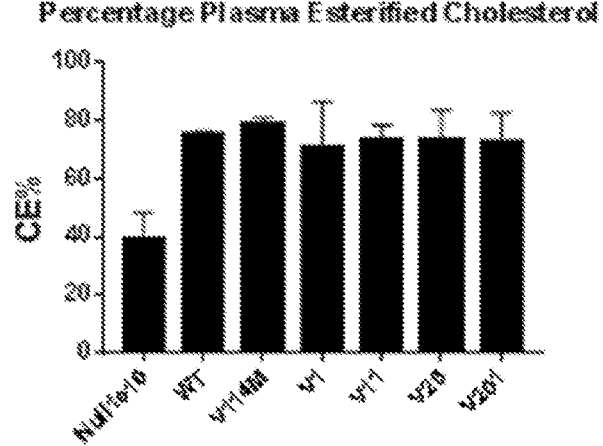
Figure 23E:
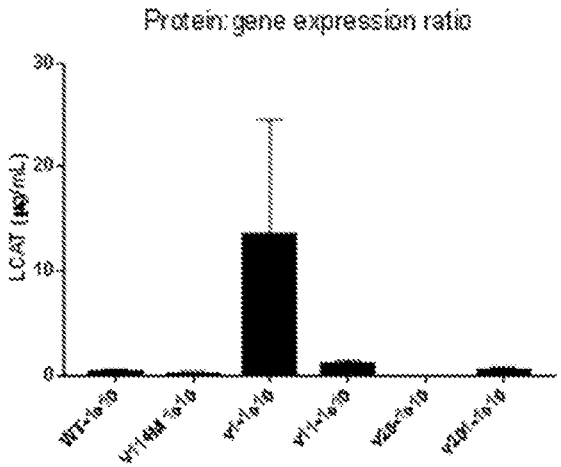

These variants were further tested in LCAT KO mice. Results in LCAT KO mice were similar to the results in C57BL/6. This time we injected only a single dose of each vector (N=7), 1e10 GC, and added AAV-hLCAT-V114M as a positive control comparison. Plasma was collected pre-injection, 2 weeks post injection and 5 weeks post injection. Plasma lipids in these mice were measure. It is found that the AAV-hLCAT-V114M had by far the highest TC, at 140±7 mg/dL and HDL-C, at 100±4 mg/dL, with AAV-hLCAT-v 1 being the second highest, although statistically comparable to AAV-hLCAT-WT at approximately 75 mg/dL of TC and 50 mg/dL of HDL-C (FIGS. 22A and 22B). Non-HDL-C was not different between any groups in this experiment, despite the increase in TC in the AAV-hLCAT-V114M group (FIG. 22C). Plasma % CE was in the normal range for all AAV-hLCAT injected groups, ranging from 63-79% (FIG. 22D). Furthermore, at 8 weeks after injection blood was collected and plasma lipids and LCAT concentration were measured. At the same time point, mice were sacrificed and liver was collected to measure LCAT gene expression via RT-qPCR. Plasma LCAT concentration for each of the experimental groups was determined by ELISA (FIG. 23A). Lipids were measured using AXCEL auto-analyzer. Mice that received a vector expressing LCAT had higher TC (FIG. 23B) and HDL-C(FIG. 23C) than mice that received null vector. Mice that received the V114M variant had higher HDL-C than the mice who received the WT LCAT vector (FIG. 23C). Mice that received a vector expressing LCAT had higher plasma cholesterol ester content (expressed as CE % of Total cholesterol, FIG. 23D) compared to Null vector injected mice. Liver LCAT gene expression was measured by RT qPCR (FIG. 23E). The panel represents the ratio between plasma LCAT protein and the respective hepatic LCAT gene expression levels. Codon optimized version v1 seems to be associated with significantly higher plasma protein to gene ratio.

Example 6—Pre-Clinical Development of AAV Based Gene Therapy for FLD-AAV.hLCAT-V114Mco The combination of the best codon optimized variant, hLCAT-v 1 with V114M is tested as described in the Examples. The coding sequences is reproduced as SEQ ID NO: 63.

Example 7—Pre-Clinical Development of AAV Based Gene Therapy for FLD-Discussion

A. The MED in LCAT KO mice: 1e10 GC of AAV-hLCAT increases plasma % CE

Although the first in vivo test of AAV-hLCAT did not produce any statistically significant responses, it was observed that at a dose of 1e10 GC there is some response to the vector and that this response is stable for a relatively long period of time, out to 12 weeks post injection (the longest post-injection timepoint sampled). Because of the lack of a significant plasma lipid response in this first experiment, we subsequently repeated the high dose and also tested two higher doses, 3e10 and e11 GC per mouse. Here, we saw that both of the two high doses induced a significant response in mice as measured by plasma lipids, CER, and LCAT mass. However, the same dose, 1e10 GC per mouse, that produced no significant increase in plasma lipids, did in fact induce a significant increase in plasma % CE, in this case to a normal level at ~70%. From these two experiments we can conclude that the MED of AAV-hLCAT to be at or below 1e10 GC per mouse. In later experiments, we tested several lower doses of AAV-hLCAT in LCAT KO mice and we found that at a dose of 3e9GC per mouse, there was a significant increase in plasma % CE in this group. These data together lead us to conclude that the tested MED of this vector in LCAT KO mice is 3e9 GC per mouse, which is approximately 1.5e11 GC per kg.

B. hApoA-I Lowers the MED: 3e9 GC of AAV-hLCAT Increases Plasma % CE

When we initially tested our AAV-hLCAT vector in LCAT KO/hApoA-I transgenic mice, we determined the MED (3e9GC) to be a half log lower than the MED in LCAT KO mice (1e10 GC). However, if we view all of our data together, including data from later experiments (FIGS. 12-15), we can conclude that the MED in LCAT KO mice is indeed also 3e9 GC per mouse.

In any case, in earlier experiments, a dose that produced only a small and not significant increase in plasma lipids in LCAT KO mice (1e10 GC) produced much more dramatic and statistically significant increases in LCAT KO/hApoA-I mice (1e10 GC). Also, while 3e9 GC had no effect on plasma lipids in LCAT KO mice, we did see a small but not significant effect in LCAT KO/hApoA-I mice, similar to the effect of 1e10 GC in LCAT KO mice. In our later experiments, we consistently see that a dose of 3e9 GC per mouse induces small increases in both TC and HDL-C (whether statistically significant or not) and produces a statistically significant increase in the plasma % CE in both LCAT KO and LCAT KO/hApoA-I mice. Altogether, this suggests to us that there may be an effect of the human cofactor, but the difference in the MED is likely less than half a log. This would explain why sometimes we see a dose difference between the two strains, and sometimes we do not.

C. Human Genetic Associations Predict the In Vitro Activity of LCAT Variants

In vitro, V114M, has ~150% the activity of WT LCAT, consistent with its human lipid association (FIG. 6). This makes V114M the first gain-of-function variant of LCAT ever described. Not only did V114M have increased activity in vitro, but this difference is robust across LCAT KO and LCAT KO/hApoAI transgenic mice, as well as in human plasma. We also showed that V114M is not the only LCAT variant to have activity consistent with its human lipid association. These data demonstrate the power of human genetic studies to identify functionally relevant sequence variants, including high activity variants which may be especially therapeutically relevant.

D. The MED of AAV-hLCAT-V 114M: 1e9 GC of AAV-hLCAT-V114M Increases % CE

We already demonstrated that hLCAT is reliably expressed via liver transduction using AAV2/8 and induces dose dependent increases in plasma lipids in both LCAT KO and LCAT KO/hApoA-I mice. Now we have identified a gain-of-function variant of human LCAT that may be ideal for use in our clinical candidate vector. The use of this naturally occurring gain-of-function variant, analogous to the strategy employed by the developers of Glybera, will likely lower the MED of our vector. When we tested the in vivo response to AAV-hLCAT-V 114M, we found that a significant increase in plasma % CE, can be seen in LCAT KO mice at a dose as low as 1e9GC per mouse (approximately equivalent to 5e10 GC per kg). In these studies, the low dose of 3e9 GC/mouse (~1.5e11 GC/kg) normalized plasma % CE in LCAT KO mice and at this dose, V114M produced plasma lipids near normal levels. In LCAT KO/hApoA-I transgenic mice, both hLCAT vectors produced normal plasma % CE, but only V114M produced significant increases in plasma lipids and CER. Given that we only tested a single dose in LCAT KO/hApoA-I mice, it is possible that an even lower dose of AAV-V114M may produce significant increases in plasma % CE in these mice. From these studies, we conclude that the MED of AAV-hLCAT-V114M is 1e9 GC per mouse (5e10 GC per kg). This dose is nearly ten fold lower than the approved dose used for Glybera (Bryant, L. M. et al. Lessons learned from the clinical development and market authorization of Glybera. Hum Gene Ther Clin Dev 24, 55-64 (2013)). 1e12GC per kg, and more than 10 fold lower than the lowest dose used in a phase I/II clinical trial for AAV gene therapy for hemophilia B, 2e12 GC per kg (Nathwani, A. C. et al. Long-term safety and efficacy of factor IX gene therapy in hemophilia B. N. Engl. J. Med. 371, 1994-2004 (2014)). Lastly, this estimate of therapeutic dose is based on changes in plasma % CE. We believe that an improvement in % CE is likely to be therapeutic, but the dose required to prevent renal failure may be quite different. Determination of the true therapeutic dose is difficult to impossible to determine without a reliable animal model of FLD renal failure and without testing in human patients. However, this dose gives us a starting point.

e. hLCAT-V114M is Better at Normalizing FLD Patient Plasma than hLCAT WT

At the time of this study, because we lacked an appropriate animal model to test the efficacy of gene therapy to prevent renal disease in FLD, we chose to test our gain-of-function LCAT in plasma from two FLD patients. When incubated with patient plasma, LCAT V114M reduced LpX-C and increased LDL-C and HDL-C, while WT hLCAT failed to reduce LpX and only increased LDL-C. The total cholesterol esterified by V114M during the incubation was nearly double that of WT LCAT, 5% in WT compared to 9.5% in V114M. We would expect similar results in a human patient, with V114M being twice as effective at reducing LpX cholesterol. Given the data demonstrating that LpX is sufficient to induce renal dysfunction in LCAT KO mice (Ossoli, A. et al. Lipoprotein X Causes Renal Disease in LCAT Deficiency. PLoS One 11, e0150083 (2016)), we would expect V114M to be a more effective at preventing renal failure in FLD than WT LCAT. This is consistent with all of our previous data and supports the idea that V114M will be a better choice for our candidate vector.

F. Molecular Dynamics Simulation Suggests V114M Increases Flexibility of the Lid Loop X-ray crystallography is the gold standard method of determining the structure of a protein. However, the determination of protein structure while immobilized in non-physiologic conditions merely provides an average or just a single version of the protein structure. In solution, the physical organization of a protein may be quite different from that represented by X-ray crystallography and this is important to keep in mind when examining the relationship between protein sequence, structure and function. While crystal structures are stationary, in a true biological system, a protein is more fluid structure with various flexible, and sometimes moving, parts. Molecular dynamics simulation attempts to fill this gap in knowledge, by combining our knowledge of protein structure, with computer modeling to form predictions of protein structure that take into account the effects of the aqueous environment.

Understanding the mechanism of gain-of-function can be useful for a variety of reasons. Firstly, one may be able to exploit this mechanism to engineer high activity variants of other enzymes, in this case, particularly lipases. Also, if a protein is to be used therapeutically, understanding the mechanism contributes to the knowledge base and potentially to the safety profile of the therapeutic product. Here we show that molecular dynamic simulation suggests V114M increases flexibility of the lid loop. In lipases, opening of the lid loop is essential for activation of the enzyme, providing the substrate access to the active site, and is facilitated by conformational changes that occur upon membrane association (Marchot, P. & Chatonnet, A. Enzymatic activity and protein interactions in alpha/beta hydrolase fold proteins: moonlighting versus promiscuity. Protein Pept. Lett. 19, 132-143 (2012)). For these reasons, the lid loop is known to be an important determinant of enzyme activity (Nardini, M. & Dijkstra, B. W. Alpha/beta hydrolase fold enzymes: the family keeps growing. Curr. Opin. Struct. Biol. 9, 732-737 (1999)).

It is therefore reasonable to assume that increased flexibility of the active site lid loop may reduce the activation energy of the enzymatic reaction thereby increasing the specific activity. In fact, this conclusion is consistent with the results of our kinetic study (FIG. 8 and Table 2), where we see an increase in the Vmax of LCAT-V 114M but no change in the Km. Given the location of V114, at the junction of the three domains, opposite the active site, and given that larger amino acids at this position predicts increased activity, we believe that V114M induces slight conformational changes via interaction with the neighboring domains, which ultimately leads to changes in the function of the lid loop. However, we cannot rule out additional mechanisms by which V 114M increases the activity of LCAT. There may be other reasons for this gain-of-function that we cannot discern from these studies alone.

G. Side by Side Comparison of Four Codon Optimized Variants of hLCAT

We designed and tested four codon optimized variants of LCAT. Only one of the four variants, variant 1, appeared to be better than WT hLCAT at increasing plasma lipids in mice. We have not yet confirmed if this variant is expressed more efficiently, as we would predict based on the theory of codon optimization and based on previous studies. The remaining three variants appear to be equivalent to or less effective than WT at increasing plasma lipids in both BL6 and LCAT KO mice. As none of the groups of mice injected with an AAV expressing one of the codon optimized variants were significantly different from mice injected with AAV expressing the WT hLCAT, these studies suggest that the LCAT gene is not strongly affected by codon optimization.

Here we have identified the first naturally occurring gain of function variant of LCAT and determined the MED of a vector expressing this variant. The MED, defined as the lowest dose which produces significant increases in plasma % CE, of this vector, our current clinical candidate, is approximately 5e10 GC per kg of bodyweight. In addition to the identification and characterization of this naturally occurring gain-of-function variant, here, we directly compared four different codon optimized variants of hLCAT. While none of the codon-optimized variants were significantly better than WT hLCAT, our data suggests that v1 might be slightly more effective. This effect, while seemingly small, may have a combinatorial benefit with our gain-of-function variant, and ultimately produce a vector that is even more effective.

Example 8—Methods

A. In vivo AAV Expression in Mice

WT LCAT and LCAT-V 114M were cloned into AAV plasmids containing the human TBG promoter and alpha mic/bik enhancer, as used in previous studies (Kassim, S. H. et al. Gene therapy in a humanized mouse model of familial hypercholesterolemia leads to marked regression of atherosclerosis. PLoS One 5, e13424 (2010)). Plasmids were then submitted to the Penn Vector core for production of our pseudotyped (serotype 8) AAV2 vectors (AAV2/8). The backbone sequence of the null control vector is the same as LCAT vectors, with a scrambled sequence in place of the transgene. LCAT KO mice (Sakai, N. et al. Targeted disruption of the mouse lecithin:cholesterol acyltransferase (LCAT) gene. Generation of a new animal model for human LCAT deficiency. J. Biol. Chem. 272, 7506-7510 (1997)) and LCAT KO/human ApoA-I transgenic mice (Rousset, X. et al. Effect of recombinant human lecithin cholesterol acyltransferase infusion on lipoprotein metabolism in mice. J. Pharmacol. Exp. Ther. 335, 140-148 (2010)) are maintained in our animal facility on standard chow diet. 6-10 week old male mice received a single intraperitoneal injection of vector diluted in sterile PBS. Blood samples were collected prior to injection and every 2 weeks thereafter via retro-orbital bleed. Animals were sacrificed for tissue collection 6 weeks after AAV injection. Livers were collected immediately following perfusion with sterile PBS. Hepatic gene expression was determined as described below.

Plasma lipids were measured using an AXCEL autoanalyzer. The following reagents were used: for Total Cholesterol, Wako TC reagent (catalog #439-17501), for Free Cholesterol, Wako FC reagent (catalog #435-35801), for HDL-C, Trinity EX HDL-Cholesterol reagent (Trinity catalog #354 LB) and for Phospholipids, the Wako Phospholipids C reagent (catalog #433-36201). Plasma Cholesterol Esters Percentage was mathematically calculated using the Unesterified and total Cholesterol concentrations according to the following formula CE=[(TC-UC)/TC]×100.

FPLC lipid profiles of injected mice were obtained by the separation of 150ul of pooled plasma using two Superose 6 columns in series (AKTA FPLC system, GE Healthcare). Lipids were measured in FPLC fractions using the Wako Cholesterol E reagent and Wako Free Cholesterol reagent.

B. Plasma Cholesterol Esterification Rate (CER) Assay

30 μl (30 ρCi) of $^3$H labeled free cholesterol was dried down under nitrogen gas and then resuspended in 300 μl of ethanol. For each sample to be run, 6 μl of the resuspended cholesterol solution was spotted onto a filter paper disc in the bottom of a glass culture tube, for a total of 0.6ρCi per reaction. Plasma from AAV injected mice, stored at −80° C., was thawed on ice. 8 μl of 1.4 mM DTNB (5,5-dithio-bis-(2-nitrobenzoic acid) solution was added to each tube before the addition of 40 μl of plasma. Each sample was run in triplicate. PBS was used as a negative control, and a pooled human plasma standard was run as a positive control. Tubes were capped and incubated in a 37° C. shaking water bath for 2 hours for equilibration. After equilibration, 8 μl of 0.1M BME solution was added to each tube and then tubes were recapped and incubated for another 60 minutes in the shaking 37° C. water bath. Reactions were terminated by the addition of 2 ml of 2:1 chloroform: methanol solution and a brief vortex. 200ul of water was added to each tube to induce phase separation and then tubes were centrifuged for 5 minutes at 400×g. The clear bottom layer was carefully moved to a clean glass tube and then dried down via centrifugal evaporator or nitrogen dryer. Dried samples were resuspended in 50ul chloroform containing unlabeled FC and CE carrier for thin layer chromatography (TLC). Labeled FC and CE in each sample was separated by TLC using 170:30:1 Hexane: Diethyl Ether: Acetic Acid. Spots were cut and quantified using scintillation counting. FC was measured in each plasma sample using Wako Free Cholesterol kit. The relative amount of cholesterol esterified per hour was determined by calculating the percentage of counts in CE spot/total counts (Sum of the counts in FC and CE spots). The absolute amount of Cholesterol esterified per hour was determined by multiplying the Percentage of Esterified cholesterol by the initial amount of Unesterified cholesterol present in the plasma sample. CER for each sample was then calculated as percent of cholesterol esterified per hour*nmol FC per ml of plasma.

C. LCAT Hepatic Gene Expression

RNA was isolated from liver tissue via homogenization and extraction with Trizol (Fisher catalog #15596018) as described by the manufacturer. Isolated RNA was washed three times before final resuspension. The concentration of RNA was measured by Nanodrop and all samples were diluted to match the concentration of the most dilute sample in the set. RNA was deemed of sufficient quality at or above a 260/280 ratio of 1.5. RNA samples with a 260/280 ratio below 1.5 were precipitated with isopropanol, washed and resuspended until the 260/280 ratio reached at least 1.5. cDNA was created using the Applied Biosystems High Capacity Reverse Transcriptions cDNA Synthesis kit (Fisher catalog #4368814) following the manufacturer's protocol. cDNA was diluted 1:50 in RNase free $H_2O$ before PCR.

Real-time quantitative PCR was performed using SYBR Green Mix (Applied Biosystems) on an Applied Biosystems QuantStudio 7 Flex Real Time PCR System. PCR reactions were set up in a 384 well optical plate. Each 10 ul reaction contained 5 μl of SYBR Green Master Mix, 3 μl of diluted cDNA and 1 μl of each primer. After loading all samples, plate was spun briefly in a tabletop centrifuge before being analyzed using Applied Biosystems QuantStudio 7 Flex Real Time PCR System. On every plate, a standard curve was created for each primer set using serial dilutions of pooled cDNA, in order to demonstrate consistent amplification efficiency and to quantify mRNA if so desired.

Relative gene expression in experiments described in FIG. 12D was determined using the ΔCT method (LCAT primer set 1, SEQ ID NOs: 68 and 69) with β-actin and 18S ribosomal RNA as housekeeper genes. FIG. 12D reports LCAT CTs (normalized by housekeeper genes).

For codon optimized variant experiments the relative gene expression in experiments was determined using the ACT method (LCAT primer set 2, SEQ ID NOs: 68 and 69) with β-actin and GAPDH as the housekeeping genes (FIG. 13F).

The following primer sequences were used. For mouse beta-actin: 5'-TTGGGTATGGAATCCTGTGG-3' (SEQ ID NO: 64) and 5'-CTTCTGCATCCTGTCAGCAA-3' (SEQ ID NO: 65). For mouse 18S: 5'-CTTAGAGGGACAAGTGGCG-3' (SEQ ID NO: 66) and 5'-ACGCTGAGCCAGTCAGTGTA-3' (SEQ ID NO: 67). For human LCAT (set 1): 5'-CCAGGGTTGTCTACAACCGG-3' (SEQ ID NO: 68) and 5'-GGCGCAGCAGGAAATAGAGC-3' (SEQ ID NO: 69). For mouse GAPDH: 5'-TGTGTCCGTCGTGGATCTGA-3' (SEQ ID NO: 73) and 5'-CCTGCTTCACCACCTTCTTGAT-3' (SEQ ID NO: 74). For human LCAT (Set 2): 5'-GNTACCTGCAYACMCTGGTG (SEQ ID NO: 75) and 5'-GCTTSCGGTAGTAYTCYTCCT-3' (SEQ ID NO: 76).

D. Cell Culture and In Vitro LCAT Activity Assay

LCAT V114M, R123H, S232T and the catalytic serine mutant S205G were created using the pcDNA3.1+expression plasmid containing the WT LCAT cDNA and the Quik-Change II XL Site Directed Mutagenesis kit from Agilent Technologies (catalog #200521). All V114 LCAT variants were created using GeneStrand fragments from Eurofins. Gene fragments were cloned into the same pcDNA3.1+-hLCAT used previously. After thawing, HEK293 cells were passaged 2-3 times in standard serum medium (such as DMEM w/FBS). Cells were then adapted to serum free medium (Freestyle 293 Expression Medium from ThermoFisher catalog #12338026) by reducing the volume of serum containing medium each passage. A trypsin inhibitor (Thermo-Fisher #T6522) was added to media immediately after trypsinizing to prevent death of the cells. Once adapted, cells were plated at $3\times10^5$ cells per well, in 12-well plates for transient transfection. At approximately 80% confluency, or 24-48 hours later, cells were transfected using Lipofectamine 2000 (Fisher catalog #11668019). 4 μg of each plasmid DNA construct was used per well, with each construct repeated in triplicate wells. Media was changed 6 hours later and then collected 48 hours post-transfection. Media samples were aliquoted and frozen at −80° C. immediately after collection.

LCAT activity assay was performed according to the method described by Vaisman et al with minor modifications (Vaisman B et al. Methods Mol Biol. 2013; 1027:343-52). Recombinant HDL (rHDL) was prepared by cholate dialysis using POPC (Avanti Lipids #850457), ApoA-I (purified in house from pooled human plasma) and free cholesterol (Avanti Lipids #250165) at amass ratio of 2.7:1:0.11 respectively. Additionally, $^3H$ labeled cholesterol was added to the rHDL at a ratio of 20 μCi/mg ApoA-I. POPC and cholesterol solutions were dried down under N2 gas then resuspended in TBS with EDTA, pH 7.4. The volume of TBS used for resuspension was calculated based on the volume of dialyzed ApoA-I such that the total volume of the mixture going into dialysis was 4 ml/mg of ApoA-I. 30 mg/ml cholate solution (in TBS with EDTA) was added to the suspension (94ul/mg ApoA-I) which was vortexed and incubated at 37° C. for 90 minutes. Dialyzed ApoA-I was then added to the mixture which was again vortexed and incubated at 37° C. for another 60 minutes. The final mixture was then dialyzed 6 times against 4L of TBS with EDTA, pH 7.4 over 72 hours. After dialysis, the rHDL was combined with an equal volume of 2% BSA with 10 mM BME (in TBS with EDTA) and stored at 4° C. until the assay was performed (within one week). Additional BME was added to the rHDL before setting up the reactions. On ice, 60 1d of rHDL mixture, as prepared above, was pipetted into labeled tubes. Each reaction was run in triplicate. After inverting each media aliquot 5-7 times, 5ul of media was added to each labeled tube containing rHDL. Reactions were then incubated in a 37° C. water bath for 2 hours. Upon removal from the water bath, reactions were terminated by the addition of 1 ml of cold 100% ethanol and placed on dry ice. Reactions were then stored at −20° C. overnight. Next, reactions were centrifuged at 13,000×g for 10 minutes to pellet any protein. The supernatant was moved into matching labeled glass culture tubes and then dried down using a centrifugal evaporator. Dried samples were resuspended in 50ul chloroform containing unlabeled FC and CE carrier for thin layer chromatography (TLC). Labeled FC and CE in each sample was separated by TLC using 170:30:1 Hexane: DEE: Acetic Acid. Spots were cut and quantified using scintillation counting. The relative amount of cholesterol esterified per hour (LCAT activity) was determined by calculating the percentage of counts in CE spot/total counts (Sum of the counts in FC and CE spots). Background activity, as measured in media samples from GFP transfected cells, was subtracted and then activity of each variant was normalized to LCAT concentration as measured by ELISA (Biovendor #RD191122200R). Because exact activity values vary between rHDL preps, data is presented as relative to WT activity (calculated for each assay).

For kinetic assays, after dialysis, recombinant HDL particles were separated by fast protein liquid chromatography (FPLC) on a Superdex 200 column and the fractions corresponding to 7-8 nm diameter were pooled and concentrated using an Amicon Centrifugal Filter Unit (Sigma-Aldrich #Z648027). Concentrated HDL was then diluted with TBS with EDTA to match the cholesterol concentration of a standard prep of 1.7 nmol/reaction. Substrate was further diluted to the appropriate concentrations using TBS with EDTA, BSA and BME to match our normal running concentrations. Final HDL-C in the substrate was determined by colorimetric assay. Different substrate concentrations (1.7, 0.85, 0.43, 0.28, 0.21, 0.14 and 0.07 nmol of Unesterified cholesterol) were then incubated with V114M and WT LCAT protein as previously described. Results were expressed as absolute specific activity (nmol of Cholesterol esterified per hour per ug of LCAT protein (nmolCE/h/ug LCAT).

E. Molecular Dynamics Simulation

Molecular dynamics simulations were performed using Maestro software (Release 2015-3; Schrodinger). The high-resolution crystal structure of LCAT (4XWG) was used as the starting structure (Piper, D. E. et al. The high-resolution crystal structure of human LCAT. J. Lipid Res. 56, 1711-1719 (2015)). Using the PRIME application, the missing residues 231-237 were replaced and Y31 was mutated back to C to obtain WT LCAT, containing all residues of the mature LCAT protein, numbered from 21-396. Using this WT LCAT structure, V114 was mutated to create the additional variants, V114G, V141, V114M, V114P, and V114Y. Starting structures for each variant were refined by restrained minimization using the following parameters: Force Field=OPLS_2005; solvent=water; iterates=2500. All-atom molecular dynamics simulations were then run for 10 ns using the Desmond application at a temperature of 310.15 K in SPC solvent with 0.15 M NaCl. Simulations were performed on the National Institutes of Health Biowulf computing cluster.

F. Incubation of LCAT-deficient human plasma with LCAT protein variants in vitro. Plasma CE %, and CER on deidentified fasting plasma samples from one LCAT deficient subject and a healthy subject were measured as outlined above. For the normalization experiment, LCAT-deficient plasma was incubated with LCAT WT or LCAT-V114M protein, or transfection media from control GFP transfected cells (Null) and then fractionated into lipoproteins by Fast Protein Liquid Chromatography (FPLC). WT and V14M LCAT-containing media were obtained by transient transfection of HEK293 cells, as previously described. Medium from GFP transfected cells was used as negative control. Media samples were concentrated using Millipore Amicon Ultra 4 centrifugal units (Merk, Millipore) and human LCAT concentration was measured by ELISA (Biovendor #RD191122200R). Concentrated media samples were diluted to a final LCAT concentration of 17 mg/ml. LCAT-deficient plasma was labeled with 3H-free cholesterol by incubating 400 uL of plasma with 15 uCi of 3H-labeled free cholesterol at 4° C. overnight. 45 µl of GFP, WT or V114M LCAT-containing medium was mixed with 135 l of 3H-free cholesterol labeled LCAT-deficient plasma. Samples were incubated in a 37° C. water bath for 15 hours. Incubation was terminated by placing the samples on ice and then freezing at 20° C. A portion of the incubation mixture was separated on a TLC plate to calculate % CE via scintillation counting. 150 µl of the sample was separated by FPLC as outlined above and then cholesterol distribution was determined using scintillation counting.

G. Design of Codon Optimized LCAT Variants

In collaboration with the lab of James Wilson, we used codon frequency tables developed in house in earlier studies for expressing various genes in liver to diversify the coding sequences for the LCAT protein. Alternative reading frames were removed from each coding sequence. The diversification was based on the inherent codon degeneracy and resulted in overall coding sequence variance presented in the SEQ ID NOs: 3(hLCAT-co-v1), 4 (hLCAT-co-v11), 5 (hLCAT-co-v26), and 6 (hLCAT-co-v201). hLCAT corresponds to the endogenous human gene. Each coding sequence was synthesized de novo and cloned into AAV cis plasmid under the control of liver specific TBG promoter. The transgene cassette is flanked by the AAV2 ITR allowing us to package those transgene expression cassettes into AAV vectors. Those plasmids were verified by end-to-end sequencing prior to packaging. All vectors were produced by Penn Vector Core.

H. Statistical Analyses

All statistical analysis was performed using GraphPad Prism 7.0. One way ANOVA with Tukey's multiple comparison test was used to compare groups of a single level. Two way ANOVA was used when comparing groups with multiple levels, such as time course data. Student t-test was used to compare pairs or triplets of single time point data. All in vitro experiments were repeated three times, using independent biological samples. In vivo experiments used a minimum of three animals per group. Animals were excluded from analysis if data was missing from one or more timepoints or if the animal was presumed to have a bad injection. An animal was presumed to have a bad injection if: at least two plasma lipid measures were more than two standard deviations below the mean of the other animals in that group AND the plasma LCAT mass or plasma CER was also two standard deviations below the mean of the other animals in that group.

I. Plasma LpX-C Measurement

Plasma samples were stored at −80° C. After thawing on ice, 150 ul of pooled plasma was mixed with an equal volume of phosphotungstic acid solution (PTA): 80 g/L phosphotungstic acid with 10 mM EDTA, to precipitate HDL. The samples were mixed by inverting 5 times and then incubated for 10 minutes on the benchtop. The samples were then centrifuged at 2,000×g for 10 minutes and then the supernatant, containing LpX was moved to a new tube. LpX was then precipitated using two times the volume of 200 mM magnesium chloride ($MgCl_2$) in Tris HDL buffer, pH 9.0. Samples were mixed well, again by inverting 5 times, incubated on the benchtop for 10 minutes and then centrifuged for 10 minutes at 2,000xg. The supernatant, containing LDL and VLDL, was removed and the pellet was resuspended in 150 pl of PBS with 0.05% SDS. Total cholesterol was measured in the samples using the Wako Total Cholesterol reagent as done previously.

J. LCAT V114 Variant Mutagenesis Strategy

Figure 25:
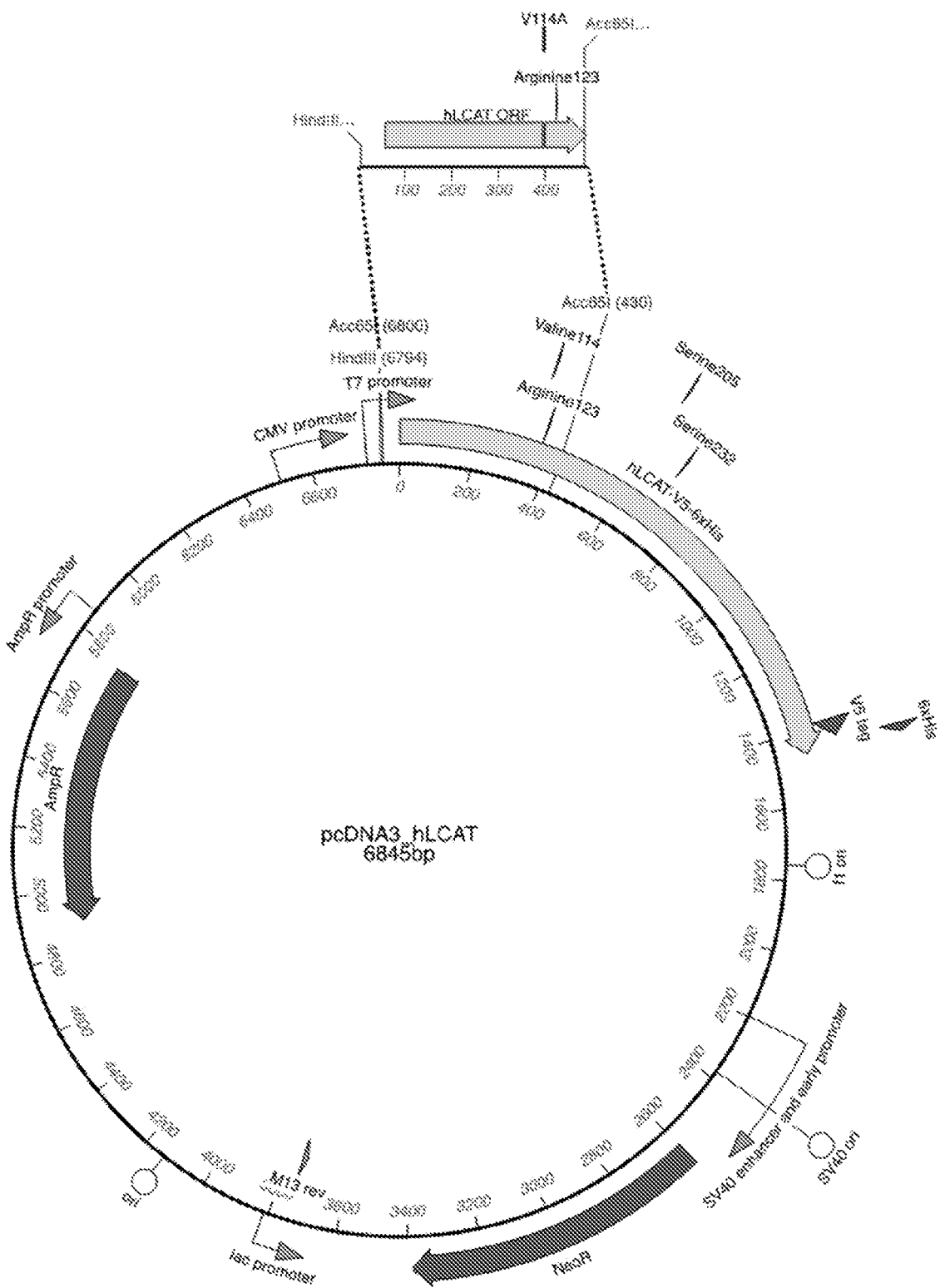
FIG. 25 illustrates LCAT V 114 variant mutagenesis strategy as described in Example 8.

The wild-type V114 residue was mutated to all possible amino acid variants, using a cassette replacement approach as illustrated in FIG. 25. Briefly, custom double-stranded DNA gene fragments (one for each variant, sequences thereof are reproduced in SEQ ID NOs: 45 to 62) were synthesized that spanned the plasmid sequence between the unique HindIII site, and the Acc65I site within the LCAT ORF, and that included extra DNA sequence at each end to promote efficient restriction digestion. The pcDNA hLCAT plasmid was digested with Acc65I and HindIII, and the linear ~6.3kb band was gel purified and separately ligated to each of the Acc65I-HindIII digested gene fragments. Successful mutagenesis of the V114 residue was confirmed by Sanger sequencing.

Plasmids for each LCAT variant were created by Site Directed Mutagenesis using the Quik-Change II XL kit (Agilent Technologies). All V14 LCAT variants were created generated using GeneStrand fragments from Eurofins. All variants were cloned into the widely used expression pcDNA3.1 expression plasmid.

K. Generation of LCAT Mutated Proteins.

LCAT protein from each variant was created by transient transfection method. After thawing, HEK293 cells were passaged 2-3 times in standard DMEM with Fetal Bovine Serum (FBS). Cells were then adapted to serum free medium (Freestyle HEK293 Expression Medium from Thermo Fisher catalog #12338026) by reducing the volume of serum containing medium each passage. A trypsin inhibitor (Thermo-Fisher #T6522) was added to media immediately after trypsinizing to prevent death of the cells. Once adapted, cells were plated at $3\times10^5$ cells per well, in 12-well plates for transient transfection. At approximately 80% confluency, or 24-48 hours later, cells were transfected using Lipofectamine reagent (Thermo Fisher Scientific). 4ug of each plasmid DNA construct was used per well, with each construct repeated in triplicate wells. Media was changed 6 hours later and then collected 48 hours post-transfection. Media samples were aliquoted and frozen at −80° C. immediately after collection.

(Sequence Listing Free Text)

The following information is provided for sequences containing free text under numeric identifier <223>.

| SEQ ID NO: (containing free text) | Free text under <223> |
|---|---|
| 3 | <223> Codon-optimized human LCAT coding sequence v1 |
| 4 | <223> Codon-optimized human LCAT coding sequence v11 |
| 5 | <223> Codon-optimized human LCAT coding sequence v26 |
| 6 | <223> Codon-optimized human LCAT coding sequence v201 |
| 8 | <223> Amino acid sequence of human LCAT protein variant V114A |
| 9 | <223> Amino acid sequence of human LCAT protein variant V114C |
| 10 | <223> Amino acid sequence of human LCAT protein variant V114D |
| 11 | <223> Amino acid sequence of human LCAT protein variant V114E |
| 12 | <223> Amino acid sequence of human LCAT protein variant V114F |
| 13 | <223> Amino acid sequence of human LCAT protein variant V114G |
| 14 | <223> Amino acid sequence of human LCAT protein variant V114H |
| 15 | <223> Amino acid sequence of human LCAT protein variant V114I |
| 16 | <223> Amino acid sequence of human LCAT protein variant V114K |
| 17 | <223> Amino acid sequence of human LCAT protein variant V114L |
| 18 | <223> Amino acid sequence of human LCAT protein variant V114N |
| 19 | <223> Amino acid sequence of human LCAT protein variant V114P |
| 20 | <223> Amino acid sequence of human LCAT protein variant V114Q |
| 21 | <223> Amino acid sequence of human LCAT protein variant V114R |
| 22 | <223> Amino acid sequence of human LCAT protein variant V114S |
| 23 | <223> Amino acid sequence of human LCAT protein variant V114T |
| 24 | <223> Amino acid sequence of human LCAT protein variant V114W |
| 25 | <223> Amino acid sequence of human LCAT protein variant V114Y |
| 27 | <223> Human LCAT V114A coding sequence |
| 28 | <223> Human LCAT V114C coding sequence |
| 29 | <223> Human LCAT V114D coding sequence |
| 30 | <223> Human LCAT V114E coding sequence |
| 31 | <223> Human LCAT V114F coding sequence |
| 32 | <223> Human LCAT V114G coding sequence |
| 33 | <223> Human LCAT V114H coding sequence |
| 34 | <223> Human LCAT V114I coding sequence |
| 35 | <223> Human LCAT V114K coding sequence |
| 36 | <223> Human LCAT V114L coding sequence |
| 37 | <223> Human LCAT V114N coding sequence |
| 38 | <223> Human LCAT V114P coding sequence |
| 39 | <223> Human LCAT V114Q coding sequence |
| 40 | <223> Human LCAT V114R coding sequence |
| 41 | <223> Human LCAT V114S coding sequence |
| 42 | <223> Human LCAT V114T coding sequence |
| 43 | <223> Human LCAT V114W coding sequence |
| 44 | <223> Human LCAT V114Y coding sequence |
| 45 | <223> Gene fragment for mutagenesis to generate human LCAT-V114A coding sequence |
| 46 | <223> Gene fragment for mutagenesis to generate human LCAT-V114C coding sequence |
| 47 | <223> Gene fragment for mutagenesis to generate human LCAT-V114D coding sequence |
| 48 | <223> Gene fragment for mutagenesis to generate human LCAT-V114E coding sequence |
| 49 | <223> Gene fragment for mutagenesis to generate human LCAT-V114F coding sequence |
| 50 | <223> Gene fragment for mutagenesis to generate human LCAT-V114G coding sequence |
| 51 | <223> Gene fragment for mutagenesis to generate human LCAT-V114H coding sequence |
| 52 | <223> Gene fragment for mutagenesis to generate human LCAT-V114I1 coding sequence |
| 53 | <223> Gene fragment for mutagenesis to generate human LCAT-V114K coding sequence |
| 54 | <223> Gene fragment for mutagenesis to generate human LCAT-V114L coding sequence |
| 55 | <223> Gene fragment for mutagenesis to generate human LCAT-V114N coding sequence |

| SEQ ID NO: (containing free text) | Free text under <223> |
|---|---|
| 56 | <223> Gene fragment for mutagenesis to generate human LCAT-V114P coding sequence |
| 57 | <223> Gene fragment for mutagenesis to generate human LCAT-V114Q coding sequence |
| 58 | <223> Gene fragment for mutagenesis to generate human LCAT-V114R coding sequence |
| 59 | <223> Gene fragment for mutagenesis to generate human LCAT-V114S coding sequence |
| 60 | <223> Gene fragment for mutagenesis to generate human LCAT-V114T coding sequence |
| 61 | <223> Gene fragment for mutagenesis to generate human LCAT-V114W coding sequence |
| 62 | <223> Gene fragment for mutagenesis to generate human LCAT-V114Y coding sequence |
| 63 | <223> Codon-optimized human LCAT V114M v1 |
| 64 | <223> PCR primer for mouse beta-actin |
| 65 | <223> PCR primer for mouse beta-actin |
| 66 | <223> PCR primer for mouse 18S |
| 67 | <223> PCR primer for mouse 18S |
| 68 | <223> PCR primer set 1 for human LCAT |
| 69 | <223> PCR primer set 1 for human LCAT |
| 70 | <223> AAV-TBG-hLCAT genome vector. <220> <221> repeat_region <222> (1) . . . (173) <223> 5' ITR <220> <221> misc_feature <222> (195) . . . (294) <223> alpha mic/bik <220> <221> promoter <222> (415) . . . (874) <223> TBG Promoter <220> <221> Intron <222> (918) . . . (1050) <223> Chimeric Intron from human beta-globin and immunoglobulin heavy chain genes <220> <221> misc_feature <222> (1109) . . . (2428) <223> coding sequence of human LCAT-V114M <220> <221> polyA_signal <222> (2493) . . . (2614) <223> SV40 polyadenylation signal <220> <221> repeat_region <222> (2736) . . . (2908) <223> 3' ITR |
| 71 | <223> AAV-TBG-hLCATco-v1 genome vector. <220> <221> repeat_region <222> (1) . . . (173) <223> 5' ITR <220> <221> enhancer <222> (195) . . . (294) <223> alpha mic/bik <220> <221> promoter <222> (415) . . . (874) <223> TBG Promoter <220> <221> Intron <222> (918) . . . (1050) <223> Chimera intron from human beta-globin and immunoglobulin heavy chain genes <220> <221> misc_feature <222> (1094) . . . (2437) <223> codon-optimized coding sequence of human LCAT, v1, LCATco-v1 <220> <221> misc_signal |

| SEQ ID NO:<br>(containing free text) | Free text under <223> |
|---|---|
|  | <222> (1104) . . . (1113)<br><223> Kozak sequence<br><220><br><221> polyA_signal<br><222> (2459) . . . (2580)<br><223> SV40 polyadenylation signal<br><220><br><221> repeat_region<br><222> (2702) . . . (2874)<br><223> 3' ITR |
| 72 | <223> AAV-TBG-hLCAT-V114M-co-v1 genome vector<br><220><br><221> repeat_region<br><222> (1) . . . (173)<br><223> 5' ITR<br><220><br><221> enhancer<br><222> (195) . . . (294)<br><223> alpha mic/bik<br><220><br><221> promoter<br><222> (415) . . . (874)<br><223> TBG Promoter<br><220><br><221> Intron<br><222> (918) . . . (1050)<br><223> Chimera intron from human beta-globin and immunoglobulin heavy chain genes<br><220><br><221> misc_feature<br><222> (1110) . . . (2429)<br><223> codon-optimized coding sequence of human LCAT V-114M variant, v1, hLCAT-V114M-co-v1<br><220><br><221> polyA_signal<br><222> (2459) . . . (2580)<br><223> SV40 polyadenylation signal<br><220><br><221> repeat_region<br><222> (2702) . . . (2874)<br><223> 3' ITR |
| 73 | <223> PCR primer for mouse GAPDH |
| 74 | <223> PCR primer for mouse GAPDH |
| 75 | <223> PCR primer set 2 for human LCAT<br><220><br><221> misc_feature<br><222> (2) . . . (2)<br><223> n is a, c, g, or t |
| 76 | <223> PCR primer set 2 for human LCAT |
| 77 | <223> pcDNA3.1-hLCAT-V114P<br><220><br><221> misc_feature<br><222> (2) . . . (1322)<br><223> hLCAT-V114P<br><220><br><221> CDS<br><222> (1389) . . . (1430)<br><223> V5 tag<br><220><br><221> CDS<br><222> (1440) . . . (1457)<br><223> 6 x His tag<br><220><br><221> polyA_signal<br><222> (1486) . . . (1710)<br><223> bGH poly(A) signal<br><220><br><221> enhancer<br><222> (6127) . . . (6506)<br><223> CMV enhancer<br><220><br><221> promoter<br><222> (6507) . . . (6710)<br><223> CMV promoter<br><220><br><221> promoter |

-continued

| SEQ ID NO: (containing free text) | Free text under <223> |
|---|---|
| | <222> (6755) ... (6773) <223> T7 promoter |
| 78 | <223> Synthetic Construct |
| 79 | <223> Synthetic Construct |

All published documents cited in this specification are incorporated herein by reference in their entireties, as is U.S. Provisional Patent Application No. 62/366,423, Filed Jul. 25, 2016. Similarly, the SEQ ID NO which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant viral vector which comprises an expression cassette comprising:
   (a) a nucleic acid sequence comprising SEQ ID NO: 26, SEQ ID NO: 63, or a sequence at least 95% identical to SEQ ID NO: 26 or 63 which encodes a functional human lecithin cholesterol acyltransferase (LCAT) variant comprising: an M amino acid substitution at amino acid residue position 114 based on the residue numbering of WT normal LCAT (V114M); and
   (b) regulatory sequences which direct expression of the LCAT V114M in a host cell, said regulatory sequences being operably linked to the LCAT V114M sequence.

2. The recombinant viral vector according to claim 1, wherein the recombinant viral vector is an adeno-associated virus.

3. The recombinant viral vector according to claim 1, wherein the vector comprises a capsid selected from an AAV8, AAVrh64R1, AAV9, or AAVrh10 capsid.

4. The recombinant viral vector according to claim 1, wherein the LCAT variant is truncated at the N-terminus or C-terminus.

5. The recombinant viral vector according to claim 1, wherein the LCAT variant is delivered as part of a fusion protein.

6. A pharmaceutical composition which comprises at least one viral vector according to claim 1 and one or more of a carrier, excipient, or preservative.

7. A recombinant adeno-associated viral (rAAV) vector which comprises an expression cassette comprising:
   (a) a nucleic acid sequence comprising SEQ ID NO: 26 or a nucleic acid sequence at least 95% identical to SEQ ID NO: 26 encoding a functional human lecithin cholesterol acyltransferase (LCAT variant V114M (SEQ ID NO: 26); and
   (b) regulatory sequences which direct expression of the LCAT variant in a host cell, said regulatory sequences being operably linked to the LCAT variant sequence.

8. The recombinant adeno-associated viral (rAAV) vector according to claim 7, wherein the nucleic acid coding sequence encoding a functional human lecithin cholesterol acyltransferase (LCAT) variant V114M is SEQ ID NO: 26.

9. The recombinant adeno-associated viral (rAAV) vector according to claim 7, wherein the regulatory sequence comprises an enhancer, a promoter, a chimeric intron and a polyA.

10. The recombinant adeno-associated viral (rAAV) vector according to claim 9, wherein the enhancer is an alpha mic/bik enhancer.

11. The recombinant adeno-associated viral (rAAV) vector according to claim 9, wherein the promoter is a TBG promoter.

12. The recombinant adeno-associated viral (rAAV) vector according to claim 9, wherein the chimeric intron comprises a human beta globin.

13. The recombinant adeno-associated viral (rAAV) vector according to claim 9, wherein the chimeric intron comprises a human beta globin and human immunoglobulin heavy chain.

14. The recombinant adeno-associated viral (rAAV) vector according to claim 9, wherein the poly A is an SV40 poly A.

15. The recombinant adeno-associated viral (rAAV) vector according to claim 7 comprising a vector genome in an AAV8 capsid, wherein the vector genome comprises an AAV 5' inverted terminal repeat (ITR), LCAT variant VI14M coding sequence of SEQ ID NO: 26, a regulatory sequence which directs expression of LCAT in a target cell, and an AAV 3' ITR.

16. The recombinant adeno-associated viral (rAAV) vector according to claim 7, wherein the LCAT variant is truncated at the N-terminus or C-terminus.

17. The recombinant adeno-associated viral (rAAV) vector according to claim 7, wherein the LCAT variant is delivered as part of a fusion protein.

18. A pharmaceutical composition which comprises at least one adeno-associated viral (rAAV) vector according to claim 7 and one or more of a carrier, excipient, or preservative.

19. A recombinant adeno-associated viral (rAAV) vector wherein the which comprises an expression cassette comprising:
a nucleic acid sequence comprising hLCAT-V1 14M-v1 of SEQ ID NO: 63 which encodes human lecithin cholesterol acyltransferase (LCAT) variant VI 14M and regulatory sequences operably linked to the coding sequence which direct expression of the LCAT variant.

20. The recombinant adeno-associated viral (rAAV) vector according to claim 19, wherein the LCAT variant is truncated at the N-terminus or C-terminus.

21. The recombinant adeno-associated viral (rAAV) vector according to claim 19, wherein the LCAT variant is delivered as part of a fusion protein.

22. A pharmaceutical composition which comprises the adeno-associated viral (rAAV) vector according to claim 19 and one or more of a carrier, excipient, or preservative.

23. A synthetic or recombinant nucleic acid molecule comprising a nucleic acid sequence comprising SEQ ID NO: 26 or SEQ ID NO: 63 encoding an LCAT variant V114M and further comprising exogenous regulatory sequences which direct expression of the LCAT variant in a target host cell.

24. The synthetic or recombinant nucleic acid molecule according to claim 23, wherein the nucleic acid sequences of the LCAT protein variant is SEQ ID NO: 26.

25. The synthetic or recombinant nucleic acid molecule according to claim 23, wherein the nucleic acid sequences of the LCAT protein variant is SEQ ID NO: 63.

* * * * *

```
                            SEQUENCE LISTING

<160> NUMBER OF SEQ ID NOS: 79

<210> SEQ ID NO 1
<211> LENGTH: 440
<212> TYPE: PRT
<213> ORGANISM: Homo sapiens

<400> SEQUENCE: 1

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
            35                  40                  45

Val Ile Leu Val Pro Gly Cys Leu Gly Asn Gln Leu Glu Ala Lys Leu
        50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu Val Ser Asn Ala Pro Gly Val Gln Ile Arg Val Pro Gly Phe Gly
        115                 120                 125

Lys Thr Tyr Ser Val Glu Tyr Leu Asp Ser Ser Lys Leu Ala Gly Tyr
    130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205

Leu His Leu Leu Tyr Phe Leu Leu Arg Gln Pro Gln Ala Trp Lys Asp
    210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255
```

```
Ile Met Ser Ser Ile Lys Leu Lys Glu Gln Arg Ile Thr Thr Thr
            260                 265                 270
Ser Pro Trp Met Phe Pro Ser Arg Met Ala Trp Pro Glu Asp His Val
        275                 280                 285
Phe Ile Ser Thr Pro Ser Phe Asn Tyr Thr Gly Arg Asp Phe Gln Arg
    290                 295                 300
Phe Phe Ala Asp Leu His Phe Glu Glu Gly Trp Tyr Met Trp Leu Gln
305                 310                 315                 320
Ser Arg Asp Leu Leu Ala Gly Leu Pro Ala Pro Gly Val Glu Val Tyr
                325                 330                 335
Cys Leu Tyr Gly Val Gly Leu Pro Thr Pro Arg Thr Tyr Ile Tyr Asp
            340                 345                 350
His Gly Phe Pro Tyr Thr Asp Pro Val Gly Val Leu Tyr Glu Asp Gly
        355                 360                 365
Asp Asp Thr Val Ala Thr Arg Ser Thr Glu Leu Cys Gly Leu Trp Gln
    370                 375                 380
Gly Arg Gln Pro Gln Pro Val His Leu Leu Pro Leu His Gly Ile Gln
385                 390                 395                 400
His Leu Asn Met Val Phe Ser Asn Leu Thr Leu Glu His Ile Asn Ala
                405                 410                 415
Ile Leu Leu Gly Ala Tyr Arg Gln Gly Pro Pro Ala Ser Pro Thr Ala
            420                 425                 430
Ser Pro Glu Pro Pro Pro Glu
        435                 440

<210> SEQ ID NO 2
<211> LENGTH: 1323
<212> TYPE: DNA
<213> ORGANISM: Homo sapiens

<400> SEQUENCE: 2
atggggccgc ccggctcccc atggcagtgg gtgacgctgc tgctggggct gctgctccct    60
cctgccgccc ccttctggct cctcaatgtg ctcttccccc gcacaccac gcccaaggct    120
gagctcagta accacacacg gcccgtcatc ctcgtgcccg ctgcctggg gaatcagcta    180
gaagccaagc tggacaaacc agatgtggtg aactggatgt gctaccgcaa gacagaggac    240
ttcttcacca tctggctgga tctcaacatg ttcctacccc ttggggtaga ctgctggatc    300
gataacacca gggttgtcta caaccggagc tctgggctcg tgtccaacgc ccctggtgtc    360
cagatccgcg tccctggctt tggcaagacc tactctgtgg agtacctgga cagcagcaag    420
ctggcagggt acctgcacac actggtgcag aacctggtca caatggcta cgtgcgggac    480
gagactgtgc gcgccgcccc ctatgactgg cggctggagc ccggccagca ggaggagtac    540
taccgcaagc tcgcagggct ggtggaggag atgcacgctg cctatgggaa gcctgtcttc    600
ctcattggcc acagcctcgg ctgtctacac ttgctctatt cctgctgcg ccagccccag    660
gcctggaagg accgctttat tgatggcttc atctctcttg ggctccctg ggtggctcc    720
atcaagccca tgctggtctt ggcctcaggt gacaaccagg catcccat catgtccagc    780
atcaagctga agaggagca cgcataacc accacctccc cctggatgtt ccctctcgc    840
atggcgtggc ctgaggacca cgtgttcatt ccacaccca gcttcaacta cacaggccgt    900
gacttccaac gcttctttgc agacctgcac tttgaggaag ctggtacat gtggctgcag    960
tcacgtgacc tcctgcagg actcccagca cctggtgtgg aagtatactg tctttacggc    1020
gtgggcctgc ccacgccccg cacctacatc tacgaccacg gcttcccta cacggaccct    1080
```

```
gtgggtgtgc tctatgagga tggtgatgac acggtggcga cccgcagcac cgagctctgt    1140
ggcctgtggc agggccgcca gccacagcct gtgcacctgc tgcccctgca cgggatacag    1200
catctcaaca tggtcttcag caacctgacc ctggagcaca tcaatgccat cctgctgggt    1260
gcctaccgcc agggtccccc tgcatccccg actgccagcc agagcccccc gcctcctgaa    1320
taa                                                                 1323
```

<210> SEQ ID NO 3
<211> LENGTH: 1323
<212> TYPE: DNA
<213> ORGANISM: Artificial Sequence
<220> FEATURE:
<223> OTHER INFORMATION: Codon-optimized human LCAT coding sequence v1

<400> SEQUENCE: 3

```
atggggcccc ccgggagccc ctggcagtgg gtgaccctgc tgctggggct gctgctgccc    60
cccgccgccc ccttctggct gctgaacgtg ctgttccccc ccacaccac ccccaaggcc    120 gagctgagca accacacccg gcccgtgatc ctggtgcccg ggtgcctggg aaccagctg    180 gaggccaagc tggacaagcc cgacgtggtg aactggatgt gctaccggaa gaccgaggac    240
ttcttcacca tctggctgga cctgaacatg ttcctgcccc tgggggtgga ctgctggatc    300
gacaacaccc cggtggtgta caaccggagc agcgggctgg tgagcaacgc ccccggggtg    360
cagatccggg tgcccgggtt cgggaagacc tacagcgtgg agtacctgga cagcagcaag    420
ctggccgggt acctgcacac cctggtgcag aacctggtga caacgggta cgtgcgggac    480 gaaaccgtgc gggccgcccc ctacgactgg cggctggagc ccggcagca ggaggagtac    540 taccggaagc tggccgggct ggtggaggag atgcacgccg cctacgggaa gcccgtgttc    600
ctgatcgggc acagcctggg tgtgctgcac ctcctgtact tcctgctgcg gcagcccag    660 gcctggaagg accggttcat cgacgggttc atcagcctgg ggccccctg ggagggagc    720 atcaagccca tgctggtgct ggccagcggg gacaaccagg ggatccccat catgagcagc    780
atcaagctga aggaggagca gcggatcacc accaccagcc cctggatgtt ccccagccgg    840
atggcctggc ccgaggacca cgtgttcatc agcacccca gcttcaacta caccgggcgg    900
gacttccagc ggttcttcgc cgacctgcac ttcgaggagg gtggtacat gtggctgcag    960 agccgggacc tgctggccgg gctgcccgcc ccggggtgg aggtgtactg cctgtacggg    1020
gtggggctgc ccacccccg gacctacatc tacgaccacg ggttccccta caccgacccc    1080 gtggggtgc tgtacgagga cggggacgac accgtggcca cccggagcac cgagctgtgc    1140
gggctgtggc aggggcggca gccccagccc gtgcacctcc tgcccctgca cgggatccag    1200
cacctgaaca tggtgttcag caacctgacc ctggagcaca tcaacgccat cctgctgggg    1260
gcctaccggc aggggccccc cgccagcccc accgccagcc ccgagccccc accccccgag    1320
tga                                                                 1323
```

<210> SEQ ID NO 4
<211> LENGTH: 1323
<212> TYPE: DNA
<213> ORGANISM: Artificial Sequence
<220> FEATURE:
<223> OTHER INFORMATION: Codon-optimized human LCAT coding sequence v11

<400> SEQUENCE: 4

```
atgggcccc ccggcagccc ctggcagtgg gtgaccctgc tgctggggcct gctgctgccc    60
```

```
cccgctgctc ccttttggct gctgaacgtg ctgtttcccc cccacaccac ccccaaggct      120
gaactgagca accacacccg gcccgtgatt ctggtgcccg gctgtctggg caaccagctg      180
gaagctaagc tggacaagcc cgacgtggtg aactggatgt gttaccggaa gaccgaagac      240
ttttttacca tttggctgga cctgaacatg tttctgcccc tgggcgtgga ctgttggatt      300
gacaacaccc gggtggtgta caaccggagc agcggcctgg tgagcaacgc tcccggcgtg      360
cagattcggg tgcccggctt tggcaagacc tacagcgtgg aatacctgga cagcagcaag      420
ctggctggct acctgcacac cctggtgcag aacctggtga caacggcta cgtgcgggac      480 gaaaccgtgc gggctgctcc ctacgactgg cggctggaac ccggccagca ggaagaatac      540
taccggaagc tggctggcct ggtggaagaa atgcacgctg cttacggcaa gcccgtgttt      600
ctgattggcc acagcctggg ctgtctgcat ctgctgtact ttctgctgcg gcagccccag      660
gcttggaagg accggtttat tgacggcttt attagcctgg gcgctccctg gggcggcagc      720
attaagccca tgctggtgct ggctagcggc gacaaccagg gcattcccat tatgagcagc      780
attaagctga aggaagaaca gcggattacc accaccagcc cctggatgtt ccccagccgg      840
atggcttggc ccgaagacca cgtgtttatt agcacccccca gctttaacta caccggccgg      900
gactttcagc ggttttttgc tgacctgcac tttgaagaag ctggtacat gtggctgcag      960 agccgggacc tgctggctgg cctgcccgct cccggcgtgg aagtgtactg tctgtacggc      1020
gtgggcctgc caccccccg gacctacatt tacgaccacg gctttcccta caccgaccccc    1080 gtgggcgtgc tgtacgaaga cggcgacgac accgtggcta cccggagcac cgaactgtgt     1140
ggcctgtggc agggccggca gccccagccc gtgcatctgc tgccccctgca cggcattcag     1200 cacctgaaca tggtgtttag caacctgacc ctggaacaca ttaacgctat tctgctgggc     1260
gcttaccggc agggccccc cgctagcccc accgctagcc ccgaacccc accccccgag      1320 tga                                                                   1323

<210> SEQ ID NO 5
<211> LENGTH: 1323
<212> TYPE: DNA
<213> ORGANISM: Artificial Sequence
<220> FEATURE:
<223> OTHER INFORMATION: Codon-optimized human LCAT coding sequence v26

<400> SEQUENCE: 5
atgggtcccc ccggttcacc ctggcagtgg gtgaccctgc tgctgggtct gctgctgccc      60
cccgctgctc ccttttggct gctgaacgtg ctgtttcccc ccataccac ccccaaggct      120 gaactgtcaa atcatacccg ccccgtgatc ctggtgcccg gttgcctggg taatcagctg      180
gaagctaagc tggacaagcc cgacgtggtg aattggatgt gctaccgcaa gaccgaagac      240
ttttttacca tctggctgga cctgaatatg tttctgcccc tgggtgtgga ctgctggatc      300
gacaataccc gcgtggtgta caatcgctca tcaggtctgg tgtcaaacgc tcccggtgtg      360
cagatccgcg tgcccggttt tggtaagacc tactcagtgg aatacctgga ctcatcaaag      420
ctggctggtt acctgcatac cctggtgcag aatctggtga ataacggtta cgtgcgcgac      480
gaaaccgtgc gcgctgctcc ctacgactgg cgcctggaac ccggtcagca ggaagaatac     540
taccgcaagc tggctggtct ggtggaagaa atgcacgctg cttacggtaa gcccgtgttt      600
ctgatcggtc attcactggg ttgcctgcat ctgctgtact ttctgctgcg ccagccccag      660
gcttggaagg accgctttat cgacggtttt atctcactgg gtgctccctg ggtggttca      720 atcaagccca tgctggtgct ggcttcaggt gacaatcagg gtatccccat catgtcatca      780
```

```
atcaagctga aggaagaaca gcgcatcacc accacctcac cctggatgtt tccctcacgc    840
atggcttggc ccgaagacca cgtgtttatc tcaaccccct catttaatta caccggtcgc    900
gactttcagc gctttttgc tgacctgcat tttgaagaag gttggtacat gtggctgcag     960
tcacgcgacc tgctggctgg tctgcccgct cccggtgtgg aagtgtactg cctgtacggt    1020
gtgggtctgc cacccccg cacctacatc tacgaccacg ttttcccta caccgacccc      1080 gtgggtgtgc tgtacgaaga cggtgacgac accgtggcta cccgctcaac cgaactgtgc    1140
ggtctgtggc agggtcgcca gccccagccc gtgcatctgc tgcccctgca tggtatccag    1200
catctgaata tggtgttttc aaatctgacc ctggaacata tcaacgctat cctgctgggt    1260
gcttaccgcc agggtccccc cgcttcaccc accgcttcac ccgaaccccc accccccgag    1320
tga                                                                 1323
```

<210> SEQ ID NO 6
<211> LENGTH: 1323
<212> TYPE: DNA
<213> ORGANISM: Artificial Sequence
<220> FEATURE:
<223> OTHER INFORMATION: Codon-optimized human LCAT coding sequence v201

<400> SEQUENCE: 6

```
atgggacctc ctggaagccc ttggcagtgg gtgaccctgc tgctgggact gctgctgcct    60
cctgccgccc ctttctggct gctgaacgtg ctgttccctc ctcacaccac ccctaaggcc    120
gagctgagca accacacccg gcctgtgatc ctggtgcctg ctgcctggg aaaccagctg    180 gaggccaagc tggacaagcc tgacgtggtg aactggatgt gctaccggaa gaccgaggac    240
ttcttcacca tctggctgga cctgaacatg ttcctgcctc tgggagtgga ctgctggatc    300
gacaacaccc gggtggtgta caaccggagc agcggactgt gagcaacgc ccctggagtg    360 cagatccggg tgcctggatt cggaaagacc tacagcgtgg agtacctgga cagcagcaag    420
ctggccggat acctgcacac cctggtgcag aacctggtga caacggata cgtgcgggac    480 gagacagtgc gggccgcccc ttacgactgg cggctggagc ctggacagca ggaggagtac    540
taccggaagc tggccggact ggtggaggag atgcacgccg cctacggaaa gcctgtgttc    600
ctgatcggac acagcctggg ctgcctgcat ctgctgtact cctgctgcg gcagcctcag    660 gcctggaagg accggttcat cgacggattc atcagcctgg agccccttg gggaggaagc    720 atcaagccta tgctggtgct ggccagcgga gacaaccagg gaatccctat catgagcagc    780
atcaagctga aggaggagca gcggatcacc accaccagcc cttggatgtt ccctagccgg    840
atggcctggc ctgaggacca cgtgttcatc agcacccta gcttcaacta caccggacgg    900
gacttccagc ggttcttcgc cgacctgcac ttcgaggagg ctggtacat gtggctgcag    960 agccgggacc tgctggccgg actgcctgcc cctggagtgg aggtgtactg cctgtacgga    1020
gtgggactgc taccccctcg gacctacatc tacgaccacg gattcccta caccgaccct    1080 gtgggagtgc tgtacgagga cggagacgac accgtggcca cccggagcac cgagctgtgc    1140
ggactgtggc agggacggca gcctcagcct gtgcatctgc tgcctctgca cggaatccag    1200
cacctgaaca tggtgttcag caacctgacc ctggagcaca tcaacgccat cctgctggga    1260
gcctaccggc agggacctcc tgccagccct accgcagcc ctgagcctcc tcctcctgag    1320
tga                                                                 1323
```

<210> SEQ ID NO 7

```
<211> LENGTH: 440
<212> TYPE: PRT
<213> ORGANISM: Homo sapiens

<400> SEQUENCE: 7

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
            20                  25                  30

Pro Pro His Thr Thr Pro Lys Ala Glu Leu Ser Asn His Thr Arg Pro
        35                  40                  45

Val Ile Leu Val Pro Gly Cys Leu Gly Asn Gln Leu Glu Ala Lys Leu
50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu Met Ser Asn Ala Pro Gly Val Gln Ile Arg Val Pro Gly Phe Gly
        115                 120                 125

Lys Thr Tyr Ser Val Glu Tyr Leu Asp Ser Ser Lys Leu Ala Gly Tyr
130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205

Leu His Leu Leu Tyr Phe Leu Leu Arg Gln Pro Gln Ala Trp Lys Asp
210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
        275                 280                 285

Phe Ile Ser Thr Pro Ser Phe Asn Tyr Thr Gly Arg Asp Phe Gln Arg
290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
        355                 360                 365

Asp Asp Thr Val Ala Thr Arg Ser Thr Glu Leu Cys Gly Leu Trp Gln
370                 375                 380

Gly Arg Gln Pro Gln Pro Val His Leu Leu Pro Leu His Gly Ile Gln
```

His Leu Asn Met Val Phe Ser Asn Leu Thr Leu Glu His Ile Asn Ala
385                 390                 395                 400

Ile Leu Leu Gly Ala Tyr Arg Gln Gly Pro Ala Ser Pro Thr Ala
            405                 410                 415

Ser Pro Glu Pro Pro Pro Glu
        435                 440

<210> SEQ ID NO 8
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114A

<400> SEQUENCE: 8

Met Gly Pro Pro Gly Ser Pro Trp Gln Trp Val Thr Leu Leu Gly
1               5                   10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
            35                  40                  45

Val Ile Leu Val Pro Gly Cys Leu Gly Asn Gln Leu Glu Ala Lys Leu
50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu Ala Ser Asn Ala Pro Gly Val Gln Ile Arg Val Pro Gly Phe Gly
            115                 120                 125

Lys Thr Tyr Ser Val Glu Tyr Leu Asp Ser Ser Lys Leu Ala Gly Tyr
            130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
            195                 200                 205

Leu His Leu Leu Tyr Phe Leu Leu Arg Gln Pro Gln Ala Trp Lys Asp
210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
            275                 280                 285

Phe Ile Ser Thr Pro Ser Phe Asn Tyr Thr Gly Arg Asp Phe Gln Arg
            290                 295                 300

```
Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
                340                 345                 350

His Gly Phe Pro Tyr Thr Asp Pro Val Gly Val Leu Tyr Glu Asp Gly
                355                 360                 365

Asp Asp Thr Val Ala Thr Arg Ser Thr Glu Leu Cys Gly Leu Trp Gln
370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
                420                 425                 430

Ser Pro Glu Pro Pro Pro Glu
                435                 440

<210> SEQ ID NO 9
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114C

<400> SEQUENCE: 9

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
            35                  40                  45

Val Ile Leu Val Pro Gly Cys Leu Gly Asn Gln Leu Glu Ala Lys Leu
        50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
                100                 105                 110

Leu Cys Ser Asn Ala Pro Gly Val Gln Ile Arg Val Pro Gly Phe Gly
            115                 120                 125

Lys Thr Tyr Ser Val Glu Tyr Leu Asp Ser Ser Lys Leu Ala Gly Tyr
            130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205

Leu His Leu Leu Tyr Phe Leu Leu Arg Gln Pro Gln Ala Trp Lys Asp
    210                 215                 220
```

-continued

```
Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
            245                 250                 255

Ile Met Ser Ser Ile Lys Leu Lys Glu Glu Gln Arg Ile Thr Thr Thr
        260                 265                 270

Ser Pro Trp Met Phe Pro Ser Arg Met Ala Trp Pro Glu Asp His Val
    275                 280                 285

Phe Ile Ser Thr Pro Ser Phe Asn Tyr Thr Gly Arg Asp Phe Gln Arg
290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
        355                 360                 365

Asp Asp Thr Val Ala Thr Arg Ser Thr Glu Leu Cys Gly Leu Trp Gln
370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
            420                 425                 430

Ser Pro Glu Pro Pro Pro Pro Glu
        435                 440

<210> SEQ ID NO 10
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114D

<400> SEQUENCE: 10

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
            20                  25                  30

Pro Pro His Thr Thr Pro Lys Ala Glu Leu Ser Asn His Thr Arg Pro
        35                  40                  45

Val Ile Leu Val Pro Gly Cys Leu Gly Asn Gln Leu Glu Ala Lys Leu
50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu Asp Ser Asn Ala Pro Gly Val Gln Ile Arg Val Pro Gly Phe Gly
        115                 120                 125

Lys Thr Tyr Ser Val Glu Tyr Leu Asp Ser Ser Lys Leu Ala Gly Tyr
```

```
                130             135             140
Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
            195                 200                 205

Leu His Leu Leu Tyr Phe Leu Leu Arg Gln Pro Gln Ala Trp Lys Asp
        210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
        275                 280                 285

Phe Ile Ser Thr Pro Ser Phe Asn Tyr Thr Gly Arg Asp Phe Gln Arg
        290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
            355                 360                 365

Asp Asp Thr Val Ala Thr Arg Ser Thr Glu Leu Cys Gly Leu Trp Gln
        370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
            420                 425                 430

Ser Pro Glu Pro Pro Pro Glu
        435                 440

<210> SEQ ID NO 11
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114E

<400> SEQUENCE: 11

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
            20                  25                  30

Pro Pro His Thr Thr Pro Lys Ala Glu Leu Ser Asn His Thr Arg Pro
        35                  40                  45
```

Val Ile Leu Val Pro Gly Cys Leu Gly Asn Gln Leu Glu Ala Lys Leu
 50                  55                  60

Asp Lys Pro Asp Val Val Asn Trp Met Cys Tyr Arg Lys Thr Glu Asp
 65                  70                  75                  80

Phe Phe Thr Ile Trp Leu Asp Leu Asn Met Phe Leu Pro Leu Gly Val
                 85                  90                  95

Asp Cys Trp Ile Asp Asn Thr Arg Val Val Tyr Asn Arg Ser Ser Gly
                100                 105                 110

Leu Glu Ser Asn Ala Pro Gly Val Gln Ile Arg Val Pro Gly Phe Gly
            115                 120                 125

Lys Thr Tyr Ser Val Glu Tyr Leu Asp Ser Ser Lys Leu Ala Gly Tyr
130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Met His
            180                 185                 190

Ala Ala Tyr Gly Lys Pro Val Phe Leu Ile Gly His Ser Leu Gly Cys
            195                 200                 205

Leu His Leu Leu Tyr Phe Leu Leu Arg Gln Pro Gln Ala Trp Lys Asp
210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
            275                 280                 285

Phe Ile Ser Thr Pro Ser Phe Asn Tyr Thr Gly Arg Asp Phe Gln Arg
290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
            355                 360                 365

Asp Asp Thr Val Ala Thr Arg Ser Thr Glu Leu Cys Gly Leu Trp Gln
370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
            420                 425                 430

Ser Pro Glu Pro Pro Pro Glu
            435                 440

<210> SEQ ID NO 12
<211> LENGTH: 440
<212> TYPE: PRT

<213> ORGANISM: Artificial Sequence
<220> FEATURE:
<223> OTHER INFORMATION: Amino acid sequence of human LCAT protein variant V114F

<400> SEQUENCE: 12

| | | | | | | | | | | | | | | |
|---|---|---|---|---|---|---|---|---|---|---|---|---|---|---|
| Met | Gly | Pro | Pro | Ser | Pro | Trp | Gln | Trp | Val | Thr | Leu | Leu | Leu | Gly |
| 1 | | | | 5 | | | | | 10 | | | | | 15 |
| Leu | Leu | Leu | Pro | Pro | Ala | Ala | Pro | Phe | Trp | Leu | Leu | Asn | Val | Leu | Phe |
| | | | 20 | | | | | 25 | | | | | 30 | | |
| Pro | Pro | His | Thr | Thr | Pro | Lys | Ala | Glu | Leu | Ser | Asn | His | Thr | Arg | Pro |
| | | | 35 | | | | | 40 | | | | | 45 | | |
| Val | Ile | Leu | Val | Pro | Gly | Cys | Leu | Gly | Asn | Gln | Leu | Glu | Ala | Lys | Leu |
| | 50 | | | | | 55 | | | | | 60 | | | | |
| Asp | Lys | Pro | Asp | Val | Val | Asn | Trp | Met | Cys | Tyr | Arg | Lys | Thr | Glu | Asp |
| 65 | | | | | 70 | | | | | 75 | | | | | 80 |
| Phe | Phe | Thr | Ile | Trp | Leu | Asp | Leu | Asn | Met | Phe | Leu | Pro | Leu | Gly | Val |
| | | | | 85 | | | | | 90 | | | | | 95 | |
| Asp | Cys | Trp | Ile | Asp | Asn | Thr | Arg | Val | Val | Tyr | Asn | Arg | Ser | Ser | Gly |
| | | | | 100 | | | | | 105 | | | | | 110 | |
| Leu | Phe | Ser | Asn | Ala | Pro | Gly | Val | Gln | Ile | Arg | Val | Pro | Gly | Phe | Gly |
| | | | 115 | | | | | 120 | | | | | 125 | | |
| Lys | Thr | Tyr | Ser | Val | Glu | Tyr | Leu | Asp | Ser | Ser | Lys | Leu | Ala | Gly | Tyr |
| | 130 | | | | | 135 | | | | | 140 | | | | |
| Leu | His | Thr | Leu | Val | Gln | Asn | Leu | Val | Asn | Asn | Gly | Tyr | Val | Arg | Asp |
| 145 | | | | | 150 | | | | | 155 | | | | | 160 |
| Glu | Thr | Val | Arg | Ala | Ala | Pro | Tyr | Asp | Trp | Arg | Leu | Glu | Pro | Gly | Gln |
| | | | | 165 | | | | | 170 | | | | | 175 | |
| Gln | Glu | Glu | Tyr | Tyr | Arg | Lys | Leu | Ala | Gly | Leu | Val | Glu | Glu | Met | His |
| | | | 180 | | | | | 185 | | | | | 190 | | |
| Ala | Ala | Tyr | Gly | Lys | Pro | Val | Phe | Leu | Ile | Gly | His | Ser | Leu | Gly | Cys |
| | | | 195 | | | | | 200 | | | | | 205 | | |
| Leu | His | Leu | Leu | Tyr | Phe | Leu | Leu | Arg | Gln | Pro | Gln | Ala | Trp | Lys | Asp |
| | 210 | | | | | 215 | | | | | 220 | | | | |
| Arg | Phe | Ile | Asp | Gly | Phe | Ile | Ser | Leu | Gly | Ala | Pro | Trp | Gly | Gly | Ser |
| 225 | | | | | 230 | | | | | 235 | | | | | 240 |
| Ile | Lys | Pro | Met | Leu | Val | Leu | Ala | Ser | Gly | Asp | Asn | Gln | Gly | Ile | Pro |
| | | | | 245 | | | | | 250 | | | | | 255 | |
| Ile | Met | Ser | Ser | Ile | Lys | Leu | Lys | Glu | Glu | Gln | Arg | Ile | Thr | Thr | Thr |
| | | | 260 | | | | | 265 | | | | | 270 | | |
| Ser | Pro | Trp | Met | Phe | Pro | Ser | Arg | Met | Ala | Trp | Pro | Glu | Asp | His | Val |
| | | | 275 | | | | | 280 | | | | | 285 | | |
| Phe | Ile | Ser | Thr | Pro | Ser | Phe | Asn | Tyr | Thr | Gly | Arg | Asp | Phe | Gln | Arg |
| | | | 290 | | | | | 295 | | | | | 300 | | |
| Phe | Phe | Ala | Asp | Leu | His | Phe | Glu | Glu | Gly | Trp | Tyr | Met | Trp | Leu | Gln |
| 305 | | | | | 310 | | | | | 315 | | | | | 320 |
| Ser | Arg | Asp | Leu | Leu | Ala | Gly | Leu | Pro | Ala | Pro | Gly | Val | Glu | Val | Tyr |
| | | | | 325 | | | | | 330 | | | | | 335 | |
| Cys | Leu | Tyr | Gly | Val | Gly | Leu | Pro | Thr | Pro | Arg | Thr | Tyr | Ile | Tyr | Asp |
| | | | 340 | | | | | 345 | | | | | 350 | | |
| His | Gly | Phe | Pro | Tyr | Thr | Asp | Pro | Val | Gly | Val | Leu | Tyr | Glu | Asp | Gly |
| | | | 355 | | | | | 360 | | | | | 365 | | |
| Asp | Asp | Thr | Val | Ala | Thr | Arg | Ser | Thr | Glu | Leu | Cys | Gly | Leu | Trp | Gln |
| | 370 | | | | | 375 | | | | | 380 | | | | |

```
Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
            405                 410                 415

Ile Leu Leu Gly Ala Tyr Arg Gln Gly Pro Pro Ala Ser Pro Thr Ala
            420                 425                 430

Ser Pro Glu Pro Pro Pro Glu
        435                 440

<210> SEQ ID NO 13
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114G

<400> SEQUENCE: 13

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
            20                  25                  30

Pro Pro His Thr Thr Pro Lys Ala Glu Leu Ser Asn His Thr Arg Pro
            35                  40                  45

Val Ile Leu Val Pro Gly Cys Leu Gly Asn Gln Leu Glu Ala Lys Leu
50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
                100                 105                 110

Leu Gly Ser Asn Ala Pro Gly Val Gln Ile Arg Val Pro Gly Phe Gly
            115                 120                 125

Lys Thr Tyr Ser Val Glu Tyr Leu Asp Ser Ser Lys Leu Ala Gly Tyr
130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
            195                 200                 205

Leu His Leu Leu Tyr Phe Leu Leu Arg Gln Pro Gln Ala Trp Lys Asp
210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
        275                 280                 285

Phe Ile Ser Thr Pro Ser Phe Asn Tyr Thr Gly Arg Asp Phe Gln Arg
290                 295                 300
```

```
Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
        355                 360                 365

Asp Asp Thr Val Ala Thr Arg Ser Thr Glu Leu Cys Gly Leu Trp Gln
370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
                420                 425                 430

Ser Pro Glu Pro Pro Pro Pro Glu
        435                 440

<210> SEQ ID NO 14
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114H

<400> SEQUENCE: 14

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
            35                  40                  45

Val Ile Leu Val Pro Gly Cys Leu Gly Asn Gln Leu Glu Ala Lys Leu
50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu His Ser Asn Ala Pro Gly Val Gln Ile Arg Val Pro Gly Phe Gly
        115                 120                 125

Lys Thr Tyr Ser Val Glu Tyr Leu Asp Ser Ser Lys Leu Ala Gly Tyr
    130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205

Leu His Leu Leu Tyr Phe Leu Leu Arg Gln Pro Gln Ala Trp Lys Asp
```

```
                210                 215                 220
Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
                260                 265                 270

Ser Pro Trp Met Phe Pro Ser Arg Met Ala Trp Pro Glu Asp His Val
                275                 280                 285

Phe Ile Ser Thr Pro Ser Phe Asn Tyr Thr Gly Arg Asp Phe Gln Arg
                290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
                340                 345                 350

His Gly Phe Pro Tyr Thr Asp Pro Val Gly Val Leu Tyr Glu Asp Gly
                355                 360                 365

Asp Asp Thr Val Ala Thr Arg Ser Thr Glu Leu Cys Gly Leu Trp Gln
                370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
                420                 425                 430

Ser Pro Glu Pro Pro Pro Glu
                435                 440

<210> SEQ ID NO 15
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114I

<400> SEQUENCE: 15

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
                35                  40                  45

Val Ile Leu Val Pro Gly Cys Leu Gly Asn Gln Leu Glu Ala Lys Leu
                50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
                100                 105                 110

Leu Ile Ser Asn Ala Pro Gly Val Gln Ile Arg Val Pro Gly Phe Gly
                115                 120                 125
```

Lys Thr Tyr Ser Val Glu Tyr Leu Asp Ser Ser Lys Leu Ala Gly Tyr
130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205

Leu His Leu Leu Tyr Phe Leu Leu Arg Gln Pro Gln Ala Trp Lys Asp
210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
        275                 280                 285

Phe Ile Ser Thr Pro Ser Phe Asn Tyr Thr Gly Arg Asp Phe Gln Arg
290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
        355                 360                 365

Asp Asp Thr Val Ala Thr Arg Ser Thr Glu Leu Cys Gly Leu Trp Gln
370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
            420                 425                 430

Ser Pro Glu Pro Pro Pro Pro Glu
        435                 440

<210> SEQ ID NO 16
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114K

<400> SEQUENCE: 16

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
            35                  40                  45

-continued

```
Val Ile Leu Val Pro Gly Cys Leu Gly Asn Gln Leu Glu Ala Lys Leu
 50                  55                  60

Asp Lys Pro Asp Val Val Asn Trp Met Cys Tyr Arg Lys Thr Glu Asp
 65                  70                  75                  80

Phe Phe Thr Ile Trp Leu Asp Leu Asn Met Phe Leu Pro Leu Gly Val
                 85                  90                  95

Asp Cys Trp Ile Asp Asn Thr Arg Val Val Tyr Asn Arg Ser Ser Gly
                100                 105                 110

Leu Lys Ser Asn Ala Pro Gly Val Gln Ile Arg Val Pro Gly Phe Gly
                115                 120                 125

Lys Thr Tyr Ser Val Glu Tyr Leu Asp Ser Ser Lys Leu Ala Gly Tyr
    130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                    165                 170                 175

Gln Glu Glu Tyr Tyr Arg Lys Leu Ala Gly Leu Val Glu Glu Met His
                180                 185                 190

Ala Ala Tyr Gly Lys Pro Val Phe Leu Ile Gly His Ser Leu Gly Cys
                195                 200                 205

Leu His Leu Leu Tyr Phe Leu Leu Arg Gln Pro Gln Ala Trp Lys Asp
210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
                260                 265                 270

Ser Pro Trp Met Phe Pro Ser Arg Met Ala Trp Pro Glu Asp His Val
                275                 280                 285

Phe Ile Ser Thr Pro Ser Phe Asn Tyr Thr Gly Arg Asp Phe Gln Arg
290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
                340                 345                 350

His Gly Phe Pro Tyr Thr Asp Pro Val Gly Val Leu Tyr Glu Asp Gly
                355                 360                 365

Asp Asp Thr Val Ala Thr Arg Ser Thr Glu Leu Cys Gly Leu Trp Gln
370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
                420                 425                 430

Ser Pro Glu Pro Pro Pro Glu
    435                 440
```

<210> SEQ ID NO 17
<211> LENGTH: 440

<212> TYPE: PRT
<213> ORGANISM: Artificial Sequence
<220> FEATURE:
<223> OTHER INFORMATION: Amino acid sequence of human LCAT protein variant V114L

<400> SEQUENCE: 17

```
Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
            20                  25                  30

Pro Pro His Thr Thr Pro Lys Ala Glu Leu Ser Asn His Thr Arg Pro
        35                  40                  45

Val Ile Leu Val Pro Gly Cys Leu Gly Asn Gln Leu Glu Ala Lys Leu
    50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu Leu Ser Asn Ala Pro Gly Val Gln Ile Arg Val Pro Gly Phe Gly
        115                 120                 125

Lys Thr Tyr Ser Val Glu Tyr Leu Asp Ser Ser Lys Leu Ala Gly Tyr
    130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205

Leu His Leu Leu Tyr Phe Leu Leu Arg Gln Pro Gln Ala Trp Lys Asp
    210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
        275                 280                 285

Phe Ile Ser Thr Pro Ser Phe Asn Tyr Thr Gly Arg Asp Phe Gln Arg
    290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
        355                 360                 365

Asp Asp Thr Val Ala Thr Arg Ser Thr Glu Leu Cys Gly Leu Trp Gln
    370                 375                 380
```

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
            405                 410                 415

Ile Leu Leu Gly Ala Tyr Arg Gln Gly Pro Pro Ala Ser Pro Thr Ala
        420                 425                 430

Ser Pro Glu Pro Pro Pro Glu
        435                 440

<210> SEQ ID NO 18
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114N

<400> SEQUENCE: 18

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
            20                  25                  30

Pro Pro His Thr Thr Pro Lys Ala Glu Leu Ser Asn His Thr Arg Pro
        35                  40                  45

Val Ile Leu Val Pro Gly Cys Leu Gly Asn Gln Leu Glu Ala Lys Leu
    50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu Asn Ser Asn Ala Pro Gly Val Gln Ile Arg Val Pro Gly Phe Gly
        115                 120                 125

Lys Thr Tyr Ser Val Glu Tyr Leu Asp Ser Ser Lys Leu Ala Gly Tyr
    130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205

Leu His Leu Leu Tyr Phe Leu Leu Arg Gln Pro Gln Ala Trp Lys Asp
    210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
        275                 280                 285

Phe Ile Ser Thr Pro Ser Phe Asn Tyr Thr Gly Arg Asp Phe Gln Arg

```
              290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
                340                 345                 350

His Gly Phe Pro Tyr Thr Asp Pro Val Gly Val Leu Tyr Glu Asp Gly
                355                 360                 365

Asp Asp Thr Val Ala Thr Arg Ser Thr Glu Leu Cys Gly Leu Trp Gln
        370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
                420                 425                 430

Ser Pro Glu Pro Pro Pro Glu
        435                 440

<210> SEQ ID NO 19
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114P

<400> SEQUENCE: 19

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
            35                  40                  45

Val Ile Leu Val Pro Gly Cys Leu Gly Asn Gln Leu Glu Ala Lys Leu
        50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu Pro Ser Asn Ala Pro Gly Val Gln Ile Arg Val Pro Gly Phe Gly
            115                 120                 125

Lys Thr Tyr Ser Val Glu Tyr Leu Asp Ser Ser Lys Leu Ala Gly Tyr
        130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205
```

```
Leu His Leu Leu Tyr Phe Leu Leu Arg Gln Pro Gln Ala Trp Lys Asp
        210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
        260                 265                 270

Ser Pro Trp Met Phe Pro Ser Arg Met Ala Trp Pro Glu Asp His Val
        275                 280                 285

Phe Ile Ser Thr Pro Ser Phe Asn Tyr Thr Gly Arg Asp Phe Gln Arg
    290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
        355                 360                 365

Asp Asp Thr Val Ala Thr Arg Ser Thr Glu Leu Cys Gly Leu Trp Gln
370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
            420                 425                 430

Ser Pro Glu Pro Pro Pro Glu
        435                 440

<210> SEQ ID NO 20
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114Q

<400> SEQUENCE: 20

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
            35                  40                  45

Val Ile Leu Val Pro Gly Cys Leu Gly Asn Gln Leu Glu Ala Lys Leu
        50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu Gln Ser Asn Ala Pro Gly Val Gln Ile Arg Val Pro Gly Phe Gly
        115                 120                 125
```

Lys Thr Tyr Ser Val Glu Tyr Leu Asp Ser Ser Lys Leu Ala Gly Tyr
            130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205

Leu His Leu Leu Tyr Phe Leu Leu Arg Gln Pro Gln Ala Trp Lys Asp
    210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
        275                 280                 285

Phe Ile Ser Thr Pro Ser Phe Asn Tyr Thr Gly Arg Asp Phe Gln Arg
    290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
        355                 360                 365

Asp Asp Thr Val Ala Thr Arg Ser Thr Glu Leu Cys Gly Leu Trp Gln
    370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
            420                 425                 430

Ser Pro Glu Pro Pro Pro Glu
        435                 440

<210> SEQ ID NO 21
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114R

<400> SEQUENCE: 21

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
            20                  25                  30

Pro Pro His Thr Thr Pro Lys Ala Glu Leu Ser Asn His Thr Arg Pro

```
                35                  40                  45
Val Ile Leu Val Pro Gly Cys Leu Gly Asn Gln Leu Glu Ala Lys Leu
 50                  55                  60

Asp Lys Pro Asp Val Val Asn Trp Met Cys Tyr Arg Lys Thr Glu Asp
 65                  70                  75                  80

Phe Phe Thr Ile Trp Leu Asp Leu Asn Met Phe Leu Pro Leu Gly Val
                     85                  90                  95

Asp Cys Trp Ile Asp Asn Thr Arg Val Val Tyr Asn Arg Ser Ser Gly
                    100                 105                 110

Leu Arg Ser Asn Ala Pro Gly Val Gln Ile Arg Val Pro Gly Phe Gly
                115                 120                 125

Lys Thr Tyr Ser Val Glu Tyr Leu Asp Ser Ser Lys Leu Ala Gly Tyr
            130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
                180                 185                 190

Ala Ala Tyr Gly Lys Pro Val Phe Leu Ile Gly His Ser Leu Gly Cys
                195                 200                 205

Leu His Leu Leu Tyr Phe Leu Leu Arg Gln Pro Gln Ala Trp Lys Asp
210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
                260                 265                 270

Ser Pro Trp Met Phe Pro Ser Arg Met Ala Trp Pro Glu Asp His Val
                275                 280                 285

Phe Ile Ser Thr Pro Ser Phe Asn Tyr Thr Gly Arg Asp Phe Gln Arg
            290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
                340                 345                 350

His Gly Phe Pro Tyr Thr Asp Pro Val Gly Val Leu Tyr Glu Asp Gly
            355                 360                 365

Asp Asp Thr Val Ala Thr Arg Ser Thr Glu Leu Cys Gly Leu Trp Gln
            370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
                420                 425                 430

Ser Pro Glu Pro Pro Pro Glu
            435                 440

<210> SEQ ID NO 22
```

```
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114S

<400> SEQUENCE: 22

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
            20                  25                  30

Pro Pro His Thr Thr Pro Lys Ala Glu Leu Ser Asn His Thr Arg Pro
        35                  40                  45

Val Ile Leu Val Pro Gly Cys Leu Gly Asn Gln Leu Glu Ala Lys Leu
50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu Ser Ser Asn Ala Pro Gly Val Gln Ile Arg Val Pro Gly Phe Gly
        115                 120                 125

Lys Thr Tyr Ser Val Glu Tyr Leu Asp Ser Ser Lys Leu Ala Gly Tyr
130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205

Leu His Leu Leu Tyr Phe Leu Leu Arg Gln Pro Gln Ala Trp Lys Asp
210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
        275                 280                 285

Phe Ile Ser Thr Pro Ser Phe Asn Tyr Thr Gly Arg Asp Phe Gln Arg
290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly
        355                 360                 365

Asp Asp Thr Val Ala Thr Arg Ser Thr Glu Leu Cys Gly Leu Trp Gln
```

```
                 370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
                420                 425                 430

Ser Pro Glu Pro Pro Pro Glu
        435                 440

<210> SEQ ID NO 23
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114T

<400> SEQUENCE: 23

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
            35                  40                  45

Val Ile Leu Val Pro Gly Cys Leu Gly Asn Gln Leu Glu Ala Lys Leu
        50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
                100                 105                 110

Leu Thr Ser Asn Ala Pro Gly Val Gln Ile Arg Val Pro Gly Phe Gly
            115                 120                 125

Lys Thr Tyr Ser Val Glu Tyr Leu Asp Ser Ser Lys Leu Ala Gly Tyr
        130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
                180                 185                 190

Ala Ala Tyr Gly Lys Pro Val Phe Leu Ile Gly His Ser Leu Gly Cys
            195                 200                 205

Leu His Leu Leu Tyr Phe Leu Leu Arg Gln Pro Gln Ala Trp Lys Asp
        210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
                260                 265                 270

Ser Pro Trp Met Phe Pro Ser Arg Met Ala Trp Pro Glu Asp His Val
            275                 280                 285
```

```
Phe Ile Ser Thr Pro Ser Phe Asn Tyr Thr Gly Arg Asp Phe Gln Arg
    290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
                340                 345                 350

His Gly Phe Pro Tyr Thr Asp Pro Val Gly Val Leu Tyr Glu Asp Gly
            355                 360                 365

Asp Asp Thr Val Ala Thr Arg Ser Thr Glu Leu Cys Gly Leu Trp Gln
370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
                420                 425                 430

Ser Pro Glu Pro Pro Pro Pro Glu
        435                 440

<210> SEQ ID NO 24
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114W

<400> SEQUENCE: 24

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
            35                  40                  45

Val Ile Leu Val Pro Gly Cys Leu Gly Asn Gln Leu Glu Ala Lys Leu
    50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
                100                 105                 110

Leu Trp Ser Asn Ala Pro Gly Val Gln Ile Arg Val Pro Gly Phe Gly
            115                 120                 125

Lys Thr Tyr Ser Val Glu Tyr Leu Asp Ser Ser Lys Leu Ala Gly Tyr
            130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
            195                 200                 205
```

Leu His Leu Leu Tyr Phe Leu Arg Gln Pro Gln Ala Trp Lys Asp
    210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                    245                 250                 255

Ile Met Ser Ser Ile Lys Leu Lys Glu Glu Gln Arg Ile Thr Thr Thr
                260                 265                 270

Ser Pro Trp Met Phe Pro Ser Arg Met Ala Trp Pro Glu Asp His Val
            275                 280                 285

Phe Ile Ser Thr Pro Ser Phe Asn Tyr Thr Gly Arg Asp Phe Gln Arg
    290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                    325                 330                 335

Cys Leu Tyr Gly Val Gly Leu Pro Thr Pro Arg Thr Tyr Ile Tyr Asp
                340                 345                 350

His Gly Phe Pro Tyr Thr Asp Pro Val Gly Val Leu Tyr Glu Asp Gly
            355                 360                 365

Asp Asp Thr Val Ala Thr Arg Ser Thr Glu Leu Cys Gly Leu Trp Gln
    370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                    405                 410                 415

Ile Leu Leu Gly Ala Tyr Arg Gln Gly Pro Pro Ala Ser Pro Thr Ala
                420                 425                 430

Ser Pro Glu Pro Pro Pro Pro Glu
        435                 440

<210> SEQ ID NO 25
<211> LENGTH: 440
<212> TYPE: PRT
<213> ORGANISM: Artificial Sequence
<220> FEATURE:
<223> OTHER INFORMATION: Amino acid sequence of human LCAT protein
      variant V114Y

<400> SEQUENCE: 25

Met Gly Pro Pro Gly Ser Pro Trp Gln Trp Val Thr Leu Leu Leu Gly
1               5                   10                  15

Leu Leu Leu Pro Pro Ala Ala Pro Phe Trp Leu Leu Asn Val Leu Phe
                20                  25                  30

Pro Pro His Thr Thr Pro Lys Ala Glu Leu Ser Asn His Thr Arg Pro
            35                  40                  45

Val Ile Leu Val Pro Gly Cys Leu Gly Asn Gln Leu Glu Ala Lys Leu
        50                  55                  60

Asp Lys Pro Asp Val Val Asn Trp Met Cys Tyr Arg Lys Thr Glu Asp
65                  70                  75                  80

Phe Phe Thr Ile Trp Leu Asp Leu Asn Met Phe Leu Pro Leu Gly Val
                85                  90                  95

Asp Cys Trp Ile Asp Asn Thr Arg Val Val Tyr Asn Arg Ser Ser Gly
            100                 105                 110

Leu Tyr Ser Asn Ala Pro Gly Val Gln Ile Arg Val Pro Gly Phe Gly

```
            115                 120                 125
Lys Thr Tyr Ser Val Glu Tyr Leu Asp Ser Lys Leu Ala Gly Tyr
        130                 135                 140
Leu His Thr Leu Val Gln Asn Leu Val Asn Asn Gly Tyr Val Arg Asp
145                 150                 155                 160
Glu Thr Val Arg Ala Ala Pro Tyr Asp Trp Arg Leu Glu Pro Gly Gln
                165                 170                 175
Gln Glu Glu Tyr Tyr Arg Lys Leu Ala Gly Leu Val Glu Met His
            180                 185                 190
Ala Ala Tyr Gly Lys Pro Val Phe Leu Ile Gly His Ser Leu Gly Cys
        195                 200                 205
Leu His Leu Leu Tyr Phe Leu Leu Arg Gln Pro Gln Ala Trp Lys Asp
    210                 215                 220
Arg Phe Ile Asp Gly Phe Ile Ser Leu Gly Ala Pro Trp Gly Gly Ser
225                 230                 235                 240
Ile Lys Pro Met Leu Val Leu Ala Ser Gly Asp Asn Gln Gly Ile Pro
                245                 250                 255
Ile Met Ser Ser Ile Lys Leu Lys Glu Glu Gln Arg Ile Thr Thr Thr
            260                 265                 270
Ser Pro Trp Met Phe Pro Ser Arg Met Ala Trp Pro Glu Asp His Val
        275                 280                 285
Phe Ile Ser Thr Pro Ser Phe Asn Tyr Thr Gly Arg Asp Phe Gln Arg
    290                 295                 300
Phe Phe Ala Asp Leu His Phe Glu Glu Gly Trp Tyr Met Trp Leu Gln
305                 310                 315                 320
Ser Arg Asp Leu Leu Ala Gly Leu Pro Ala Pro Gly Val Glu Val Tyr
                325                 330                 335
Cys Leu Tyr Gly Val Gly Leu Pro Thr Pro Arg Thr Tyr Ile Tyr Asp
            340                 345                 350
His Gly Phe Pro Tyr Thr Asp Pro Val Gly Val Leu Tyr Glu Asp Gly
        355                 360                 365
Asp Asp Thr Val Ala Thr Arg Ser Thr Glu Leu Cys Gly Leu Trp Gln
370                 375                 380
Gly Arg Gln Pro Gln Pro Val His Leu Leu Pro Leu His Gly Ile Gln
385                 390                 395                 400
His Leu Asn Met Val Phe Ser Asn Leu Thr Leu Glu His Ile Asn Ala
                405                 410                 415
Ile Leu Leu Gly Ala Tyr Arg Gln Gly Pro Pro Ala Ser Pro Thr Ala
            420                 425                 430
Ser Pro Glu Pro Pro Pro Glu
        435                 440

<210> SEQ ID NO 26
<211> LENGTH: 1320
<212> TYPE: DNA
<213> ORGANISM: Homo sapiens

<400> SEQUENCE: 26
atggggccgc ccggctcccc atggcagtgg gtgacgctgc tgctggggct gctgctccct      60
cctgccgccc ccttctggct cctcaatgtg ctcttccccc gcacaccac gcccaaggct      120 gagctcagta accacacacg gcccgtcatc ctcgtgcccg ctgcctggg gaatcagcta      180 gaagccaagc tggacaaacc agatgtggtg aactggatgt gctaccgcaa gacagaggac      240
ttcttcacca tctggctgga tctcaacatg ttcctacccc ttggggtaga ctgctggatc      300
```

```
gataacacca gggttgtcta caaccggagc tctgggctca tgtccaacgc ccctggtgtc    360
cagatccgcg tccctggctt tggcaagacc tactctgtgg agtacctgga cagcagcaag    420
ctggcagggt acctgcacac actggtgcag aacctggtca acaatggcta cgtgcgggac    480
gagactgtgc gcgccgcccc ctatgactgg cggctggagc ccggccagca ggaggagtac    540
taccgcaagc tcgcagggct ggtggaggag atgcacgctg cctatgggaa gcctgtcttc    600
ctcattggcc acagcctcgg ctgtctacac ttgctctatt cctgctgcg ccagccccag    660 gcctggaagg accgctttat tgatggcttc atctctcttg gggctccctg ggtggctcc    720 atcaagccca tgctggtctt ggcctcaggt gacaaccagg gcatccccat catgtccagc    780
atcaagctga agaggagca gcgcataacc accacctccc cctggatgtt tccctctcgc    840
atggcgtggc ctgaggacca cgtgttcatt tccacaccca gcttcaacta cacaggccgt    900
gacttccaac gcttctttgc agacctgcac tttgaggaag gctggtacat gtggctgcag    960
tcacgtgacc tcctggcagg actcccagca cctggtgtgg aagtatactg tctttacggc    1020
gtgggcctgc ccacgccccg cacctacatc tacgaccacg gcttccccta cacggaccct    1080
gtgggtgtgc tctatgagga tggtgatgac acggtggcga cccgcagcac cgagctctgt    1140
ggcctgtggc agggccgcca gccacagcct gtgcacctgc tgccctgca cgggatacag    1200 catctcaaca tggtcttcag caacctgacc ctggagcaca tcaatgccat cctgctgggt    1260
gcctaccgcc agggtccccc tgcatccccg actgccagcc cagagccccc gcctcctgag    1320
```

```
<210> SEQ ID NO 27
<211> LENGTH: 1320
<212> TYPE: DNA
<213> ORGANISM: Artificial Sequence
<220> FEATURE:
<223> OTHER INFORMATION: Human LCAT V114A coding sequence

<400> SEQUENCE: 27
```

```
atggggccgc ccggctcccc atggcagtgg gtgacgctgc tgctggggct gctgctccct    60
cctgccgccc ccttctggct cctcaatgtg ctcttccccc gcacaccac gcccaaggct    120 gagctcagta accacacacg gccgtcatc ctcgtgcccg gctgcctggg gaatcagcta    180
gaagccaagc tggacaaaac agatgtggtg aactggatgt gctaccgcaa gacagaggac    240
ttcttcacca tctggctgga tctcaacatg ttcctacccc ttggggtaga ctgctggatc    300
gataacacca gggttgtcta caaccggagc tctgggctcg cctccaacgc ccctggtgtc    360
cagatccgcg tccctggctt tggcaagacc tactctgtgg agtacctgga cagcagcaag    420
ctggcagggt acctgcacac actggtgcag aacctggtca acaatggcta cgtgcgggac    480
gagactgtgc gcgccgcccc ctatgactgg cggctggagc ccggccagca ggaggagtac    540
taccgcaagc tcgcagggct ggtggaggag atgcacgctg cctatgggaa gcctgtcttc    600
ctcattggcc acagcctcgg ctgtctacac ttgctctatt cctgctgcg ccagccccag    660 gcctggaagg accgctttat tgatggcttc atctctcttg gggctccctg ggtggctcc    720 atcaagccca tgctggtctt ggcctcaggt gacaaccagg gcatccccat catgtccagc    780
atcaagctga agaggagca gcgcataacc accacctccc cctggatgtt tccctctcgc    840
atggcgtggc ctgaggacca cgtgttcatt tccacaccca gcttcaacta cacaggccgt    900
gacttccaac gcttctttgc agacctgcac tttgaggaag gctggtacat gtggctgcag    960
tcacgtgacc tcctggcagg actcccagca cctggtgtgg aagtatactg tctttacggc    1020
```

-continued

| | |
|---|---|
| gtgggcctgc ccacgccccg cacctacatc tacgaccacg gcttccccta cacggaccct | 1080 |
| gtgggtgtgc tctatgagga tggtgatgac acggtggcga cccgcagcac cgagctctgt | 1140 |
| ggcctgtggc agggccgcca gccacagcct gtgcacctgc tgcccctgca cgggatacag | 1200 |
| catctcaaca tggtcttcag caacctgacc ctggagcaca tcaatgccat cctgctgggt | 1260 |
| gcctaccgcc agggtccccc tgcatccccg actgccagcc cagagccccc gcctcctgag | 1320 |

<210> SEQ ID NO 28
<211> LENGTH: 1320
<212> TYPE: DNA
<213> ORGANISM: Artificial Sequence
<220> FEATURE:
<223> OTHER INFORMATION: Human LCAT V114C coding sequence

<400> SEQUENCE: 28

| | |
|---|---|
| atggggccgc ccggctcccc atggcagtgg gtgacgctgc tgctggggct gctgctccct | 60 |
| cctgccgccc ccttctggct cctcaatgtg ctcttccccc cgcacaccac gcccaaggct | 120 |
| gagctcagta accacacacg gcccgtcatc ctcgtgcccg gctgcctggg gaatcagcta | 180 |
| gaagccaagc tggacaaacc agatgtggtg aactggatgt gctaccgcaa gacagaggac | 240 |
| ttcttcacca tctggctgga tctcaacatg ttcctacccc ttggggtaga ctgctggatc | 300 |
| gataacacca gggttgtcta caaccggagc tctgggctct gctccaacgc cctggtgtc | 360 |
| cagatccgcg tccctggctt tggcaagacc tactctgtgg agtacctgga cagcagcaag | 420 |
| ctggcagggt acctgcacac actggtgcag aacctggtca caatggcta cgtgcgggac | 480 |
| gagactgtgc gcgccgcccc ctatgactgg cggctggagc ccggccagca ggaggagtac | 540 |
| taccgcaagc tcgcagggct ggtggaggag atgcacgctg cctatgggaa gcctgtcttc | 600 |
| ctcattggcc acagcctcgg ctgtctacac ttgctctatt tcctgctgcg ccagccccag | 660 |
| gcctggaagg accgctttat tgatggcttc atctctcttg ggctccctg gggtggctcc | 720 |
| atcaagccca tgctggtctt ggcctcaggt gacaaccagg gcatccccat catgtccagc | 780 |
| atcaagctga agaggagca gcgcataacc accacctccc cctggatgtt ccctctcgc | 840 |
| atggcgtggc tgaggaccca cgtgttcatt tccacaccca gcttcaacta cacaggccgt | 900 |
| gacttccaac gcttctttgc agacctgcac tttgaggaag ctggtacat gtggctgcag | 960 |
| tcacgtgacc tcctgcagg actcccagca cctggtgtgg aagtatactg tctttacggc | 1020 |
| gtgggcctgc ccacgccccg cacctacatc tacgaccacg gcttccccta cacggaccct | 1080 |
| gtgggtgtgc tctatgagga tggtgatgac acggtggcga cccgcagcac cgagctctgt | 1140 |
| ggcctgtggc agggccgcca gccacagcct gtgcacctgc tgcccctgca cgggatacag | 1200 |
| catctcaaca tggtcttcag caacctgacc ctggagcaca tcaatgccat cctgctgggt | 1260 |
| gcctaccgcc agggtccccc tgcatccccg actgccagcc cagagccccc gcctcctgag | 1320 |

<210> SEQ ID NO 29
<211> LENGTH: 1320
<212> TYPE: DNA
<213> ORGANISM: Artificial Sequence
<220> FEATURE:
<223> OTHER INFORMATION: Human LCAT V114D coding sequence

<400> SEQUENCE: 29

| | |
|---|---|
| atggggccgc ccggctcccc atggcagtgg gtgacgctgc tgctggggct gctgctccct | 60 |
| cctgccgccc ccttctggct cctcaatgtg ctcttccccc cgcacaccac gcccaaggct | 120 |
| gagctcagta accacacacg gcccgtcatc ctcgtgcccg gctgcctggg gaatcagcta | 180 |

| | |
|---|---|
| gaagccaagc tggacaaacc agatgtggtg aactggatgt gctaccgcaa gacagaggac | 240 |
| ttcttcacca tctggctgga tctcaacatg ttcctacccc ttggggtaga ctgctggatc | 300 |
| gataacacca gggttgtcta caaccggagc tctgggctcg actccaacgc ccctggtgtc | 360 |
| cagatccgcg tccctggctt tggcaagacc tactctgtgg agtacctgga cagcagcaag | 420 |
| ctggcagggt acctgcacac actggtgcag aacctggtca caatggcta cgtgcgggac | 480 |
| gagactgtgc gcgccgcccc ctatgactgg cggctggagc ccggccagca ggaggagtac | 540 |
| taccgcaagc tcgcagggct ggtggaggag atgcacgctg cctatgggaa gcctgtcttc | 600 |
| ctcattggcc acagcctcgg ctgtctacac ttgctctatt cctgctgcg ccagccccag | 660 |
| gcctggaagg accgctttat tgatggcttc atctctcttg gggctccctg ggtggctcc | 720 |
| atcaagccca tgctggtctt ggcctcaggt gacaaccagg gcatccccat catgtccagc | 780 |
| atcaagctga agaggagca gcgcataacc accacctccc cctggatgtt tccctctcgc | 840 |
| atggcgtggc ctgaggacca cgtgttcatt tccacaccca gcttcaacta cacaggccgt | 900 |
| gacttccaac gcttctttgc agacctgcac tttgaggaag gctggtacat gtggctgcag | 960 |
| tcacgtgacc tcctggcagg actcccagca cctggtgtgg aagtatactg tctttacggc | 1020 |
| gtgggcctgc ccacgccccg cacctacatc tacgaccacg gcttccccta cacggaccct | 1080 |
| gtgggtgtgc tctatgagga tggtgatgac acggtggcga cccgcagcac cgagctctgt | 1140 |
| ggcctgtggc agggccgcca gccacagcct gtgcacctgc tgccctgca cgggatacag | 1200 |
| catctcaaca tggtcttcag caacctgacc ctggagcaca tcaatgccat cctgctgggt | 1260 |
| gcctaccgcc agggtccccc tgcatccccg actgccagcc cagagccccc gcctcctgag | 1320 |

<210> SEQ ID NO 30
<211> LENGTH: 1320
<212> TYPE: DNA
<213> ORGANISM: Artificial Sequence
<220> FEATURE:
<223> OTHER INFORMATION: Human LCAT V114E coding sequence

<400> SEQUENCE: 30

| | |
|---|---|
| atggggccgc ccggctcccc atggcagtgg gtgacgctgc tgctggggct gctgctccct | 60 |
| cctgccgccc ccttctggct cctcaatgtg ctcttccccc gcacaccac gcccaaggct | 120 |
| gagctcagta accacacacg gcccgtcatc ctcgtgcccg gctgcctggg gaatcagcta | 180 |
| gaagccaagc tggacaaacc agatgtggtg aactggatgt gctaccgcaa gacagaggac | 240 |
| ttcttcacca tctggctgga tctcaacatg ttcctacccc ttggggtaga ctgctggatc | 300 |
| gataacacca gggttgtcta caaccggagc tctgggctcg agtccaacgc ccctggtgtc | 360 |
| cagatccgcg tccctggctt tggcaagacc tactctgtgg agtacctgga cagcagcaag | 420 |
| ctggcagggt acctgcacac actggtgcag aacctggtca caatggcta cgtgcgggac | 480 |
| gagactgtgc gcgccgcccc ctatgactgg cggctggagc ccggccagca ggaggagtac | 540 |
| taccgcaagc tcgcagggct ggtggaggag atgcacgctg cctatgggaa gcctgtcttc | 600 |
| ctcattggcc acagcctcgg ctgtctacac ttgctctatt cctgctgcg ccagccccag | 660 |
| gcctggaagg accgctttat tgatggcttc atctctcttg gggctccctg ggtggctcc | 720 |
| atcaagccca tgctggtctt ggcctcaggt gacaaccagg gcatccccat catgtccagc | 780 |
| atcaagctga agaggagca gcgcataacc accacctccc cctggatgtt tccctctcgc | 840 |
| atggcgtggc ctgaggacca cgtgttcatt tccacaccca gcttcaacta cacaggccgt | 900 |

| | |
|---|---|
| gacttccaac gcttctttgc agacctgcac tttgaggaag gctggtacat gtggctgcag | 960 |
| tcacgtgacc tcctggcagg actcccagca cctggtgtgg aagtatactg tctttacggc | 1020 |
| gtgggcctgc ccacgccccg cacctacatc tacgaccacg gcttccccta cacggaccct | 1080 |
| gtgggtgtgc tctatgagga tggtgatgac acggtggcga cccgcagcac cgagctctgt | 1140 |
| ggcctgtggc agggccgcca gccacagcct gtgcacctgc tgcccctgca cgggatacag | 1200 |
| catctcaaca tggtcttcag caacctgacc ctggagcaca tcaatgccat cctgctgggt | 1260 |
| gcctaccgcc agggtccccc tgcatccccg actgccagcc agagcccccc gcctcctgag | 1320 |

<210> SEQ ID NO 31
<211> LENGTH: 1320
<212> TYPE: DNA
<213> ORGANISM: Artificial Sequence
<220> FEATURE:
<223> OTHER INFORMATION: Human LCAT V114F coding sequence

<400> SEQUENCE: 31

| | |
|---|---|
| atggggccgc ccggctcccc atggcagtgg gtgacgctgc tgctggggct gctgctccct | 60 |
| cctgccgccc ccttctggct cctcaatgtg ctcttccccc gcacaccac gcccaaggct | 120 |
| gagctcagta accacacacg gcccgtcatc ctcgtgcccg gctgcctggg gaatcagcta | 180 |
| gaagccaagc tggacaaacc agatgtggtg aactggatgt gctaccgcaa gacagaggac | 240 |
| ttcttcacca tctggctgga tctcaacatg ttcctacccc ttggggtaga ctgctggatc | 300 |
| gataacacca gggttgtcta aaccggagc tctgggctct ctccaacgc cctggtgtc | 360 |
| cagatccgcg tccctggctt tggcaagacc tactctgtgg agtacctgga cagcagcaag | 420 |
| ctggcagggt acctgcacac actggtgcag aacctggtca caatggcta cgtgcgggac | 480 |
| gagactgtgc gcgccgcccc ctatgactgg cggctggagc ccggccagca ggaggagtac | 540 |
| taccgcaagc tcgcagggct ggtggaggag atgcacgctg cctatgggaa gcctgtcttc | 600 |
| ctcattggcc acagcctcgg ctgtctacac ttgctctatt tcctgctgcg ccagccccag | 660 |
| gcctggaagg accgctttat tgatggcttc atctctcttg ggctcccctg ggtggctcc | 720 |
| atcaagccca tgctggtctt ggcctcaggt gacaaccagg gcatccccat catgtccagc | 780 |
| atcaagctga agaggagca gcgcataacc accacctccc cctggatgtt ccctctcgc | 840 |
| atggcgtggc ctgaggacca cgtgttcatt tccacaccca gcttcaacta cacaggccgt | 900 |
| gacttccaac gcttctttgc agacctgcac tttgaggaag gctggtacat gtggctgcag | 960 |
| tcacgtgacc tcctggcagg actcccagca cctggtgtgg aagtatactg tctttacggc | 1020 |
| gtgggcctgc ccacgccccg cacctacatc tacgaccacg gcttccccta cacggaccct | 1080 |
| gtgggtgtgc tctatgagga tggtgatgac acggtggcga cccgcagcac cgagctctgt | 1140 |
| ggcctgtggc agggccgcca gccacagcct gtgcacctgc tgcccctgca cgggatacag | 1200 |
| catctcaaca tggtcttcag caacctgacc ctggagcaca tcaatgccat cctgctgggt | 1260 |
| gcctaccgcc agggtccccc tgcatccccg actgccagcc agagcccccc gcctcctgag | 1320 |

<210> SEQ ID NO 32
<211> LENGTH: 1320
<212> TYPE: DNA
<213> ORGANISM: Artificial Sequence
<220> FEATURE:
<223> OTHER INFORMATION: Human LCAT V114G coding sequence

<400> SEQUENCE: 32

| | |
|---|---|
| atggggccgc ccggctcccc atggcagtgg gtgacgctgc tgctggggct gctgctccct | 60 |

```
cctgccgccc ccttctggct cctcaatgtg ctcttccccc cgcacaccac gcccaaggct      120
gagctcagta accacacacg gcccgtcatc ctcgtgcccg gctgcctggg gaatcagcta      180
gaagccaagc tggacaaacc agatgtggtg aactggatgt gctaccgcaa gacagaggac      240
ttcttcacca tctggctgga tctcaacatg ttcctacccc ttggggtaga ctgctggatc      300
gataacacca gggttgtcta caaccggagc tctgggctcg gctccaacgc ccctggtgtc      360
cagatccgcg tccctggctt tggcaagacc tactctgtgg agtacctgga cagcagcaag      420
ctggcagggt acctgcacac actggtgcag aacctggtca caatggcta cgtgcgggac       480 gagactgtgc gcgccgcccc ctatgactgg cggctggagc ccggccagca ggaggagtac      540
taccgcaagc tcgcagggct ggtggaggag atgcacgctg cctatgggaa gcctgtcttc      600
ctcattggcc acagcctcgg ctgtctacac ttgctctatt tcctgctgcg ccagccccag      660
gcctggaagg accgctttat tgatggcttc atctctcttg gggctccctg ggtggctcc       720 atcaagccca tgctggtctt ggcctcaggt gacaaccagg gcatcccat catgtccagc       780 atcaagctga aagaggagca gcgcataacc accacctccc cctggatgtt tccctctcgc      840
atggcgtggc ctgaggacca cgtgttcatt tccacaccca gcttcaacta cacaggccgt      900
gacttccaac gcttctttgc agacctgcac tttgaggaag gctggtacat gtggctgcag      960
tcacgtgacc tcctggcagg actcccagca cctggtgtgg aagtatactg tctttacggc     1020
gtgggcctgc ccacgccccg cacctacatc tacgaccacg gcttccccta cacggaccct     1080
gtgggtgtgc tctatgagga tggtgatgac acggtggcga cccgcagcac cgagctctgt     1140
ggcctgtggc agggccgcca gccacagcct gtgcacctgc tgccctgca gggatacag       1200 catctcaaca tggtcttcag caacctgacc ctggagcaca tcaatgccat cctgctgggt     1260
gcctaccgcc agggtccccc tgcatccccg actgccagcc cagagccccc gcctcctgag     1320
```

<210> SEQ ID NO 33
<211> LENGTH: 1320
<212> TYPE: DNA
<213> ORGANISM: Artificial Sequence
<220> FEATURE:
<223> OTHER INFORMATION: Human LCAT V114H coding sequence

<400> SEQUENCE: 33

```
atggggccgc ccggctcccc atggcagtgg gtgacgctgc tgctggggct gctgctccct       60
cctgccgccc ccttctggct cctcaatgtg ctcttccccc cgcacaccac gcccaaggct      120
gagctcagta accacacacg gcccgtcatc ctcgtgcccg gctgcctggg gaatcagcta      180
gaagccaagc tggacaaacc agatgtggtg aactggatgt gctaccgcaa gacagaggac      240
ttcttcacca tctggctgga tctcaacatg ttcctacccc ttggggtaga ctgctggatc      300
gataacacca gggttgtcta caaccggagc tctgggctcc actccaacgc ccctggtgtc      360
cagatccgcg tccctggctt tggcaagacc tactctgtgg agtacctgga cagcagcaag      420
ctggcagggt acctgcacac actggtgcag aacctggtca caatggcta cgtgcgggac       480 gagactgtgc gcgccgcccc ctatgactgg cggctggagc ccggccagca ggaggagtac      540
taccgcaagc tcgcagggct ggtggaggag atgcacgctg cctatgggaa gcctgtcttc      600
ctcattggcc acagcctcgg ctgtctacac ttgctctatt tcctgctgcg ccagccccag      660
gcctggaagg accgctttat tgatggcttc atctctcttg gggctccctg ggtggctcc       720 atcaagccca tgctggtctt ggcctcaggt gacaaccagg gcatcccat catgtccagc       780
```

| | |
|---|---|
| atcaagctga aagaggagca gcgcataacc accacctccc cctggatgtt tccctctcgc | 840 |
| atggcgtggc ctgaggacca cgtgttcatt tccacaccca gcttcaacta cacaggccgt | 900 |
| gacttccaac gcttctttgc agacctgcac tttgaggaag gctggtacat gtggctgcag | 960 |
| tcacgtgacc tcctggcagg actcccagca cctggtgtgg aagtatactg tctttacggc | 1020 |
| gtgggcctgc ccacgccccg cacctacatc tacgaccacg gcttcccta cacggaccct | 1080 |
| gtgggtgtgc tctatgagga tggtgatgac acggtggcga cccgcagcac cgagctctgt | 1140 |
| ggcctgtggc agggccgcca gccacagcct gtgcacctgc tgcccctgca cgggatacag | 1200 |
| catctcaaca tggtcttcag caacctgacc ctggagcaca tcaatgccat cctgctgggt | 1260 |
| gcctaccgcc agggtccccc tgcatccccg actgccagcc cagagccccc gcctcctgag | 1320 |

<210> SEQ ID NO 34
<211> LENGTH: 1320
<212> TYPE: DNA
<213> ORGANISM: Artificial Sequence
<220> FEATURE:
<223> OTHER INFORMATION: Human LCAT V114I coding sequence

<400> SEQUENCE: 34

| | |
|---|---|
| atggggccgc ccggctcccc atggcagtgg gtgacgctgc tgctggggct gctgctccct | 60 |
| cctgccgccc ccttctggct cctcaatgtg ctcttccccc gcacaccac gcccaaggct | 120 |
| gagctcagta accacacacg gcccgtcatc ctcgtgcccg gctgcctggg gaatcagcta | 180 |
| gaagccaagc tggacaaaac agatgtggtg aactggatgt gctaccgcaa gacagaggac | 240 |
| ttcttcacca tctggctgga tctcaacatg ttcctacccc ttggggtaga ctgctggatc | 300 |
| gataacacca gggttgtcta caaccggagc tctgggctca tctccaacgc cctggtgtc | 360 |
| cagatccgcg tccctggctt tggcaagacc tactctgtgg agtacctgga cagcagcaag | 420 |
| ctggcagggt acctgcacac actggtgcag aacctggtca caatggcta cgtgcgggac | 480 |
| gagactgtgc gcgccgcccc ctatgactgg cggctggagc ccggccagca ggaggagtac | 540 |
| taccgcaagc tcgcagggct ggtggaggag atgcacgctg cctatgggaa gcctgtcttc | 600 |
| ctcattggcc acagcctcgg ctgtctacac ttgctctatt tcctgctgcg ccagccccag | 660 |
| gcctggaagg accgctttat tgatggcttc atctctcttg ggctccctg ggtggctcc | 720 |
| atcaagccca tgctggtctt ggcctcaggt gacaaccagg gcatccccat catgtccagc | 780 |
| atcaagctga aagaggagca gcgcataacc accacctccc cctggatgtt tccctctcgc | 840 |
| atggcgtggc ctgaggacca cgtgttcatt tccacaccca gcttcaacta cacaggccgt | 900 |
| gacttccaac gcttctttgc agacctgcac tttgaggaag gctggtacat gtggctgcag | 960 |
| tcacgtgacc tcctggcagg actcccagca cctggtgtgg aagtatactg tctttacggc | 1020 |
| gtgggcctgc ccacgccccg cacctacatc tacgaccacg gcttcccta cacggaccct | 1080 |
| gtgggtgtgc tctatgagga tggtgatgac acggtggcga cccgcagcac cgagctctgt | 1140 |
| ggcctgtggc agggccgcca gccacagcct gtgcacctgc tgcccctgca cgggatacag | 1200 |
| catctcaaca tggtcttcag caacctgacc ctggagcaca tcaatgccat cctgctgggt | 1260 |
| gcctaccgcc agggtccccc tgcatccccg actgccagcc cagagccccc gcctcctgag | 1320 |

<210> SEQ ID NO 35
<211> LENGTH: 1320
<212> TYPE: DNA
<213> ORGANISM: Artificial Sequence
<220> FEATURE:
<223> OTHER INFORMATION: Human LCAT V114K coding sequence

<400> SEQUENCE: 35

```
atggggccgc ccggctcccc atggcagtgg gtgacgctgc tgctggggct gctgctccct      60
cctgccgccc ccttctggct cctcaatgtg ctcttccccc cgcacaccac gcccaaggct     120
gagctcagta accacacacg gcccgtcatc ctcgtgcccg gctgcctggg aatcagcta      180
gaagccaagc tggacaaacc agatgtggtg aactggatgt gctaccgcaa gacagaggac     240
ttcttcacca tctggctgga tctcaacatg ttcctacccc ttggggtaga ctgctggatc     300
gataacacca gggttgtcta caaccggagc tctgggctca gtccaacgc ccctggtgtc      360
cagatccgcg tccctggctt tggcaagacc tactctgtgg agtacctgga cagcagcaag     420
ctggcagggt acctgcacac actggtgcag aacctggtca caatggcta cgtgcgggac     480
gagactgtgc gcgccgcccc ctatgactgg cggctggagc ccggccagca ggaggagtac     540
taccgcaagc tcgcagggct ggtggaggag atgcacgctg cctatgggaa gcctgtcttc     600
ctcattggcc acagcctcgg ctgtctacac ttgctctatt tcctgctgcg ccagccccag     660
gcctggaagg accgctttat tgatggcttc atctctcttg ggctccctg ggtggctcc       720
atcaagccca tgctggtctt ggcctcaggt gacaaccagg gcatccccat catgtccagc     780
atcaagctga agaggagca gcgcataacc accacctccc cctggatgtt tccctctcgc      840
atggcgtggc ctgaggacca cgtgttcatt tccacaccca gcttcaacta cacaggccgt     900
gacttccaac gcttctttgc agacctgcac tttgaggaag ctggtacat gtggctgcag      960
tcacgtgacc tcctggcagg actcccagca cctggtgtgg aagtatactg tctttacggc    1020
gtgggcctgc ccacgccccg cacctacatc tacgaccacg gcttcccta cacggaccct    1080
gtgggtgtgc tctatgagga tggtgatgac acggtggcga cccgcagcac cgagctctgt    1140
ggcctgtggc agggccgcca gccacagcct gtgcacctgc tgcccctgca cgggatacag    1200
catctcaaca tggtcttcag caacctgacc ctggagcaca tcaatgccat cctgctgggt    1260
gcctaccgcc agggtccccc tgcatccccg actgccagcc cagagccccc gcctcctgag    1320
```

<210> SEQ ID NO 36
<211> LENGTH: 1320
<212> TYPE: DNA
<213> ORGANISM: Artificial Sequence
<220> FEATURE:
<223> OTHER INFORMATION: Human LCAT V114L coding sequence

<400> SEQUENCE: 36

```
atggggccgc ccggctcccc atggcagtgg gtgacgctgc tgctggggct gctgctccct      60
cctgccgccc ccttctggct cctcaatgtg ctcttccccc cgcacaccac gcccaaggct     120
gagctcagta accacacacg gcccgtcatc ctcgtgcccg gctgcctggg aatcagcta      180
gaagccaagc tggacaaacc agatgtggtg aactggatgt gctaccgcaa gacagaggac     240
ttcttcacca tctggctgga tctcaacatg ttcctacccc ttggggtaga ctgctggatc     300
gataacacca gggttgtcta caaccggagc tctgggctcc tgtccaacgc ccctggtgtc     360
cagatccgcg tccctggctt tggcaagacc tactctgtgg agtacctgga cagcagcaag     420
ctggcagggt acctgcacac actggtgcag aacctggtca caatggcta cgtgcgggac     480
gagactgtgc gcgccgcccc ctatgactgg cggctggagc ccggccagca ggaggagtac     540
taccgcaagc tcgcagggct ggtggaggag atgcacgctg cctatgggaa gcctgtcttc     600
ctcattggcc acagcctcgg ctgtctacac ttgctctatt tcctgctgcg ccagccccag     660
```

```
gcctggaagg accgctttat tgatggcttc atctctcttg gggctccctg ggtggctcc      720 atcaagccca tgctggtctt ggcctcaggt gacaaccagg gcatccccat catgtccagc      780
atcaagctga agaggagca gcgcataacc accacctccc cctggatgtt tccctctcgc       840
atggcgtggc ctgaggacca cgtgttcatt tccacaccca gcttcaacta cacaggccgt      900
gacttccaac gcttctttgc agacctgcac tttgaggaag ctggtacat gtggctgcag       960 tcacgtgacc tcctggcagg actcccagca cctggtgtgg aagtatactg tctttacggc     1020
gtgggcctgc ccacgccccg cacctacatc tacgaccacg gcttccccta cacggaccct     1080
gtgggtgtgc tctatgagga tggtgatgac acggtggcga cccgcagcac cgagctctgt    1140
ggcctgtggc agggccgcca gccacagcct gtgcacctgc tgcccctgca cgggatacag     1200
catctcaaca tggtcttcag caacctgacc ctggagcaca tcaatgccat cctgctgggt     1260
gcctaccgcc agggtccccc tgcatccccg actgccagcc cagagccccc gcctcctgag    1320
```

<210> SEQ ID NO 37
<211> LENGTH: 1320
<212> TYPE: DNA
<213> ORGANISM: Artificial Sequence
<220> FEATURE:
<223> OTHER INFORMATION: Human LCAT V114N coding sequence

<400> SEQUENCE: 37

```
atggggccgc ccggctcccc atggcagtgg gtgacgctgc tgctggggct gctgctccct      60
cctgccgccc ccttctggct cctcaatgtg ctcttccccc gcacaccac gcccaaggct       120 gagctcagta accacacacg gcccgtcatc ctcgtgcccg gctgcctggg gaatcagcta     180
gaagccaagc tggacaaacc agatgtggtg aactggatgt gctaccgcaa gacagaggac     240
ttcttcacca tctggctgga tctcaacatg ttcctacccc ttggggtaga ctgctggatc     300
gataacacca gggttgtcta acccggagc tctgggctca actccaacgc ccctggtgtc     360
cagatccgcg tccctggctt tggcaagacc tactctgtgg agtacctgga cagcagcaag    420
ctggcagggt acctgcacac actggtgcag aacctggtca caatggcta cgtgcgggac     480 gagactgtgc gcgccgcccc ctatgactgg cggctggagc ccggccagca ggaggagtac     540
taccgcaagc tcgcagggct ggtggaggag atgcacgctg cctatgggaa gcctgtcttc    600
ctcattggcc acagcctcgg ctgtctacac ttgctctatt tcctgctgcg ccagccccag    660
gcctggaagg accgctttat tgatggcttc atctctcttg gggctccctg ggtggctcc     720 atcaagccca tgctggtctt ggcctcaggt gacaaccagg gcatccccat catgtccagc      780
atcaagctga agaggagca gcgcataacc accacctccc cctggatgtt tccctctcgc       840
atggcgtggc ctgaggacca cgtgttcatt tccacaccca gcttcaacta cacaggccgt      900
gacttccaac gcttctttgc agacctgcac tttgaggaag ctggtacat gtggctgcag       960 tcacgtgacc tcctggcagg actcccagca cctggtgtgg aagtatactg tctttacggc     1020
gtgggcctgc ccacgccccg cacctacatc tacgaccacg gcttccccta cacggaccct     1080
gtgggtgtgc tctatgagga tggtgatgac acggtggcga cccgcagcac cgagctctgt    1140
ggcctgtggc agggccgcca gccacagcct gtgcacctgc tgcccctgca cgggatacag     1200
catctcaaca tggtcttcag caacctgacc ctggagcaca tcaatgccat cctgctgggt     1260
gcctaccgcc agggtccccc tgcatccccg actgccagcc cagagccccc gcctcctgag    1320
```

<210> SEQ ID NO 38
<211> LENGTH: 1320

```
<212> TYPE: DNA
<213> ORGANISM: Artificial Sequence
<220> FEATURE:
<223> OTHER INFORMATION: Human LCAT V114P coding sequence

<400> SEQUENCE: 38
atggggccgc cggctccc atggcagtgg gtgacgctgc tgctggggct gctgctccct      60
cctgccgccc ccttctggct cctcaatgtg ctcttccccc cgcacaccac gcccaaggct    120
gagctcagta accacacacg gcccgtcatc ctcgtgcccg gctgcctggg gaatcagcta    180
gaagccaagc tggacaaacc agatgtggtg aactggatgt gctaccgcaa gacagaggac    240
ttcttcacca tctggctgga tctcaacatg ttcctacccc ttggggtaga ctgctggatc    300
gataacacca gggttgtcta caaccggagc tctgggctcc cctccaacgc ccctggtgtc    360
cagatccgcg tccctggctt tggcaagacc tactctgtgg agtacctgga cagcagcaag    420
ctggcagggt acctgcacac actggtgcag aacctggtca caatggcta cgtgcgggac    480 gagactgtgc gcgccgcccc ctatgactgg cggctggagc ccggccagca ggaggagtac    540
taccgcaagc tcgcagggct ggtggaggag atgcacgctg cctatgggaa gcctgtcttc    600
ctcattggcc acagcctcgg ctgtctacac ttgctctatt tcctgctgcg ccagccccag    660
gcctggaagg accgctttat tgatggcttc atctctcttg ggctccctg ggtggctcc     720 atcaagccca tgctggtctt ggcctcaggt gacaaccagg gcatccccat catgtccagc    780
atcaagctga agaggagca gcgcataacc accacctccc cctggatgtt tccctctcgc    840
atggcgtggc ctgaggacca cgtgttcatt tccacaccca gcttcaacta cacaggccgt    900
gacttccaac gcttcttgc agacctgcac tttgaggaag ctggtacat gtggctgcag    960 tcacgtgacc tcctggcagg actcccagca cctggtgtgg aagtatactg tctttacggc   1020
gtgggcctgc ccacgcccg cacctacatc tacgaccacg gcttcccta cggacccct   1080 gtgggtgtgc tctatgagga tggtgatgac acggtggcga cccgcagcac cgagctctgt   1140
ggcctgtggc agggccgcca gccacagcct gtgcacctgc tgcccctgca cgggatacag   1200
catctcaaca tggtcttcag caacctgacc ctggagcaca tcaatgccat cctgctgggt   1260
gcctaccgcc agggtccccc tgcatcccg actgccagcc cagagccccc gcctcctgag   1320

<210> SEQ ID NO 39
<211> LENGTH: 1320
<212> TYPE: DNA
<213> ORGANISM: Artificial Sequence
<220> FEATURE:
<223> OTHER INFORMATION: Human LCAT V114Q coding sequence

<400> SEQUENCE: 39
atggggccgc ccggctcccc atggcagtgg gtgacgctgc tgctggggct gctgctccct      60
cctgccgccc ccttctggct cctcaatgtg ctcttccccc cgcacaccac gcccaaggct    120
gagctcagta accacacacg gcccgtcatc ctcgtgcccg gctgcctggg gaatcagcta    180
gaagccaagc tggacaaacc agatgtggtg aactggatgt gctaccgcaa gacagaggac    240
ttcttcacca tctggctgga tctcaacatg ttcctacccc ttggggtaga ctgctggatc    300
gataacacca gggttgtcta caaccggagc tctgggctcc agtccaacgc ccctggtgtc    360
cagatccgcg tccctggctt tggcaagacc tactctgtgg agtacctgga cagcagcaag    420
ctggcagggt acctgcacac actggtgcag aacctggtca caatggcta cgtgcgggac    480 gagactgtgc gcgccgcccc ctatgactgg cggctggagc ccggccagca ggaggagtac    540
```

| | |
|---|---|
| taccgcaagc tcgcagggct ggtggaggag atgcacgctg cctatgggaa gcctgtcttc | 600 |
| ctcattggcc acagcctcgg ctgtctacac ttgctctatt tcctgctgcg ccagcccag | 660 |
| gcctggaagg accgctttat tgatggcttc atctctcttg gggctccctg ggtggctcc | 720 |
| atcaagccca tgctggtctt ggcctcaggt gacaaccagg gcatcccat catgtccagc | 780 |
| atcaagctga aagaggagca gcgcataacc accacctccc cctggatgtt tccctctcgc | 840 |
| atggcgtggc ctgaggacca cgtgttcatt tccacacca gcttcaacta cacaggccgt | 900 |
| gacttccaac gcttctttgc agacctgcac tttgaggaag gctggtacat gtggctgcag | 960 |
| tcacgtgacc tcctggcagg actcccagca cctggtgtgg aagtatactg tctttacggc | 1020 |
| gtgggcctgc ccacgccccg cacctacatc tacgaccacg gcttcccta cacggaccct | 1080 |
| gtgggtgtgc tctatgagga tggtgatgac acggtggcga cccgcagcac cgagctctgt | 1140 |
| ggcctgtggc agggccgcca gccacagcct gtgcacctgc tgccctgca cgggatacag | 1200 |
| catctcaaca tggtcttcag caacctgacc ctggagcaca tcaatgccat cctgctgggt | 1260 |
| gcctaccgcc agggtccccc tgcatccccg actgccagcc cagagccccc gcctcctgag | 1320 |

<210> SEQ ID NO 40
<211> LENGTH: 1320
<212> TYPE: DNA
<213> ORGANISM: Artificial Sequence
<220> FEATURE:
<223> OTHER INFORMATION: Human LCAT V114R coding sequence

<400> SEQUENCE: 40

| | |
|---|---|
| atggggccgc ccggctcccc atggcagtgg gtgacgctgc tgctggggct gctgctccct | 60 |
| cctgccgccc ccttctggct cctcaatgtg ctcttccccc gcacaccac gcccaaggct | 120 |
| gagctcagta accacacacg gcccgtcatc ctcgtgcccg gctgcctggg gaatcagcta | 180 |
| gaagccaagc tggacaaacc agatgtggtg aactggatgt gctaccgcaa gacagaggac | 240 |
| ttcttcacca tctggctgga tctcaacatg ttcctacccc ttggggtaga ctgctggatc | 300 |
| gataacacca gggttgtcta caaccggagc tctgggctcc ggtccaacgc ccctggtgtc | 360 |
| cagatccgcg tccctggctt tggcaagacc tactctgtgg agtacctgga cagcagcaag | 420 |
| ctggcagggt acctgcacac actggtgcag aacctggtca caatggcta cgtgcgggac | 480 |
| gagactgtgc gcgccgcccc ctatgactgg cggctggagc ccggccagca ggaggagtac | 540 |
| taccgcaagc tcgcagggct ggtggaggag atgcacgctg cctatgggaa gcctgtcttc | 600 |
| ctcattggcc acagcctcgg ctgtctacac ttgctctatt tcctgctgcg ccagcccag | 660 |
| gcctggaagg accgctttat tgatggcttc atctctcttg gggctccctg ggtggctcc | 720 |
| atcaagccca tgctggtctt ggcctcaggt gacaaccagg gcatcccat catgtccagc | 780 |
| atcaagctga aagaggagca gcgcataacc accacctccc cctggatgtt tccctctcgc | 840 |
| atggcgtggc ctgaggacca cgtgttcatt tccacacca gcttcaacta cacaggccgt | 900 |
| gacttccaac gcttctttgc agacctgcac tttgaggaag gctggtacat gtggctgcag | 960 |
| tcacgtgacc tcctggcagg actcccagca cctggtgtgg aagtatactg tctttacggc | 1020 |
| gtgggcctgc ccacgccccg cacctacatc tacgaccacg gcttcccta cacggaccct | 1080 |
| gtgggtgtgc tctatgagga tggtgatgac acggtggcga cccgcagcac cgagctctgt | 1140 |
| ggcctgtggc agggccgcca gccacagcct gtgcacctgc tgccctgca cgggatacag | 1200 |
| catctcaaca tggtcttcag caacctgacc ctggagcaca tcaatgccat cctgctgggt | 1260 |
| gcctaccgcc agggtccccc tgcatccccg actgccagcc cagagccccc gcctcctgag | 1320 |

<210> SEQ ID NO 41
<211> LENGTH: 1320
<212> TYPE: DNA
<213> ORGANISM: Artificial Sequence
<220> FEATURE:
<223> OTHER INFORMATION: Human LCAT V114S coding sequence

<400> SEQUENCE: 41

| | | |
|---|---|---|
| atggggccgc ccggctcccc atggcagtgg gtgacgctgc tgctggggct gctgctccct | 60 |
| cctgccgccc ccttctggct cctcaatgtg ctcttccccc gcacaccac gcccaaggct | 120 |
| gagctcagta accacacacg gcccgtcatc ctcgtgcccg gctgcctggg aatcagcta | 180 |
| gaagccaagc tggacaaacc agatgtggtg aactggatgt gctaccgcaa gacagaggac | 240 |
| ttcttcacca tctggctgga tctcaacatg ttcctacccc ttggggtaga ctgctggatc | 300 |
| gataacacca gggttgtcta caaccggagc tctgggctca gctccaacgc ccctggtgtc | 360 |
| cagatccgcg tccctggctt tggcaagacc tactctgtgg agtacctgga cagcagcaag | 420 |
| ctggcagggt acctgcacac actggtgcag aacctggtca caatggcta cgtgcgggac | 480 |
| gagactgtgc gcgccgcccc ctatgactgg cggctggagc ccggccagca ggaggagtac | 540 |
| taccgcaagc tcgcagggct ggtggaggag atgcacgctg cctatgggaa gcctgtcttc | 600 |
| ctcattggcc acagcctcgg ctgtctacac ttgctctatt tcctgctgcg ccagccccag | 660 |
| gcctggaagg accgctttat tgatggcttc atctctcttg ggctccctg gggtggctcc | 720 |
| atcaagccca tgctggtctt ggcctcaggt gacaaccagg gcatccccat catgtccagc | 780 |
| atcaagctga agaggagca gcgcataacc accacctccc cctggatgtt ccctctcgc | 840 |
| atggcgtggc ctgaggacca cgtgttcatt tccacaccca gcttcaacta cacaggccgt | 900 |
| gacttccaac gcttctttgc agacctgcac tttgaggaag ctggtacat gtggctgcag | 960 |
| tcacgtgacc tcctggcagg actcccagca cctggtgtgg aagtatactg tctttacggc | 1020 |
| gtgggcctgc ccacgccccg cacctacatc tacgaccacg gcttcccta cggaccct | 1080 |
| gtgggtgtgc tctatgagga tggtgatgac acggtggcga cccgcagcac cgagctctgt | 1140 |
| ggcctgtggc agggccgcca gccacagcct gtgcacctgc tgccctgca cgggatacag | 1200 |
| catctcaaca tggtcttcag caacctgacc ctggagcaca tcaatgccat cctgctgggt | 1260 |
| gcctaccgcc agggtccccc tgcatccccg actgccagcc cagagccccc gcctcctgag | 1320 |

<210> SEQ ID NO 42
<211> LENGTH: 1320
<212> TYPE: DNA
<213> ORGANISM: Artificial Sequence
<220> FEATURE:
<223> OTHER INFORMATION: Human LCAT V114T coding sequence

<400> SEQUENCE: 42

| | | |
|---|---|---|
| atggggccgc ccggctcccc atggcagtgg gtgacgctgc tgctggggct gctgctccct | 60 |
| cctgccgccc ccttctggct cctcaatgtg ctcttccccc gcacaccac gcccaaggct | 120 |
| gagctcagta accacacacg gcccgtcatc ctcgtgcccg gctgcctggg aatcagcta | 180 |
| gaagccaagc tggacaaacc agatgtggtg aactggatgt gctaccgcaa gacagaggac | 240 |
| ttcttcacca tctggctgga tctcaacatg ttcctacccc ttggggtaga ctgctggatc | 300 |
| gataacacca gggttgtcta caaccggagc tctgggctca cctccaacgc ccctggtgtc | 360 |
| cagatccgcg tccctggctt tggcaagacc tactctgtgg agtacctgga cagcagcaag | 420 |

```
ctggcagggt acctgcacac actggtgcag aacctggtca acaatggcta cgtgcgggac     480
gagactgtgc gcgccgcccc ctatgactgg cggctggagc ccggccagca ggaggagtac     540
taccgcaagc tcgcagggct ggtggaggag atgcacgctg cctatgggaa gcctgtcttc     600
ctcattggcc acagcctcgg ctgtctacac ttgctctatt cctgctgcg ccagccccag      660 gcctggaagg accgctttat tgatggcttc atctctcttg gggctccctg ggtggctcc      720 atcaagccca tgctggtctt ggcctcaggt gacaaccagg gcatcccat catgtccagc      780 atcaagctga aagaggagca gcgcataacc accacctccc cctggatgtt ccctctcgc      840 atggcgtggc ctgaggacca cgtgttcatt ccacaccca gcttcaacta cacaggccgt      900
gacttccaac gcttctttgc agacctgcac tttgaggaag gctggtacat gtggctgcag     960
tcacgtgacc tcctggcagg actcccagca cctggtgtgg aagtatactg tctttacggc    1020
gtgggcctgc ccacgccccg cacctacatc tacgaccacg gcttcccta cacggaccct    1080 gtgggtgtgc tctatgagga tggtgatgac acggtggcga cccgcagcac cgagctctgt    1140
ggcctgtggc agggccgcca gccacagcct gtgcacctgc tgcccctgca cgggatacag    1200
catctcaaca tggtcttcag caacctgacc ctggagcaca tcaatgccat cctgctgggt    1260
gcctaccgcc agggtccccc tgcatccccg actgccagcc cagagccccc gcctcctgag    1320

<210> SEQ ID NO 43
<211> LENGTH: 1320
<212> TYPE: DNA
<213> ORGANISM: Artificial Sequence
<220> FEATURE:
<223> OTHER INFORMATION: Human LCAT V114W coding sequence

<400> SEQUENCE: 43
atggggccgc ccggctcccc atggcagtgg gtgacgctgc tgctggggct gctgctccct      60
cctgccgccc ccttctggct cctcaatgtg ctcttccccc gcacaccac gcccaaggct      120 gagctcagta accacacacg gcccgtcatc ctcgtgcccg gctgcctggg gaatcagcta     180
gaagccaagc tggacaaacc agatgtggtg aactggatgt gctaccgcaa gacagaggac     240
ttcttcacca tctggctgga tctcaacatg ttcctacccc ttggggtaga ctgctggatc     300
gataacacca gggttgtcta caaccggagc tctgggctct ggtccaacgc ccctggtgtc     360
cagatccgcg tccctggctt tggcaagacc tactctgtgg agtacctgga cagcagcaag     420
ctggcagggt acctgcacac actggtgcag aacctggtca acaatggcta cgtgcgggac     480
gagactgtgc gcgccgcccc ctatgactgg cggctggagc ccggccagca ggaggagtac     540
taccgcaagc tcgcagggct ggtggaggag atgcacgctg cctatgggaa gcctgtcttc     600
ctcattggcc acagcctcgg ctgtctacac ttgctctatt cctgctgcg ccagccccag      660 gcctggaagg accgctttat tgatggcttc atctctcttg gggctccctg ggtggctcc      720 atcaagccca tgctggtctt ggcctcaggt gacaaccagg gcatcccat catgtccagc      780 atcaagctga aagaggagca gcgcataacc accacctccc cctggatgtt ccctctcgc      840 atggcgtggc ctgaggacca cgtgttcatt ccacaccca gcttcaacta cacaggccgt      900
gacttccaac gcttctttgc agacctgcac tttgaggaag gctggtacat gtggctgcag     960
tcacgtgacc tcctggcagg actcccagca cctggtgtgg aagtatactg tctttacggc    1020
gtgggcctgc ccacgccccg cacctacatc tacgaccacg gcttcccta cacggaccct    1080 gtgggtgtgc tctatgagga tggtgatgac acggtggcga cccgcagcac cgagctctgt    1140
ggcctgtggc agggccgcca gccacagcct gtgcacctgc tgcccctgca cgggatacag    1200
```

```
catctcaaca tggtcttcag caacctgacc ctggagcaca tcaatgccat cctgctgggt    1260
gcctaccgcc agggtccccc tgcatccccg actgccagcc cagagccccc gcctcctgag    1320
```

<210> SEQ ID NO 44
<211> LENGTH: 1320
<212> TYPE: DNA
<213> ORGANISM: Artificial Sequence
<220> FEATURE:
<223> OTHER INFORMATION: Human LCAT V114Y coding sequence

<400> SEQUENCE: 44

```
atggggccgc ccggctcccc atggcagtgg gtgacgctgc tgctggggct gctgctccct     60
cctgccgccc ccttctggct cctcaatgtg ctcttccccc gcacaccac gcccaaggct    120 gagctcagta accacacacg gcccgtcatc ctcgtgcccg ctgcctggg gaatcagcta    180 gaagccaagc tggacaaacc agatgtggtg aactggatgt gctaccgcaa gacagaggac    240
ttcttcacca tctggctgga tctcaacatg ttcctacccc ttggggtaga ctgctggatc    300
gataacacca gggttgtcta accggagc tctgggctct actccaacgc ccctggtgtc    360
cagatccgcg tccctggctt tggcaagacc tactctgtgg agtacctgga cagcagcaag    420
ctggcagggt acctgcacac actggtgcag aacctggtca caatggcta cgtgcgggac    480 gagactgtgc gcgccgcccc ctatgactgg cggctggagc ccggccagca ggaggagtac    540
taccgcaagc tcgcagggct ggtggaggag atgcacgctg cctatgggaa gcctgtcttc    600
ctcattggcc acagcctcgg ctgtctacac ttgctctatt cctgctgcg ccagccccag    660 gcctggaagg accgctttat tgatggcttc atctctcttg ggctccctg ggtggctcc    720 atcaagccca tgctggtctt ggcctcaggt gacaaccagg gcatccccat catgtccagc    780
atcaagctga agaggagca gcgcataacc accacctccc cctggatgtt tccctctcgc    840
atggcgtggc ctgaggacca cgtgttcatt tccacaccca gcttcaacta cacaggccgt    900
gacttccaac gcttctttgc agacctgcac tttgaggaag ctggtacat gtggctgcag    960 tcacgtgacc tcctggcagg actcccagca cctggtgtgg aagtatactg tctttacggc    1020
gtgggcctgc ccacgccccg cacctacatc tacgaccacg gcttccccta cggaccct    1080 gtgggtgtgc tctatgagga tggtgatgac acggtggcga cccgcagcac cgagctctgt    1140
ggcctgtggc agggccgcca gccacagcct gtgcacctgc tgcccctgca gggatacag    1200 catctcaaca tggtcttcag caacctgacc ctggagcaca tcaatgccat cctgctgggt    1260
gcctaccgcc agggtccccc tgcatccccg actgccagcc cagagccccc gcctcctgag    1320
```

<210> SEQ ID NO 45
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114A coding sequence

<400> SEQUENCE: 45

```
aaataagctt gaattcgagc tcggatccac tagtccagtg tggtggaatt gcccttcaat     60
ggggccgccc ggctccccat ggcagtgggt gacgctgctg ctgggctgc tgctccctcc    120 tgccgccccc ttctggctcc tcaatgtgct cttcccccg cacaccacgc ccaaggctga    180
gctcagtaac cacacacggc ccgtcatcct cgtgcccggc tgcctgggga atcagctaga    240
agccaagctg gacaaaccag atgtggtgaa ctggatgtgc taccgcaaga cagaggactt    300
```

```
cttcaccatc tggctggatc tcaacatgtt cctacccctt ggggtagact gctggatcga    360
taacaccagg gttgtctaca accggagctc tgggctcgcc tccaacgccc tggtgtcca    420 gatccgcgtc cctggctttg gcaagaccta ctctgtggag tacctggaca gcagcaagct    480
ggcagggtac cttat                                                    495

<210> SEQ ID NO 46
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114C coding sequence

<400> SEQUENCE: 46
aaataagctt gaattcgagc tcggatccac tagtccagtg tggtggaatt gcccttcaat    60
ggggccgccc ggctccccat ggcagtgggt gacgctgctg ctggggctgc tgctccctcc    120
tgccgccccc ttctggctcc tcaatgtgct cttcccccccg cacaccacgc ccaaggctga    180
gctcagtaac cacacacggc ccgtcatcct cgtgcccggc tgcctgggga atcagctaga    240
agccaagctg gacaaaccag atgtggtgaa ctggatgtgc taccgcaaga cagaggactt    300
cttcaccatc tggctggatc tcaacatgtt cctacccctt ggggtagact gctggatcga    360
taacaccagg gttgtctaca accggagctc tgggctctgc tccaacgccc tggtgtcca    420 gatccgcgtc cctggctttg gcaagaccta ctctgtggag tacctggaca gcagcaagct    480
ggcagggtac cttat                                                    495

<210> SEQ ID NO 47
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114D coding sequence

<400> SEQUENCE: 47
aaataagctt gaattcgagc tcggatccac tagtccagtg tggtggaatt gcccttcaat    60
ggggccgccc ggctccccat ggcagtgggt gacgctgctg ctggggctgc tgctccctcc    120
tgccgccccc ttctggctcc tcaatgtgct cttcccccccg cacaccacgc ccaaggctga    180
gctcagtaac cacacacggc ccgtcatcct cgtgcccggc tgcctgggga atcagctaga    240
agccaagctg gacaaaccag atgtggtgaa ctggatgtgc taccgcaaga cagaggactt    300
cttcaccatc tggctggatc tcaacatgtt cctacccctt ggggtagact gctggatcga    360
taacaccagg gttgtctaca accggagctc tgggctcgac tccaacgccc tggtgtcca    420 gatccgcgtc cctggctttg gcaagaccta ctctgtggag tacctggaca gcagcaagct    480
ggcagggtac cttat                                                    495

<210> SEQ ID NO 48
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114E coding sequence

<400> SEQUENCE: 48
aaataagctt gaattcgagc tcggatccac tagtccagtg tggtggaatt gcccttcaat    60
```

```
ggggccgccc ggctccccat ggcagtgggt gacgctgctg ctggggctgc tgctccctcc    120
tgccgccccc ttctggctcc tcaatgtgct cttccccccg cacaccacgc ccaaggctga    180
gctcagtaac cacacacggc ccgtcatcct cgtgcccggc tgcctgggga atcagctaga    240
agccaagctg gacaaaccag atgtggtgaa ctggatgtgc taccgcaaga cagaggactt    300
cttcaccatc tggctggatc tcaacatgtt cctacccctt ggggtagact gctggatcga    360
taacaccagg gttgtctaca accggagctc tgggctcgag tccaacgccc tggtgtcca    420 gatccgcgtc cctggctttg gcaagaccta ctctgtggag tacctggaca gcagcaagct    480
ggcagggtac cttat                                                    495
```

<210> SEQ ID NO 49
<211> LENGTH: 495
<212> TYPE: DNA
<213> ORGANISM: Artificial Sequence
<220> FEATURE:
<223> OTHER INFORMATION: Gene fragment for mutagenesis to generate human LCAT-V114F coding sequence

<400> SEQUENCE: 49

```
aaataagctt gaattcgagc tcggatccac tagtccagtg tggtggaatt gcccttcaat     60
ggggccgccc ggctccccat ggcagtgggt gacgctgctg ctggggctgc tgctccctcc    120
tgccgccccc ttctggctcc tcaatgtgct cttccccccg cacaccacgc ccaaggctga    180
gctcagtaac cacacacggc ccgtcatcct cgtgcccggc tgcctgggga atcagctaga    240
agccaagctg gacaaaccag atgtggtgaa ctggatgtgc taccgcaaga cagaggactt    300
cttcaccatc tggctggatc tcaacatgtt cctaccccctt ggggtagact gctggatcga    360
taacaccagg gttgtctaca accggagctc tgggctcttc tccaacgccc tggtgtcca    420 gatccgcgtc cctggctttg gcaagaccta ctctgtggag tacctggaca gcagcaagct    480
ggcagggtac cttat                                                    495
```

<210> SEQ ID NO 50
<211> LENGTH: 495
<212> TYPE: DNA
<213> ORGANISM: Artificial Sequence
<220> FEATURE:
<223> OTHER INFORMATION: Gene fragment for mutagenesis to generate human LCAT-V114G coding sequence

<400> SEQUENCE: 50

```
aaataagctt gaattcgagc tcggatccac tagtccagtg tggtggaatt gcccttcaat     60
ggggccgccc ggctccccat ggcagtgggt gacgctgctg ctggggctgc tgctccctcc    120
tgccgccccc ttctggctcc tcaatgtgct cttccccccg cacaccacgc ccaaggctga    180
gctcagtaac cacacacggc ccgtcatcct cgtgcccggc tgcctgggga atcagctaga    240
agccaagctg gacaaaccag atgtggtgaa ctggatgtgc taccgcaaga cagaggactt    300
cttcaccatc tggctggatc tcaacatgtt cctaccccctt ggggtagact gctggatcga    360
taacaccagg gttgtctaca accggagctc tgggctcggc tccaacgccc tggtgtcca    420 gatccgcgtc cctggctttg gcaagaccta ctctgtggag tacctggaca gcagcaagct    480
ggcagggtac cttat                                                    495
```

<210> SEQ ID NO 51
<211> LENGTH: 495
<212> TYPE: DNA

<213> ORGANISM: Artificial Sequence
<220> FEATURE:
<223> OTHER INFORMATION: Gene fragment for mutagenesis to generate human
      LCAT-V114H coding sequence

<400> SEQUENCE: 51

```
aaataagctt gaattcgagc tcggatccac tagtccagtg tggtggaatt gcccttcaat    60
ggggccgccc ggctccccat ggcagtgggt gacgctgctg ctgggctgc tgctccctcc    120
tgccgccccc ttctggctcc tcaatgtgct cttcccccg cacaccacgc ccaaggctga   180
gctcagtaac cacacacggc ccgtcatcct cgtgcccggc tgcctgggga atcagctaga   240
agccaagctg gacaaaccag atgtggtgaa ctggatgtgc taccgcaaga cagaggactt   300
cttcaccatc tggctggatc tcaacatgtt cctaccccctt ggggtagact gctggatcga   360
taacaccagg gttgtctaca accggagctc tgggctccac tccaacgccc ctggtgtcca   420
gatccgcgtc cctggctttg caagaccta ctctgtggag tacctggaca gcagcaagct   480
ggcagggtac cttat                                                   495
```

<210> SEQ ID NO 52
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114I coding sequence

<400> SEQUENCE: 52

```
aaataagctt gaattcgagc tcggatccac tagtccagtg tggtggaatt gcccttcaat    60
ggggccgccc ggctccccat ggcagtgggt gacgctgctg ctgggctgc tgctccctcc    120
tgccgccccc ttctggctcc tcaatgtgct cttcccccg cacaccacgc ccaaggctga   180
gctcagtaac cacacacggc ccgtcatcct cgtgcccggc tgcctgggga atcagctaga   240
agccaagctg gacaaaccag atgtggtgaa ctggatgtgc taccgcaaga cagaggactt   300
cttcaccatc tggctggatc tcaacatgtt cctaccccctt ggggtagact gctggatcga   360
taacaccagg gttgtctaca accggagctc tgggctcatc tccaacgccc ctggtgtcca   420
gatccgcgtc cctggctttg caagaccta ctctgtggag tacctggaca gcagcaagct   480
ggcagggtac cttat                                                   495
```

<210> SEQ ID NO 53
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114K coding sequence

<400> SEQUENCE: 53

```
aaataagctt gaattcgagc tcggatccac tagtccagtg tggtggaatt gcccttcaat    60
ggggccgccc ggctccccat ggcagtgggt gacgctgctg ctgggctgc tgctccctcc    120
tgccgccccc ttctggctcc tcaatgtgct cttcccccg cacaccacgc ccaaggctga   180
gctcagtaac cacacacggc ccgtcatcct cgtgcccggc tgcctgggga atcagctaga   240
agccaagctg gacaaaccag atgtggtgaa ctggatgtgc taccgcaaga cagaggactt   300
cttcaccatc tggctggatc tcaacatgtt cctaccccctt ggggtagact gctggatcga   360
taacaccagg gttgtctaca accggagctc tgggctcaag tccaacgccc ctggtgtcca   420
```

```
gatccgcgtc cctggctttg gcaagaccta ctctgtggag tacctggaca gcagcaagct    480
ggcagggtac cttat                                                    495
```

<210> SEQ ID NO 54
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114L coding sequence

<400> SEQUENCE: 54

```
aaataagctt gaattcgagc tcggatccac tagtccagtg tggtggaatt gcccttcaat     60
ggggccgccc ggctccccat ggcagtgggt gacgctgctg ctgggctgc tgctccctcc    120 tgccgccccc ttctggctcc tcaatgtgct cttcccccg cacaccacgc ccaaggctga    180
gctcagtaac cacacacggc ccgtcatcct cgtgcccggc tgcctgggga atcagctaga    240
agccaagctg gacaaaccag atgtggtgaa ctggatgtgc taccgcaaga cagaggactt    300
cttcaccatc tggctggatc tcaacatgtt cctaccccct tggggtagact gctggatcga    360 taacaccagg gttgtctaca accggagctc tgggctcctg tccaacgccc ctggtgtcca    420
gatccgcgtc cctggctttg gcaagaccta ctctgtggag tacctggaca gcagcaagct    480
ggcagggtac cttat                                                    495
```

<210> SEQ ID NO 55
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114N coding sequence

<400> SEQUENCE: 55

```
aaataagctt gaattcgagc tcggatccac tagtccagtg tggtggaatt gcccttcaat     60
ggggccgccc ggctccccat ggcagtgggt gacgctgctg ctgggctgc tgctccctcc    120 tgccgccccc ttctggctcc tcaatgtgct cttcccccg cacaccacgc ccaaggctga    180
gctcagtaac cacacacggc ccgtcatcct cgtgcccggc tgcctgggga atcagctaga    240
agccaagctg gacaaaccag atgtggtgaa ctggatgtgc taccgcaaga cagaggactt    300
cttcaccatc tggctggatc tcaacatgtt cctaccccct tggggtagact gctggatcga    360 taacaccagg gttgtctaca accggagctc tgggctcaac tccaacgccc ctggtgtcca    420
gatccgcgtc cctggctttg gcaagaccta ctctgtggag tacctggaca gcagcaagct    480
ggcagggtac cttat                                                    495
```

<210> SEQ ID NO 56
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114P coding sequence

<400> SEQUENCE: 56

```
aaataagctt gaattcgagc tcggatccac tagtccagtg tggtggaatt gcccttcaat     60
ggggccgccc ggctccccat ggcagtgggt gacgctgctg ctgggctgc tgctccctcc    120 tgccgccccc ttctggctcc tcaatgtgct cttcccccg cacaccacgc ccaaggctga    180
```

| | | |
|---|---|---|
| gctcagtaac cacacacggc ccgtcatcct cgtgcccggc tgcctgggga atcagctaga | 240 | |
| agccaagctg gacaaaccag atgtggtgaa ctggatgtgc taccgcaaga cagaggactt | 300 | |
| cttcaccatc tggctggatc tcaacatgtt cctaccccct ggggtagact gctggatcga | 360 | |
| taacaccagg gttgtctaca accggagctc tgggctcccc tccaacgccc tggtgtcca | 420 | |
| gatccgcgtc cctggctttg gcaagaccta ctctgtggag tacctggaca gcagcaagct | 480 | |
| ggcagggtac cttat | 495 | |

<210> SEQ ID NO 57
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114Q coding sequence

<400> SEQUENCE: 57

| | | |
|---|---|---|
| aaataagctt gaattcgagc tcggatccac tagtccagtg tggtggaatt gcccttcaat | 60 | |
| ggggccgccc ggctccccat ggcagtgggt gacgctgctg ctgggctgc tgctccctcc | 120 | |
| tgccgccccc ttctggctcc tcaatgtgct cttcccccccg cacaccacgc ccaaggctga | 180 | |
| gctcagtaac cacacacggc ccgtcatcct cgtgcccggc tgcctgggga atcagctaga | 240 | |
| agccaagctg gacaaaccag atgtggtgaa ctggatgtgc taccgcaaga cagaggactt | 300 | |
| cttcaccatc tggctggatc tcaacatgtt cctaccccct ggggtagact gctggatcga | 360 | |
| taacaccagg gttgtctaca accggagctc tgggctccag tccaacgccc tggtgtcca | 420 | |
| gatccgcgtc cctggctttg gcaagaccta ctctgtggag tacctggaca gcagcaagct | 480 | |
| ggcagggtac cttat | 495 | |

<210> SEQ ID NO 58
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114R coding sequence

<400> SEQUENCE: 58

| | | |
|---|---|---|
| aaataagctt gaattcgagc tcggatccac tagtccagtg tggtggaatt gcccttcaat | 60 | |
| ggggccgccc ggctccccat ggcagtgggt gacgctgctg ctgggctgc tgctccctcc | 120 | |
| tgccgccccc ttctggctcc tcaatgtgct cttcccccccg cacaccacgc ccaaggctga | 180 | |
| gctcagtaac cacacacggc ccgtcatcct cgtgcccggc tgcctgggga atcagctaga | 240 | |
| agccaagctg gacaaaccag atgtggtgaa ctggatgtgc taccgcaaga cagaggactt | 300 | |
| cttcaccatc tggctggatc tcaacatgtt cctaccccct ggggtagact gctggatcga | 360 | |
| taacaccagg gttgtctaca accggagctc tgggctccgg tccaacgccc tggtgtcca | 420 | |
| gatccgcgtc cctggctttg gcaagaccta ctctgtggag tacctggaca gcagcaagct | 480 | |
| ggcagggtac cttat | 495 | |

<210> SEQ ID NO 59
<211> LENGTH: 495
<212> TYPE: DNA
<213> ORGANISM: Artificial Sequence
<220> FEATURE:
<223> OTHER INFORMATION: Gene fragment for mutagenesis to generate human
      LCAT-V114S coding sequence

<400> SEQUENCE: 59

```
aaataagctt gaattcgagc tcggatccac tagtccagtg tggtggaatt gcccttcaat    60
ggggccgccc ggctccccat ggcagtgggt gacgctgctg ctggggctgc tgctccctcc   120
tgccgccccc ttctggctcc tcaatgtgct cttcccccg cacaccacgc ccaaggctga    180
gctcagtaac cacacacggc ccgtcatcct cgtgcccggc tgcctgggga atcagctaga   240
agccaagctg gacaaaccag atgtggtgaa ctggatgtgc taccgcaaga cagaggactt   300
cttcaccatc tggctggatc tcaacatgtt cctaccccct tggggtagact gctggatcga   360
taacaccagg gttgtctaca accggagctc tgggctcagc tccaacgccc ctggtgtcca   420
gatccgcgtc cctggctttg gcaagaccta ctctgtggag tacctggaca gcagcaagct   480
ggcagggtac cttat                                                   495
```

<210> SEQ ID NO 60
<211> LENGTH: 495
<212> TYPE: DNA
<213> ORGANISM: Artificial Sequence
<220> FEATURE:
<223> OTHER INFORMATION: Gene fragment for mutagenesis to generate human LCAT-V114T coding sequence

<400> SEQUENCE: 60

```
aaataagctt gaattcgagc tcggatccac tagtccagtg tggtggaatt gcccttcaat    60
ggggccgccc ggctccccat ggcagtgggt gacgctgctg ctggggctgc tgctccctcc   120
tgccgccccc ttctggctcc tcaatgtgct cttcccccg cacaccacgc ccaaggctga    180
gctcagtaac cacacacggc ccgtcatcct cgtgcccggc tgcctgggga atcagctaga   240
agccaagctg gacaaaccag atgtggtgaa ctggatgtgc taccgcaaga cagaggactt   300
cttcaccatc tggctggatc tcaacatgtt cctaccccct tggggtagact gctggatcga   360
taacaccagg gttgtctaca accggagctc tgggctcacc tccaacgccc ctggtgtcca   420
gatccgcgtc cctggctttg gcaagaccta ctctgtggag tacctggaca gcagcaagct   480
ggcagggtac cttat                                                   495
```

<210> SEQ ID NO 61
<211> LENGTH: 495
<212> TYPE: DNA
<213> ORGANISM: Artificial Sequence
<220> FEATURE:
<223> OTHER INFORMATION: Gene fragment for mutagenesis to generate human LCAT-V114W coding sequence

<400> SEQUENCE: 61

```
aaataagctt gaattcgagc tcggatccac tagtccagtg tggtggaatt gcccttcaat    60
ggggccgccc ggctccccat ggcagtgggt gacgctgctg ctggggctgc tgctccctcc   120
tgccgccccc ttctggctcc tcaatgtgct cttcccccg cacaccacgc ccaaggctga    180
gctcagtaac cacacacggc ccgtcatcct cgtgcccggc tgcctgggga atcagctaga   240
agccaagctg gacaaaccag atgtggtgaa ctggatgtgc taccgcaaga cagaggactt   300
cttcaccatc tggctggatc tcaacatgtt cctaccccct tggggtagact gctggatcga   360
taacaccagg gttgtctaca accggagctc tgggctctgg tccaacgccc ctggtgtcca   420
gatccgcgtc cctggctttg gcaagaccta ctctgtggag tacctggaca gcagcaagct   480
ggcagggtac cttat                                                   495
```

<210> SEQ ID NO 62
<211> LENGTH: 478
<212> TYPE: DNA
<213> ORGANISM: Artificial Sequence
<220> FEATURE:
<223> OTHER INFORMATION: Gene fragment for mutagenesis to generate human
      LCAT-V114Y coding sequence

<400> SEQUENCE: 62

| aaataagctt | gaattcgagc | tcggatccac | tagtccagtg | tggtggaatt | gcccttcaat | 60 |
| ggggccgccc | ggctccccat | ggcagtgggt | gacgctgctg | ctggggctgc | tgctccctcc | 120 |
| tgccgcccccc | ttctggctcc | tcaatgtgct | cttcccccccg | cacaccacgc | ccaaggctga | 180 |
| gctcagtaac | cacacacggc | ccgtcatcct | cgtgcccggc | tgcctgggga | atcagctaga | 240 |
| agccaagctg | gacaaaccag | atgtggtgaa | ctggatgtgc | taccgcaaga | cagaggactt | 300 |
| cttcaccatc | tggctggatc | tcaacatgtt | cctaccccctt | ggggtagact | gctggatcga | 360 |
| taacaccagg | gttgtctaca | accggagctc | tgggctctac | tccaacgccc | tggtgtcca | 420 |
| gatccgcgtc | cctggctttg | caagaccta | ctctgtggag | tacctggaca | gcagcaag | 478 |

<210> SEQ ID NO 63
<211> LENGTH: 1323
<212> TYPE: DNA
<213> ORGANISM: Artificial Sequence
<220> FEATURE:
<223> OTHER INFORMATION: Codon-optimized human LCAT V114M v1

<400> SEQUENCE: 63

| atggggcccc | ccgggagccc | ctggcagtgg | gtgaccctgc | tgctggggct | gctgctgccc | 60 |
| cccgccgccc | ccttctggct | gctgaacgtg | ctgttccccc | ccacaccac | ccccaaggcc | 120 |
| gagctgagca | ccacacccg | gcccgtgatc | ctggtgcccg | gtgcctggg | gaaccagctg | 180 |
| gaggccaagc | tggacaagcc | cgacgtggtg | aactggatgt | gctaccggaa | gaccgaggac | 240 |
| ttcttcacca | tctggctgga | cctgaacatg | ttcctgcccc | tgggggtgga | ctgctggatc | 300 |
| gacaacaccc | gggtggtgta | caaccggagc | agcgggctga | tgagcaacgc | cccggggtg | 360 |
| cagatccggg | tgcccgggtt | cggaagacc | tacagcgtgg | agtacctgga | cagcagcaag | 420 |
| ctggccgggt | acctgcacac | cctggtgcag | aacctggtga | caacgggta | cgtgcgggac | 480 |
| gaaaccgtgc | gggccgcccc | ctacgactgg | cggctgagc | ccgggcagca | ggaggagtac | 540 |
| taccggaagc | tggccgggct | ggtggaggag | atgcacgccg | cctacgggaa | gcccgtgttc | 600 |
| ctgatcgggc | acagcctggg | gtgcctgcac | ctcctgtact | cctgctgcg | gcagccccag | 660 |
| gcctggaagg | accggttcat | cgacgggttc | atcagcctgg | ggcccccctg | ggagggagc | 720 |
| atcaagccca | tgctggtgct | ggccagcggg | gacaaccagg | ggatccccat | catgagcagc | 780 |
| atcaagctga | aggaggagca | gcggatcacc | accaccagcc | cctggatgtt | ccccagccgg | 840 |
| atggcctggc | ccgaggacca | cgtgttcatc | agcaccccca | gcttcaacta | cacccgggcgg | 900 |
| gacttccagc | ggttcttcgc | cgacctgcac | ttcgaggagg | gtggtacat | gtggctgcag | 960 |
| agccgggacc | tgctggccgg | gctgcccgcc | ccggggtgg | aggtgtactg | cctgtacggg | 1020 |
| gtggggctgc | ccaccccccg | gacctacatc | tacgaccacg | gttccccta | caccgacccc | 1080 |
| gtgggggtgc | tgtacgagga | cggggacgac | accgtggcca | ccggagcac | cgagctgtgc | 1140 |
| gggctgtggc | aggggcggca | gcccagccc | gtgcacctcc | tgcccctgca | cgggatccag | 1200 |
| cacctgaaca | tggtgttcag | caacctgacc | ctggagcaca | tcaacgccat | cctgctgggg | 1260 |
| gcctaccggc | agggggcccc | cgccagcccc | accgccagcc | ccgagccccc | accccccgag | 1320 |

-continued tga                                                                    1323

<210> SEQ ID NO 64
<211> LENGTH: 20
<212> TYPE: DNA
<213> ORGANISM: Artificial Sequence
<220> FEATURE:
<223> OTHER INFORMATION: PCR primer for mouse beta-actin

<400> SEQUENCE: 64
ttgggtatgg aatcctgtgg                                                    20

<210> SEQ ID NO 65
<211> LENGTH: 20
<212> TYPE: DNA
<213> ORGANISM: Artificial Sequence
<220> FEATURE:
<223> OTHER INFORMATION: PCR primer for mouse beta-actin

<400> SEQUENCE: 65
cttctgcatc ctgtcagcaa                                                    20

<210> SEQ ID NO 66
<211> LENGTH: 19
<212> TYPE: DNA
<213> ORGANISM: Artificial Sequence
<220> FEATURE:
<223> OTHER INFORMATION: PCR primer for mouse 18S

<400> SEQUENCE: 66
cttagaggga caagtggcg                                                     19

<210> SEQ ID NO 67
<211> LENGTH: 20
<212> TYPE: DNA
<213> ORGANISM: Artificial Sequence
<220> FEATURE:
<223> OTHER INFORMATION: PCR primer for mouse 18S

<400> SEQUENCE: 67
acgctgagcc agtcagtgta                                                    20

<210> SEQ ID NO 68
<211> LENGTH: 20
<212> TYPE: DNA
<213> ORGANISM: Artificial Sequence
<220> FEATURE:
<223> OTHER INFORMATION: PCR primer set 1 for human LCAT

<400> SEQUENCE: 68
ccagggttgt ctacaaccgg                                                    20

<210> SEQ ID NO 69
<211> LENGTH: 20
<212> TYPE: DNA
<213> ORGANISM: Artificial Sequence
<220> FEATURE:
<223> OTHER INFORMATION: PCR primer set 1 for human LCAT

<400> SEQUENCE: 69
ggcgcagcag gaaatagagc                                                    20

<210> SEQ ID NO 70
<211> LENGTH: 2908
<212> TYPE: DNA

```
<213> ORGANISM: Artificial Sequence
<220> FEATURE:
<223> OTHER INFORMATION: AAV-TBG-hLCAT genome vector.
<220> FEATURE:
<221> NAME/KEY: repeat_region
<222> LOCATION: (1)..(173)
<223> OTHER INFORMATION: 5' ITR
<220> FEATURE:
<221> NAME/KEY: misc_feature
<222> LOCATION: (195)..(294)
<223> OTHER INFORMATION: alpha mic/bik
<220> FEATURE:
<221> NAME/KEY: promoter
<222> LOCATION: (415)..(874)
<223> OTHER INFORMATION: TBG Promoter
<220> FEATURE:
<221> NAME/KEY: Intron
<222> LOCATION: (918)..(1050)
<223> OTHER INFORMATION: Chimeric Intron from human beta-globin and
      immunoglobulin heavy chain genes
<220> FEATURE:
<221> NAME/KEY: misc_feature
<222> LOCATION: (1109)..(2428)
<223> OTHER INFORMATION: coding sequence of human LCAT-V114M
<220> FEATURE:
<221> NAME/KEY: polyA_signal
<222> LOCATION: (2493)..(2614)
<223> OTHER INFORMATION: SV40 polyadenylation signal
<220> FEATURE:
<221> NAME/KEY: repeat_region
<222> LOCATION: (2736)..(2908)
<223> OTHER INFORMATION: 3' ITR

<400> SEQUENCE: 70
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt ccttgtagtt aatgattaac ccgccatgct acttatctac gtagccatgc     180
tctaggaaga tccaggttaa ttttttaaaaa gcagtcaaaa gtccaagtgg cccttggcag    240
catttactct ctctgtttgc tctggttaat aatctcagga gcacaaacat tccagatcca     300
ggttaatttt taaaaagcag tcaaaagtcc aagtggccct tggcagcatt tactctctct    360
gtttgctctg gttaataatc tcaggagcac aaacattcca gatccggcgc gccagggctg    420
gaagctacct ttgacatcat ttcctctgcg aatgcatgta taatttctac agaacctatt    480
agaaaggatc acccagcctc tgcttttgta caactttccc ttaaaaaact gccaattcca    540
ctgctgtttg gcccaatagt gagaactttt tcctgctgcc tcttggtgct tttgcctatg    600 gccactatc tgcctgctga agacactctt gccagcatgg acttaaaccc ctccagctct    660
gacaatcctc tttctctttt gttttacatg aagggtctgg cagccaaagc aatcactcaa    720
agttcaaacc ttatcatttt ttgctttgtt cctcttggcc ttggttttgt acatcagctt    780
tgaaaatacc atcccagggt taatgctggg gttaatttat aactaagagt gctctagttt    840
tgcaatacag gacatgctat aaaaatggaa agatgttgct ttctgagaga tctgcttcag    900
ctggaggcac tgggcaggta agtatcaagg ttacaagaca ggtttaagga gaccaataga    960
aactgggctt gtcgagacag agaagactct tgcgtttctg ataggcacct attggtctta   1020
ctgacatcca ctttgccttt ctctccacag gtgcagctgc tgcagcggga attccagaag   1080
ccactcgagg aggctagcgc gcgtccgaat ggggccgccc ggctccccat ggcagtgggt   1140
gacgctgctg ctggggctgc tgctccctcc tgccgccccc ttctggctcc tcaatgtgct   1200
cttccccccg cacaccacgc ccaaggctga gctcagtaac cacacacggc ccgtcatcct   1260
cgtgcccggc tgcctgggga atcagctaga agccaagctg gacaaaccag atgtggtgaa   1320
```

```
ctggatgtgc taccgcaaga cagaggactt cttcaccatc tggctggatc tcaacatgtt    1380
cctaccccctt ggggtagact gctggatcga taacaccagg gttgtctaca accggagctc   1440
tgggctcatg tccaacgccc ctggtgtcca gatccgcgtc cctggctttg gcaagaccta    1500
ctctgtggag tacctggaca gcagcaagct ggcagggtac ctgcacacac tggtgcagaa    1560
cctggtcaac aatggctacg tgcgggacga gactgtgcgc gccgccccct atgactggcg    1620
gctggagccc ggccagcagg aggagtacta ccgcaagctc gcagggctgg tggaggagat    1680
gcacgctgcc tatgggaagc ctgtcttcct cattggccac agcctcggct gtctacactt    1740
gctctatttc ctgctgcgcc agccccaggc ctggaaggac cgctttattg atggcttcat    1800
ctctcttggg gctccctggg gtggctccat caagcccatg ctggtcttgg cctcaggtga    1860
caaccagggc atccccatca tgtccagcat caagctgaaa gaggagcagc gcataaccac    1920
cacctccccc tggatgtttc cctctcgcat ggcgtggcct gaggaccacg tgttcatttc    1980
cacacccagc ttcaactaca caggccgtga cttccaacgc ttctttgcag acctgcactt    2040
tgaggaaggc tggtacatgt ggctgcagtc acgtgacctc ctggcaggac tcccagcacc    2100
tggtgtggaa gtatactgtc tttacggcgt gggcctgccc acgccccgca cctacatcta    2160
cgaccacggc ttcccctaca cggacccgtg gggtgtgctc tatgaggatg gtgatgacac    2220
ggtggcgacc cgcagcaccg agctctgtgg cctgtggcag ggccgccagc acagcctgt    2280
gcacctgctg cccctgcacg ggatacagca tctcaacatg gtcttcagca acctgaccct    2340
ggagcacatc aatgccatcc tgctgggtgc ctaccgccag ggtcccccctg catccccgac    2400
tgccagccca gagcccccgc ctcctgaata aagaccttcc tttgctaccg taaaaaaaaa    2460
aaaaaaggg cggccgcttc gagcagacat gataagatac attgatgagt ttggacaaac    2520
cacaactaga atgcagtgaa aaaaatgctt tatttgtgaa atttgtgatg ctattgcttt    2580
atttgtaacc attataagct gcaataaaca agttaacaac aacaattgca ttcattttat    2640
gtttcaggtt cagggggaga tgtgggaggt tttttaaagc aagtaaaacc tctacaaatg    2700
tggtaaaatc gataaggatc ttcctagagc atggctacgt agataagtag catggcgggt    2760
taatcattaa ctacaaggaa cccctagtga tggagttggc cactccctct ctgcgcgctc    2820
gctcgctcac tgaggccggg cgaccaaagg tcgcccgacg cccgggcttt gcccgggcgg    2880
cctcagtgag cgagcgagcg cgcagctg                                       2908
```

<210> SEQ ID NO 71
<211> LENGTH: 2874
<212> TYPE: DNA
<213> ORGANISM: Artificial Sequence
<220> FEATURE:
<223> OTHER INFORMATION: AAV-TBG-hLCATco-v1 genome vector.
<220> FEATURE:
<221> NAME/KEY: repeat_region
<222> LOCATION: (1)..(173)
<223> OTHER INFORMATION: 5' ITR
<220> FEATURE:
<221> NAME/KEY: enhancer
<222> LOCATION: (195)..(294)
<223> OTHER INFORMATION: alpha mic/bik
<220> FEATURE:
<221> NAME/KEY: promoter
<222> LOCATION: (415)..(874)
<223> OTHER INFORMATION: TBG Promoter
<220> FEATURE:
<221> NAME/KEY: Intron
<222> LOCATION: (918)..(1050)
<223> OTHER INFORMATION: Chimera intron from human beta-globin and
      immunoglobulin heavy chain genes
<220> FEATURE:

```
<221> NAME/KEY: misc_feature
<222> LOCATION: (1094)..(2437)
<223> OTHER INFORMATION: codon-optimized coding sequence of human LCAT,
      v1, LCATco-v1
<220> FEATURE:
<221> NAME/KEY: misc_signal
<222> LOCATION: (1104)..(1113)
<223> OTHER INFORMATION: Kozak sequence
<220> FEATURE:
<221> NAME/KEY: polyA_signal
<222> LOCATION: (2459)..(2580)
<223> OTHER INFORMATION: SV40 polyadenylation signal
<220> FEATURE:
<221> NAME/KEY: repeat_region
<222> LOCATION: (2702)..(2874)
<223> OTHER INFORMATION: 3' ITR

<400> SEQUENCE: 71
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt ccttgtagtt aatgattaac ccgccatgct acttatctac gtagccatgc     180
tctaggaaga tccaggttaa ttttaaaaa gcagtcaaaa gtccaagtgg cccttggcag      240
catttactct ctctgtttgc tctggttaat aatctcagga gcacaaacat tccagatcca     300
ggttaatttt taaaaagcag tcaaaagtcc aagtggccct tggcagcatt tactctctct     360
gtttgctctg gttaataatc tcaggagcac aaacattcca gatccggcgc gccagggctg     420
gaagctacct ttgacatcat ttcctctgcg aatgcatgta aatttctac agaacctatt      480 agaaaggatc acccagcctc tgcttttgta caactttccc ttaaaaaact gccaattcca     540
ctgctgtttg gcccaatagt gagaactttt tcctgctgcc tcttggtgct tttgcctatg     600 gccctattc tgcctgctga agacactctt gccagcatgg acttaaaccc ctccagctct     660
gacaatcctc tttctctttt gttttacatg aagggtctgg cagccaaagc aatcactcaa     720
agttcaaacc ttatcatttt ttgctttgtt cctcttggcc ttggttttgt acatcagctt     780
tgaaaatacc atcccagggt taatgctggg gttaattat aactaagagt gctctagttt      840
tgcaatacag gacatgctat aaaaatggaa agatgttgct ttctgagaga tctgcttcag     900
ctggaggcac tgggcaggta agtatcaagg ttacaagaca ggtttaagga gaccaataga     960
aactgggctt gtcgagacag agaagactct tgcgtttctg ataggcacct attggtctta    1020
ctgacatcca ctttgccttt ctctccacag gtgcagctgc tgcagcggga attccagaag    1080
ccactcgagg aggctagtcc taggccacca tggggcccccc cgggagcccc tggcagtggg    1140
tgaccctgct gctggggctg ctgctgcccc ccgccgcccc cttctggctg ctgaacgtgc    1200
tgttcccccc ccacaccacc cccaaggccg agctgagcaa ccacaccgg cccgtgatcc    1260 tggtgccccgg gtgcctgggg aaccagctgg aggccaagct ggacaagccc gacgtggtga    1320
actggatgtg ctaccggaag accgaggact cttcaccat ctggctggac ctgaacatgt     1380 tcctgccccct gggggtggac tgctggatcg acaacacccg ggtggtgtac aaccggagca    1440
gcgggctggt gagcaacgcc cccggggtgc agatccgggt gcccgggttc gggaagacct    1500
acagcgtgga gtacctggac agcagcaagc tggccgggta cctgcacacc ctggtgcaga    1560
acctggtgaa caacgggtac gtgcgggacg aaaccgtgcg ggccgccccc tacgactggc    1620
ggctggagcc cggcagcag gaggagtact accggaagct ggccgggctg gtggaggaga    1680
tgcacgccgc ctacgggaag cccgtgttcc tgatcgggca cagcctgggg tgcctgcacc    1740
tcctgtactt cctgctgcgg cagccccagg cctggaagga ccggttcatc gacgggttca    1800
```

```
tcagcctggg ggcccctgg ggagggagca tcaagcccat gctggtgctg gccagcgggg    1860
acaaccaggg gatccccatc atgagcagca tcaagctgaa ggaggagcag cggatcacca    1920
ccaccagccc ctggatgttc cccagccgga tggcctggcc cgaggaccac gtgttcatca    1980 gcaccccag cttcaactac accgggcggg acttccagcg gttcttcgcc gacctgcact    2040
tcgaggaggg gtggtacatg tggctgcaga gccgggacct gctggccggg ctgcccgccc    2100
ccggggtgga ggtgtactgc ctgtacgggg tggggctgcc cacccccgg acctacatct    2160 acgaccacgg gttcccctac accgaccccg tggggtgct gtacgaggac ggggacgaca    2220
ccgtggccac ccggagcacc gagctgtgcg ggctgtggca ggggcggcag ccccagcccg    2280
tgcacctcct gcccctgcac gggatccagc acctgaacat ggtgttcagc aacctgaccc    2340
tggagcacat caacgccatc ctgctggggg cctaccggca ggggcccccc gccagcccca    2400
ccgccagccc cgagcccca ccccccgagt gataagcggc cgcttcgagc agacatgata    2460
agatacattg atgagtttgg acaaaccaca actagaatgc agtgaaaaaa atgctttatt    2520
tgtgaaattt gtgatgctat tgcttttattt gtaaccatta taagctgcaa taaacaagtt    2580
aacaacaaca attgcattca ttttatgttt caggttcagg gggagatgtg ggaggttttt    2640
taaagcaagt aaaacctcta caaatgtggt aaaatcgata aggatcttcc tagagcatgg    2700
ctacgtagat aagtagcatg gcgggttaat cattaactac aaggaacccc tagtgatgga    2760
gttggccact ccctctctgc gcgctcgctc gctcactgag gccgggcgac caaaggtcgc    2820
ccgacgcccg ggctttgccc gggcggcctc agtgagcgag cgagcgcgca gctg          2874
```

```
<210> SEQ ID NO 72
<211> LENGTH: 2874
<212> TYPE: DNA
<213> ORGANISM: Artificial Sequence
<220> FEATURE:
<223> OTHER INFORMATION: AAV-TBG-hLCAT-V114M-co-v1 genome vector
<220> FEATURE:
<221> NAME/KEY: repeat_region
<222> LOCATION: (1)..(173)
<223> OTHER INFORMATION: 5' ITR
<220> FEATURE:
<221> NAME/KEY: enhancer
<222> LOCATION: (195)..(294)
<223> OTHER INFORMATION: alpha mic/bik
<220> FEATURE:
<221> NAME/KEY: promoter
<222> LOCATION: (415)..(874)
<223> OTHER INFORMATION: TBG Promoter
<220> FEATURE:
<221> NAME/KEY: Intron
<222> LOCATION: (918)..(1050)
<223> OTHER INFORMATION: Chimera intron from human beta-globin and
    immunoglobulin heavy chain genes
<220> FEATURE:
<221> NAME/KEY: misc_feature
<222> LOCATION: (1110)..(2429)
<223> OTHER INFORMATION: codon-optimized coding sequence of human LCAT
    V-114M variant, v1, hLCAT-V114M-co-v1
<220> FEATURE:
<221> NAME/KEY: polyA_signal
<222> LOCATION: (2459)..(2580)
<223> OTHER INFORMATION: SV40 polyadenylation signal
<220> FEATURE:
<221> NAME/KEY: repeat_region
<222> LOCATION: (2702)..(2874)
<223> OTHER INFORMATION: 3' ITR

<400> SEQUENCE: 72
cagctgcgcg ctcgctcgct cactgaggcc gcccgggcaa agcccgggcg tcgggcgacc       60
tttggtcgcc cggcctcagt gagcgagcga gcgcgcagag agggagtggc caactccatc      120
```

```
actaggggtt ccttgtagtt aatgattaac ccgccatgct acttatctac gtagccatgc    180
tctaggaaga tccaggttaa tttttaaaaa gcagtcaaaa gtccaagtgg cccttggcag    240
catttactct ctctgtttgc tctggttaat aatctcagga gcacaaacat tccagatcca    300
ggttaatttt taaaaagcag tcaaaagtcc aagtggccct tggcagcatt tactctctct    360
gtttgctctg gttaataatc tcaggagcac aaacattcca gatccggcgc gccagggctg    420
gaagctacct ttgacatcat ttcctctgcg aatgcatgta taatttctac agaacctatt    480
agaaaggatc acccagcctc tgcttttgta caactttccc ttaaaaaact gccaattcca    540
ctgctgtttg gcccaatagt gagaactttt tcctgctgcc tcttggtgct tttgcctatg    600
gcccctattc tgcctgctga agacactctt gccagcatgg acttaaaccc ctccagctct    660
gacaatcctc tttctctttt gttttacatg aagggtctgg cagccaaagc aatcactcaa    720
agttcaaacc ttatcatttt ttgctttgtt cctcttggcc ttggttttgt acatcagctt    780
tgaaaatacc atcccagggt taatgctggg gttaatttat aactaagagt gctctagttt    840
tgcaatacag gacatgctat aaaaatggaa agatgttgct ttctgagaga tctgcttcag    900
ctggaggcac tggcaggta agtatcaagg ttacaagaca ggtttaagga gaccaataga    960
aactgggctt gtcgagacag agaagactct tgcgtttctg ataggcacct attggtctta   1020
ctgacatcca ctttgccttt ctctccacag gtgcagctgc tgcagcggga attccagaag   1080
ccactcgagg aggctagtcc taggccacca tggggccccc cgggagcccc tggcagtggg   1140
tgaccctgct gctggggctg ctgctgcccc ccgccgcccc cttctggctg ctaacgtgc    1200 tgttcccccc ccacaccacc cccaaggccg agctgagcaa ccacacccgg cccgtgatcc   1260
tggtgcccgg gtgcctgggg aaccagctgg aggccaagct ggacaagccc gacgtggtga   1320
actggatgtg ctaccggaag accgaggact tcttcaccat ctggctggac ctgaacatgt   1380 tcctgccccct gggggtggac tgctggatcg acaacacccg ggtggtgtac aaccggagca   1440
gcgggctgat gagcaacgcc cccggggtgc agatccgggt gcccgggttc gggaagacct   1500
acagcgtgga gtacctggac agcagcaagc tggccgggta cctgcacacc ctggtgcaga   1560
acctggtgaa caacgggtac gtgcgggacg aaaccgtgcg ggccgccccc tacgactggc   1620
ggctggagcc cggcagcag gaggagtact accggaagct ggccgggctg gtggaggaga   1680
tgcacgccgc ctacggaaag cccgtgttcc tgatcgggca cagcctgggg tgcctgcacc   1740
tcctgtactt cctgctgcgg cagccccagg cctggaagga ccggttcatc gacgggttca   1800
tcagcctggg ggcccctgg ggagggagca tcaagcccat gctggtgctg gccagcgggg   1860
acaaccaggg gatccccatc atgagcagca tcaagctgaa ggaggagcag cggatcacca   1920
ccaccagccc ctggatgttc cccagccgga tggcctggcc cgaggaccac gtgttcatca   1980
gcacccccag cttcaactac accgggcggg acttccagcg gttcttcgcc gacctgcact   2040
tcgaggagtg gtgtacatg tggctgcaga gccgggacct gctggccggg ctgccgccc    2100 ccgggggtgga ggtgtactgc ctgtacgggg tgggctgcc caccccccgg acctacatct   2160
acgaccacgg gttccccctac accgacccccg tggggtgct gtacgaggac ggggacgaca   2220
ccgtggccac ccggagcacc gagctgtgcg gctgtggca gggcggcag cccagcccg    2280 tgcacctcct gccccgtgcac gggatccagc acctgaacat ggtgttcagc aacctgaccc   2340
tggagcacat caacgccatc ctgctggggg cctaccggca gggcccccc gccagcccca   2400 ccgccagccc cgagccccca cccccgagt gataagcggc cgcttcgagc agacatgata   2460
```

```
agatacattg atgagtttgg acaaaccaca actagaatgc agtgaaaaaa atgctttatt    2520
tgtgaaattt gtgatgctat tgctttattt gtaaccatta taagctgcaa taaacaagtt    2580
aacaacaaca attgcattca ttttatgttt caggttcagg gggagatgtg ggaggttttt    2640
taaagcaagt aaaacctcta caaatgtggt aaaatcgata aggatcttcc tagagcatgg    2700
ctacgtagat aagtagcatg gcgggttaat cattaactac aaggaacccc tagtgatgga    2760
gttggccact ccctctctgc gcgctcgctc gctcactgag gccgggcgac caaaggtcgc    2820
ccgacgcccg ggctttgccc gggcggcctc agtgagcgag cgagcgcgca gctg          2874

<210> SEQ ID NO 73
<211> LENGTH: 20
<212> TYPE: DNA
<213> ORGANISM: Artificial Sequence
<220> FEATURE:
<223> OTHER INFORMATION: PCR primer for mouse GAPDH

<400> SEQUENCE: 73
tgtgtccgtc gtggatctga                                                 20

<210> SEQ ID NO 74
<211> LENGTH: 22
<212> TYPE: DNA
<213> ORGANISM: Artificial Sequence
<220> FEATURE:
<223> OTHER INFORMATION: PCR primer for mouse GAPDH

<400> SEQUENCE: 74
cctgcttcac caccttcttg at                                              22

<210> SEQ ID NO 75
<211> LENGTH: 20
<212> TYPE: DNA
<213> ORGANISM: Artificial Sequence
<220> FEATURE:
<223> OTHER INFORMATION: PCR primer set 2 for human LCAT
<220> FEATURE:
<221> NAME/KEY: misc_feature
<222> LOCATION: (2)..(2)
<223> OTHER INFORMATION: n is a, c, g, or t

<400> SEQUENCE: 75
gntacctgca yacmctggtg                                                 20

<210> SEQ ID NO 76
<211> LENGTH: 21
<212> TYPE: DNA
<213> ORGANISM: Artificial Sequence
<220> FEATURE:
<223> OTHER INFORMATION: PCR primer set 2 for human LCAT

<400> SEQUENCE: 76
gcttscggta gtaytcytcc t                                               21

<210> SEQ ID NO 77
<211> LENGTH: 6845
<212> TYPE: DNA
<213> ORGANISM: Artificial Sequence
<220> FEATURE:
<223> OTHER INFORMATION: pcDNA3.1-hLCAT-V114P
<220> FEATURE:
<221> NAME/KEY: misc_feature
<222> LOCATION: (2)..(1322)
<223> OTHER INFORMATION: hLCAT-V114P
<220> FEATURE:
<221> NAME/KEY: CDS
```

```
<222> LOCATION: (1389)..(1430)
<223> OTHER INFORMATION: V5 tag
<220> FEATURE:
<221> NAME/KEY: CDS
<222> LOCATION: (1440)..(1457)
<223> OTHER INFORMATION: 6 x His tag
<220> FEATURE:
<221> NAME/KEY: polyA_signal
<222> LOCATION: (1486)..(1710)
<223> OTHER INFORMATION: bGH poly(A) signal
<220> FEATURE:
<221> NAME/KEY: enhancer
<222> LOCATION: (6127)..(6506)
<223> OTHER INFORMATION: CMV enhancer
<220> FEATURE:
<221> NAME/KEY: promoter
<222> LOCATION: (6507)..(6710)
<223> OTHER INFORMATION: CMV promoter
<220> FEATURE:
<221> NAME/KEY: promoter
<222> LOCATION: (6755)..(6773)
<223> OTHER INFORMATION: T7 promoter

<400> SEQUENCE: 77
```

| | |
|---|---:|
| caatggggcc gcccggctcc ccatggcagt gggtgacgct gctgctgggg ctgctgctcc | 60 |
| ctcctgccgc ccccttctgg ctcctcaatg tgctcttccc cccgcacacc acgcccaagg | 120 |
| ctgagctcag taaccacaca cggcccgtca tcctcgtgcc cggctgcctg gggaatcagc | 180 |
| tagaagccaa gctggacaaa ccagatgtgg tgaactggat gtgctaccgc aagacagagg | 240 |
| acttcttcac catctggctg gatctcaaca tgttcctacc ccttggggta gactgctgga | 300 |
| tcgataacac cagggttgtc tacaaccgga gctctgggct ccctccaac gcccctggtg | 360 |
| tccagatccg cgtccctggc tttggcaaga cctactctgt ggagtacctg gacagcagca | 420 |
| agctggcagg gtacctgcac acactggtgc agaacctggt caacaatggc tacgtgcggg | 480 |
| acgagactgt gcgcgccgcc ccctatgact ggcggctgga gccggccag caggaggagt | 540 |
| actaccgcaa gctcgcaggg ctggtggagg agatgcacgc tgcctatggg aagcctgtct | 600 |
| tcctcattgg ccacagcctc ggctgtctac acttgctcta tttcctgctg cgccagcccc | 660 |
| aggcctggaa ggaccgcttt attgatggct tcatctctct tggggctccc tggggtggct | 720 |
| ccatcaagcc catgctggtc ttggcctcag gtgacaacca gggcatcccc atcatgtcca | 780 |
| gcatcaagct gaaagaggag cagcgcataa ccaccacctc cccctggatg tttccctctc | 840 |
| gcatggcgtg gcctgaggac cacgtgttca tttccacacc cagcttcaac tacacaggcc | 900 |
| gtgacttcca acgcttcttt gcagacctgc actttgagga aggctggtac atgtggctgc | 960 |
| agtcacgtga cctcctggca ggactcccag cacctggtgt ggaagtatac tgtctttacg | 1020 |
| gcgtgggcct gcccacgccc cgcacctaca tctacgacca cggcttcccc tacacggacc | 1080 |
| ctgtgggtgt gctctatgag gatggtgatg acacggtggc gacccgcagc accgagctct | 1140 |
| gtggcctgtg gcagggccgc cagccacagc ctgtgcacct gctgcccctg cacggataca | 1200 |
| agcatctcaa catggtcttc agcaacctga ccctggagca catcaatgcc atcctgctgg | 1260 |
| gtgcctaccg ccagggtccc cctgcatccc cgactgccag cccagagccc cgcctcctg | 1320 |
| agaagggcaa ttctgcagat atccagcaca gtggcggccg ctcgagtcta gagggcccgc | 1380 |
| ggttcgaa ggt aag cct atc cct aac cct ctc ctc ggt ctc gat tct acg | 1430 |
|             Gly Lys Pro Ile Pro Asn Pro Leu Leu Gly Leu Asp Ser Thr | |
|               1               5                  10                | |
| cgtaccggt cat cat cac cat cac cat tgagtttaaa cccgctgatc | 1477 |
|           His His His His His His | |
|            15              20 | |

```
agcctcgact gtgccttcta gttgccagcc atctgttgtt tgcccctccc ccgtgccttc    1537
cttgaccctg gaaggtgcca ctcccactgt cctttcctaa taaaatgagg aaattgcatc    1597
gcattgtctg agtaggtgtc attctattct gggggggtggg gtggggcagg acagcaaggg    1657
ggaggattgg gaagacaata gcaggcatgc tggggatgcg gtgggctcta tggcttctga    1717
ggcggaaaga accagctggg gctctagggg gtatccccac gcgccctgta gcggcgcatt    1777
aagcgcggcg ggtgtggtgg ttacgcgcag cgtgaccgct acacttgcca gcgccctagc    1837
gcccgctcct ttcgctttct tcccttcctt tctcgccacg ttcgccggct ttccccgtca    1897
agctctaaat cggggcatcc ctttagggtt ccgatttagt gctttacggc acctcgaccc    1957
caaaaaactt gattagggtg atggttcacg tagtgggcca tcgccctgat agacggtttt    2017
tcgccctttg acgttggagt ccacgttctt aatagtggac tcttgttcc aaactggaac     2077 aacactcaac cctatctcgg tctattcttt tgatttataa gggattttgg ggatttcggc    2137
ctattggtta aaaaatgagc tgatttaaca aaaatttaac gcgaattaat tctgtggaat    2197
gtgtgtcagt tagggtgtgg aaagtcccca ggctccccag gcaggcagaa gtatgcaaag    2257
catgcatctc aattagtcag caaccaggtg tggaaagtcc ccaggctccc cagcaggcag    2317
aagtatgcaa agcatgcatc tcaattagtc agcaaccata gtcccgcccc taactccgcc    2377
catcccgccc ctaactccgc ccagttccgc ccattctccg ccccatggct gactaatttt    2437
ttttatttat gcagaggccg aggccgcctc tgcctctgag ctattccaga agtagtgagg    2497 aggcttttt ggaggcctag gcttttgcaa aaagctcccg ggagcttgta tatccattt      2557 cggatctgat caagagacag gatgaggatc gtttcgcatg attgaacaag atggattgca    2617
cgcaggttct ccggccgctt gggtggagag gctattcggc tatgactggg cacaacagac    2677
aatcggctgc tctgatgccg ccgtgttccg gctgtcagcg caggggcgcc cggttctttt    2737
tgtcaagacc gacctgtccg gtgccctgaa tgaactgcag gacgaggcag cgcggctatc    2797
gtggctggcc acgacgggcg ttccttgcgc agctgtgctc gacgttgtca ctgaagcggg    2857
aagggactgg ctgctattgg gcgaagtgcc ggggcaggat ctcctgtcat ctcaccttgc    2917
tcctgccgag aaagtatcca tcatggctga tgcaatgcgg cggctgcata cgcttgatcc    2977
ggctacctgc ccattcgacc accaagcgaa acatcgcatc gagcgagcac gtactcggat    3037
ggaagccggt cttgtcgatc aggatgatct ggacgaagag catcagggc tcgcgccagc     3097 cgaactgttc gccaggctca aggcgcgcat gcccgacggc gaggatctcg tcgtgaccca    3157
tggcgatgcc tgcttgccga atatcatggt ggaaaatggc cgcttttctg gattcatcga    3217
ctgtggccgg ctgggtgtgg cggaccgcta tcaggacata gcgttggcta cccgtgatat    3277
tgctgaagag cttggcggcg aatgggctga ccgcttcctc gtgctttacg gtatcgccgc    3337
tcccgattcg cagcgcatcg ccttctatcg ccttcttgac gagttcttct gagcgggact    3397
ctggggttcg cgaaatgacc gaccaagcga cgcccaacct gccatcacga gatttcgatt    3457
ccaccgccgc cttctatgaa aggttgggct tcggaatcgt tttccgggac gccggctgga    3517
tgatcctcca gcgcggggat ctcatgctgg agttcttcgc ccaccccaac ttgtttattg    3577
cagcttataa tggttacaaa taaagcaata gcatcacaaa tttcacaaat aaagcatttt    3637
tttcactgca ttctagttgt ggtttgtcca aactcatcaa tgtatcttat catgtctgta    3697
taccgtcgac ctctagctag agcttggcgt aatcatggtc atagctgttt cctgtgtgaa    3757
attgttatcc gctcacaatt ccacacaaca tacgagccgg aagcataaag tgtaaagcct    3817
ggggtgccta atgagtgagc taactcacat taattgcgtt gcgctcactg cccgctttcc    3877
```

```
agtcgggaaa cctgtcgtgc cagctgcatt aatgaatcgg ccaacgcgcg gggagaggcg    3937
gtttgcgtat tgggcgctct tccgcttcct cgctcactga ctcgctgcgc tcggtcgttc    3997
ggctgcggcg agcggtatca gctcactcaa aggcggtaat acggttatcc acagaatcag    4057
gggataacgc aggaaagaac atgtgagcaa aaggccagca aaaggccagg aaccgtaaaa    4117
aggccgcgtt gctggcgttt ttccataggc tccgcccccc tgacgagcat cacaaaaatc    4177
gacgctcaag tcagaggtgg cgaaacccga caggactata aagataccag gcgtttcccc    4237
ctggaagctc cctcgtgcgc tctcctgttc cgaccctgcc gcttaccgga tacctgtccg    4297
cctttctccc ttcgggaagc gtggcgcttt ctcaatgctc acgctgtagg tatctcagtt    4357
cggtgtaggt cgttcgctcc aagctgggct gtgtgcacga accccccgtt cagcccgacc    4417
gctgcgcctt atccggtaac tatcgtcttg agtccaaccc ggtaagacac gacttatcgc    4477
cactggcagc agccactggt aacaggatta gcagagcgag gtatgtaggc ggtgctacag    4537
agttcttgaa gtggtggcct aactacggct acactagaag gacagtattt ggtatctgcg    4597
ctctgctgaa gccagttacc ttcggaaaaa gagttggtag ctcttgatcc ggcaaacaaa    4657
ccaccgctgg tagcggtggt ttttttgttt gcaagcagca gattacgcgc agaaaaaaag    4717
gatctcaaga agatcctttg atcttttcta cggggtctga cgctcagtgg aacgaaaact    4777
cacgttaagg gattttggtc atgagattat caaaaaggat cttcacctag atccttttaa    4837
attaaaaatg aagttttaaa tcaatctaaa gtatatatga gtaaacttgg tctgacagtt    4897
accaatgctt aatcagtgag gcacctatct cagcgatctg tctatttcgt tcatccatag    4957
ttgcctgact ccccgtcgtg tagataacta cgatacggga gggcttacca tctggcccca    5017
gtgctgcaat gataccgcga gacccacgct caccggctcc agatttatca gcaataaacc    5077
agccagccgg aagggccgag cgcagaagtg gtcctgcaac tttatccgcc tccatccagt    5137
ctattaattg ttgccgggaa gctagagtaa gtagttcgcc agttaatagt ttgcgcaacg    5197
ttgttgccat tgctacaggc atcgtggtgt cacgctcgtc gtttggtatg gcttcattca    5257
gctccggttc ccaacgatca aggcgagtta catgatcccc catgttgtgc aaaaaagcgg    5317
ttagctcctt cggtcctccg atcgttgtca gaagtaagtt ggccgcagtg ttatcactca    5377
tggttatggc agcactgcat aattctctta ctgtcatgcc atccgtaaga tgcttttctg    5437
tgactggtga gtactcaacc aagtcattct gagaatagtg tatgcggcga ccgagttgct    5497
cttgcccggc gtcaatacgg gataataccg cgccacatag cagaacttta aaagtgctca    5557
tcattggaaa acgttcttcg gggcgaaaac tctcaaggat cttaccgctg ttgagatcca    5617
gttcgatgta acccactcgt gcacccaact gatcttcagc atcttttact ttcaccagcg    5677
tttctgggtg agcaaaaaca ggaaggcaaa atgccgcaaa aaagggaata agggcgacac    5737
ggaaatgttg aatactcata ctcttccttt ttcaatatta ttgaagcatt tatcagggtt    5797
attgtctcat gagcggatac atatttgaat gtatttagaa aaataaacaa ataggggttc    5857
cgcgcacatt tccccgaaaa gtgccacctg acgtcgacgg atcgggagat ctcccgatcc    5917
cctatggtcg actctcagta caatctgctc tgatgccgca tagttaagcc agtatctgct    5977
ccctgcttgt gtgttggagg tcgctgagta gtgcgcgagc aaaatttaag ctacaacaag    6037
gcaaggcttg accgacaatt gcatgaagaa tctgcttagg gttaggcgtt ttgcgctgct    6097
tcgcgatgta cgggccagat atacgcgttg acattgatta ttgactagtt attaatagta    6157
atcaattacg gggtcattag ttcatagccc atatatggag ttccgcgtta cataacttac    6217
```

```
ggtaaatggc ccgcctggct gaccgcccaa cgacccccgc ccattgacgt caataatgac    6277
gtatgttccc atagtaacgc caatagggac tttccattga cgtcaatggg tggactattt    6337
acggtaaact gcccacttgg cagtacatca agtgtatcat atgccaagta cgcccctat    6397 tgacgtcaat gacggtaaat ggcccgcctg gcattatgcc cagtacatga ccttatggga    6457
ctttcctact tggcagtaca tctacgtatt agtcatcgct attaccatgg tgatgcggtt    6517
ttggcagtac atcaatgggc gtggatagcg gtttgactca cggggatttc caagtctcca    6577
ccccattgac gtcaatggga gtttgttttg gcaccaaaat caacgggact ttccaaaatg    6637
tcgtaacaac tccgccccat tgacgcaaat gggcggtagg cgtgtacggt gggaggtcta    6697
tataagcaga gctctctggc taactagaga acccactgct tactggctta tcgaaattaa    6757
tacgactcac tatagggaga cccaagctgg ctagttaagc ttggtaccga gctcggatcc    6817
actagtccag tgtggtggaa ttgcccctt                                      6845
```

```
<210> SEQ ID NO 78
<211> LENGTH: 14
<212> TYPE: PRT
<213> ORGANISM: Artificial Sequence
<220> FEATURE:
<223> OTHER INFORMATION: Synthetic Construct

<400> SEQUENCE: 78

Gly Lys Pro Ile Pro Asn Pro Leu Leu Gly Leu Asp Ser Thr
1               5                   10

<210> SEQ ID NO 79
<211> LENGTH: 6
<212> TYPE: PRT
<213> ORGANISM: Artificial Sequence
<220> FEATURE:
<223> OTHER INFORMATION: Synthetic Construct

<400> SEQUENCE: 79

His His His His His His
1               5
```